United States Patent
Cheney et al.

(10) Patent No.: US 11,806,059 B2
(45) Date of Patent: Nov. 7, 2023

(54) SHAPE MEMORY IMPLANTS AND METHODS AND APPARATUS FOR THE LOADING AND IMPLANTING THEREOF

(71) Applicant: DEPUY SYNTHES PRODUCTS, INC., Raynham, MA (US)

(72) Inventors: Daniel F. Cheney, Downingtown, PA (US); Adam T. Knight, Douglassville, PA (US); Joseph P. Ritz, Castroville, TX (US)

(73) Assignee: DePuy Synthes Products, Inc., Raynham, MA (US)

( * ) Notice: Subject to any disclaimer, the term of this patent is extended or adjusted under 35 U.S.C. 154(b) by 25 days.

(21) Appl. No.: 17/371,810

(22) Filed: Jul. 9, 2021

(65) Prior Publication Data

US 2022/0015812 A1   Jan. 20, 2022

Related U.S. Application Data

(60) Provisional application No. 63/051,702, filed on Jul. 14, 2020.

(51) Int. Cl.
| | |
|---|---|
| *A61B 17/80* | (2006.01) |
| *A61B 17/064* | (2006.01) |
| *A61B 17/00* | (2006.01) |
| *A61B 17/10* | (2006.01) |

(52) U.S. Cl.
CPC ...... *A61B 17/8085* (2013.01); *A61B 17/0642* (2013.01); *A61B 17/808* (2013.01); *A61B 17/8057* (2013.01); *A61B 17/10* (2013.01); *A61B 2017/00867* (2013.01); *A61B 2017/0645* (2013.01)

(58) Field of Classification Search
CPC .... A61B 2017/0641; A61B 2017/0645; A61B 2017/00867; A61B 17/1728; A61B 17/808; A61B 17/8057; A61B 17/8004; A61B 17/8085; A61B 17/10; A61B 17/0642
USPC ........................................................ 606/281
See application file for complete search history.

(56) References Cited

U.S. PATENT DOCUMENTS

| | | |
|---|---|---|
| 6,685,708 B2 | 2/2004 | Monassevitch et al. |
| 7,115,129 B2 | 10/2006 | Heggeness |
| 7,931,679 B2 | 4/2011 | Heggeness |
| 8,137,351 B2 | 3/2012 | Prandi |

(Continued)

FOREIGN PATENT DOCUMENTS

EP   0826340 A2   3/1998

OTHER PUBLICATIONS

International Search Report for PCT/IB2021/056364, dated Dec. 23, 2021 for PCT Application Counterpart to US 17371810.

*Primary Examiner* — Marcela I. Shirsat
(74) *Attorney, Agent, or Firm* — Christopher L. Makay

(57) ABSTRACT

An orthopedic fixation system includes an orthopedic implant and an implant retainer. The orthopedic implant transitions between a natural shape and an insertion shape whereby a transition of the orthopedic implant from the natural shape to the insertion shape stores deliverable energy and a transition of the orthopedic implant from the insertion shape to the natural shape delivers stored energy. The implant retainer is configured to engage the orthopedic implant and constrain the orthopedic implant in the insertion shape such that the implant grip prevents a transition of the orthopedic implant from the insertion shape to the natural shape.

21 Claims, 72 Drawing Sheets

(56) References Cited

U.S. PATENT DOCUMENTS

| | | |
|---|---|---|
| 9,011,507 B2 | 4/2015 | Schelling |
| 9,220,546 B2 | 12/2015 | Medoff et al. |
| 9,597,130 B2 | 3/2017 | Pappalardo et al. |
| 9,615,874 B2 | 4/2017 | Orbay et al. |
| 9,883,897 B2 | 2/2018 | Taber |
| 9,918,762 B2 | 3/2018 | Federspiel et al. |
| 10,064,619 B2 | 9/2018 | Palmer et al. |
| 10,123,831 B2 | 11/2018 | Gephardt |
| 10,194,959 B2 | 2/2019 | Gephardt et al. |
| 2009/0182345 A1 | 7/2009 | Medoff et al. |
| 2010/0133316 A1 | 6/2010 | Lizee et al. |
| 2011/0118842 A1* | 5/2011 | Bernard ............... A61F 2/4455 623/17.11 |
| 2011/0178555 A1 | 7/2011 | Heggeness |
| 2016/0199060 A1* | 7/2016 | Morgan ............... A61B 17/10 227/175.1 |
| 2017/0196604 A1 | 7/2017 | Hartdegen et al. |
| 2017/0209193 A1* | 7/2017 | Hartdegen ......... A61B 17/8863 |
| 2017/0252036 A1* | 9/2017 | Palmer ............... A61B 17/8685 |
| 2017/0281157 A1 | 10/2017 | Hartdegen et al. |
| 2018/0271521 A1 | 9/2018 | Wahl |

\* cited by examiner

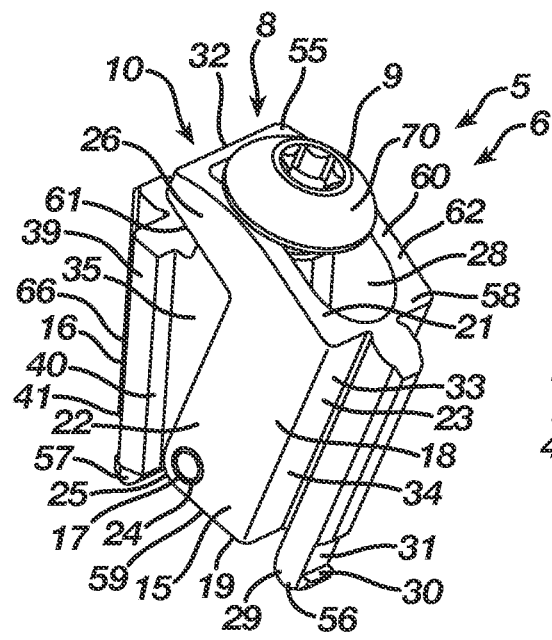
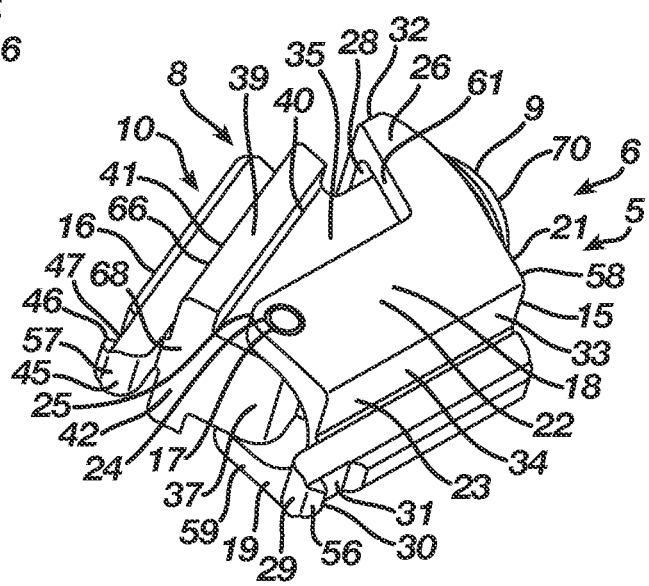
FIG. 1A
FIG. 1B
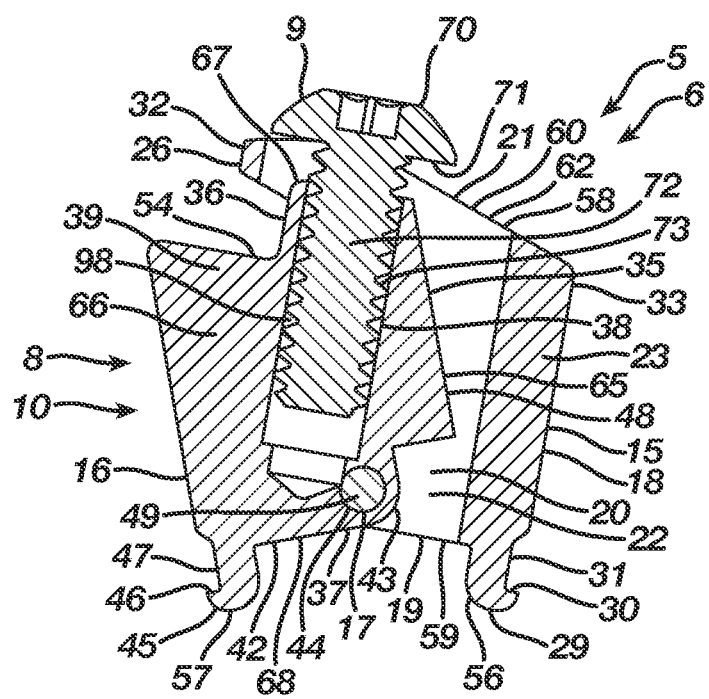
FIG. 1C

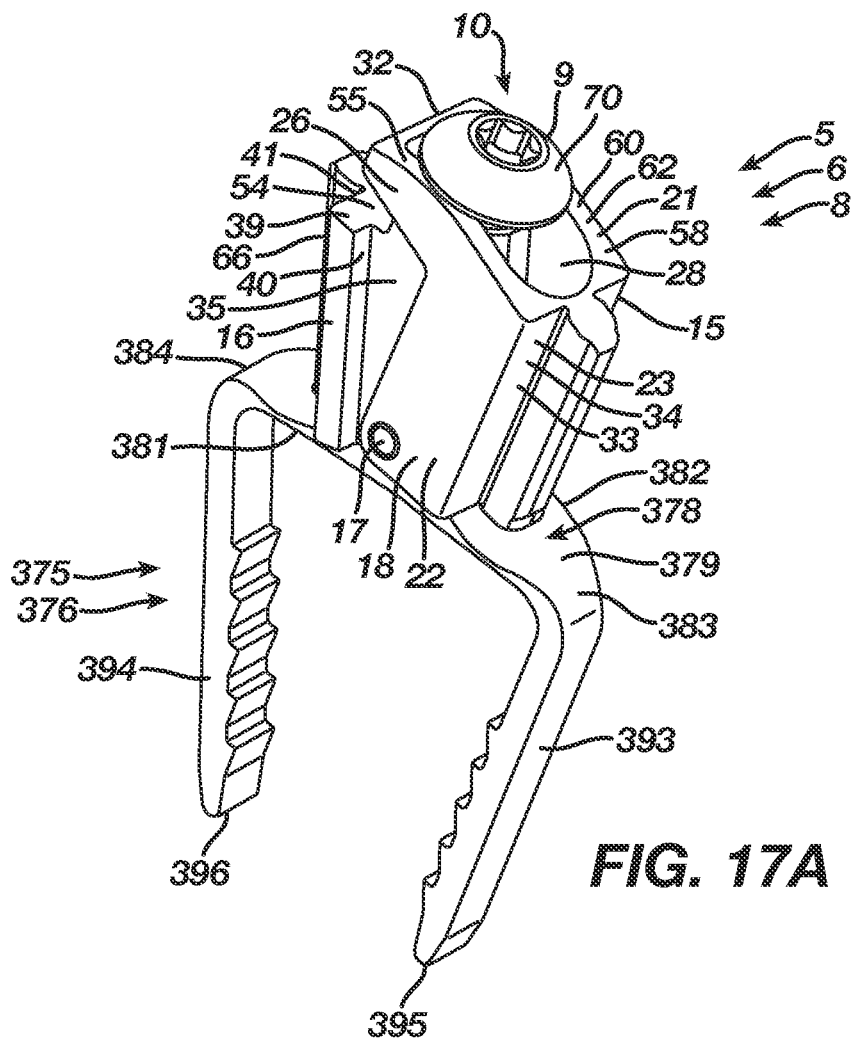
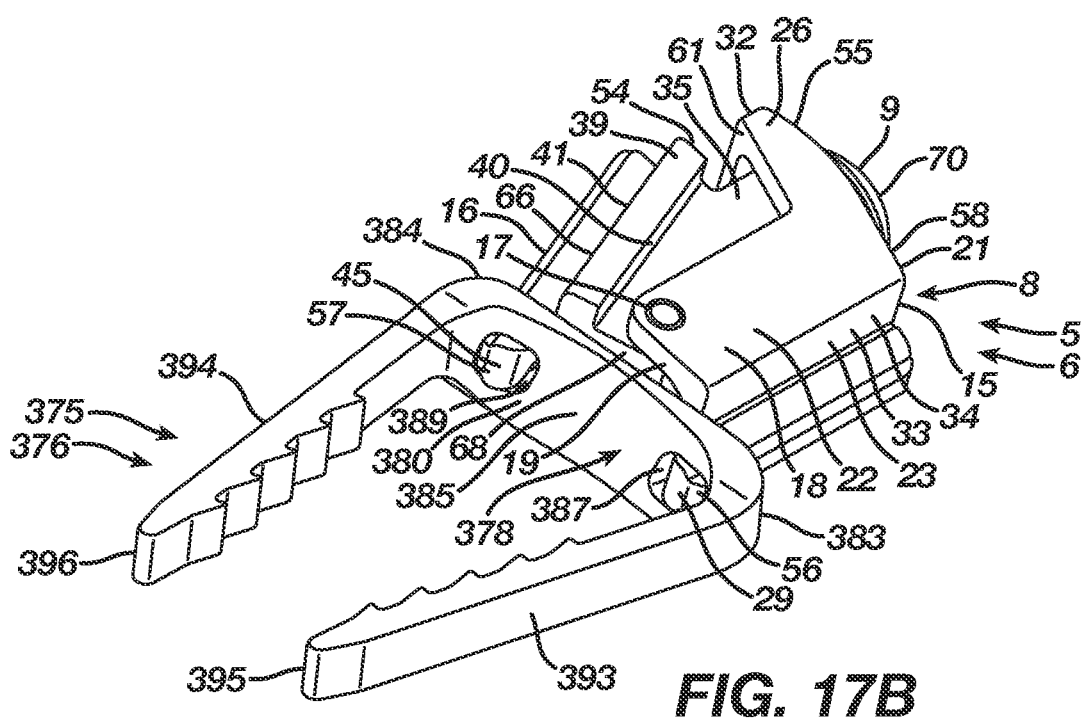

SHAPE MEMORY IMPLANTS AND METHODS AND APPARATUS FOR THE LOADING AND IMPLANTING THEREOF

BACKGROUND OF THE INVENTION

1. Field of the Invention

The present invention relates generally to shape memory implants and the implantation thereof using an implant retention device and, more particularly, but not way of limitation, to an orthopedic fixation system including a shape memory implant and an implant retention device designed for loading with the shape memory implant and for subsequent delivery of the shape memory implant utilizing the implant retention device.

2. Description of the Related Art

Shape memory implants are commonly used in surgical procedures that require the reattachment or fusing of tissue or bone. Shape memory implants can be composed of a shape memory material such as Nitinol that allows the shape memory implants to have a first final shape and the ability to transform into a second shape. A shape memory implant can be either thermally activated, in which an external heating source or body temperature would be required to activate the implant, or mechanically activated, in which a constraining instrument would be required. A shape memory implant that requires mechanical constraint stores mechanical energy due to elastic (recoverable) deformation, and then releases the stored mechanical energy when the constraining instrument is removed. In these types of implants, the implants are mechanically deformed into their second shape and maintained in their second shape by instrumentation such that, upon release from the instrumentation, the implants elastically return to their first final shape from their second shape.

In surgical procedures, the elastic property of constrained shape memory implants is used as follows. Bones that require fixating are aligned, and the shape memory implant, which has been mechanically deformed to its second shape, is maintained in instrumentation and inserted across the bones. After insertion, the shape memory implant is released from the instrumentation, whereupon the shape memory implant elastically tries to return to its first final shape such that the shape memory implant maintains the bones fixated together. The shape memory implant because it stores mechanical energy continuously applies force to the fixated bones as the shape memory implant tries to transition from the second shape to the first final shape, which aids in the healing process.

Various types of instrumentation can be used for either maintaining the shape memory implants in their second shape or moving an implant from its first final shape to a temporary second shape. Metal forceps are often employed to open and then insert the implant. These forceps have to be sterilized by a hospital, and then the implant can be placed on the forceps, opened to a desired position, and used for inserting the implant. Although potentially effective, forceps require the implant to be loaded into the forceps during surgery, which might be cumbersome and time consuming. In addition, forceps might be large and grip the implant at an underside thereof such that the forceps hinder implantation of the implant into a patient during surgery. It is also possible that a physician using the forceps might damage the implant in various ways, such as stretching the implant beyond the second shape, fatiguing the implant, or causing metal-on-metal scraping of the implant with the instrument. Furthermore, forceps can be expensive instruments that require cleaning and sterilization after each surgery.

Metal instrumentation alternative to forceps engage a shape memory implant at securing features thereof such as screw holes. This type of instrumentation allows preloading and sterilization of the implant with the implant already in the second shape, and the implant can be pre-activated so that it does not require heating with an external heater or body temperature after implantation. Although potentially effective, the instrumentation typically must be employed with an implant sufficiently large to include multiple securing features at each end unless the instrumentation releases the securing features of the implant prior to a complete engagement of the implant with bones, which may result in an improper delivery of the implant.

Other instrumentation includes plastic and disposable tools to maintain a shape memory implant in the second shape. This type of instrumentation can be preloaded and sterilized with the implant already in the second shape, and the implant can be pre-activated so that it does not require heating with an external heater or body temperature after use. One type of plastic and disposable instrument operates by having the implant fit inside a passage that is substantially the same diameter as the shape memory implant. By using this method, the instrumentation allows the shape memory implant to be preloaded prior to surgery. However, using instrumentation that substantially conforms to the profile of the shape memory implant can create several problems for a surgeon. First, this type of instrumentation often makes disengagement of the shape memory staple after implantation problematic. In particular, the shape memory implant sticks to the instrumentation due to the frictional engagement between the shape memory implant, which is trying to compress, and the passage of the instrumentation, resulting in a more difficult surgical procedure and the potential for a less than satisfactory fixation of tissue or bone. Second, this type of instrumentation results in an abrupt and sudden release of stored mechanical energy as the implant is removed from the device. This type of instrumentation accordingly provides no method of slowly transitioning the stored energy in the implant from the instrumentation to the bones being fixated. Finally, this type of instrumentation can result in entanglement during release, in which the implant begins to compress upon release thereby making extraction of this type of instrumentation more difficult.

Another type of plastic and disposable instrument includes arms movable between a disengaged position and an engaged position. The arms terminate in jaws such that, when the arms reside in their engaged position, the jaws contact the shape memory implant to maintain the shape memory implant open for insertion. While the movable arms and jaws release the implant without entanglement and further allow the slow transitioning of the implant, the jaws, due to their location when contacting the shape memory implant as well as their path of travel during removal from the shape memory implant, leave the implant situated above the bone surface such that tamping of the implant to a position flush with the bone surface is required. As a result, the instrument can be impractical for certain surgeries because it is not always possible to tamp and thus seat the implant flush with a bone surface after its release from the instrument, particularly when the implant includes anchoring members of limited length.

Accordingly, an instrument that constrains a shape memory implant in its second shape, allows the shape memory implant to be preloaded and sterilized prior to surgery, controls the rate of tension release, simplifies removal of the shape memory implant after implantation, and releases the shape memory implant at a bone surface thereby eliminating tamping would be beneficial.

SUMMARY OF THE INVENTION

In accordance with the present invention, an orthopedic fixation system includes an orthopedic implant and an implant retainer. The orthopedic implant transitions between a natural shape and an insertion shape whereby a transition of the orthopedic implant from the natural shape to the insertion shape stores deliverable energy and a transition of the orthopedic implant from the insertion shape to the natural shape delivers stored energy. The implant retainer is configured to engage the orthopedic implant and constrain the orthopedic implant in the insertion shape thereby preventing a transition of the orthopedic implant from the insertion shape to the natural shape.

The orthopedic implant includes a bridge with a first end and a second end. The orthopedic implant includes a transition section disposed in the bridge, whereby the transition section deforms to move the orthopedic implant between the natural shape and the insertion shape. The orthopedic implant includes a first anchoring segment disposed at the first end of the bridge and a second anchoring segment disposed at the second end of the bridge. The orthopedic implant includes a first aperture extending through the bridge adjacent the transition section at a first side thereof and a second aperture extending through the bridge adjacent the transition section at a second side thereof. The first aperture and the second aperture are spaced apart across the transition section. The orthopedic implant includes a first catch protruding into the first aperture and a second catch protruding into the second aperture.

The first anchoring segment includes a first opening extending through the bridge at the first end thereof adapted to receive a screw therethrough. Likewise, the second anchoring segment includes a second opening extending through the bridge at the second end thereof adapted to receive a screw therethrough. The first anchoring segment may include a third opening extending through the bridge at the first end thereof exterior of the first opening adapted to receive a screw therethrough. Likewise, the second anchoring segment may include a fourth opening extending through the bridge at the second end thereof exterior of the second opening adapted to receive a screw therethrough.

The first anchoring segment alternatively includes a first leg extending from the bridge at the first end thereof. Likewise, the second anchoring segment alternatively includes a second leg extending from the bridge at the second end thereof. The first anchoring segment may include a third leg extending from the bridge interior of the first leg. Likewise, the second anchoring segment may include a fourth leg extending from the bridge interior of the second leg.

The orthopedic implant further includes a third anchoring segment disposed at the first end of the bridge adjacent the first anchoring segment. The third anchoring segment includes a third opening extending through the bridge at the first end thereof adjacent the first opening adapted to receive a screw therethrough. The third anchoring segment alternatively includes a third leg extending from the bridge at the first end thereof adjacent the first leg. The orthopedic implant still further includes a fourth anchoring segment disposed at the second end of the bridge adjacent the second anchoring segment. The fourth anchoring segment includes a fourth opening extending through the bridge at the second end thereof adjacent the second opening adapted to receive a screw therethrough. The fourth anchoring segment alternatively includes a fourth leg extending from the bridge at the second end thereof adjacent the second leg.

The implant retainer is configured to engage the orthopedic implant at the first aperture and the second aperture and constrain the orthopedic implant in the insertion shape thereby preventing a transition of the orthopedic implant from the insertion shape to the natural shape. The implant retainer includes an implant grip and an actuator coupled with the implant grip.

The implant grip is movable between a disengaged position whereby the implant grip releases the orthopedic implant and an engaged position whereby the implant grip constrains the orthopedic implant in the insertion shape. The implant grip includes a first fastener adapted to engage the orthopedic implant at the first aperture and a second fastener adapted to engage of the orthopedic implant at the second aperture. The first fastener and the second fastener are spaced apart at a first distance when the implant grip resides in the disengaged position and at a second distance greater than the first distance when the implant grip resides in the engaged position.

The actuator is operable to move the implant grip between the disengaged position and the engaged position. Upon operation of the actuator to move the implant grip to the disengaged position with the first fastener and the second fastener residing at the first distance, the first fastener inserts into and removes from the first aperture of the orthopedic implant and the second fastener inserts into and removes from the second aperture of the orthopedic implant. Conversely, upon operation of the actuator to move the implant grip to the engaged position with the first fastener and the second fastener residing at the second distance, the first fastener engages with the bridge of the orthopedic implant at the first aperture and the second fastener engages with the bridge of the orthopedic implant at the second aperture. The implant grip accordingly secures with the orthopedic implant across the transition section of the bridge such that the implant grip constrains the bridge and holds the orthopedic implant in the insertion shape to prevent a transition of the orthopedic implant from the insertion shape to the natural shape.

The first fastener includes a first detent and the second fastener includes a second detent. Upon operation of the actuator to move the implant grip to the disengaged position with the first fastener and the second fastener residing at the first distance, the first fastener inserts into and removes from the first aperture of the orthopedic implant such that the first detent bypasses the first catch and the second fastener inserts into and removes from the second aperture of the orthopedic implant such that the second detent bypasses the second catch. Conversely, upon operation of the actuator to move the implant grip to the engaged position with the first fastener and the second fastener residing at the second distance, the first detent interlocks with the first catch such that the first fastener engages with the bridge of the orthopedic implant at the first aperture and the second detent interlocks with the second catch such that the second fastener engages with the bridge of the orthopedic implant at the second aperture. The implant grip accordingly secures with the orthopedic implant across the transition section of the bridge such that the implant grip constrains the bridge and holds the orthopedic implant in the insertion shape to prevent a transition of the orthopedic implant from the insertion shape to the natural shape.

The implant grip includes a frame and a body pivotally secured at a pivot point. The frame defines a chamber and includes a front, a rear, a top, and a bottom. The front is elevated relative to the rear whereby the top angles downward between the front and the rear. The frame at the top thereof includes a slot communicating with the chamber. The frame further at the top thereof about the slot includes a bearing surface with a slope due to the front being elevated relative to the rear. The frame at the rear thereof includes the first fastener extending below the bottom of the frame. The body includes a front, a rear, a top, and a bottom. The body defines an actuator aperture beginning at the top thereof and extending into the body. The actuator aperture is adapted to receive therein at least a portion of the actuator whereby the actuator aperture facilitates linear travel of the actuator relative thereto. The body is configured to insert into the chamber of the frame such that the actuator aperture of the body is accessible through the slot of the frame. The body at the rear thereof includes the second fastener extending below the bottom of the body.

The actuator engages with the frame and the body and is operable to impart angular motion to the frame and the body about the pivot point such that the implant grip moves between the disengaged position and the engaged position. The actuator includes a head coupled with a shaft, The shaft inserts through the slot of the frame and into the actuator aperture of the body such that the head resides atop the bearing surface at the top of the frame in abutting relationship therewith.

The frame and the body, when the implant grip resides in the disengaged position, pivot relative thereto about the pivot point such that the top of the body defining the actuator aperture is positioned in the slot adjacent the front of the frame and the front of the body is spaced apart from the rear of the frame. The actuator, when the implant grip resides in the disengaged position, includes the head thereof being located atop the bearing surface adjacent the front of the frame and the shaft thereof being inserted in the actuator aperture a first distance. Conversely, the frame and the body, when the implant grip resides in the engaged position, pivot relative thereto about the pivot point such that the top of the body defining the actuator aperture is positioned in the slot adjacent the rear of the frame and the front of the body is positioned adjacent the rear of the frame. The actuator, when the implant grip resides in the engaged position, includes the head thereof being located atop the bearing surface adjacent the rear of the frame and the shaft thereof being inserted in the actuator aperture a second distance greater than the first distance based upon the front of the frame being elevated relative to the rear of the frame.

The actuator, in moving the implant grip from the disengaged position to the engaged position, is rotationally operable to facilitate a rotational motion of the head and a linear progression of the shaft. In accordance therewith, the head traverses the bearing surface of the frame from adjacent the front of the frame to adjacent the rear of the frame. Concurrently, the shaft progresses within the actuator aperture from the first distance to the second distance based upon the abutting relationship of the head with the bearing surface of the frame and the slope of the bearing surface being negative relative to the head. Responsive thereto, the pivot point of the frame and the body translates the rotational motion of the head and the linear progression of the shaft into a linear motion imparted to the frame and the body that pivots the frame and the body about the pivot point along a decreasing arc until the top of the body defining the actuator aperture traverses the slot from adjacent the front of the frame to adjacent the rear of the frame and the front of the body inserts into the chamber of the frame adjacent the rear of the frame. The first fastener and the second fastener accordingly progress from the first distance to the second distance such that the first fastener engages with the bridge of the orthopedic implant at the first aperture and the second fastener engages with the bridge of the orthopedic implant at the second aperture. More particularly, the first fastener and the second fastener progress from the first distance to the second distance such that the first detent interlocks with the first catch thereby engaging with the bridge of the orthopedic implant at the first aperture and the second detent interlocks with the second catch thereby engaging with the bridge of the orthopedic implant at the second aperture.

The actuator, in moving the implant grip from the engaged position to the disengaged position, is rotationally operable to facilitate a rotational motion of the head and a linear retraction of the shaft. In accordance therewith, the head traverses the bearing surface of the frame from adjacent the rear of the frame to adjacent the front of the frame. Concurrently, the shaft retracts within the actuator aperture from the second distance to the first distance based upon the abutting relationship of the head with the bearing surface of the frame and the slope of the bearing surface being positive relative to the head. Responsive thereto, the pivot point of the frame and the body translates the rotational motion of the head and the linear retraction of the shaft into a linear motion imparted to the frame and the body that pivots the frame and the body about the pivot point along an increasing arc until the top of the body defining the actuator aperture traverses the slot from adjacent the rear of the frame to adjacent the front of the frame and the front of the body is spaced apart from the rear of the frame. The first fastener and the second fastener accordingly progress from the second distance to the first distance such that the first fastener disengages from the bridge of the orthopedic implant at the first aperture and the second fastener disengages from the bridge of the orthopedic implant at the second aperture. More particularly, the first fastener and the second fastener progress from the second distance to the first distance such that the first detent releases the first catch thereby disengaging with the bridge of the orthopedic implant at the first aperture and the second detent releases the second catch thereby disengaging with the bridge of the orthopedic implant at the second aperture.

It is therefore an object of the present invention to provide an orthopedic fixation system with an orthopedic implant transitionable between a natural shape and an insertion shape whereby a transition of the orthopedic implant from the natural shape to the insertion shape stores deliverable energy and a transition of the orthopedic implant from the insertion shape to the natural shape delivers stored energy.

It is another object of the present invention to provide an orthopedic fixation system with an implant retainer configured to mechanically engage the orthopedic implant such the implant retainer constrains the orthopedic implant in the insertion shape thereby preventing a transition of the orthopedic implant from the insertion shape to the natural shape.

It is a further object of the present invention to provide an orthopedic fixation system with an implant retainer that simplifies removal of an orthopedic implant therefrom and releases the orthopedic implant at a bone surface thereby eliminating tamping.

Still other objects, features, and advantages of the present invention will become evident to those of ordinary skill in the art in light of the following. Also, it should be understood that the scope of this invention is intended to be broad, and any combination of any subset of the features, elements, or steps described herein is part of the intended scope of the invention.

BRIEF DESCRIPTION OF DRAWINGS

FIG. 1A is a top isometric view illustrating an implant retainer according to a first embodiment in an unloaded position.

FIG. 1B is a bottom isometric view thereof.

FIG. 1C is a side view in cross-section thereof.

FIG. 17A is a top isometric view illustrating the implant retainer according to the first embodiment in an unloaded position relative to the shape memory implant according to the fourth embodiment in its natural shape.

FIG. 17B is a bottom isometric view thereof.

DETAILED DESCRIPTION OF THE PREFERRED EMBODIMENT

Figure 2:
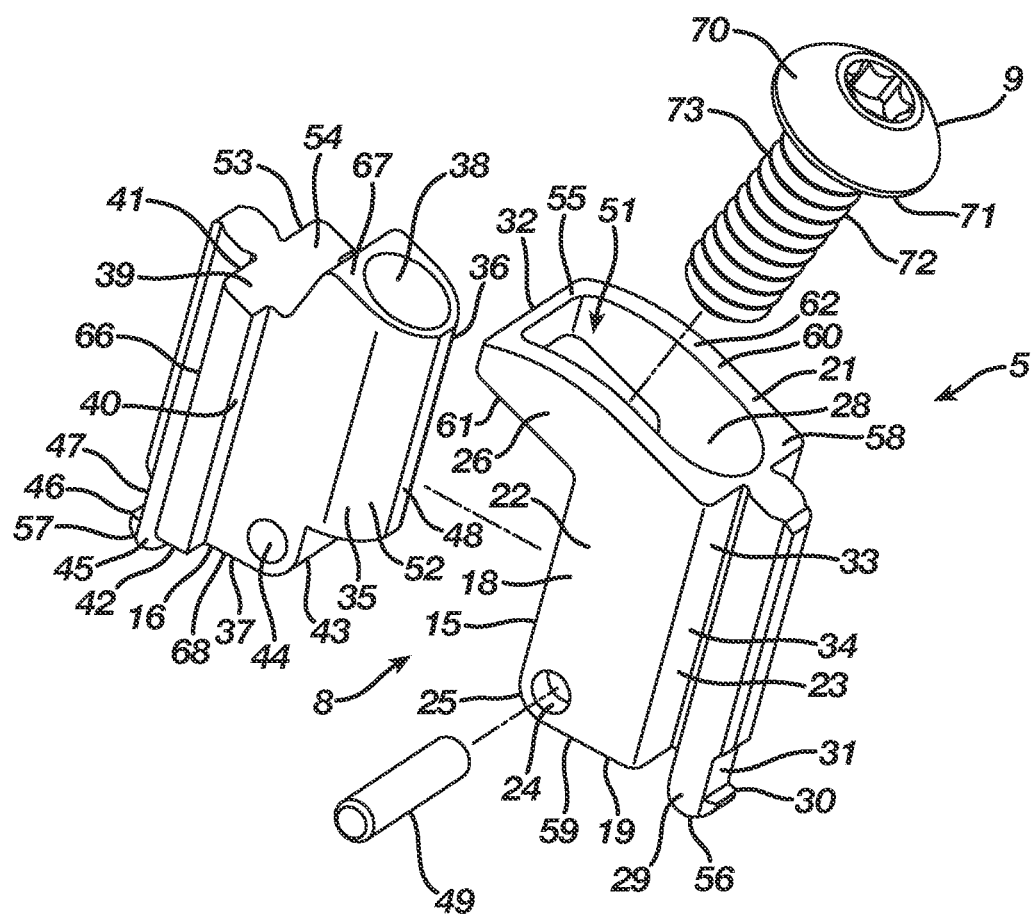
FIG. 2 is an exploded isometric view illustrating the implant retainer according to the first embodiment.
Figure 3A:
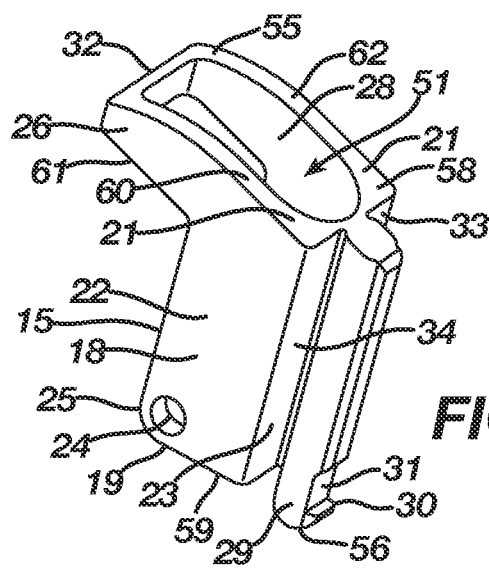
FIG. 3A is an isometric view illustrating a frame of an implant grip for the implant retainer according to the first embodiment.
Figure 3B:
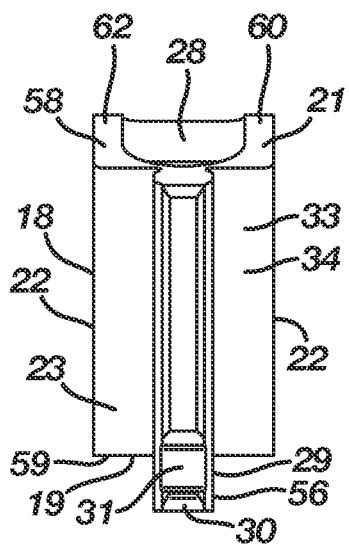
FIG. 3B is a rear view thereof.
Figure 3C:
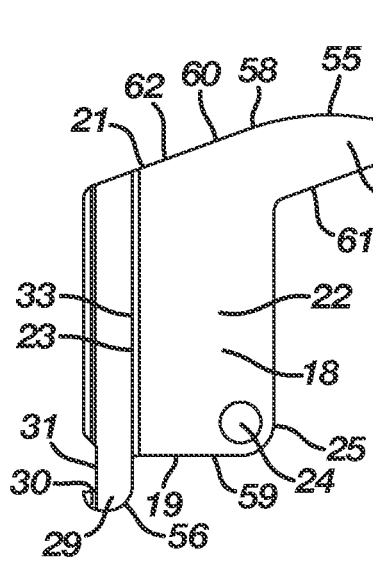
FIG. 3C is a side view thereof.
Figure 3D:
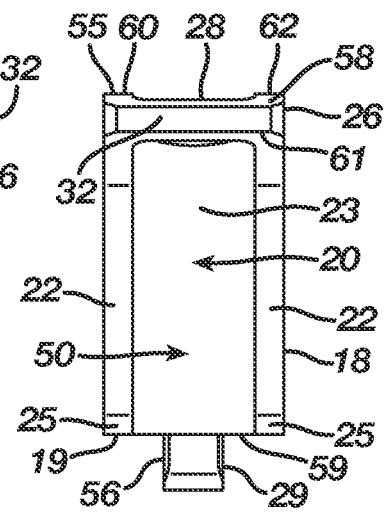
FIG. 3D is a front view thereof.
Figure 3E:
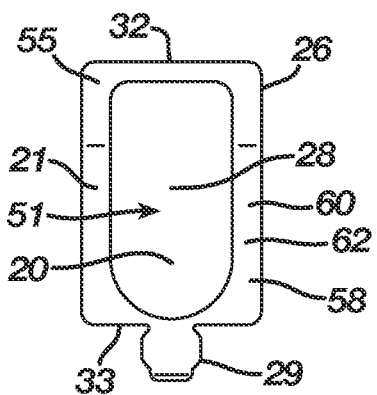
FIG. 3E is a top view thereof.
Figure 3F:
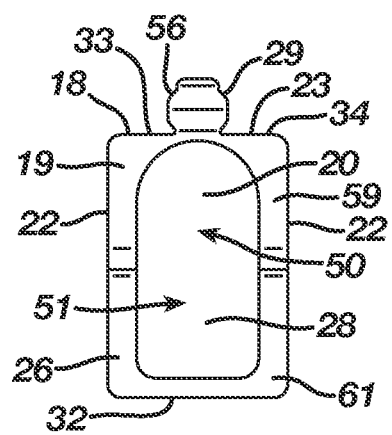
FIG. 3F is a bottom view thereof.
Figure 4A:
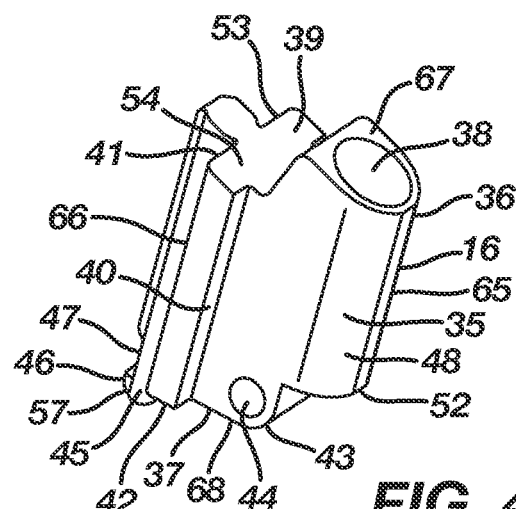
FIG. 4A is an isometric view illustrating a body of an implant grip for the implant retainer according to the first embodiment.
Figure 4B:
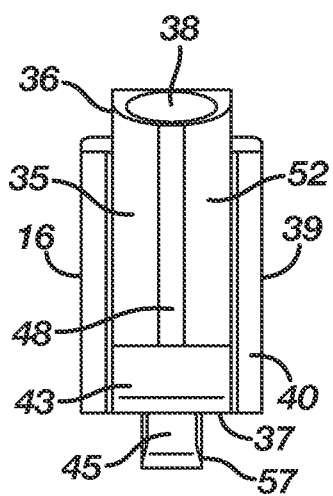
FIG. 4B is a front view thereof.
Figure 4C:
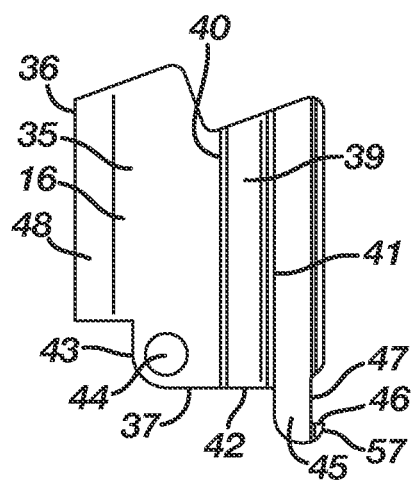
FIG. 4C is a side view thereof.
Figure 4D:
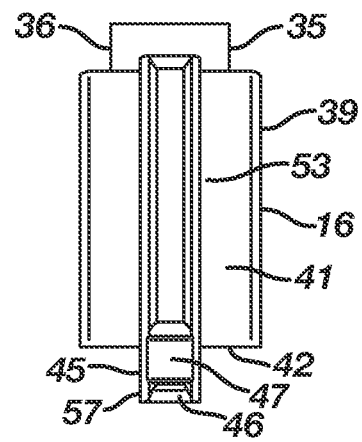
FIG. 4D is a rear view thereof.
Figure 4E:
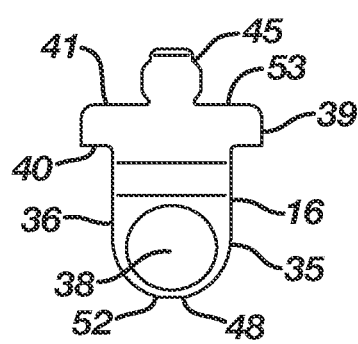
FIG. 4E is a top view thereof.
Figure 4F:
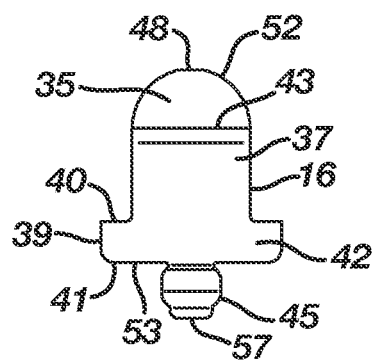
FIG. 4F is a bottom view thereof.

As required, detailed embodiments of the present invention are disclosed herein; however, it is to be understood that the disclosed embodiments are merely exemplary of the invention, which may be embodied in various forms. Figures are not necessarily to scale, and some features may be exaggerated to show details of particular components or steps.

FIGS. 1A-4F and 6A-7C illustrate an implant retainer 5 according to a first embodiment adapted for use with an implant transitionable between a natural shape and an insertion shape. The implant retainer 5 includes an unloaded position 6 whereby the implant retainer 5 releases the implant to return to its natural shape and a loaded position 7 whereby the implant retainer 5 constrains the implant in its insertion shape. The implant retainer 5 includes an implant grip 8 engageable with the implant and an actuator 9 coupled with the implant grip 8. Operating the actuator 9 moves the implant grip 8 between a disengaged position 10 whereby the implant grip 8 releases the implant and an engaged position 11 whereby the implant grip 8 retains the implant in its insertion shape. The implant grip 8 includes a frame 15 and a body 16 pivotally secured at a pivot point 17 using a pin 49. The actuator 9 engages the frame 15 and the body 16 such that manipulation of the actuator 9 imparts angular motion to the frame 15 and the body 16 about their pivot point 17 resulting in the implant grip 8 moving between its disengaged position 10 and its engaged position 11.

The frame 15, which includes a front 32, a rear 33, a top 58, and a bottom 59, defines a chamber 20 having a width 50. The frame 15 at the top 58 includes a slot 28 communicating with the chamber 20 whereby the slot 28 has a width 51 substantially equal to the width 50 of the chamber 20. The front 32 of the frame 15 is elevated with respect to the rear 33 of the frame 15 whereby the top 58 of the frame 15 angles downward between the front 32 and the rear 33 such that there is a vertical distance between the rear 33 and the front 32 of the frame 15. The top 58 of the frame 15 about the slot 28 includes a bearing surface 60 with a slope 62 due to the elevation of the front 32 with respect to the rear 33 of the frame 15. The frame 15 at bottom corners 25 thereof each include an opening 24 therethrough aligned to facilitate formation of the pivot point 17. The frame 15 at its rear 33 includes a fastener 29 extending therefrom. In the first embodiment, the fastener 29 resides centrally with respect to the rear 33 of the frame 15 and extends therefrom below the bottom 59 of the frame 15 such that the fastener 29 provides an engagement point 56 for the frame 15 with the implant. The fastener 29 at the engagement point 56 includes a detent 30 located below a cutout 31 in the fastener 29. While the first embodiment includes a single fastener 29 positioned centrally with respect to the rear 33 of the frame 15, the frame 15 in an alternative embodiment may include first and second fasteners located at each side of the rear 33 for the alternative frame such that the first and second fasteners provide first and second engagement points for the alternative frame with an implant in order to facilitate a more secure engagement of the implant with the alternative frame including first and second fasteners and first and second engagement points.

The frame 15 includes a wall 18 with a top 21 and a bottom 19 and an arm 26 with a top 55 and a bottom 61 whereby the arm 26 extends from the wall 18 at the top 21 thereof. The wall 18 defines the chamber 20 and includes sidewalls 22 that angle downward to an end wall 23. In the first embodiment, the arm 26 and the wall 18 at their respective tops 55 and 21 define the slot 28 of the frame 15, whereas the tops 55 and 21 of the arm 26 and the wall 18, respectively, define the bearing surface 60 of the frame 15. The arm 26 extends from the wall 18 elevated relative thereto while the sidewalls 22 angle downward such that the top 55 of the arm 26 and the top 21 of the wall 18 define the bearing surface 60 with the slope 62. The sidewalls 22, which incorporate the bottom corners 25 of the frame 15, each include one of the openings 24 therethrough such that the openings 24 are aligned to facilitate formation of the pivot point 17. The wall 18 at an exterior face 34 of the end wall 23 includes the fastener 29 extending therefrom. The fastener 29 in the first embodiment resides centrally with respect to the end wall 23 and extends therefrom below the bottom 19 of the wall 18 such that the fastener 29 provides the engagement point 56 for the frame 15 with the implant. While the first embodiment includes a single fastener 29 positioned centrally with respect to the end wall 23, the frame 15 in an alternative embodiment may include first and second fasteners located at each side of the end wall 23 for the wall 18 such that the first and second fasteners provide first and second engagement points for the alternative frame with an implant in order to facilitate a more secure engagement of the implant with the alternative frame including first and second fasteners and first and second engagement points.

The body 16, which includes a front 65, a rear 66, a top 67, a bottom 68, defines an actuator aperture 38 beginning at the top 67 of the body 16 and extending into the body 16 whereby the actuator aperture 38 receives at least a portion of the actuator 9 therein and engages the actuator 9 such that the actuator aperture 38 facilitates linear travel of the actuator 9 within the actuator aperture 38. The actuator aperture 38 in the first embodiment includes threads 98 that facilitate the securing of the actuator 9 with the body 16 as well as the linear travel of the actuator 9 within the actuator aperture 38. The front 65 of the body 16 has a width 52 less than the width 50 of the chamber 20 and the width 51 of the slot 28, whereas the rear 66 of the body 16 has a width 53 greater than the width 50 of the chamber 20 and the width 51 of the slot 28. The body 16 at a bottom corner 43 thereof includes a passage 44 that aligns with the openings 24 of the frame 15 to facilitate formation of the pivot point 17. The body 16 at its rear 66 includes a fastener 45 extending therefrom. In the first embodiment, the fastener 45 resides centrally with respect to the rear 66 of the body 16 and extends therefrom below the bottom 68 of the body 16 such that the fastener 45 provides an engagement point 57 for the body 16 with the implant. The fastener 45 at the engagement point 57 includes a detent 46 located below a cutout 47 in the fastener 45. While the first embodiment includes a single fastener 45 positioned centrally with respect to the rear 66 of the body 16, the body 16 in an alternative embodiment may include first and second fasteners located at each side of the rear 66 for the alternative body such that the first and second fasteners provide first and second engagement points for the alternative body with an implant in order to facilitate a more secure engagement of the implant with the alternative body including first and second fasteners and first and second engagement points.

The body 16 includes an actuator carrier 35 with a top segment 36, a bottom 37, and a front surface 48 therebetween, which in the first embodiment is rounded. The actuator carrier 35 defines the actuator aperture 38 beginning at the top segment 36 and extending into the actuator carrier 35. In the first embodiment, the actuator carrier 35 at the actuator aperture 38 includes the threads 98 that facilitate the securing of the actuator 9 with the actuator carrier 35 as well as the linear travel of the actuator 9 within the actuator aperture 38. The body 16 includes a wall 39 with an interior face 40, an exterior face 41, a top 54, and a bottom 42 whereby the wall 39 at its interior face 40 supports the actuator carrier 35 such that the top segment 36 of the actuator carrier 35 extends above the top 54 of the wall 39. The actuator carrier 35 includes the width 52 that is less than the width 50 of the chamber 20 and the width 51 of the slot 28, whereas the wall 39 includes the width 53 that is greater than the width 50 of the chamber 20 and the width 51 of the slot 28. The actuator carrier 35, which incorporates the bottom corner 43 of the body 16, includes the passage 44 that aligns with the openings 24 of the frame 15 to facilitate formation of the pivot point 17. The wall 39 at the exterior face 41 includes the fastener 45 extending therefrom. The fastener 45 in the first embodiment resides centrally with respect to the wall 39 and extends therefrom below the bottom 42 of the wall 39 such that the fastener 45 provides the engagement point 57 for the body 16 with the implant. While the first embodiment includes a single fastener 45 positioned centrally with respect to the wall 39 of the body 16, the body 16 in an alternative embodiment may include first and second fasteners located at each side of the wall 39 such that the first and second fasteners provide first and second engagement points for the alternative body with an implant in order to facilitate a more secure engagement of the implant with the alternative body including first and second fasteners and first and second engagement points.

The actuator 9 includes a head 70 with a bearing surface 71 and a shaft 72 coupled with the head 72. The shaft 72 is engageable with the actuator aperture 38 whereby rotation of the head 70 facilitates linear travel of the shaft 72 within the actuator aperture 38. In the first embodiment, the shaft 72 includes threads 73 engageable with the threads 98 of the actuator carrier 35 at the actuator aperture 38 such that the threads 98 and 73 create linear travel of the shaft 72 within the actuator aperture 38 in response to the rotation of the head 70.

Assembly of the implant retainer 5 includes the frame 15 and the body 16 pivotally securing at the pivot point 17 to form the implant grip 8. The frame 15 and the body 16 are positioned in opposed relationship with the front 65 of the body 16 facing the front 32 of the frame 15 and aligned with the chamber 20 thereof. The body 16, due to the lesser width 52 of the front 65, inserts into the chamber 20 of the frame 15 with its top 67 disposed in the slot 28 of the frame 15 such that the actuator aperture 38 is accessible through the slot 28. The rear 66 of the body 16, due to its greater width 53, limits the insertion of the body 16 into the chamber 20 of the frame 15. Along with the insertion of the body 16 into the frame 15, the passage 44 of the body 16 aligns with the openings 24 of the frame 15 whereby insertion of the pin 49 into the openings 24 and the passage 44 forms the pivot point 17, thereby pivotally securing the frame 15 with the body 16 and producing the implant grip 8. More particularly, the frame 15 and the body 16 are positioned in opposed relationship with the actuator carrier 35 of the body 16 at its front surface 48 facing the arm 26 of the frame 15 and aligned with the chamber 20 thereof. The actuator carrier 35 of the body 16, due to the lesser width 52, inserts into the chamber 20 of the frame 15 while its top segment 36 inserts into the slot 28 of the frame 15 at the arm 26 thereof such that the actuator aperture 38 is accessible through the slot 28. With the actuator carrier 35 inserted into the chamber 20 of the frame 15, the actuator carrier 35 is located interior of the wall 18 between the sidewalls 22 thereof. The wall 39 of the body 16, due to the greater width 53, resides exterior to wall 18 such that the wall 39 limits the insertion of the body 16 into the chamber 20 of the frame 15. The insertion of the actuator carrier 35 into the chamber 20 includes aligning the passage 44 of the body 16 with the openings 24 in the sidewalls 22 whereby insertion of the pin 49 into the openings 24 and the passage 44 forms the pivot point 17, thereby pivotally securing the actuator carrier 35 with the sidewalls 22 and producing the implant grip 8.

After forming of the implant grip 18, assembly of the implant retainer 5 includes coupling the actuator 9 with the implant grip 8. The actuator 9 inserts through the slot 28 and into the actuator aperture 38 until the actuator 9 contacts the top 58 of the frame 15 at the bearing surface 60. More particularly, the shaft 72, which is sized to pass through the slot 28, inserts through the slot 28 and into the actuator aperture 38 until the head 70 at the bearing surface 71 contacts the top 58 of the frame 15 at the bearing surface 60. In the first embodiment, rotation of the head 70 results in the shaft 72 progressing linearly within the actuator aperture 38 due to the threads 98 and 73 and their engagement which translate the rotational motion of the head 70 into linear motion of the shaft 72 within the actuator aperture 38.

The implant retainer 5 preferably is assembled in, or progressed to, its unloaded position 6 whereby the implant grip 8 resides in its disengaged position 10 since loading of the implant retainer 5 with an implant begins with the implant grip 8 located in its disengaged position 10. In the unloaded position 6 of the implant retainer 5 with the implant grip 8 in its disengaged position 10, the frame 15 and the body 16 pivot about the pivot point 17 relative thereto due to the chamber 20 of the frame 15 such that the top 67 of the body 16 defining the actuator aperture 38 is positioned in the slot 28 adjacent the front 32 of the frame 15 while the front 65 of the body 16 is spaced apart from the rear 33 of the frame 15. With the frame 15 and the body 16 pivoted until the top 67 of the body 16 is positioned adjacent the front 32 of the frame 15, the fasteners 29 and 45 of the frame 15 and the body 16, due to their location underneath the pivot point 17 and extension respectively below the bottoms 59 and 68 of the frame 15 and the body 16, pivot opposite to the frame 15 and the body 16 to an unclasped position whereby the fasteners 29 and 45 reside at a first distance. Additionally, when the top 67 of the body 16 defining the actuator aperture 38 is positioned adjacent the front 32 of the frame 15, the actuator 9, due to its insertion through the slot 28 and into the actuator aperture 38, seats atop the bearing surface 60 adjacent the front 32 of the frame 15 in an unlocking position while also remaining spaced apart from the bearing surface 60 adjacent the rear 33 of the frame 15 due to the elevation of the front 32 of the frame 15 relative to the rear 33 of the frame 15. The seating of the actuator 9 atop the bearing surface 63 while remaining spaced apart therefrom retains the implant retainer 5 in its unloaded position 6 with the implant grip 8 in its disengaged position 10. More particularly, when the implant retainer 5 is in the unloaded position 6 with the implant grip 8 in its disengaged position 10, the top segment 36 of the actuator carrier 35 defining the actuator aperture 38 is located in the slot 28 at the arm 26 while the actuator carrier 35 at its front surface 48 is spaced apart from the end wall 23 of the wall 18. With the frame 15 and the body 16 pivoted until the actuator carrier 35 defining the actuator aperture 38 is located in the slot 28 at the arm 26, the bearing surface 71 of the head 70 for the actuator 9, due to insertion of the shaft 72 for the actuator 9 through the slot 28 and into the actuator aperture 38 via rotation of the head 70, seats atop the bearing surface 60 at the arm 26 in an unlocking position while remaining spaced apart from the bearing surface 60 at the wall 18 due to the elevation of the arm 26 relative to the wall 18. Moreover, the shaft 72 based upon the elevation of the arm 26 relative to the wall 18 inserts a first distance into the actuator aperture 38, which, in the first embodiment, is partially within the actuator aperture 38. The seating of the bearing surface 71 of the actuator 9 atop the bearing surface 60 at the arm 26 while remaining spaced apart from the bearing surface 60 at the wall 18 retains the implant retainer 5 in its unloaded position 6 with the implant grip 8 in its disengaged position 10.

Conversely, in the loaded position 7 of the implant retainer 5 with the implant grip 8 in its engaged position 11, the frame 15 and the body 16 pivot about the pivot point 17 relative thereto due to the chamber 20 of the frame 15 such that the top 67 of the body 16 defining the actuator aperture 38 is positioned in the slot 28 adjacent the rear 33 of the frame 15 while the front 65 of the body 16 is adjacent the rear 33 of the frame 15. With the frame 15 and the body 16 pivoted until the top 67 of the body 16 is positioned adjacent the rear 33 of the frame 15, the fasteners 29 and 45 of the frame 15 and the body 16, due to their location underneath the pivot point 17 and extension respectively below the bottoms 59 and 68 of the frame 15 and the body 16, pivot opposite to the frame 15 and the body 16 to a clasped position whereby the fasteners 29 and 45 reside at a second distance that is greater than the first distance. Additionally, when the top 67 of the body 16 defining the actuator aperture 38 is positioned adjacent the rear 33 of the frame 15, the actuator 9, due to its insertion through the slot 28 and into the actuator aperture 38, no longer seats atop the bearing surface 60 adjacent the front 32 of the frame 15 and instead seats atop the bearing surface 60 adjacent the rear 33 of the frame 15 in a locking position due to the lesser elevation of the rear 33 of the frame 15 relative to the front 32 of the frame 15. The seating of the actuator 9 solely atop the bearing surface 60 adjacent the rear 33 of the frame 15 retains the implant retainer 5 in its loaded position 7 with the implant grip 8 in its engaged position 11. More particularly, when the implant retainer 5 is in the loaded position 7 with the implant grip 8 in its engaged position 11, the top segment 36 of the actuator carrier 35 defining the actuator aperture 38 is located in the slot 28 adjacent the end wall 23 of the wall 18 while the actuator carrier 35 at its front surface 48 is adjacent the end wall 23 of the wall 18. With the frame 15 and the body 16 pivoted until the actuator carrier 35 defining the actuator aperture 38 is located in the slot 28 adjacent the end wall 23, the bearing surface 71 of the head 70 for the actuator 9, due to insertion of the shaft 72 for the actuator 9 through the slot 28 and into the actuator aperture 38 via rotation of the head 70, no longer seats atop the bearing surface 60 at the arm 26 and instead seats atop the bearing surface 60 at the wall 18 in a locking position due to the lesser elevation of the wall 18 relative to the arm 26. Moreover, the shaft 72 based upon the lesser elevation of the wall 18 relative to the arm 26 inserts into the actuator aperture 38 a second distance greater than the first distance, which, in the first embodiment, is substantially, completely within the actuator aperture 38. The seating of the bearing surface 71 of the actuator 9 solely atop the bearing surface 60 at the wall 18 retains the implant retainer 5 in its loaded position 7 with the implant grip 8 in its engaged position 11.

When the implant retainer 5 is positioned in its unloaded position 6 with the implant grip 8 in its disengaged position 10, rotation of the actuator 9 in a first direction, which, in the first embodiment, is a direction that facilitates insertion of the actuator 9 into the actuator aperture 38, results in the actuator 9 progressing the implant retainer 5 from its unloaded position 6 with the implant grip 8 in its disengaged position 10 to its loaded position 7 with the implant grip 8 in its engaged position 11. In the first embodiment, a driver imparts rotational motion to the actuator 9, nevertheless, one of ordinary skill in the art will recognize the actuator 9 may be provided with a grip that allows rotation of the actuator 9 directly by hand. Rotational motion imparted to the actuator 9 in the first direction progresses the implant grip 8 to its engaged position 11 based upon the pivotal connection of the frame 15 and the body 16 at the pivot point 17 and the elevation of the front 32 of the frame 15 with respect to its rear 33, resulting in the bearing surface 60 having the slope 62 that is negative relative to the actuator 9. The pivot point 17, due to the frictional engagement of the actuator 9 with the bearing surface 60 at the front 32 of the frame 15, translates the rotational motion of the actuator 9 in the first direction and its consequent linear progression into the actuator aperture 38 into linear motion imparted to the frame 15 and the body 16 that pivots the frame 15 and the body 16 about the pivot point 17 towards each other along a decreasing arc whereby the body 16 inserts into the chamber 20 of the frame 15 as the top 67 of the body 16 and the rear 33 of the frame 15 concurrently pivot together via the slot 28. Moreover, the vertical distance between the rear 33 and the front 32 of the frame 15, which creates the bearing surface 60 and the negative orientation of its slope 62 relative to the actuator 9, results in a separation of the actuator 9 from the bearing surface 60 adjacent the rear 33 of the frame 15 such that, during rotation of the actuator 9 in the first direction and its traversing of the bearing surface 60 toward the rear 33 of the frame 15, the actuator 9 maintains frictional engagement with the bearing surface 60 while there exists space sufficient for the actuator 9 to insert into the actuator aperture 38, whereas, without inclusion of the sloped bearing surface 60 in the frame 15, the actuator 9 would bind against the bearing surface 60 thereby failing to insert into the actuator aperture 38. Rotation of the actuator 9 in the first direction and its consequent linear progression into the actuator aperture 38 occurs until the actuator 9 traverses the bearing surface 60 such that the actuator 9 in its locking position resides atop the bearing surface 60 adjacent the rear 33 of the frame 15 and travels within the actuator aperture 38 from its first distance to its second distance. When the actuator 9 is positioned adjacent the rear 33 of the frame 15, the frame 15 and the body 16 pivot into the engaged position 11 of the implant grip 8 whereby the top 67 of the body 16 defining the actuator aperture 38 is positioned in the slot 28 adjacent the rear 33 of the frame 15 while the front 65 of the body 16 is adjacent the rear 33 of the frame 15. The pivoting of the frame 15 and the body 16 towards one another into the engaged position 11 of the implant grip 8 pivots the fasteners 29 and 45 of the frame 15 and the body 16 away from each other such that the fasteners 29 and 45 move from their unclasped position at the first distance to their clasped position at the second distance based upon the location of the fasteners 29 and 45 underneath the pivot point 17 and their extension respectively below the bottoms 59 and 68 of the frame 15 and the body 16. With the fasteners 29 and 45 progressed to their clasped position at their second distance, engagement of the implant retainer 5 via the fasteners 29 and 45 with an implant constrains the implant in its insertion shape.

More particularly, rotational motion imparted to the head 70 of the actuator 9 in the first direction progresses the implant grip 8 to its engaged position 11 based upon the pivotal connection between the sidewalls 22 of the frame 15 and the actuator carrier 35 of the body 16 at the pivot point 17 and the elevation of the arm 26 with respect to the wall 18 and its angled sidewalls 22, resulting in the bearing surface 60 having the slope 62 that is negative relative to the head 70 of the actuator 9. The pivot point 17, due to the frictional engagement of the bearing surface 71 for the actuator 9 with the bearing surface 60 at the arm 26 of the frame 15, translates the rotational motion of the head 70 in the first direction and the consequent linear progression of the shaft 72 into the actuator aperture 38 into linear motion imparted to the frame 15 and the body 16 that pivots the frame 15 and the body 16 about the pivot point 17 towards each other along a decreasing arc whereby the actuator carrier 35 at its front surface 48 inserts into the chamber 20 of the wall 18 as the top segment 36 of the actuator carrier 35 defining the actuator aperture 38 and the end wall 23 of the wall 18 concurrently pivot together via the slot 28. Moreover, the vertical distance between the arm 26 and the end wall 23 of the wall 18, which creates the bearing surface 60 and the negative orientation of its slope 62 relative to the head 70 of the actuator 9, results in a separation of the head 70 from the bearing surface 60 adjacent the end wall 23 of the frame 18 such that, during rotation of the head 70 in the first direction and its traversing of the bearing surface 60 toward the end wall 23 of the wall 18, the head 70 via its bearing surface 71 maintains frictional engagement with the bearing surface 60 while there exists space sufficient for the shaft 72 of the actuator 9 to insert into the actuator aperture 38, whereas, without inclusion of the sloped bearing surface 60 in the frame 15, the head 70 would bind against the bearing surface 60 thereby failing to insert the shaft 72 into the actuator aperture 38. Rotation of the head 70 in the first direction and the consequent linear progression of the shaft 72 into the actuator aperture 38 occurs until the head 70 traverses the bearing surface 60 such that the head 70 in its locking position of the actuator 9 resides atop the bearing surface 60 adjacent the end wall 23 of the wall 18 and the shaft 72 travels within the actuator aperture 38 from its first distance to its second distance. When the head 70 of the actuator 9 is positioned adjacent the end wall 23 of the wall 18, the frame 15 and the body 16 pivot into the engaged position 11 of the implant grip 8 whereby the top segment 36 of the actuator carrier 35 defining the actuator aperture 38 is positioned in the slot 28 adjacent the end wall 23 of the wall 18 while the actuator carrier 35 at its front surface 48 is adjacent the end wall 23 of the wall 18. The pivoting of the frame 15 and the body 16 towards one another into the engaged position 11 of the implant grip 8 pivots the fasteners 29 and 45 of the frame 15 and the body 16 away from each other such that the fasteners 29 and 45 move from their unclasped position at the first distance to their clasped position at the second distance based upon the location of the fasteners 29 and 45 underneath the pivot point 17 and their extension respectively below the end wall 23 and the wall 39 of the frame 15 and the body 16. With the fasteners 29 and 45 progressed to their clasped position at the second distance, engagement of the implant retainer 5 via the fasteners 29 and 45 with an implant constrains the implant in its insertion shape.

When the implant retainer 5 is positioned in its loaded position 7 with the implant grip 8 in its engaged position 11, rotation of the actuator 9 in a second direction, which, in the first embodiment, is a direction that facilitates retraction of the actuator 9 from the actuator aperture 38, results in the actuator 9 progressing the implant retainer 5 from its loaded position 7 with the implant grip 8 in its engaged position 11 to its unloaded position 6 with the implant grip 8 in its disengaged position 10. Rotational motion imparted to the actuator 9 in the second direction progresses the implant grip 8 to its disengaged position 10 based upon the pivotal connection of the frame 15 and the body 16 at the pivot point 17 and the elevation of the front 32 of the frame 15 with respect to its rear 33, resulting in the bearing surface 60 having the slope 62 that is positive relative to the actuator 9. The pivot point 17, due to the frictional engagement of the actuator 9 with the bearing surface 60 at the rear 33 of the frame 15, translates the rotational motion of the actuator 9 in the second direction and its consequent linear retraction from the actuator aperture 38 into linear motion imparted to the frame 15 and the body 16 that pivots the frame 15 and the body 16 about the pivot point 17 away from each other along an increasing arc whereby the body 16 exits the chamber 20 of the frame 15 as the top 67 of the body 16 and the rear 33 of the frame 15 concurrently pivot away via the slot 28. Moreover, the vertical distance between the rear 33 and the front 32 of the frame 15, which creates the bearing surface 60 and the positive orientation of its slope 62 relative to the actuator 9, results in the actuator 9 seating substantially, completely atop the bearing surface 60 adjacent the rear 33 of the frame 15 such that, during rotation of the actuator 9 in the second direction and its traversing of the bearing surface 60 toward the front 32 of the frame 15, the actuator 9 maintains frictional engagement with the bearing surface 60 even though the actuator 9 retracts from the actuator aperture 38, whereas, without inclusion of the sloped bearing surface 60 in the frame 15, the actuator 9 would disengage from the bearing surface 60 thereby ceasing operation of the implant grip 8. Rotation of the actuator 9 in the second direction and its consequent linear retraction from the actuator aperture 38 occurs until the actuator 9 traverses the bearing surface 60 such that the actuator 9 in its unlocking position resides atop the bearing surface 60 adjacent the front 32 of the frame 15 and travels within the actuator aperture 38 from its second distance to its first distance. When the actuator 9 is positioned adjacent the front 32 of the frame 15, the frame 15 and the body 16 pivot into the disengaged position 10 of the implant grip 8 whereby the top 67 of the body 16 defining the actuator aperture 38 is positioned in the slot 28 adjacent the front 32 of the frame 15 while the front 65 of the body 16 is spaced apart from the rear 33 of the frame 15. The pivoting of the frame 15 and the body 16 away from one another into the disengaged position 10 of the implant grip 8 pivots the fasteners 29 and 45 of the frame 15 and the body 16 toward each other such that the fasteners 29 and 45 move from their clasped position at the second distance to their unclasped position at the first distance based upon the location of the fasteners 29 and 45 underneath the pivot point 17 and their extension respectively below the bottoms 59 and 68 of the frame 15 and the body 16. With the fasteners 29 and 45 progressed to their unclasped position at the first distance, the implant retainer 5 via the fasteners 29 and 45 releases an implant in its insertion shape whereby the implant attempts to return to its natural shape.

More particularly, rotational motion imparted to the head 70 of the actuator 9 in the second direction progresses the implant grip 8 to its disengaged position 10 based upon the pivotal connection between the sidewalls 22 of the frame 15 and the actuator carrier 35 of the body 16 at the pivot point 17 and the elevation of the arm 26 with respect to the wall 18 and its angled sidewalls 22, resulting in the bearing surface 60 having the slope 62 that is positive relative to the head 70 of the actuator 9. The pivot point 17, due to the frictional engagement of the bearing surface 71 for the actuator 9 with the bearing surface 60 at the end wall 23 of the wall 18, translates the rotational motion of the head 70 in the second direction and the consequent linear retraction of the shaft 72 from the actuator aperture 38 into linear motion imparted to the frame 15 and the body 16 that pivots the frame 15 and the body 16 about the pivot point 17 away from each other along an increasing arc whereby the actuator carrier 35 at its front surface 48 exits the chamber 20 of the wall 18 as the top segment 36 of the actuator carrier 35 defining the actuator aperture 38 and the end wall 23 of the wall 18 concurrently pivot away via the slot 28. Moreover, the vertical distance between the arm 26 and the end wall 23 of the wall 18, which creates the bearing surface 60 and the positive orientation of its slope 62 relative to the head 70 of the actuator 9, results in the head 70 seating substantially, completely atop the bearing surface 60 adjacent the end wall 23 of the frame 18 such that, during rotation of the head 70 in the second direction and its traversing of the bearing surface 60 toward the arm 26, the head 70 via its bearing surface 71 maintains frictional engagement with the bearing surface 60 even though the shaft 72 of the actuator 9 retracts from the actuator aperture 38, whereas, without inclusion of the sloped bearing surface 60 in the frame 15, the head 70 would disengage from the bearing surface 60 thereby stopping operation of the implant grip 8. Rotation of the head 70 in the second direction and the consequent linear retraction of the shaft 72 within the actuator aperture 38 occurs until the head 70 traverses the bearing surface 60 such that the head 70 in the unlocking position of the actuator 9 resides atop the bearing surface 60 at the arm 26 and the shaft 72 travels within the actuator aperture 38 from its second distance to its first distance. When the head 70 of the actuator 9 is positioned at the arm 26, the frame 15 and the body 16 pivot into the disengaged position 10 of the implant grip 8 whereby the top segment 36 of the actuator carrier 35 defining the actuator aperture 38 is positioned in the slot 28 at the arm 26 while the actuator carrier 35 at its front surface 48 is spaced apart from the end wall 23 of the wall 18. The pivoting of the frame 15 and the body 16 away from one another into the disengaged position 10 of the implant grip 8 pivots the fasteners 29 and 45 of the frame 15 and the body 16 toward each other such that the fasteners 29 and 45 move from their clasped position at the second distance to their unclasped position at the first distance based upon the location of the fasteners 29 and 45 underneath the pivot point 17 and their extension respectively below the end wall 23 and the wall 39 of the frame 15 and the body 16. With the fasteners 29 and 45 progressed to their unclasped position at the first distance, the implant retainer 5 via the fasteners 29 and 45 releases an implant in its insertion shape whereby the implant attempts to return to its natural shape.

Figure 5A:
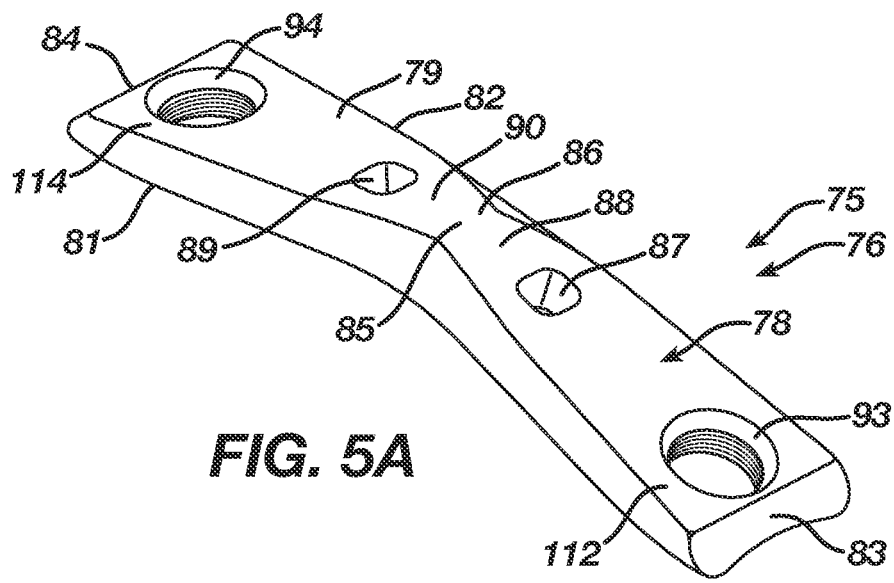
FIG. 5A is a top isometric view illustrating a shape memory implant according to a first embodiment in a natural shape.
Figure 5B:
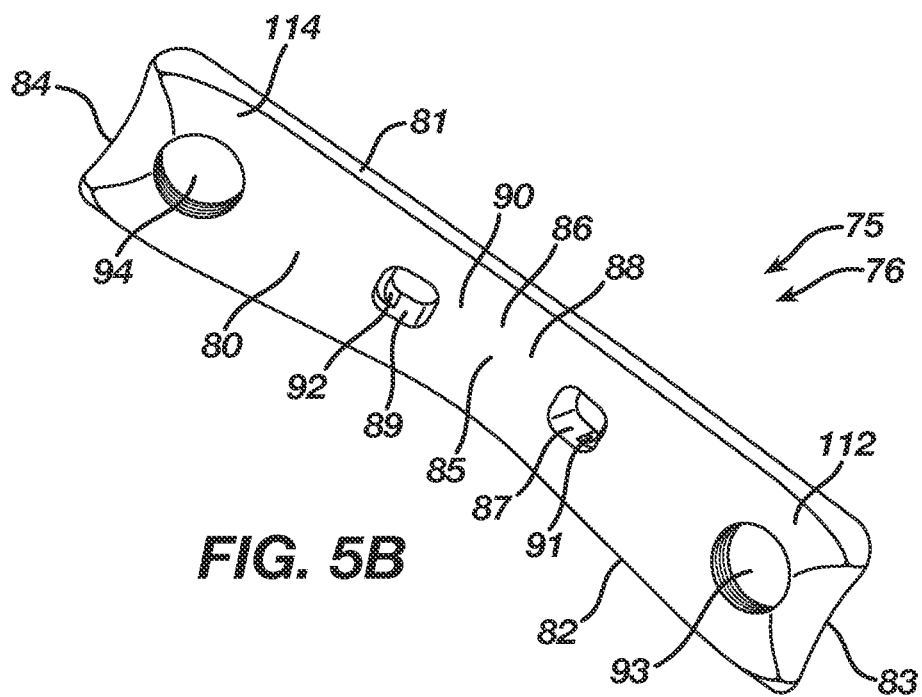
FIG. 5B is a bottom isometric view thereof.
Figure 5C:
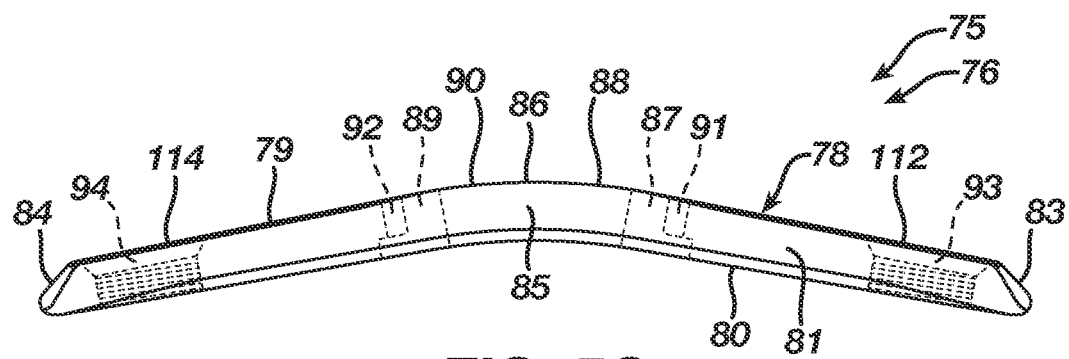
FIG. 5C is a side view thereof.
Figure 5D:
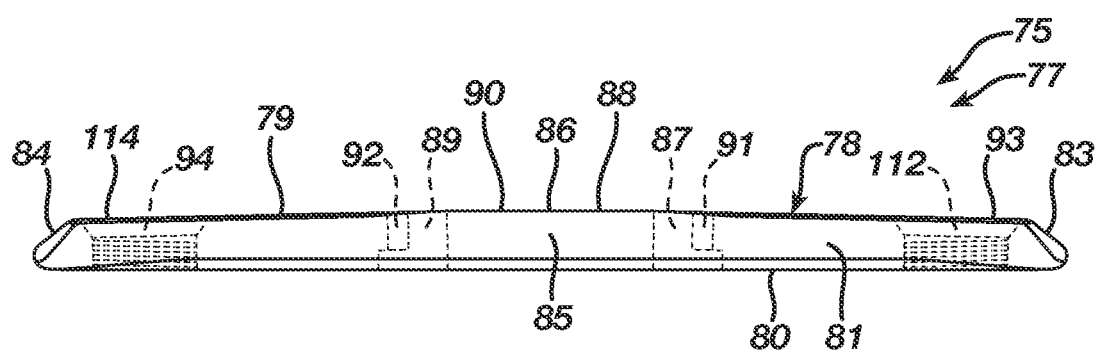
FIG. 5D is a side view illustrating the shape memory implant according to the first embodiment in an insertion shape.

FIGS. 5A-5C illustrate an orthopedic implant 75 according to a first embodiment in a natural shape 76, whereas FIG. 5D illustrates the orthopedic implant 75 in an insertion shape 77. The implant 75 in the first embodiment may be manufactured from a shape memory material with superelastic or temperature dependent properties (e.g., Nitinol) such that the implant 75 transitions between its natural shape 76 and its insertion shape 77. The implant 75 when deformed from its natural shape 76 to its insertion shape 77 stores energy deliverable to bone, bones, or bone pieces. In accordance with its manufacture from shape memory material, the implant 75 begins in its natural shape 76, is transitionable to its insertion shape 77, and, once implanted in bone, bones, or bone pieces, attempts to transition from its insertion shape 77 to its natural shape 76 whereby the implant 75 delivers the energy stored therein to the bone, bones, or bone pieces in order to affix the bone, bones, or bone pieces and promote a healing thereof. In the first embodiment, attempted transition of the implant 75 from its insertion shape 77 to its natural shape 76 continuously compresses the bone, bones, or bone pieces to promote fusion thereof.

The implant 75 includes a bridge 78 with upper and lower surfaces 79 and 80, first and second sides 81 and 82, and first and second ends 83 and 84. The implant 75 includes a transition section 85 located at a center section 86 of the implant 75 and thus the bridge 78. The implant 75, and thus the bridge 78, includes a first opening 93 extending therethrough from the upper surface 79 to the lower surface 80 whereby the first opening 93 is located adjacent the first end 83 of the bridge 78 to provide the implant 75 and thus the bridge 78 with an anchoring segment 112. Likewise, the implant 75, and thus the bridge 78, includes a second opening 94 extending therethrough from the upper surface 79 to the lower surface 80 whereby the second opening 94 is located adjacent the second end 84 of the bridge 78 to provide the implant 75 and thus the bridge 78 with an anchoring segment 114. The first and second openings 93 and 94 receive anchoring members in the form of screws therethrough in order to facilitate a securing of the implant 75 at the first and second anchoring segments 112 and 114 with bone, bones, or bone pieces whereby the bridge 78 between the first and second openings 93 and 94 traverses a fixation zone of the bone, bones, or bone pieces such that the implant 75, after its insertion and attempted transition from the insertion shape 77 to the natural shape 76, delivers energy to the bone, bones, or bone pieces at the fixation zone. Although the first and second openings 93 and 94 of the implant 75 primarily operate to receive therethrough anchoring members, the first and second openings 93 and 94 may receive therein respectively drill guides 110 and 111 that facilitate a drilling of holes in the bone, bones, or bone pieces that assist in inserting anchoring members through the first and second openings 93 and 94 and into the bone, bones, or bone pieces. The first and second openings 93 and 94 in the first embodiment include threads that facilitate engagement of the first and second openings 93 and 94 with anchoring members or the drill guides 110 and 111. The implant 75, and thus the bridge 78, includes a first aperture 87 extending therethrough from the upper surface 79 to the lower surface 80 whereby the first aperture 87 is located adjacent the transition section 85 at a first side 88 thereof. The implant 75, and thus the bridge 78, includes a catch 91 protruding into the first aperture 87. Similarly, the implant 75, and thus the bridge 78, includes a second aperture 89 extending therethrough from the upper surface 79 to the lower surface 80 whereby the second aperture 89 is located adjacent the transition section 85 at a second side 90 thereof. The implant 75, and thus the bridge 78, includes a catch 92 protruding into the second aperture 89. The first aperture 87 and its catch 91 and the second aperture 89 and its catch 92 provide engagement points for the implant retainer 5 with the implant 75. As such, the first and second apertures 87 and 89 are spaced apart across the transition section 85 a distance that allows receipt therein, respectively, of the fasteners 29 and 45 when the fasteners 29 and 45 reside at their first distance. When the fasteners 29 and 45 reside at their second distance, the fasteners 29 and 45, respectively, engage the catches 91 and 92 thereby securing the implant retainer 5 with the implant 75. The implant retainer 5 and its fasteners 29 and 45 and the first and second apertures 87 and 89 are correspondingly designed with respect to their size, location, and distances to interact and engage such that the implant retainer 5 optimally constrains the implant 75 in its insertion shape 77.

The regular inherent shape of the implant 75, as illustrated in FIGS. 5A-5C, is its natural shape 76 where the transition section 85 locates the bridge 78 in a natural form consisting of a closed or angular profile whereby the first and second ends 83 and 84 reside at a first distance. Nevertheless, as illustrated in FIG. 5D, the implant 75 is deformable under the action of superelasticity or temperature dependent shape memory to its insertion shape 77 where the transition section 85 deforms to store energy while also moving the bridge 78 from its natural form to an insertion form which is an open or substantially linear profile whereby the first and second ends 83 and 84 reside at a second distance that is greater than the first distance. Since the insertion shape 77 is not the regular inherent shape of the implant 75, the bridge 78 typically is mechanically constrained using the implant retainer 5 whereby the implant retainer 5 maintains the bridge 78 in its insertion form. In particular, the implant retainer 5 inserts into the first and second apertures 87 and 89 and engages the catches 91 and 92 such that the implant retainer 5 holds the bridge 78, resulting in the implant retainer 5 constraining the deformed transition section 85 in order to maintain the implant 75 in its insertion shape 77. After implantation into bone, bones, or bone pieces and a release of the implant retainer 5, including if necessary a heating of the implant 75, the implant 75 delivers the energy stored in the transition section 85 whereby the bridge 78 attempts to transition from its insertion form to its natural form such that the implant 75 affixes the bone, bones, or bone pieces through an application of a compressive force thereto.

Figure 5E:
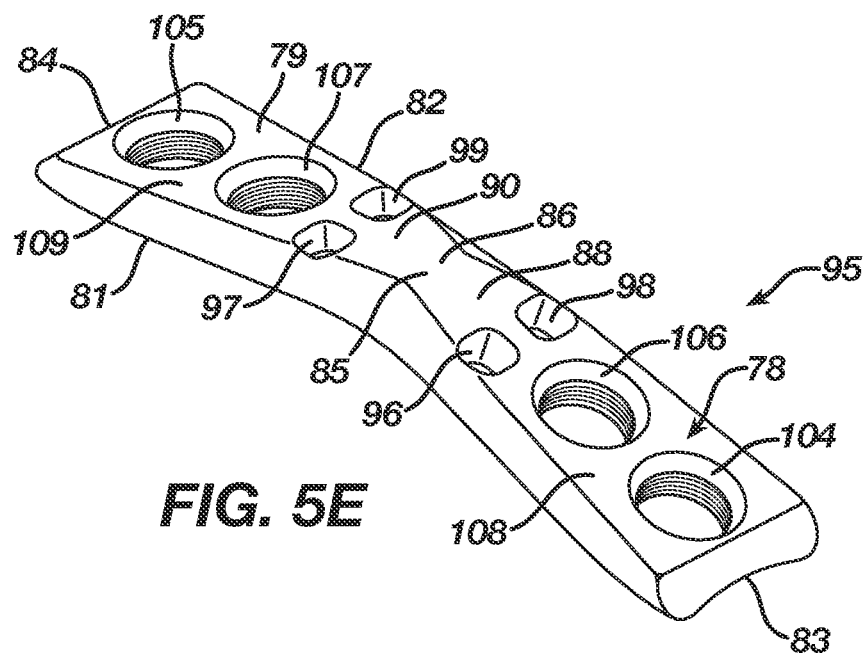
FIG. 5E is a top isometric view illustrating a shape memory implant alternative to the shape memory implant according to the first embodiment.
Figure 5F:
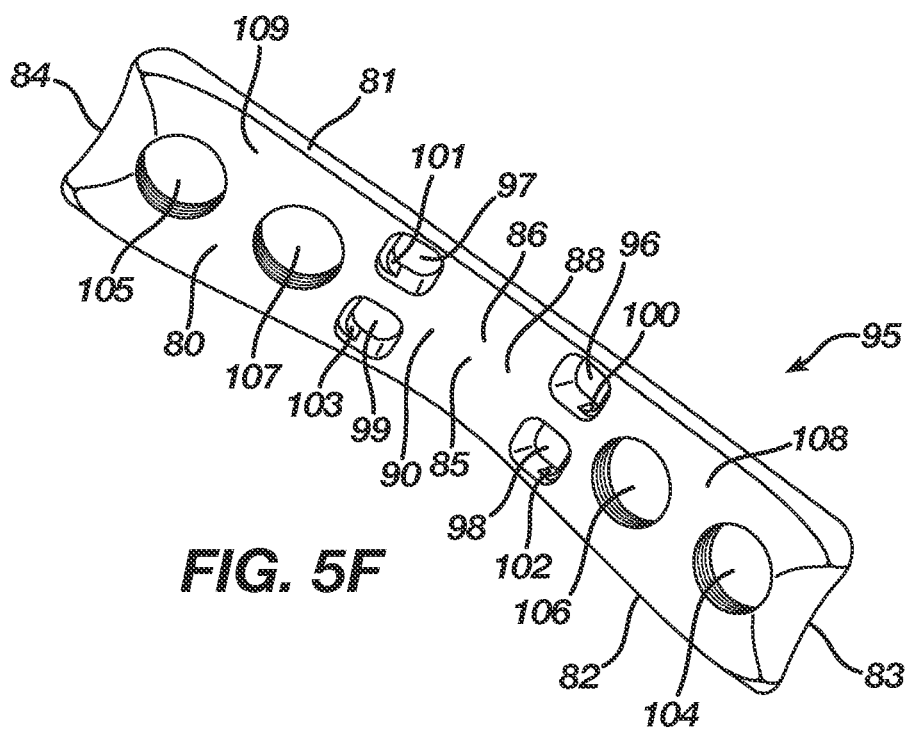
FIG. 5F is a bottom isometric view thereof.

FIGS. 5E-5F illustrate an orthopedic implant 95 alternative to the orthopedic implant 75 according to a first embodiment. The implant 95 is substantially similar in design and operation relative to the implant 75 according to the first embodiment such that, for the sake of brevity, only differences therebetween will be described herein. Moreover, one of ordinary skill in the art will recognize that like parts of the implant 95 labeled with like numerals of the implant 75 incorporate a design and function as previously set forth in the detailed description of the implant 75 according to the first embodiment. The implant 75 includes the first and second apertures 87 and 89 and the catches 91 and 92, whereas the implant 95 includes first, second, third, and fourth apertures 96-99 and respective catches 100-103 that provide additional engagement points for a more secure engagement of the implant 95 with an implant retainer including four fasteners. The implant 75 includes the first and second openings 93 and 94, whereas the implant 95 includes first and third openings 104 and 106 at an anchoring segment 108 and second and fourth openings 105 and 107 at an anchoring segment 109 that receive additional drill guides or anchoring members in the form of screws therethrough in order to more securely affix the implant 95 to bone, bones, or bone pieces.

Figure 6A:
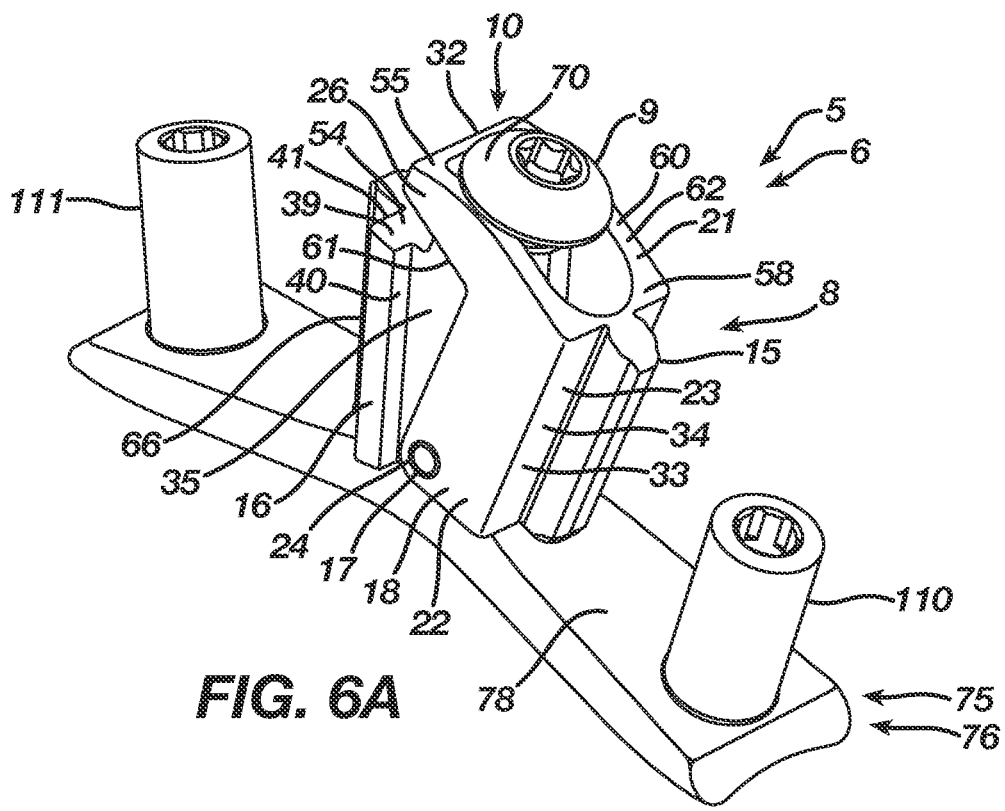
FIG. 6A is a top isometric view illustrating the implant retainer according to the first embodiment in an unloaded position relative to the shape memory implant according to the first embodiment in its natural shape.
Figure 6B:
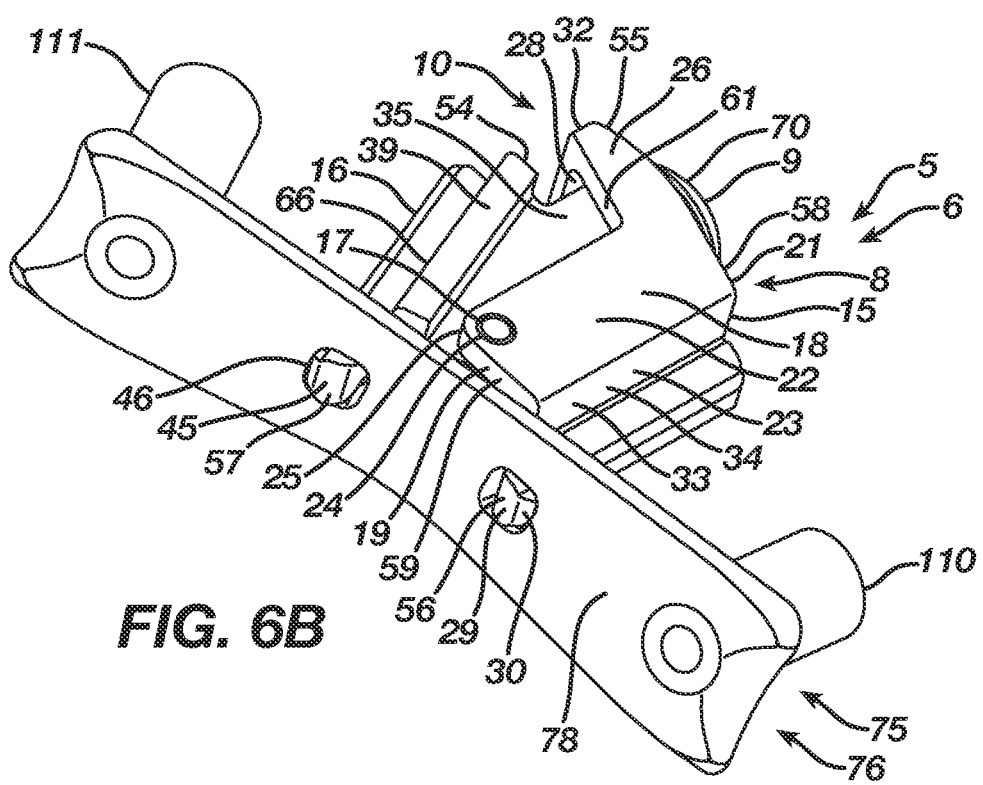
FIG. 6B is a bottom isometric view thereof.
Figure 6C:
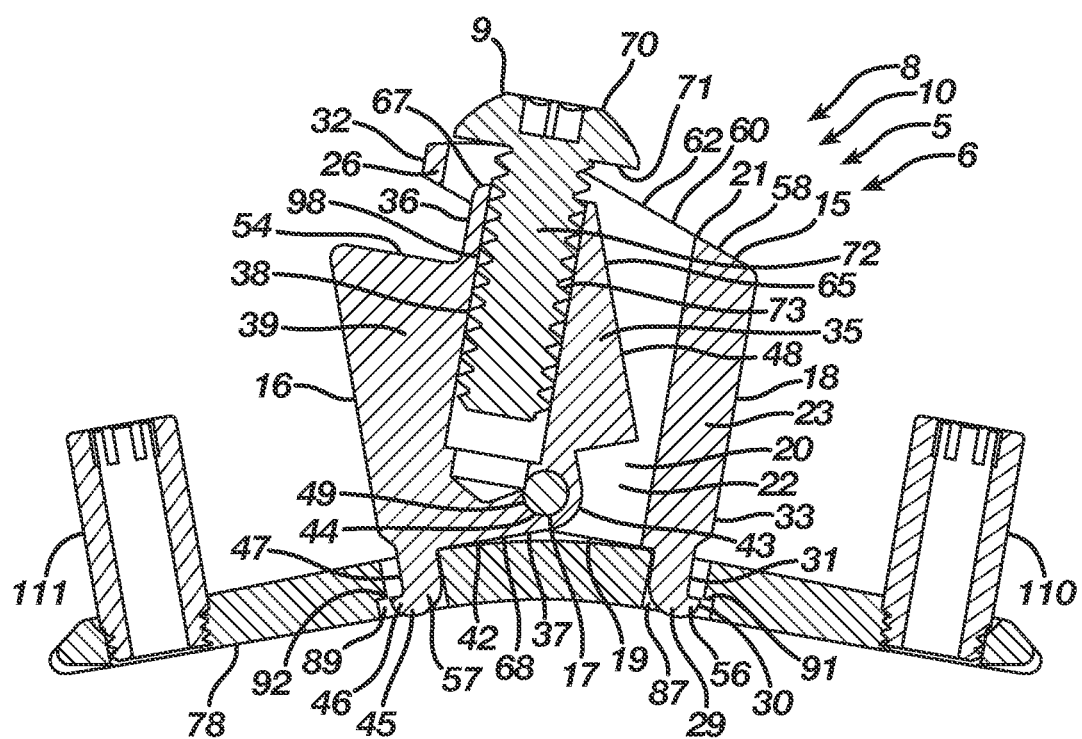
FIG. 6C is a side view in cross-section thereof.

When receiving the implant 75 in an orthopedic fixation system, the implant retainer 5 as illustrated in FIGS. 6A-6C begins in its unloaded position 6 wherein the implant grip 8 resides in its disengaged position 10 such that the fasteners 29 and 45 are in their unclasped position spaced apart at the first distance. The implant 75 is mechanically deformed from its natural shape 76 to its insertion shape 77 as illustrated in FIG. 5D such that the implant 75 stores mechanical energy. Mechanical deformation of the implant 75 may include cooling of the implant 75 such that the implant 75 transitions from its austenite phase to its martensite phase prior to loading of the implant 75 on the implant retainer 5. After deformation of the implant 75, the implant retainer 5 is positioned adjacent the deformed implant 75 at the upper surface 79 thereof whereby the fastener 29 of the implant retainer 5 is located at the first aperture 87 of the implant 75 while the fastener 45 of the implant retainer 5 is located at the second aperture 89 of the implant 75.

With the implant retainer 5 positioned adjacent the deformed implant 75, the fasteners 29 and 45 respectively insert into the first apertures 87 and 89 until the bottoms 59 and 68 of the frame 15 and body 16 contact the upper surface 79 of the implant 75. The fastener 29, due to its unclasped position residing from the fastener 45 at the first distance, inserts into the first aperture 87 spaced apart from the catch 91 whereby its cutout 31 is adjacent the catch 91 while its detent 30 is positioned underneath the catch 91 but separated therefrom. Likewise, the fastener 45, due to its unclasped position residing from the fastener 29 at the first distance, inserts into the second aperture 89 spaced apart from the catch 92 whereby its cutout 47 is adjacent the catch 92 while its detent 46 is positioned underneath the catch 92 but separated therefrom. In the first embodiment, the fasteners 29 and 45 respectively extend below the end wall 23 of the wall 18 for the frame 15 and the wall 39 for the body 16 a length that permits their respective insertions into the first and second apertures 87 and 89 such that their detents 30 and 46 are located respectively below the catches 91 and 92. Nevertheless, the lengths of the fasteners 29 and 45 are equal to or less than the thickness of the implant 75 between its upper and lower surfaces 79 and 80 whereby the fasteners 29 and 45 do not extend respectively from the first and second apertures 87 and 89 below the lower surface 80 of the implant 75 in order to ensure the implant 75 sits flush atop bone, bones, or bone pieces.

Figure 7A:
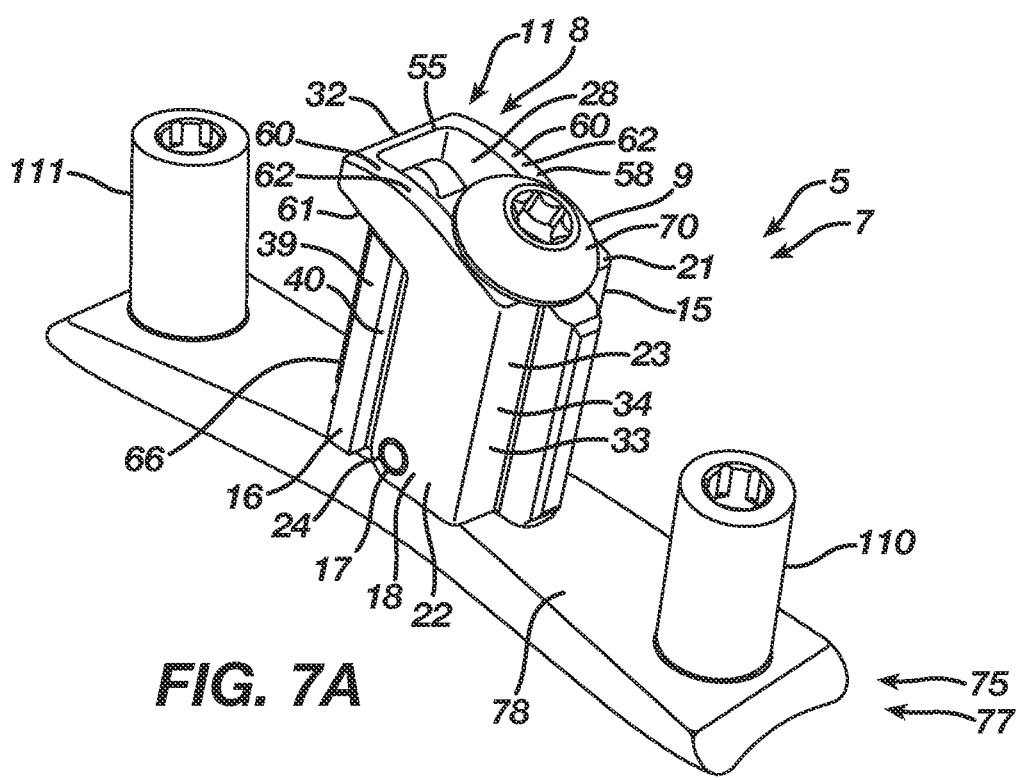
FIG. 7A is a top isometric view illustrating the implant retainer according to the first embodiment in a loaded position constraining the shape memory implant according to the first embodiment in its insertion shape.
Figure 7B:
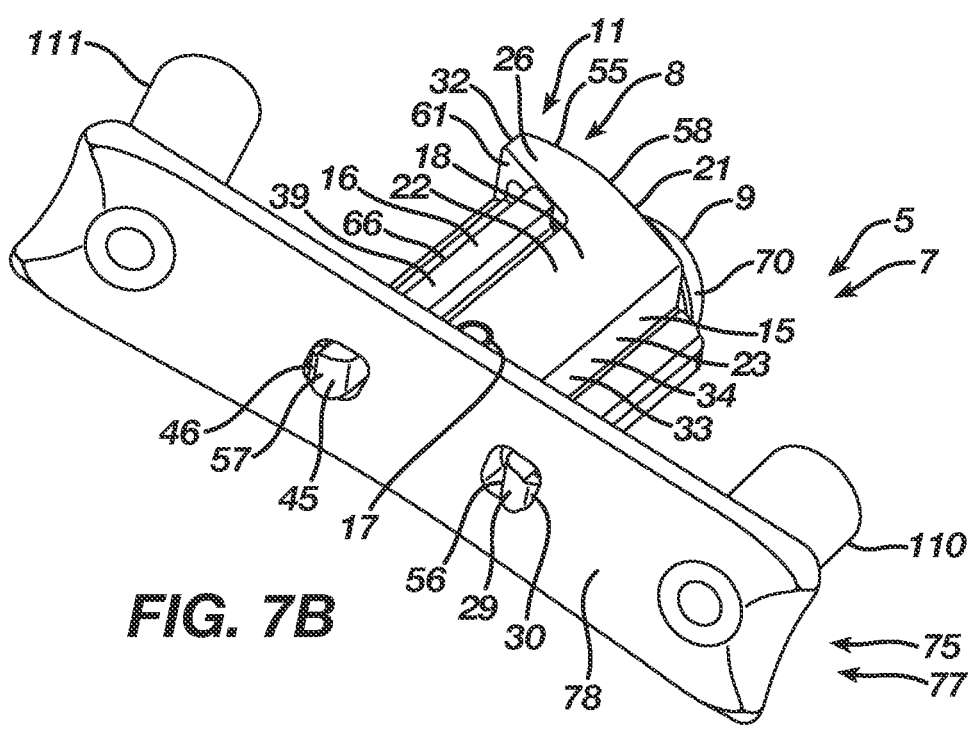
FIG. 7B is a bottom isometric view thereof.
Figure 7C:
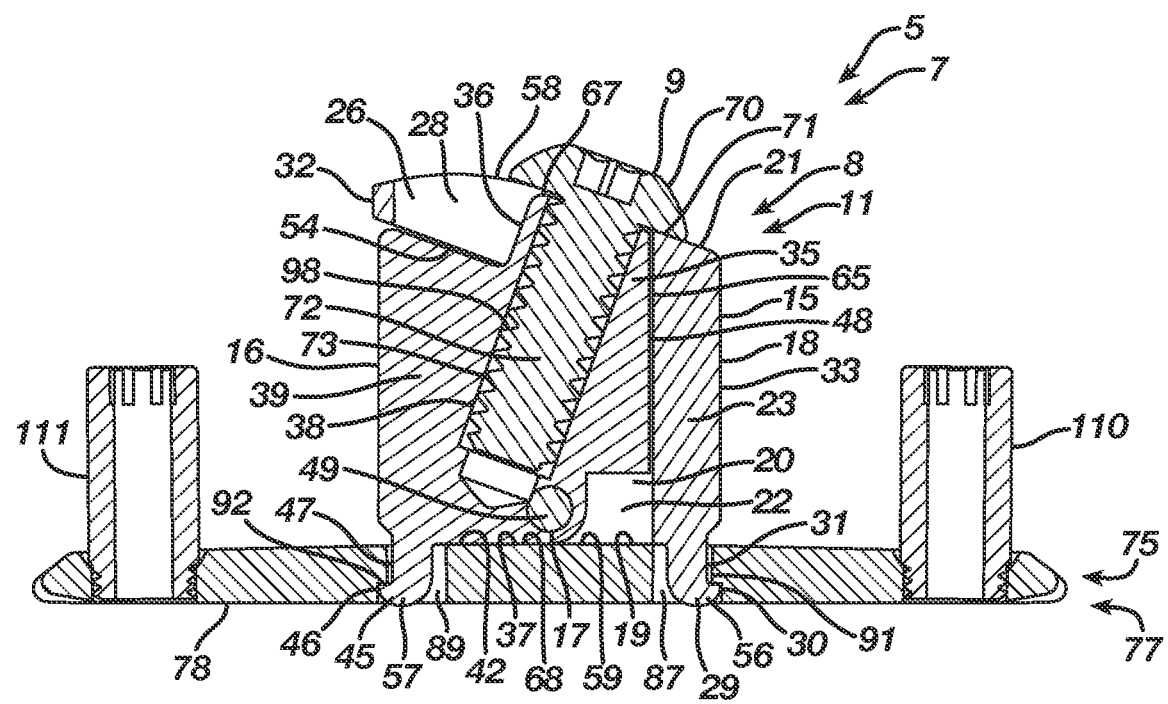
FIG. 7C is a side view in cross-section thereof.
Figure 8A:
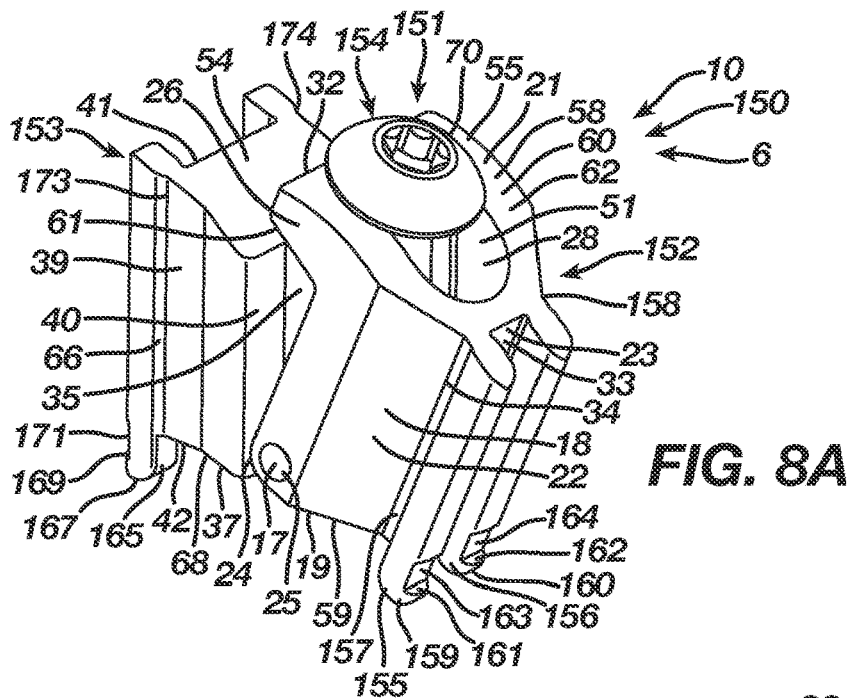
FIG. 8A is a top isometric view illustrating an implant retainer according to a second embodiment in an unloaded position.
Figure 8B:
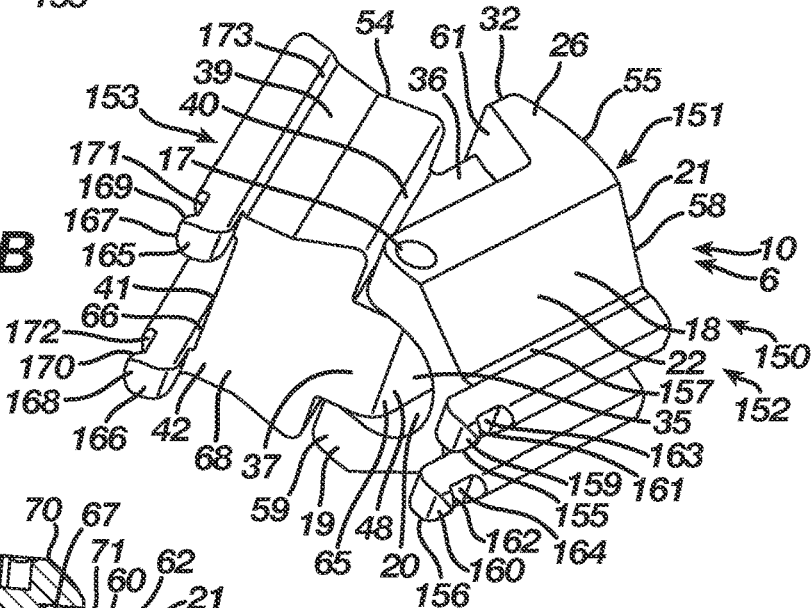
FIG. 8B is a bottom isometric view thereof.
Figure 8C:
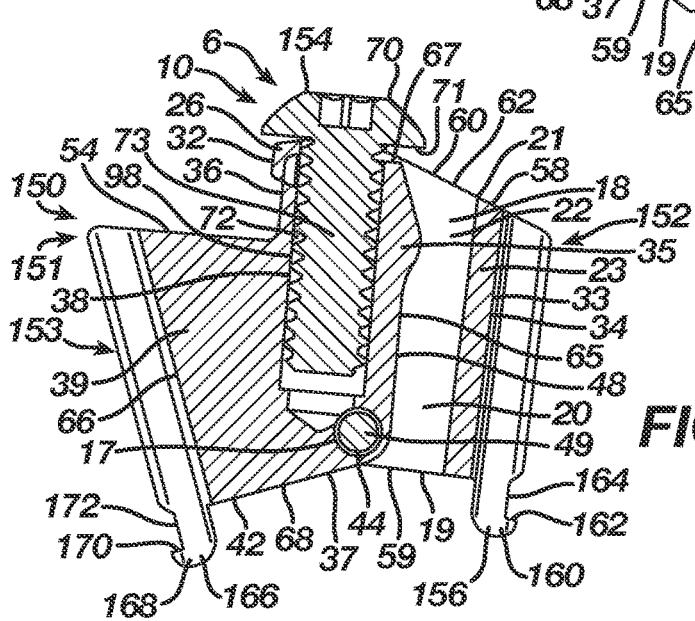
FIG. 8C is a side view in cross-section thereof.

After insertion respectively of the fasteners 29 and 45 in their unclasped position into the first and second apertures 87 and 89 with their detents 30 and 46 respectively underneath the catches 91 and 92, the implant retainer 5 is positioned relative to the implant 75 for engagement therewith whereby the implant retainer 5 constrains the implant 75 in its insertion shape 77. The constraining of the implant 75 in its insertion shape 77 utilizing the implant retainer 5 includes rotation of the head 70 for the actuator 9 in the first direction and the consequent linear progression of the shaft 72 into the actuator aperture 38. Rotation of the head 70 for the actuator 9 in the first direction occurs until the head 70 traverses the bearing surface 60 from its unlocking position to its locking position whereby the head 70 resides atop the bearing surface 60 adjacent the end wall 23 of the wall 18 and the shaft 72 travels within the actuator aperture 38 from its first distance to its second distance. With the traversal of the head 70 for the actuator 9 to its locking position adjacent the end wall 23 of the wall 18, the frame 15 and the body 16 pivot into the engaged position 11 of the implant grip 8 whereby the top segment 36 of the actuator carrier 35 defining the actuator aperture 38 is positioned in the slot 28 adjacent the end wall 23 of the wall 18 while the actuator carrier 35 at its front surface 48 is adjacent the end wall 23 of the wall 18. The pivoting of the frame 15 and the body 16 towards one another into the engaged position 11 of the implant grip 8 pivots the fasteners 29 and 45 of the frame 15 and the body 16 away from each other such that the fasteners 29 and 45 move from their unclasped position at the first distance to their clasped position at the second distance based upon the location of the fasteners 29 and 45 underneath the pivot point 17 and their extension respectively below the end wall 23 and the wall 39 of the frame 15 and the body 16. Upon the progression of the fasteners 29 and 45 to their clasped position at the second distance, the fasteners 29 and 45 respectively via the detents 30 and 46 abut the catches 91 and 92 at undersides thereof. As a result, the implant retainer 5, now in its loaded position 7 with the actuator 9 in its locking position holding the implant grip 8 in its engaged position 11 as illustrated in FIG. 7A-7C, constrains the implant 75 in its insertion shape 77 via engagement of the implant retainer 5 with the implant 75 at the fasteners 29 and 45 and the bottoms 59 and 68 of the frame 15 and body 16 at the upper surface 79 of the implant 75.

While the implant 75 may be mechanically deformed from its natural shape 76 to its insertion shape 77 prior to its loading on the implant retainer 5 in an orthopedic fixation system, the implant retainer 5 may be employed during its loading with the implant 75 to mechanically deform the implant 75 from its natural shape 76 to its insertion shape 77. The implant retainer 5 is positioned adjacent the implant 75 at the upper surface 79 thereof when the implant 75 resides in its natural shape 76 whereby the fastener 29 of the implant retainer 5 is located at the first aperture 87 of the implant 75 while the fastener 45 of the implant retainer 5 is located at the second aperture 89 of the implant 75.

With the implant retainer 5 positioned adjacent the implant 75 in its natural shape 76, the fasteners 29 and 45 respectively insert into the first apertures 87 and 89 until the bottoms 59 and 68 of the frame 15 and body 16 contact the upper surface 79 of the implant 75. The fastener 29, due to its unclasped position residing from the fastener 45 at the first distance, inserts into the first aperture 87 spaced apart from the catch 91 whereby its cutout 31 is adjacent the catch 91 while its detent 30 is positioned underneath the catch 91 but separated therefrom. Likewise, the fastener 45, due to its unclasped position residing from the fastener 29 at the first distance, inserts into the second aperture 89 spaced apart from the catch 92 whereby its cutout 47 is adjacent the catch 92 while its detent 46 is positioned underneath the catch 92 but separated therefrom.

After insertion respectively of the fasteners 29 and 45 in their unclasped position into the first and second apertures 87 and 89 with their detents 30 and 46 respectively underneath the catches 91 and 92, the implant retainer 5 is positioned relative to the implant 75 in its natural shape 76 for engagement therewith whereby the implant retainer 5 transitions the implant 75 from its natural shape 76 to its insertion shape 77 and constrains the implant 75 in its insertion shape 77. The transitioning of the implant 75 from its natural shape 76 to its insertion shape 77 and the constraining thereof in its insertion shape 77 utilizing the implant retainer 5 includes rotation of the head 70 for the actuator 9 in the first direction and the consequent linear progression of the shaft 72 into the actuator aperture 38. Rotation of the head 70 for the actuator 9 in the first direction occurs until the head 70 traverses the bearing surface 60 from its unlocking position to its locking position whereby the head 70 resides atop the bearing surface 60 adjacent the end wall 23 of the wall 18 and the shaft 72 travels within the actuator aperture 38 from its first distance to its second distance. With the traversal of the head 70 for the actuator 9 to its locking position adjacent the end wall 23 of the wall 18, the frame 15 and the body 16 pivot into the engaged position 11 of the implant grip 8 whereby the top segment 36 of the actuator carrier 35 defining the actuator aperture 38 is positioned in the slot 28 adjacent the end wall 23 of the wall 18 while the actuator carrier 35 at its front surface 48 is adjacent the end wall 23 of the wall 18. The pivoting of the frame 15 and the body 16 towards one another into the engaged position 11 of the implant grip 8 pivots the fasteners 29 and 45 of the frame 15 and the body 16 away from each other such that the fasteners 29 and 45 move from their unclasped position at the first distance to their clasped position at the second distance based upon the location of the fasteners 29 and 45 underneath the pivot point 17 and their extension respectively below the end wall 23 and the wall 39 of the frame 15 and the body 16. Upon the progression of the fasteners 29 and 45 to their clasped position at the second distance, the fasteners 29 and 45 respectively via the detents 30 and 46 abut the catches 91 and 92 at undersides thereof and further impart a force into the implant 75 that facilitates transition of the implant 75 from its natural shape 76 to its insertions shape 77. As a result, the implant retainer 5, now in its loaded position 7 with the actuator 9 in its locking position holding the implant grip 8 in its engaged position 11 as illustrated in FIG. 7A-7C, transitions the implant 75 from its natural shape 76 to its insertion shape 77 and further constrains the implant 75 in its insertion shape 77 via engagement of the implant retainer 5 with the implant 75 at the fasteners 29 and 45 and the bottoms 59 and 68 of the frame 15 and body 16 at the upper surface 79 of the implant 75.

When delivering the implant 75 to bone, bones, or bone pieces, the implant retainer 5 as illustrated in FIGS. 7A-7C begins in its loaded position 7 wherein the implant grip 8 in its engaged position 11 constrains the implant 75 in its insertion shape 77. Release of the implant 75 from the implant retainer 5 for delivery into bone, bones, or bone pieces includes rotation of the head 70 for the actuator 9 in the second direction and the consequent linear retraction of the shaft 72 within the actuator aperture 38. Rotation of the head 70 for the actuator 9 in the second direction occurs until the head 70 traverses the bearing surface 60 from its locking position to its unlocking position whereby the head 70 resides atop the bearing surface 60 at the arm 26 and the shaft 72 travels within the actuator aperture 38 from its second distance to its first distance. With the traversing of the head 70 for the actuator 9 to its unlocking position at the arm 26, the frame 15 and the body 16 pivot into the disengaged position 10 of the implant grip 8 whereby the top segment 36 of the actuator carrier 35 defining the actuator aperture 38 is positioned in the slot 28 at the arm 26 while the actuator carrier 35 at its front surface 48 is spaced apart from the end wall 23 of the wall 18. The pivoting of the frame 15 and the body 16 away from one another into the disengaged position 10 of the implant grip 8 pivots the fasteners 29 and 45 of the frame 15 and the body 16 toward each other such that the fasteners 29 and 45 move from their clasped position at the second distance to their unclasped position at the first distance based upon the location of the fasteners 29 and 45 underneath the pivot point 17 and their extension respectively below the end wall 23 and the wall 39 of the frame 15 and the body 16. Upon the progression of the fasteners 29 and 45 to their unclasped position at the first distance, the fasteners 29 and 45 and thus the detents 30 and 46 respectively move away from and thus release the catches 91 and 92 at undersides thereof. As a result, the implant retainer 5, now in its unloaded position 6 with the actuator 9 in its unlocking position holding the implant grip 8 in its disengaged position 10 as illustrated in FIGS. 6A-6C, removes from atop the upper surface 79 of the implant 75 while the fasteners 29 and 45 respectively discharge from the first and second apertures 87 and 89 such that the released implant 75 attempts transition from its insertion shape 77 to its natural shape 76 whereby the implant 75 delivers the energy stored therein to the bone, bones, or bone pieces.

As illustrated in FIGS. 8A-C and 10A-11C, the implant retainer 150 according to a second embodiment, including its implant grip 151, comprised of a frame 152 and a body 153, and its actuator 154, is substantially similar in design and operation relative to the implant retainer 5 according to the first embodiment, including its implant grip 8, comprised of the frame 15 and the body 16, and its actuator 9, such that, for the sake of brevity, only differences therebetween will be described herein. Moreover, one of ordinary skill in the art will recognize that like parts of the implant grip 151, including its frame 152 and body 153, and the actuator 154 for the implant retainer 150 labeled with like numerals of the implant grip 8, including its frame 15 and body 16, and the actuator 9 for the implant retainer 5 incorporate a design and function as previously set forth in the detailed description of the implant retainer 5 according to the first embodiment.

The implant retainer 150 and, in particular, the implant grip 151 and its frame 152 are substantially similar to the implant grip 8 and its frame 15 with the exception of the following. The frame 152 at its rear 33 or its end wall 23 of the wall 18 includes first and second fasteners 155 and 156 extending therefrom. In the second embodiment, the first and second fasteners 155 and 156 reside respectively at each side 157 and 158 of the rear 33 for the frame 152 or the end wall 23 for the wall 18. The first and second fasteners 155 and 156 extend below the bottom 59 of the frame 152 or the end wall 23 such that the first and second fasteners 155 and 156 provide first and second engagement points 159 and 160 for the frame 152 with an implant. The first and second fasteners 155 and 156 at the engagement points 159 and 160 respectively include detents 161 and 162 located below cutouts 163 and 164. While the second embodiment includes the first and second fasteners 155 and 156, the frame 152 may include a single fastener located centrally with respect to the rear 33 or the end wall 23 for the wall 18.

The implant retainer 150 and, in particular, the implant grip 151 and its body 153 are substantially similar to the implant grip 8 and its body 16 with the exception of the following. The body 153 at its rear 66 or its wall 39 at the exterior face 41 thereof includes first and second fasteners 165 and 166 extending therefrom. In the second embodiment, the first and second fasteners 165 and 166 reside respectively at each side 173 and 174 of the rear 66 of the body 153 or the wall 39 at the exterior face 41. The first and second fasteners 165 and 166 extend below the bottom 68 of the body 153 or the wall 39 such that first and second fasteners 165 and 166 provide first and second engagement points 167 and 168 for the body 153 with an implant. The first and second fasteners 165 and 166 at the first and second engagement points 167 and 168 respectively include detents 169 and 170 located below cutouts 171 and 172. While the second embodiment includes the first and second fasteners 165 and 166, the body 153 may include a single fastener located centrally with respect to the rear 66 or the wall 39 of the body 153.

Based upon the foregoing, the implant retainer 150 according to the second embodiment primarily is different from the implant retainer 5 according to the first embodiment in that the implant retainer 250 is different in size from the implant retainer 5 whereby the implant retainer 150 is engageable with different size and shape implants such as an implant with a Y-shaped configuration. Although two or three fasteners will facilitate engagement of the implant retainer 150 with an implant, the four fasteners of the implant grip 151 provide for a more secure engagement of the implant retainer 150 with an implant including a Y-shaped configuration.

Figure 9A:
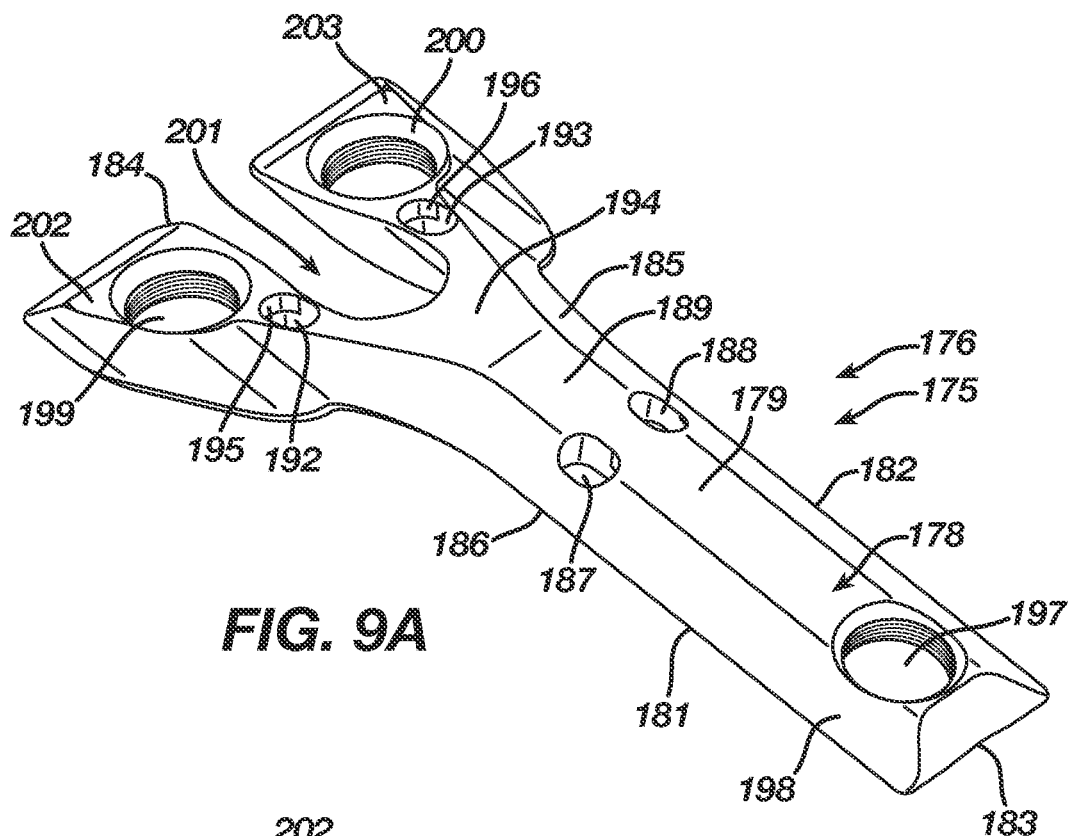
FIG. 9A is a top isometric view illustrating a shape memory implant according to a second embodiment in a natural shape.
Figure 9B:
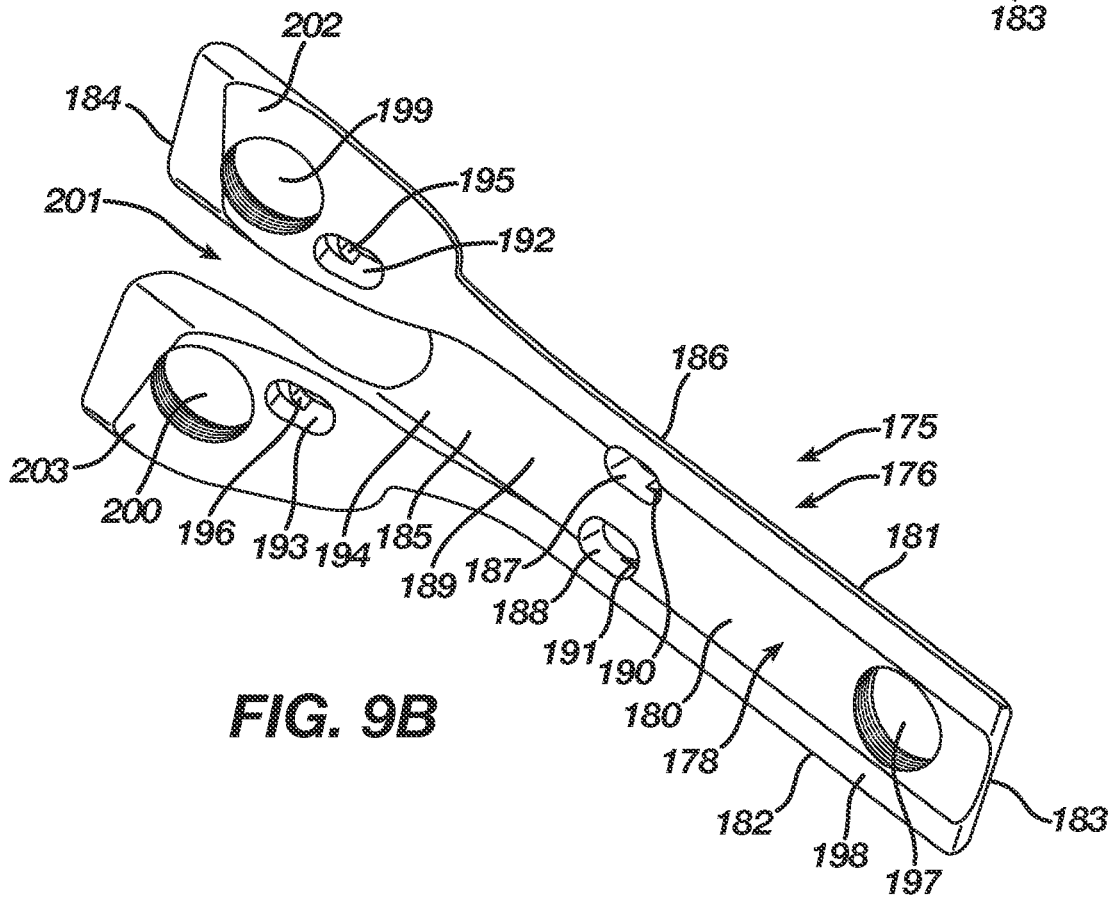
FIG. 9B is a bottom isometric view thereof.
Figure 9C:
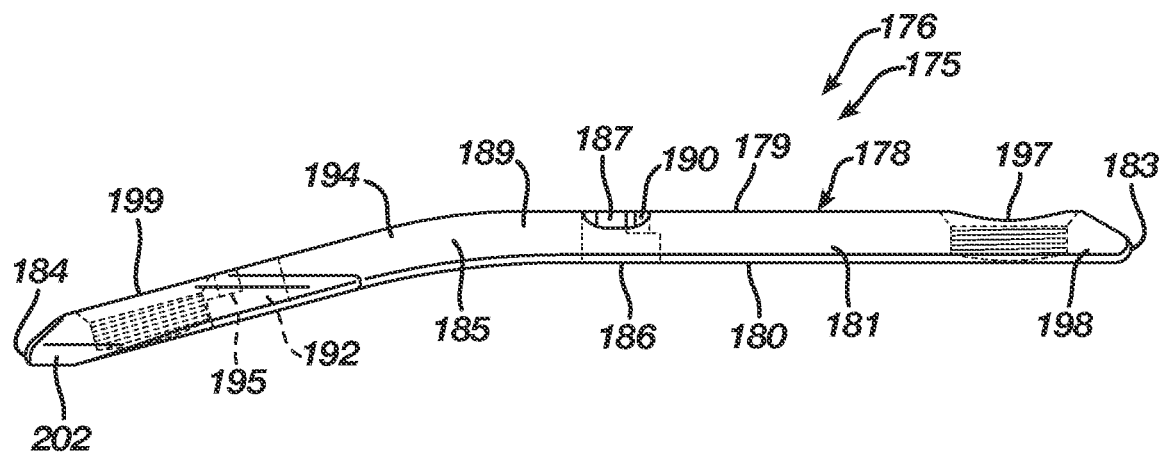
FIG. 9C is a side view thereof.
Figure 9D:
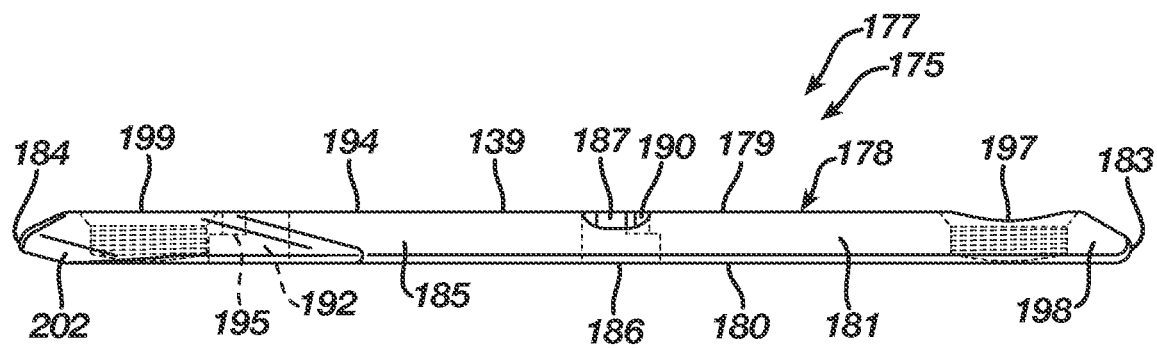
FIG. 9D is a side view illustrating the shape memory implant according to the second embodiment in an insertion shape.

FIGS. 9A-9C illustrate an orthopedic implant 175 according to a second embodiment in a natural shape 176, whereas FIG. 9D illustrates the orthopedic implant 175 in an insertion shape 177. The implant 175 in the second embodiment may be manufactured from a shape memory material with superelastic or temperature dependent properties (e.g., Nitinol) such that the implant 175 transitions between its natural shape 176 and its insertion shape 177. The implant 175 when deformed from its natural shape 176 to its insertion shape 177 stores energy deliverable to bone, bones, or bone pieces. In accordance with its manufacture from shape memory material, the implant 175 begins in its natural shape 176, is transitionable to its insertion shape 177, and, once implanted in bone, bones, or bone pieces, attempts to transition from its insertion shape 177 to its natural shape 176 whereby the implant 175 delivers the energy stored therein to the bone, bones, or bone pieces in order to affix the bone, bones, or bone pieces and promote a healing thereof. In the second embodiment, attempted transition of the implant 175 from its insertion shape 177 to its natural shape 176 continuously compresses the bone, bones, or bone pieces to promote fusion thereof.

The implant 175 includes a bridge 178 with upper and lower surfaces 179 and 180, first and second sides 181 and 182, and first and second ends 183 and 184. The implant 175 includes a transition section 185 located adjacent a center section 186 of the implant 175 and thus the bridge 178 between the center section 186 and the second end 184. The implant 175, and thus the bridge 178, includes a first opening 197 extending therethrough from the upper surface 179 to the lower surface 180 whereby the first opening 197 is located adjacent the first end 183 of the bridge 178 to provide the implant 175 and thus the bridge 178 with a first anchoring segment 198. The implant 175, and thus the bridge 178, includes second and third openings 199 and 200 extending therethrough from the upper surface 179 to the lower surface 180 whereby the second and third openings 199 and 200 are aligned and located adjacent the second end 184 of the bridge 178. In the second embodiment, the implant 175, and thus the bridge 178, at the second end 184 divides via a cut-out 201 into a second anchoring segment 202 incorporating the second opening 199 and a third anchoring segment 203 incorporating the third opening 201, thereby producing a Y-shaped configuration for the implant 175. The first, second, and third openings 197, 199, and 200 receive anchoring members in the form of screws therethrough in order to facilitate a securing of the implant 175 at the first, second, and third anchoring segments 198, 202, and 203 with bone, bones, or bone pieces whereby the bridge 178 between the first opening 197 and the second and third openings 199 and 200 traverses a fixation zone of the bone, bones, or bone pieces such that the implant 175, after its insertion and attempted transition from the insertion shape 177 to the natural shape 176, delivers energy to the bone, bones, or bone pieces at the fixation zone. Although the first, second, and third openings 197, 199, and 200 of the implant 175 primarily operate to receive therethrough anchoring members, the first, second, and third openings 197, 199, and 200 may receive therein respectively drill guides 204, 205, and 206 that facilitate a drilling of holes in the bone, bones, or bone pieces that assist in inserting anchoring members through the first, second, and third openings 197, 199, and 200 and into the bone, bones, or bone pieces. The first, second, and third openings 197, 199, and 200 in the second embodiment include threads that facilitate engagement of the first, second, and third openings 197, 199, and 200 with anchoring members or the drill guides 204, 205, and 206.

The implant 175, and thus the bridge 178, includes first and second apertures 187 and 188 extending therethrough from the upper surface 179 to the lower surface 180 whereby the first and second apertures 187 are aligned and located adjacent the transition section 185 at a first side 189 thereof. The implant 175, and thus the bridge 178, includes first and second catches 190 and 191 protruding respectively into the first and second apertures 187 and 188. The implant 175, and thus the bridge 178, includes third and fourth apertures 192 and 193 extending therethrough from the upper surface 179 to the lower surface 180 whereby the third and fourth apertures 192 and 193 are aligned and located adjacent the transition section 185 at a second side 194 thereof. The implant 175, and thus the bridge 178, includes third and fourth catches 195 and 196 protruding respectively into the third and fourth apertures 192 and 193. In the second embodiment, the second and third anchoring segments 202 and 203 respectively incorporate the third and fourth apertures 192 and 193, whereby the third and fourth apertures 192 and 193 are aligned across the cut-out 201. The first and second apertures 187 and 188 and their respective first and second catches 190 and 191 and the third and fourth apertures 192 and 193 and their respective third and fourth catches 195 and 196 provide engagement points for the implant retainer 150 with the implant 175. As such, the first and second apertures 187 and 188 are aligned and spaced apart a distance that allows receipt therein, respectively, of the fasteners 155 and 156 of the frame 152. Likewise, the third and fourth apertures 192 and 193 are aligned and spaced apart a distance that allows receipt therein, respectively, of the fasteners 165 and 166 of the body 153. Moreover, the first and second apertures 187 and 188 are spaced apart across the transition section 185 from the third and fourth apertures 192 and 193 a distance that allows receipt therein, respectively, of the fasteners 155 and 156 for the frame 152 and the fasteners 165 and 166 for the body 153 when the fasteners 155 and 156 for the frame 152 and the fasteners 165 and 166 for the body 153 reside at their first distance. When the fasteners 155 and 156 for the frame 152 and the fasteners 165 and 166 for the body 153 reside at their second distance, the fasteners 155 and 156 for the frame 152 and the fasteners 165 and 166 for the body 153, respectively, engage the first, second, third, and fourth catches 190, 191, 195, and 196 thereby securing the implant retainer 150 with the implant 175. The implant retainer 150 and its fasteners 155, 156, 165, and 166 and the first, second, third, and fourth apertures 187, 188, 192, and 193 are correspondingly designed with respect to their size, location, and distances to interact and engage such that the implant retainer 150 optimally constrains the implant 175 in its insertion shape 177.

The regular inherent shape of the implant 175, as illustrated in FIGS. 9A-9C, is its natural shape 176 where the transition section 185 locates the bridge 178 in a natural form consisting of a closed or angular profile whereby the first and second ends 183 and 184 reside at a first distance. Nevertheless, as illustrated in FIG. 9D, the implant 175 is deformable under the action of superelasticity or temperature dependent shape memory to its insertion shape 177 where the transition section 185 deforms to store energy while also moving the bridge 178 from its natural form to an insertion form which is an open or substantially linear profile whereby the first and second ends 183 and 184 reside at a second distance that is greater than the first distance. Since the insertion shape 177 is not the regular inherent shape of the implant 175, the bridge 178 typically is mechanically constrained using the implant retainer 150 whereby the implant retainer 150 maintains the bridge 178 in its insertion form. In particular, the implant retainer 150 inserts into the first, second, third, and fourth apertures 187, 188, 192, and 193 and engages the first, second, third, and fourth catches 190, 191, 195, and 196 such that the implant retainer 150 holds the bridge 178, resulting in the implant retainer 150 constraining the deformed transition section 185 in order to maintain the implant 175 in its insertion shape 177. After implantation into bone, bones, or bone pieces and a release of the implant retainer 150, including if necessary a heating of the implant 175, the implant 175 delivers the energy stored in the transition section 185 whereby the bridge 178 attempts to transition from its insertion form to its natural form such that the implant 175 affixes the bone, bones, or bone pieces through an application of a compressive force thereto.

Although the implant 175 in the second embodiment includes the first, second, third, and fourth apertures 187, 188, 192, and 193 and their respective first, second, third, and fourth catches 190, 191, 195, and 196, one of ordinary skill in the art will recognize that the implant 175 may include two apertures with a first aperture and respective catch located adjacent the transition section 185 at a first side 189 thereof and a second aperture and respective catch located adjacent the transition section 185 at a second side 194 thereof such that the implant 175 is engageable with an implant retainer including two fasteners. Alternatively, one of ordinary skill in the art will recognize that the implant 175 may include three apertures with a first aperture and respective catch located adjacent the transition section 185 at a first side 189 thereof and second and third apertures and respective catches located adjacent the transition section 185 at a second side 194 thereof such that the implant 175 is engageable with an implant retainer including three fasteners. Moreover, while the implant 175 in the second embodiment includes the first, second, and third openings 197, 199, and 200 in the first, second, and third anchoring segments 198, 202, and 203, one of ordinary skill in the art will recognize that the implant 175 may include additional openings in the first, second, and third anchoring segments 198, 202, and 203 that receive additional anchoring members in the form of screws therethrough in order to more securely affix the implant 175 to bone, bones, or bone pieces.

Figure 10A:
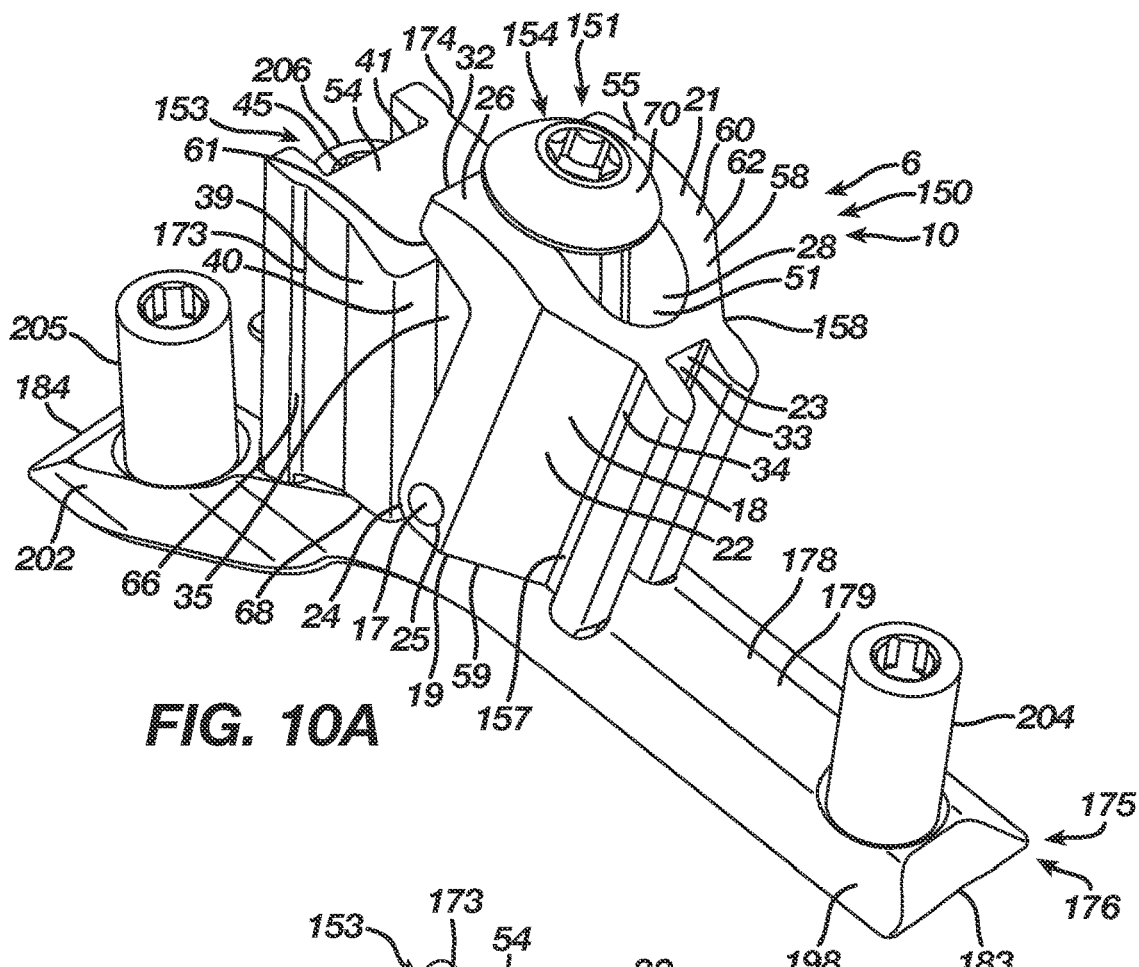
FIG. 10A is a top isometric view illustrating the implant retainer according to the second embodiment in an unloaded position relative to the shape memory implant according to the second embodiment in its natural shape.
Figure 10B:
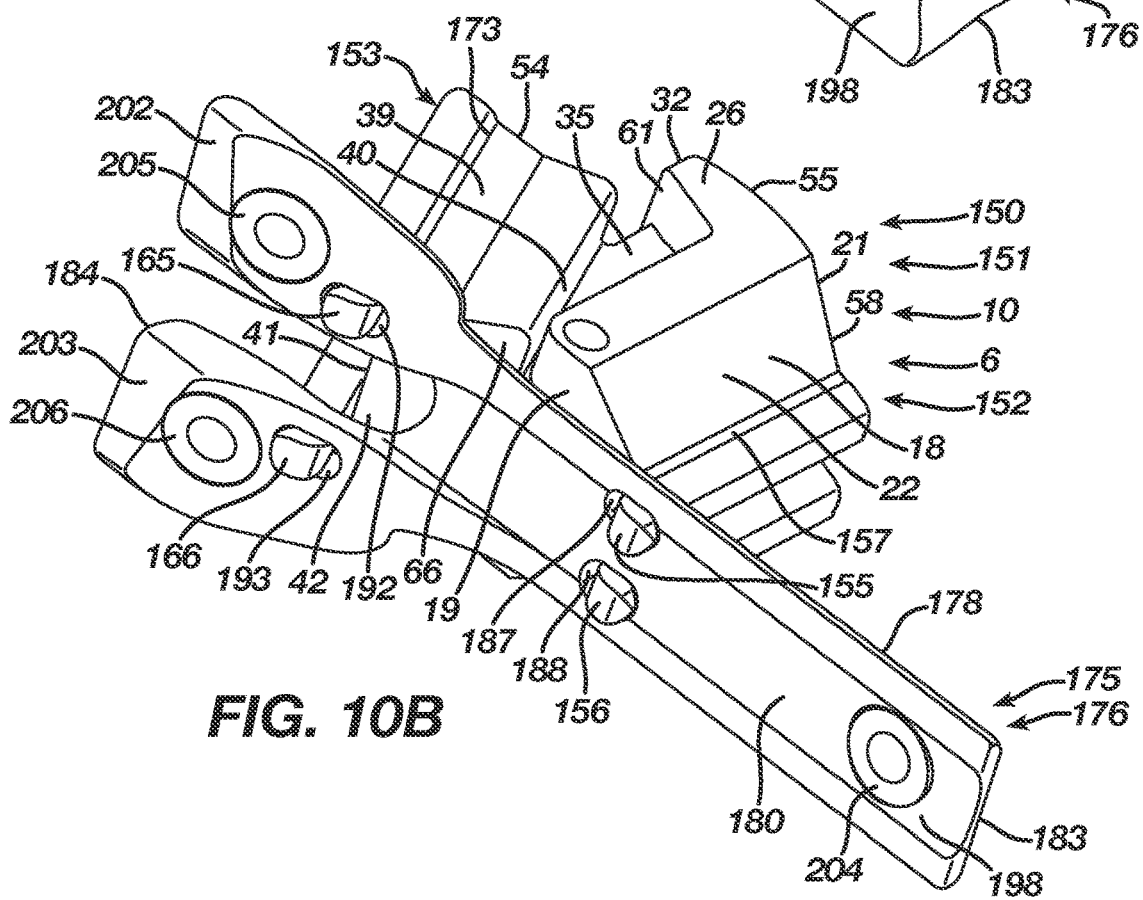
FIG. 10B is a bottom isometric view thereof.
Figure 10C:
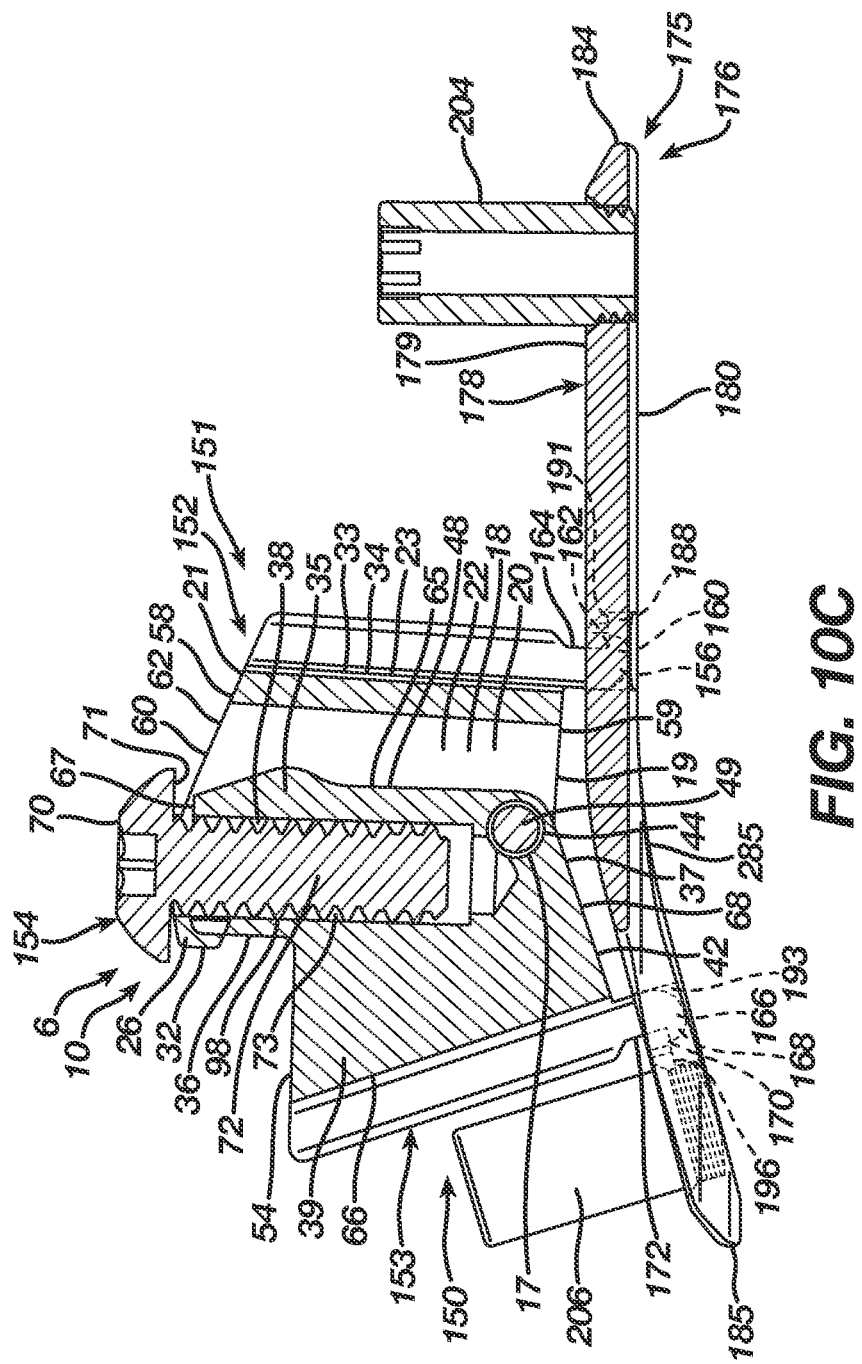
FIG. 10C is a side view in cross-section thereof.
Figure 11A:
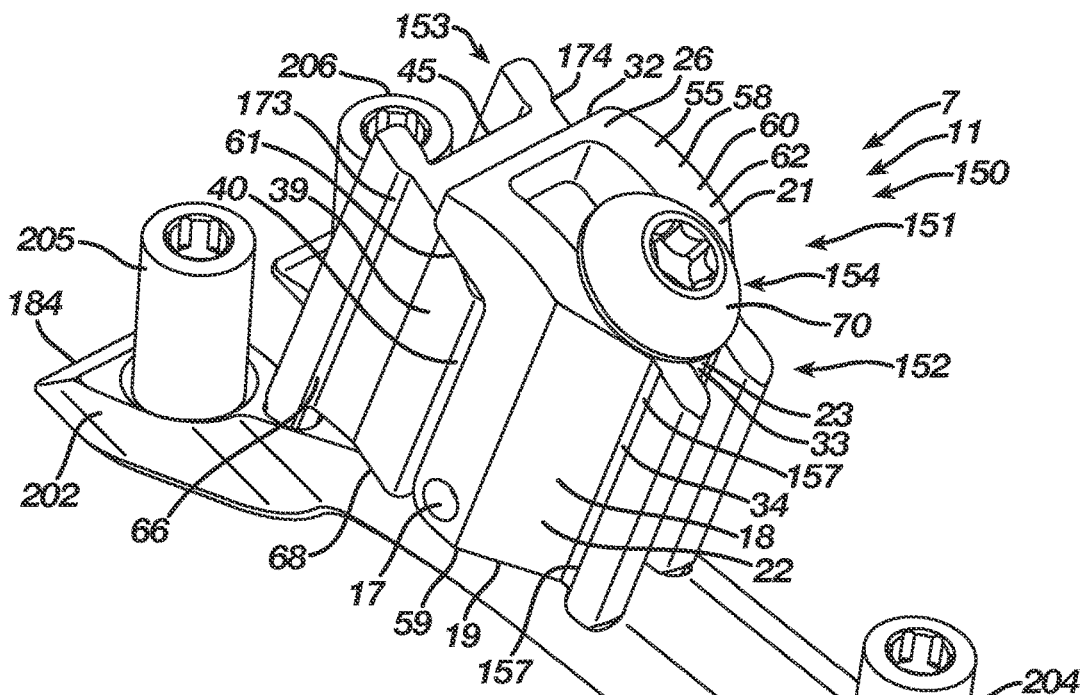
FIG. 11A is a top isometric view illustrating the implant retainer according to the second embodiment in a loaded position constraining the shape memory implant according to the second embodiment in its insertion shape.
Figure 11B:
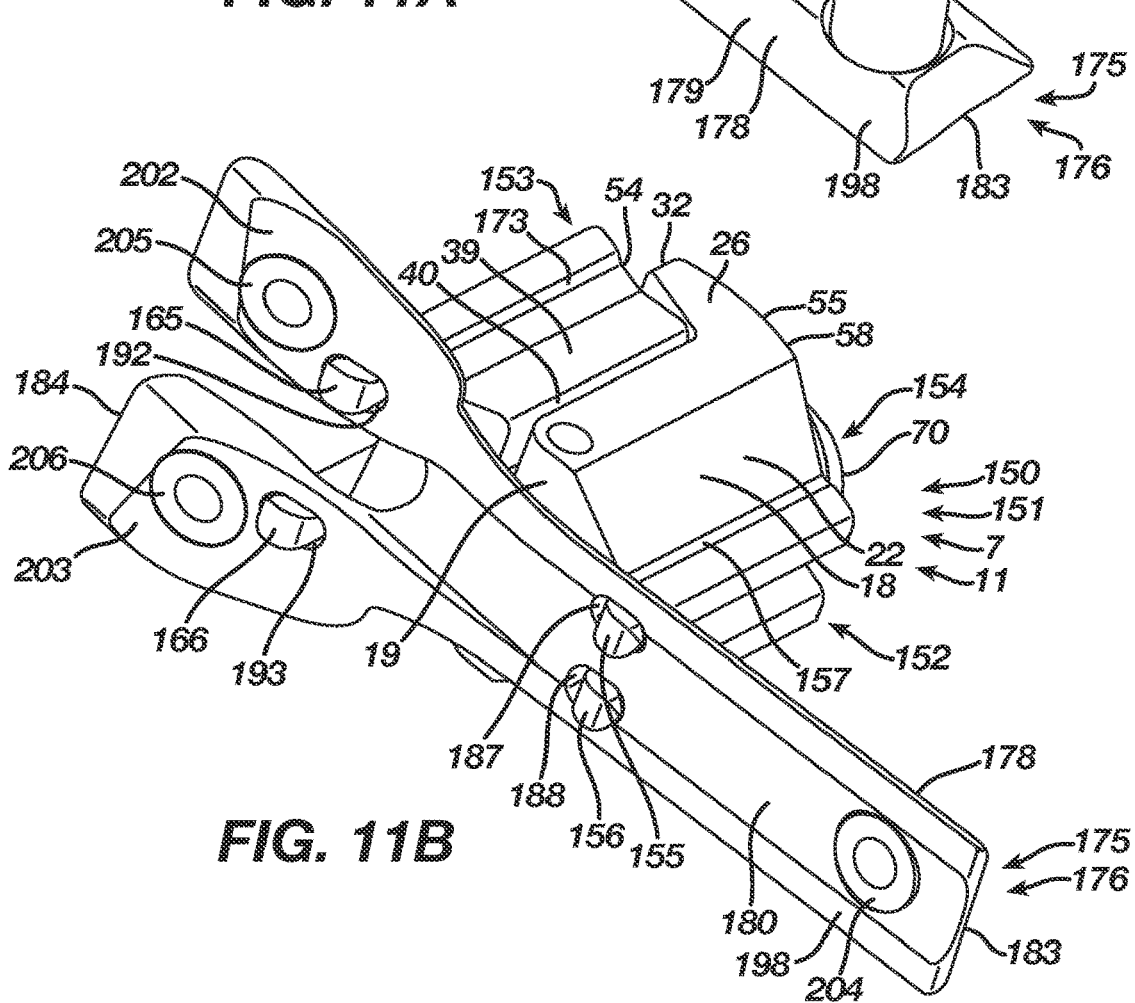
FIG. 11B is a bottom isometric view thereof.
Figure 11C:
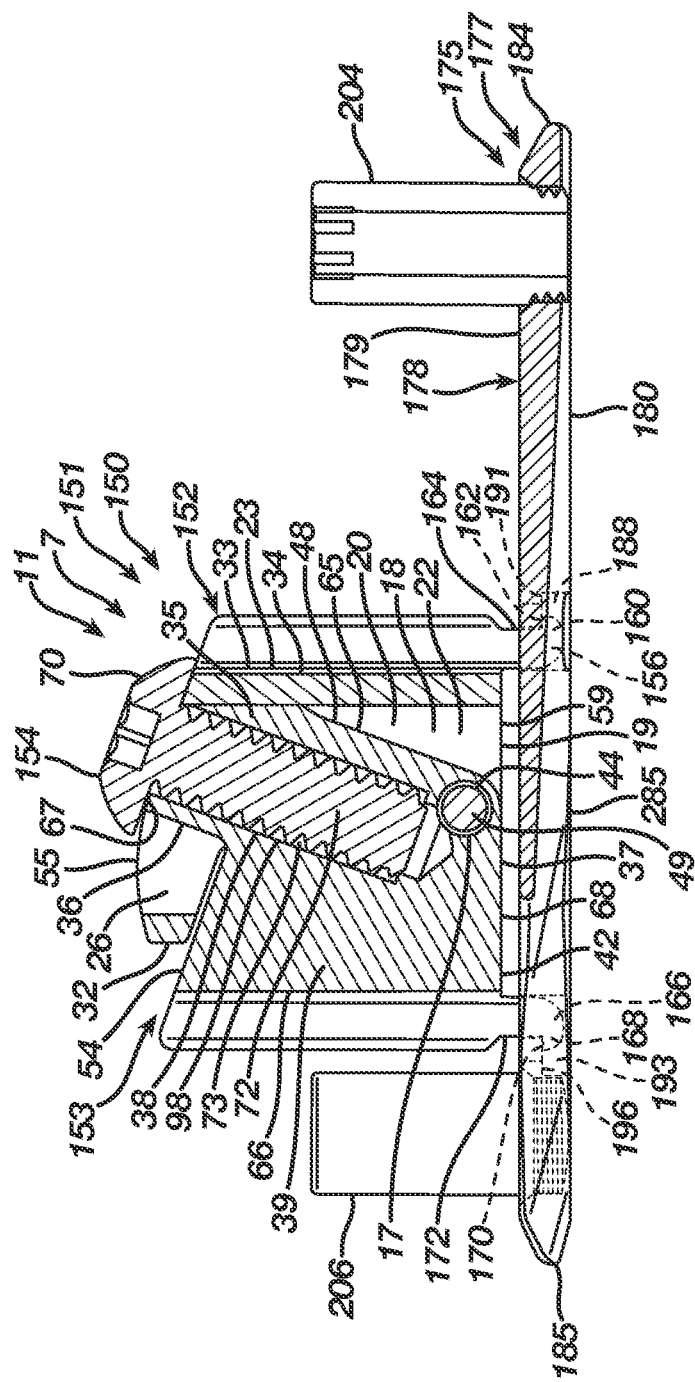
FIG. 11C is a side view in cross-section thereof.
Figure 12A:
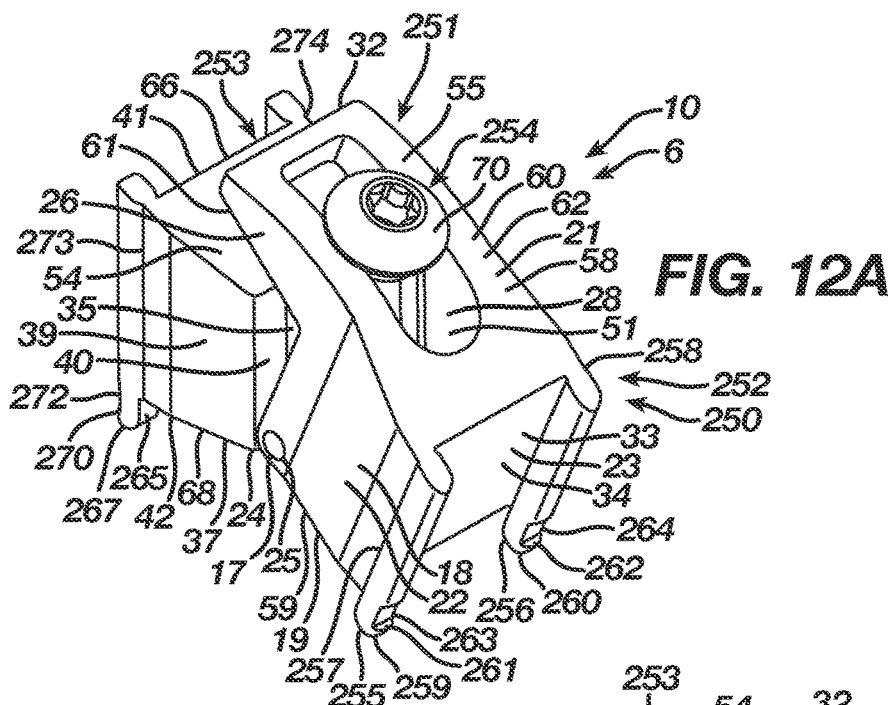
FIG. 12A is a top isometric view illustrating an implant retainer according to a third embodiment in an unloaded position.
Figure 12B:
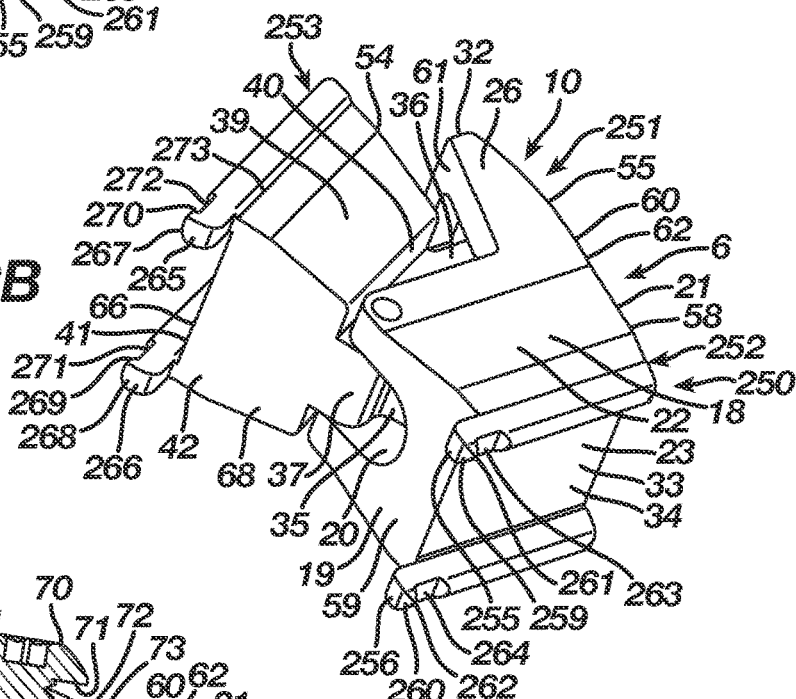
FIG. 12B is a bottom isometric view thereof.
Figure 12C:
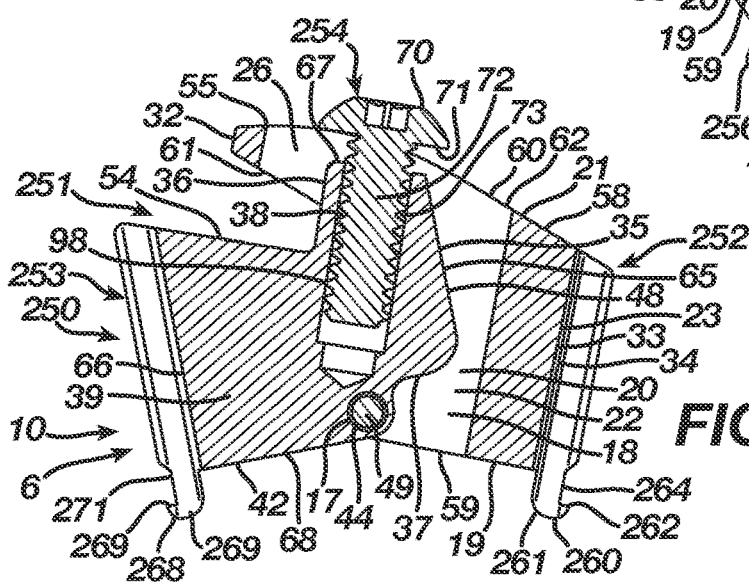
FIG. 12C is a side view in cross-section thereof.

As illustrated in FIGS. 10A-11C, the implant retainer 150 according to the second embodiment operates substantially identical in constraining the implant 175 in its insertion shape 177 relative to the implant retainer 5 according to the first embodiment and its constraining of the implant 75 in its insertion shape 77. In particular, after the implant retainer 150 is positioned adjacent the implant 175 at the upper surface 179 thereof, the fasteners 155 and 156 of the frame 152 and the fasteners 165 and 166 of the body 153, due to their unclasped position residing at the first distance, insert respectively into the first, second, third and fourth apertures 187, 188, 192, and 193 of the implant 175, whereby the cutouts 163, 164, 171, and 172 respectively are adjacent the first, second, third, and fourth catches 190, 191, 195, and 196 while the detents 161, 162, 169, and 170 are positioned underneath the first, second, third, and fourth catches 190, 191, 195, and 196 but separated therefrom. In the second embodiment, the fasteners 155, 156, 165, and 166 respectively extend below the end wall 23 of the wall 18 for the frame 152 and the wall 39 for the body 153 a length that permits their respective insertions into the first, second, third and fourth apertures 187, 188, 192, and 193 such that their detents 161, 162, 169, and 170 are located respectively below the first, second, third, and fourth catches 190, 191, 195, and 196. Nevertheless, the lengths of the fasteners 155, 156, 165, and 166 are equal to or less than the thickness of the implant 175 between its upper and lower surfaces 179 and 180 whereby the fasteners 155, 156, 165, and 166 do not extend respectively from the first, second, third and fourth apertures 187, 188, 192, and 193 below the lower surface 180 of the implant 175 in order to ensure the implant 175 sits flush atop bone, bones, or bone pieces. Rotation of the head 70 for the actuator 154 in the first direction and the subsequent traversing of the head 70 along the bearing surface 60 from its unlocking position to its locking position progresses the fasteners 155, 156, 165, and 166 to their clasped position at the second distance such that the fasteners 155, 156, 165, and 166 respectively via the detents 161, 162, 169, and 170 abut the first, second, third, and fourth catches 190, 191, 195, and 196 at undersides thereof. As a result, the implant retainer 150, now in its loaded position 7 with the actuator 154 in its locking position holding the implant grip 151 in its engaged position 11 as illustrated in FIG. 11A-11C, has moved the implant 175, if necessary, to its insertion shape 177 and constrains the implant 175 in its insertion shape 177 via engagement of the implant retainer 150 with the implant 175 at the fasteners 155, 156, 165, and 166 and the bottoms 59 and 68 of the frame 152 and body 153 at the upper surface 179 of the implant 175.

When delivering the implant 175 to bone, bones, or bone pieces, the implant retainer 150 as illustrated in FIGS. 11A-11C begins in its loaded position 7 wherein the implant grip 151 in its engaged position 11 constrains the implant 175 in its insertion shape 177. Rotation of the head 70 for the actuator 154 in the second direction and the subsequent traversing of the head 70 along the bearing surface 60 from its locking position to its unlocking position progresses the fasteners 155, 156, 165, and 166 to their unclasped position at the first distance such that the fasteners 155, 156, 165, and 166 and thus the detents 161, 162, 169, and 170 respectively move away from and thus release the first, second, third, and fourth catches 190, 191, 195, and 196 at undersides thereof. As a result, the implant retainer 150, now in its unloaded position 6 with the actuator 154 in its unlocking position holding the implant grip 151 in its disengaged position 10 as illustrated in FIGS. 10A-610, removes from atop the upper surface 179 of the implant 175 while the fasteners 155, 156, 165, and 166 respectively discharge from the first, second, third and fourth apertures 187, 188, 192, and 193 such that the released implant 175 attempts transition from its insertion shape 177 to its natural shape 176 whereby the implant 175 delivers the energy stored therein to the bone, bones, or bone pieces.

As illustrated in FIGS. 12A-C and 14A-15C, the implant retainer 250 according to a third embodiment, including its implant grip 251, comprised of a frame 252 and a body 253, and its actuator 254, is substantially similar in design and operation relative to the implant retainer 5 according to the first embodiment, including its implant grip 8, comprised of the frame 15 and the body 16, and its actuator 9, such that, for the sake of brevity, only differences therebetween will be described herein. Moreover, one of ordinary skill in the art will recognize that like parts of the implant grip 251, including its frame 252 and body 253, and the actuator 254 for the implant retainer 250 labeled with like numerals of the implant grip 8, including its frame 15 and body 16, and the actuator 9 for the implant retainer 5 incorporate a design and function as previously set forth in the detailed description of the implant retainer 5 according to the first embodiment.

The implant retainer 250 and, in particular, the implant grip 251 and its frame 252 are substantially similar to the implant grip 8 and its frame 15 with the exception of the following. The frame 252 at its rear 33 or its end wall 23 of the wall 18 includes first and second fasteners 255 and 256 extending therefrom. In the third embodiment, the first and second fasteners 255 and 256 reside respectively at each side 257 and 258 of the rear 33 for the frame 252 or the end wall 23 for the wall 18. The first and second fasteners 255 and 256 extend below the bottom 59 of the frame 252 or the end wall 23 such that the first and second fasteners 255 and 256 provide first and second engagement points 259 and 260 for the frame 252 with an implant. The first and second fasteners 255 and 256 at the engagement points 259 and 260 respectively include detents 261 and 262 located below cutouts 263 and 264. While the third embodiment includes the first and second fasteners 255 and 156, the frame 252 may include a single fastener located centrally with respect to the rear 33 or the end wall 23 for the wall 18.

The implant retainer 250 and, in particular, the implant grip 251 and its body 253 are substantially similar to the implant grip 8 and its body 16 with the exception of the following. The body 253 at its rear 66 or its wall 39 at the exterior face 41 thereof includes first and second fasteners 265 and 266 extending therefrom. In the third embodiment, the first and second fasteners 265 and 266 reside respectively at each side 273 and 274 of the rear 66 of the body 253 or the wall 39 at the exterior face 41. The first and second fasteners 265 and 266 extend below the bottom 68 of the body 253 or the wall 39 such that first and second fasteners 265 and 266 provide first and second engagement points 267 and 268 for the body 253 with an implant. The first and second fasteners 265 and 266 at the first and second engagement points 267 and 268 respectively include detents 269 and 270 located below cutouts 271 and 272. While the third embodiment includes the first and second fasteners 265 and 266, the body 253 may include a single fastener located centrally with respect to the rear 66 or the wall 39 of the body 253.

Based upon the foregoing, the implant retainer 250 according to the third embodiment primarily is different from the implant retainer 5 according to the first embodiment in that the implant retainer 250 is different in size from the implant retainer 5 whereby the implant retainer 250 is engageable with different size and shape implants such as an implant with an H-shaped configuration. Although two fasteners will facilitate engagement of the implant retainer 250 with an implant, the four fasteners of the implant grip 251 provide for a more secure engagement of the implant retainer 250 with an implant including an H-shaped configuration.

Figure 13A:
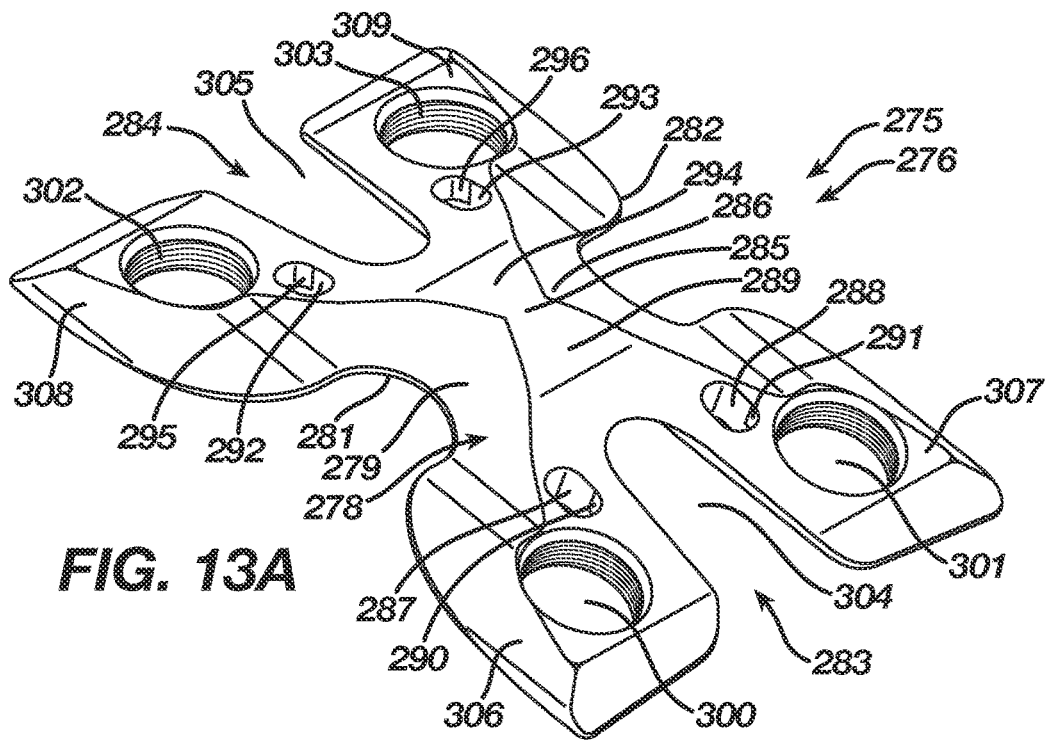
FIG. 13A is a top isometric view illustrating a shape memory implant according to a third embodiment in a natural shape.
Figure 13B:
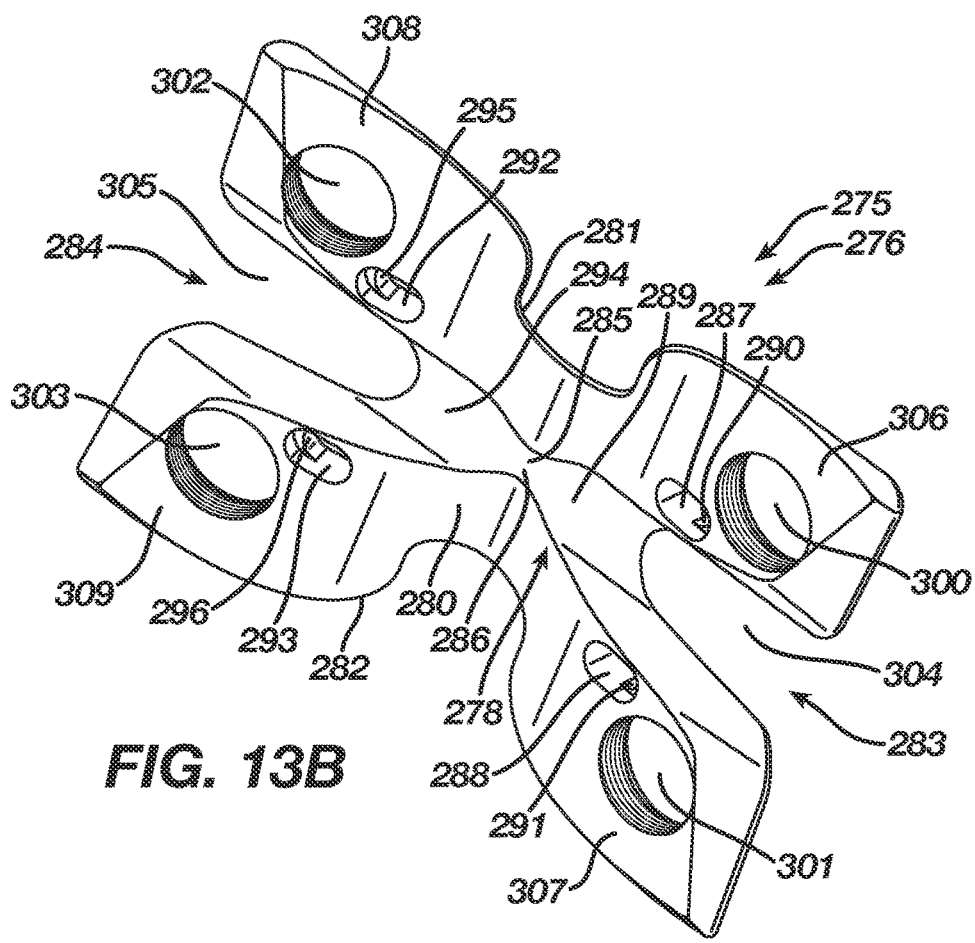
FIG. 13B is a bottom isometric view thereof.
Figure 13C:
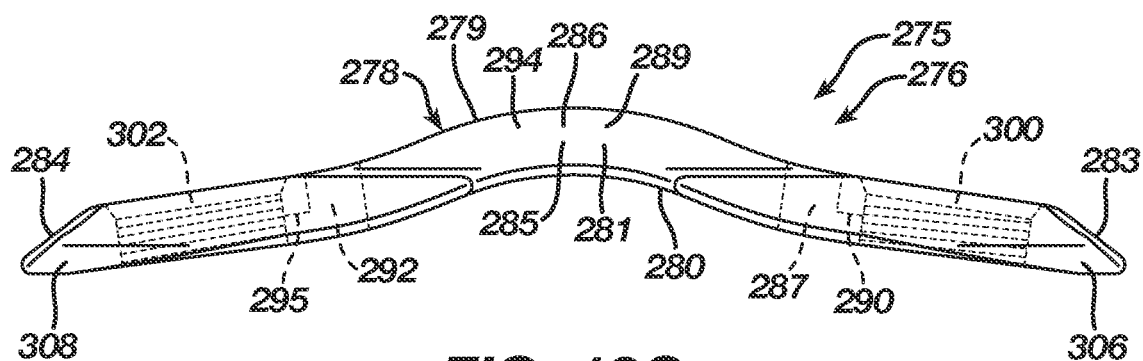
FIG. 13C is a side view thereof.
Figure 13D:
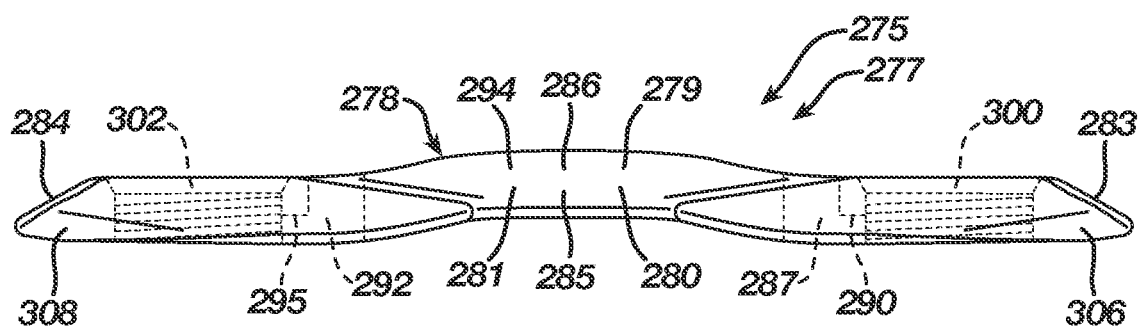
FIG. 13D is a side view illustrating the shape memory implant according to the third embodiment in an insertion shape.

FIGS. 13A-13C illustrate an orthopedic implant 275 according to a third embodiment in a natural shape 276, whereas FIG. 13D illustrates the orthopedic implant 275 in an insertion shape 277. The implant 275 in the third embodiment may be manufactured from a shape memory material with superelastic or temperature dependent properties (e.g., Nitinol) such that the implant 275 transitions between its natural shape 276 and its insertion shape 277. The implant 275 when deformed from its natural shape 276 to its insertion shape 277 stores energy deliverable to bone, bones, or bone pieces. In accordance with its manufacture from shape memory material, the implant 275 begins in its natural shape 276, is transitionable to its insertion shape 277, and, once implanted in bone, bones, or bone pieces, attempts to transition from its insertion shape 277 to its natural shape 276 whereby the implant 275 delivers the energy stored therein to the bone, bones, or bone pieces in order to affix the bone, bones, or bone pieces and promote a healing thereof.

In the third embodiment, attempted transition of the implant 275 from its insertion shape 277 to its natural shape 276 continuously compresses the bone, bones, or bone pieces to promote fusion thereof.

The implant 275 includes a bridge 278 with upper and lower surfaces 279 and 280, first and second sides 281 and 282, and first and second ends 283 and 284. The implant 275 includes a transition section 285 located at a center section 286 of the implant 275 and thus the bridge 278. The implant 275, and thus the bridge 278, includes first and second openings 300 and 301 extending therethrough from the upper surface 279 to the lower surface 280 whereby the first and second openings 300 and 301 are aligned and located adjacent the first end 283 of the bridge 278. In the third embodiment, the implant 275, and thus the bridge 278, at the first end 283 divides via a cut-out 304 into a first anchoring segment 306 incorporating the first opening 300 and a second anchoring segment 307 incorporating the second opening 301, thereby producing an H-shaped configuration for the implant 275. The implant 275, and thus the bridge 278, includes third and fourth openings 302 and 303 extending therethrough from the upper surface 279 to the lower surface 280 whereby the third and fourth openings 302 and 303 are aligned and located adjacent the second end 284 of the bridge 278. In the third embodiment, the implant 275, and thus the bridge 278, at the second end 284 divides via a cut-out 305 into a third anchoring segment 308 incorporating the third opening 302 and a fourth anchoring segment 309 incorporating the fourth opening 303, thereby producing an H-shaped configuration for the implant 275. The first, second, third, and fourth openings 300-303 receive anchoring members in the form of screws therethrough in order to facilitate a securing of the implant 275 at the first, second, and third anchoring segments 306-309 with bone, bones, or bone pieces whereby the bridge 278 between the first and second openings 300 and 301 and the third and fourth openings 302 and 303 traverses a fixation zone of the bone, bones, or bone pieces such that the implant 275, after its insertion and attempted transition from the insertion shape 277 to the natural shape 276, delivers energy to the bone, bones, or bone pieces at the fixation zone. Although the first, second, third, and fourth openings 300-303 of the implant 275 primarily operate to receive therethrough anchoring members, the first, second, third, and fourth openings 300-303 may receive therein respectively drill guides 310-313 that facilitate a drilling of holes in the bone, bones, or bone pieces that assist in inserting anchoring members through the first, second, third, and fourth openings 300-303 and into the bone, bones, or bone pieces. The first, second, third, and fourth openings 300-303 in the third embodiment include threads that facilitate engagement of the first, second, third, and fourth openings 300-303 with anchoring members or the drill guides 310-313. The implant 275, and thus the bridge 278, includes first and second apertures 287 and 288 extending therethrough from the upper surface 279 to the lower surface 280 whereby the first and second apertures 287 and 288 are aligned and located adjacent the transition section 285 at a first side 289 thereof. The implant 275, and thus the bridge 278, includes first and second catches 290 and 291 protruding respectively into the first and second apertures 287 and 288. In the third embodiment, the first and second anchoring segments 306 and 307 respectively incorporate the first and second apertures 287 and 288, whereby the first and second apertures 287 and 288 are aligned across the cut-out 304. The implant 275, and thus the bridge 278, includes third and fourth apertures 292 and 293 extending therethrough from the upper surface 279 to the lower surface 280 whereby the third and fourth apertures 292 and 293 are aligned and located adjacent the transition section 285 at a second side 294 thereof. The implant 275, and thus the bridge 278, includes third and fourth catches 295 and 296 protruding respectively into the third and fourth apertures 292 and 293. In the third embodiment, the third and fourth anchoring segments 308 and 309 respectively incorporate the third and fourth apertures 292 and 293, whereby the third and fourth apertures 292 and 293 are aligned across the cut-out 305. The first and second apertures 287 and 288 and their respective first and second catches 290 and 291 and the third and fourth apertures 292 and 293 and their respective third and fourth catches 295 and 296 provide engagement points for the implant retainer 250 with the implant 275. As such, the first and second apertures 287 and 288 are aligned and spaced apart a distance that allows receipt therein, respectively, of the fasteners 255 and 256 of the frame 252. Likewise, the third and fourth apertures 292 and 293 are aligned and spaced apart a distance that allows receipt therein, respectively, of the fasteners 265 and 266 of the body 253. Moreover, the first and second apertures 287 and 288 are spaced apart across the transition section 285 from the third and fourth apertures 292 and 293 a distance that allows receipt therein, respectively, of the fasteners 255 and 256 for the frame 252 and the fasteners 265 and 266 for the body 253 when the fasteners 255 and 256 for the frame 252 and the fasteners 265 and 266 for the body 253 reside at their first distance. When the fasteners 255 and 256 for the frame 252 and the fasteners 265 and 266 for the body 253 reside at their second distance, the fasteners 255 and 256 for the frame 252 and the fasteners 265 and 266 for the body 253, respectively, engage the first, second, third, and fourth catches 290, 291, 295, and 296 thereby securing the implant retainer 250 with the implant 275. The implant retainer 250 and its fasteners 255, 256, 265, and 266 and the first, second, third, and fourth apertures 287, 288, 292, and 293 are correspondingly designed with respect to their size, location, and distances to interact and engage such that the implant retainer 250 optimally constrains the implant 275 in its insertion shape 277.

The regular inherent shape of the implant 275, as illustrated in FIGS. 13A-13C, is its natural shape 276 where the transition section 285 locates the bridge 278 in a natural form consisting of a closed or angular profile whereby the first and second ends 283 and 284 reside at a first distance. Nevertheless, as illustrated in FIG. 13D, the implant 275 is deformable under the action of superelasticity or temperature dependent shape memory to its insertion shape 277 where the transition section 285 deforms to store energy while also moving the bridge 278 from its natural form to an insertion form which is an open or substantially linear profile whereby the first and second ends 283 and 284 reside at a second distance that is greater than the first distance. Since the insertion shape 277 is not the regular inherent shape of the implant 275, the bridge 278 typically is mechanically constrained using the implant retainer 250 whereby the implant retainer 250 maintains the bridge 278 in its insertion form. In particular, the implant retainer 250 inserts into the first, second, third, and fourth apertures 287, 288, 292, and 293 and engages the first, second, third, and fourth catches 290, 291, 295, and 296 such that the implant retainer 250 holds the bridge 278, resulting in the implant retainer 250 constraining the deformed transition section 285 in order to maintain the implant 275 in its insertion shape 277. After implantation into bone, bones, or bone pieces and a release of the implant retainer 250, including if necessary a heating of the implant 275, the implant 275 delivers the energy stored in the transition section 285 whereby the bridge 278 attempts to transition from its insertion form to its natural form such that the implant 275 affixes the bone, bones, or bone pieces through an application of a compressive force thereto.

Although the implant 275 in the third embodiment includes the first, second, third, and fourth apertures 287, 288, 292, and 293 and their respective first, second, third, and fourth catches 290, 291, 295, and 296, one of ordinary skill in the art will recognize that the implant 275 may include two apertures with a first aperture and respective catch located adjacent the transition section 285 at a first side 289 thereof and a second aperture and respective catch located adjacent the transition section 285 at a second side 294 thereof such that the implant 275 is engageable with an implant retainer including two fasteners. Moreover, while the implant 275 in the third embodiment includes the first, second, third, and fourth openings 300-303 in the first, second, third, and fourth anchoring segments 306-309, one of ordinary skill in the art will recognize that the implant 175 may include additional openings in the first, second, third, and fourth anchoring segments 306-309 that receive additional anchoring members in the form of screws therethrough in order to more securely affix the implant 275 to bone, bones, or bone pieces.

Figure 14A:
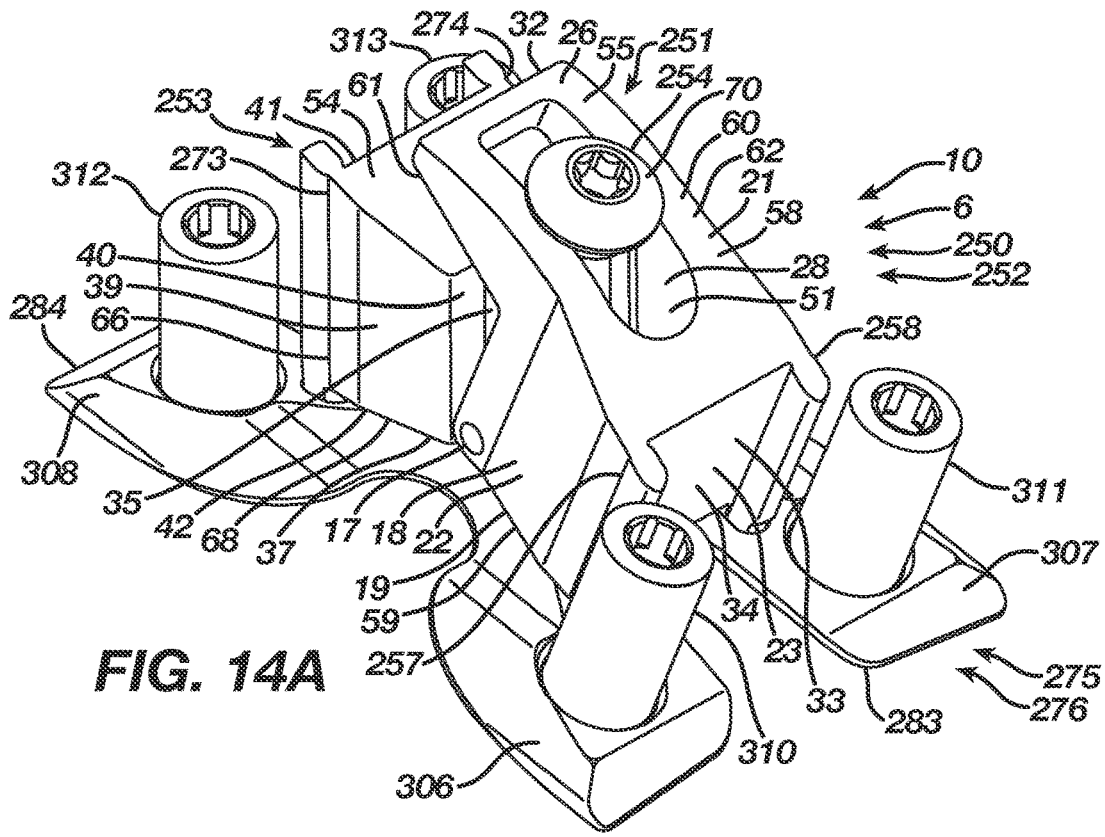
FIG. 14A is a top isometric view illustrating the implant retainer according to the third embodiment in an unloaded position relative to the shape memory implant according to the third embodiment in its natural shape.
Figure 14B:
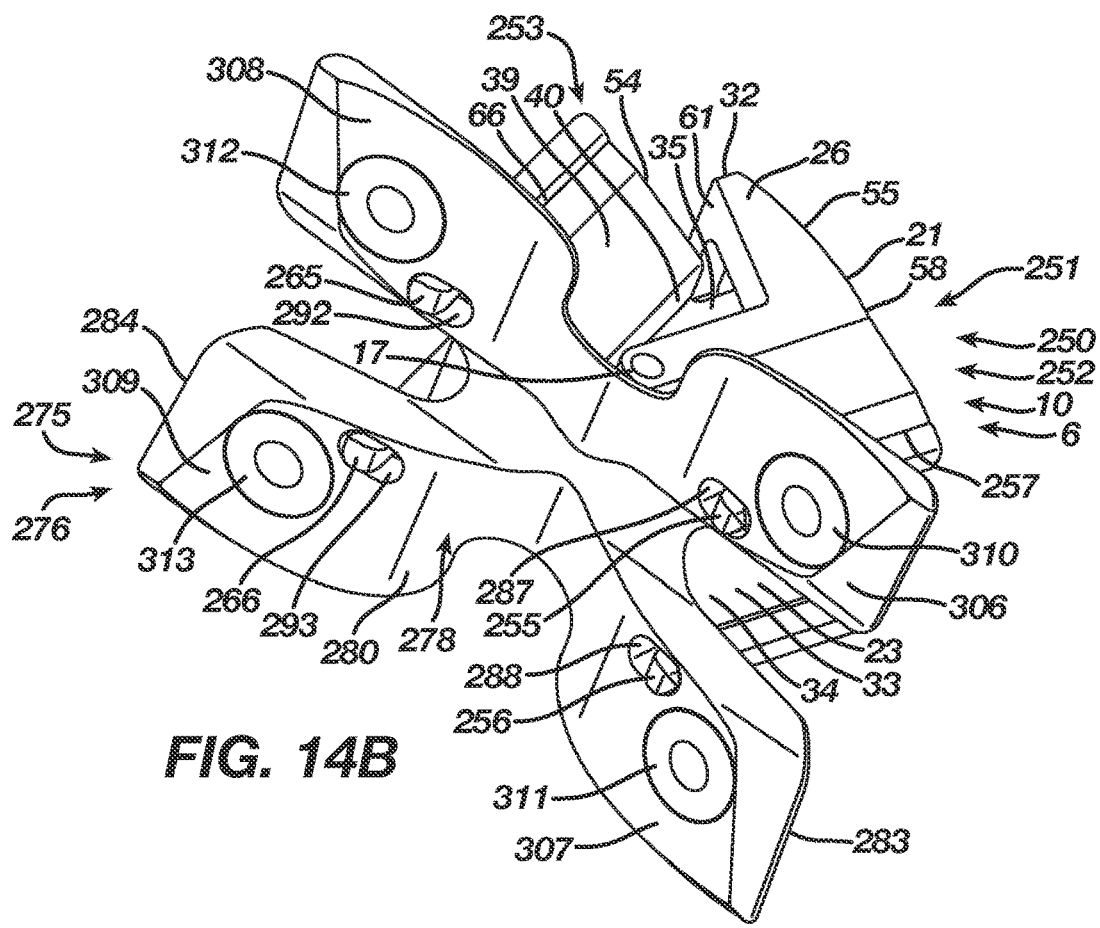
FIG. 14B is a bottom isometric view thereof.
Figure 14C:
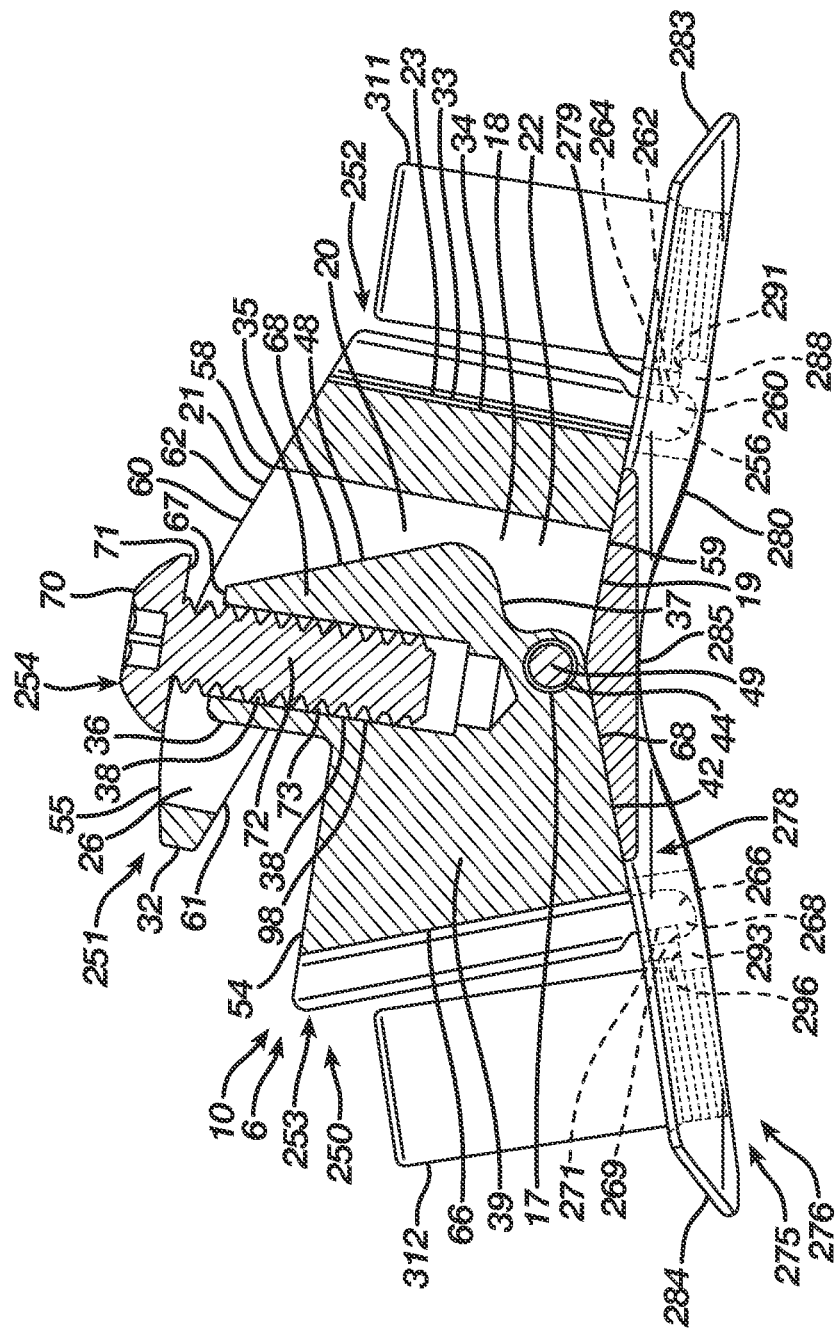
FIG. 14C is a side view in cross-section thereof.
Figure 15A:
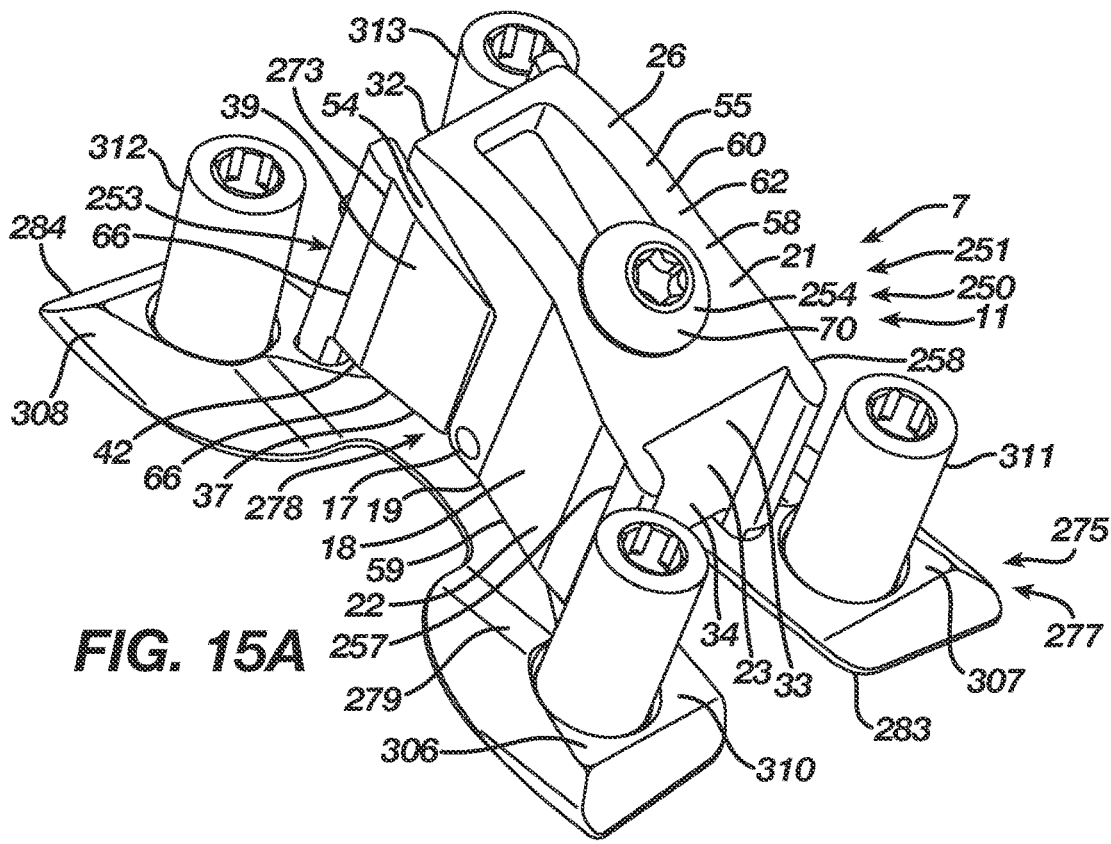
FIG. 15A is a top isometric view illustrating the implant retainer according to the third embodiment in a loaded position constraining the shape memory implant according to the third embodiment in its insertion shape.
Figure 15B:
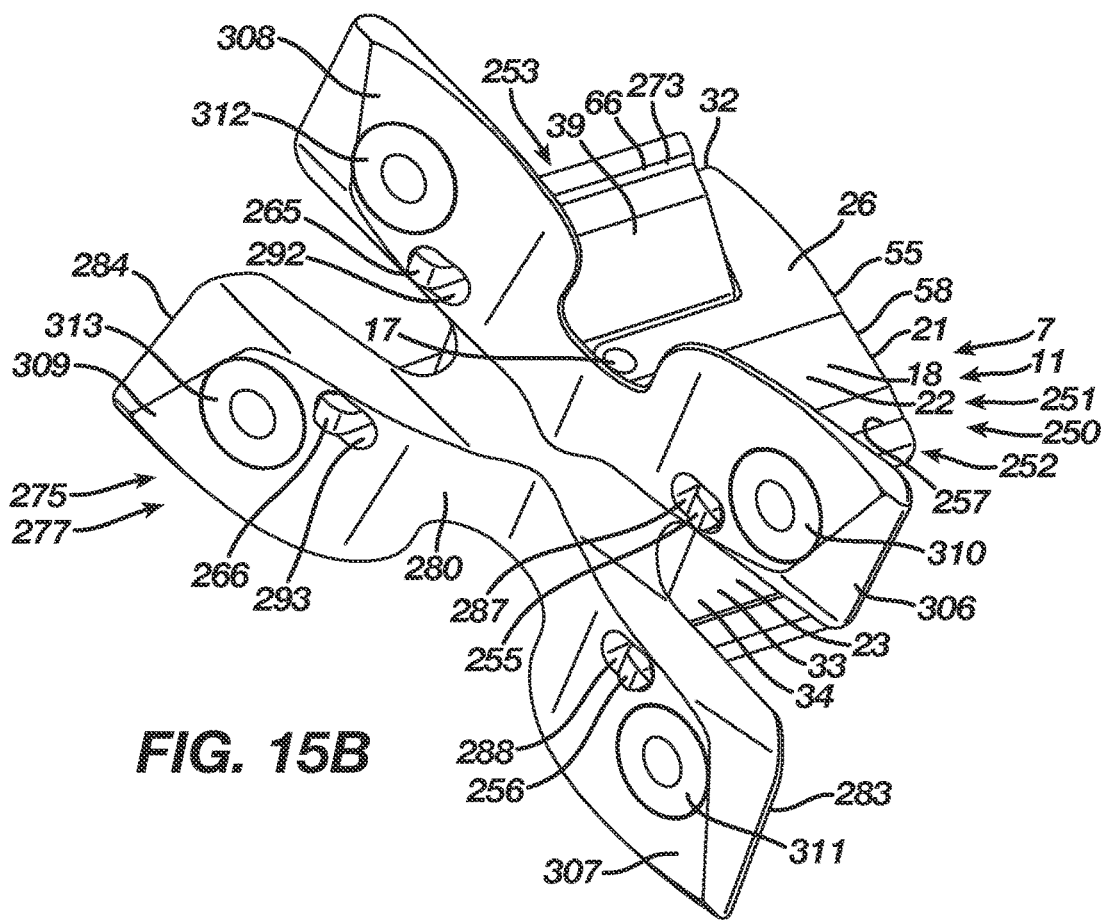
FIG. 15B is a bottom isometric view thereof.
Figure 15C:
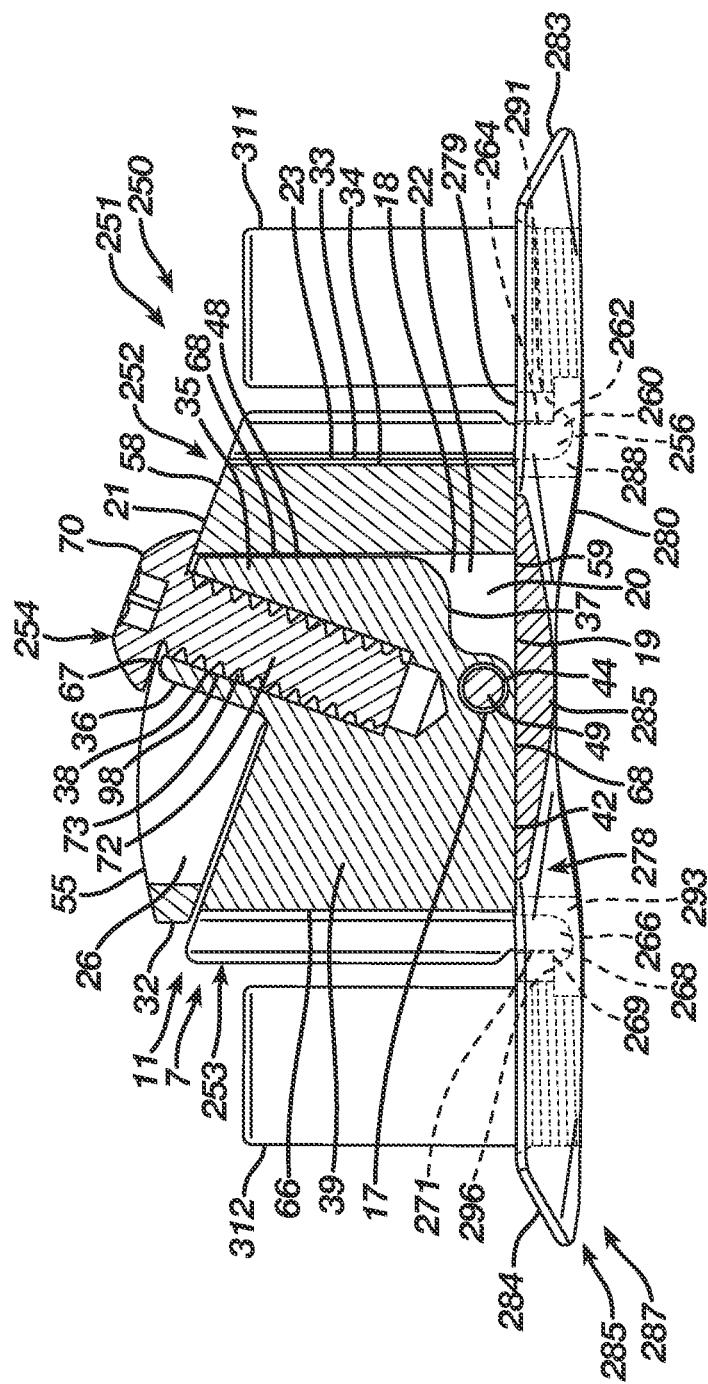
FIG. 15C is a side view in cross-section thereof.

As illustrated in FIGS. 14A-15C, the implant retainer 250 according to the third embodiment operates substantially identical in constraining the implant 275 in its insertion shape 277 relative to the implant retainer 5 according to the first embodiment and its constraining of the implant 75 in its insertion shape 77. In particular, after the implant retainer 250 is positioned adjacent the implant 275 at the upper surface 279 thereof, the fasteners 255 and 256 of the frame 252 and the fasteners 265 and 266 of the body 253, due to their unclasped position residing at the first distance, insert respectively into the first, second, third and fourth apertures 287, 288, 292, and 293 of the implant 275, whereby the cutouts 263, 264, 271, and 272 respectively are adjacent the first, second, third, and fourth catches 290, 291, 295, and 296 while the detents 261, 262, 269, and 270 are positioned underneath the first, second, third, and fourth catches 290, 291, 295, and 296 but separated therefrom. In the third embodiment, the fasteners 255, 256, 265, and 266 respectively extend below the end wall 23 of the wall 18 for the frame 252 and the wall 39 for the body 253 a length that permits their respective insertions into the first, second, third and fourth apertures 287, 288, 292, and 293 such that their detents 261, 262, 269, and 270 are located respectively below the first, second, third, and fourth catches 290, 291, 295, and 296. Nevertheless, the lengths of the fasteners 255, 256, 265, and 266 are equal to or less than the thickness of the implant 275 between its upper and lower surfaces 279 and 280 whereby the fasteners 255, 256, 265, and 266 do not extend respectively from the first, second, third and fourth apertures 287, 288, 292, and 293 below the lower surface 280 of the implant 275 in order to ensure the implant 275 sits flush atop bone, bones, or bone pieces. Rotation of the head 70 for the actuator 254 in the first direction and the subsequent traversing of the head 70 along the bearing surface 60 from its unlocking position to its locking position progresses the fasteners 255, 256, 265, and 266 to their clasped position at the second distance such that the fasteners 255, 256, 265, and 266 respectively via the detents 261, 262, 269, and 270 abut the first, second, third, and fourth catches 290, 291, 295, and 296 at undersides thereof. As a result, the implant retainer 250, now in its loaded position 7 with the actuator 254 in its locking position holding the implant grip 251 in its engaged position 11 as illustrated in FIG. 15A-15C, has moved the implant 275, if necessary, to its insertion shape 277 and constrains the implant 275 in its insertion shape 277 via engagement of the implant retainer 250 with the implant 275 at the fasteners 255, 256, 265, and 266 and the bottoms 59 and 68 of the frame 252 and body 253 at the upper surface 279 of the implant 275.

When delivering the implant 275 to bone, bones, or bone pieces, the implant retainer 250 as illustrated in FIGS. 15A-15C begins in its loaded position 7 wherein the implant grip 251 in its engaged position 11 constrains the implant 275 in its insertion shape 277. Rotation of the head 70 for the actuator 254 in the second direction and the subsequent traversing of the head 70 along the bearing surface 60 from its locking position to its unlocking position progresses the fasteners 255, 256, 265, and 266 to their unclasped position at the first distance such that the fasteners 255, 256, 265, and 266 respectively move away from and thus release the first, second, third, and fourth catches 290, 291, 295, and 296 at undersides thereof. As a result, the implant retainer 250, now in its unloaded position 6 with the actuator 254 in its unlocking position holding the implant grip 251 in its disengaged position 10 as illustrated in FIGS. 14A-14C, removes from atop the upper surface 279 of the implant 275 while the fasteners 255, 256, 265, and 266 respectively discharge from the first, second, third and fourth apertures 287, 288, 292, and 293 such that the released implant 275 attempts transition from its insertion shape 277 to its natural shape 276 whereby the implant 275 delivers the energy stored therein to the bone, bones, or bone pieces.

Figure 16A:
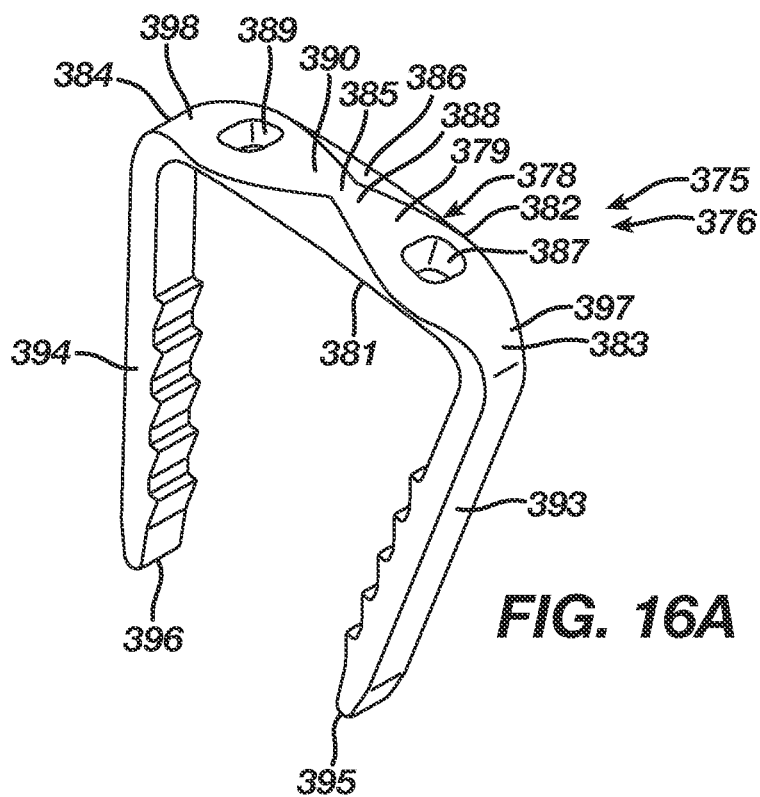
FIG. 16A is a top isometric view illustrating a shape memory implant according to a fourth embodiment in a natural shape.
Figure 16B:
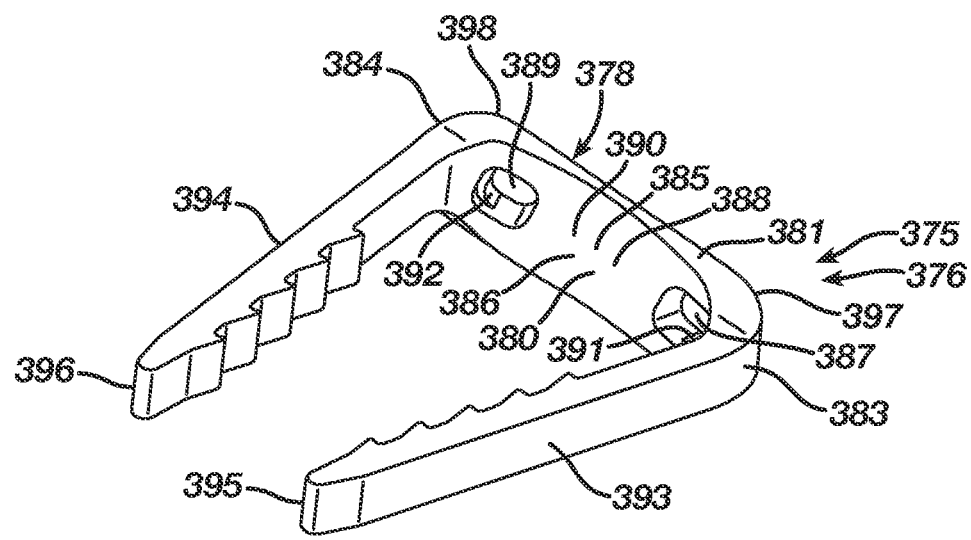
FIG. 16B is a bottom isometric view thereof.
Figure 16C:
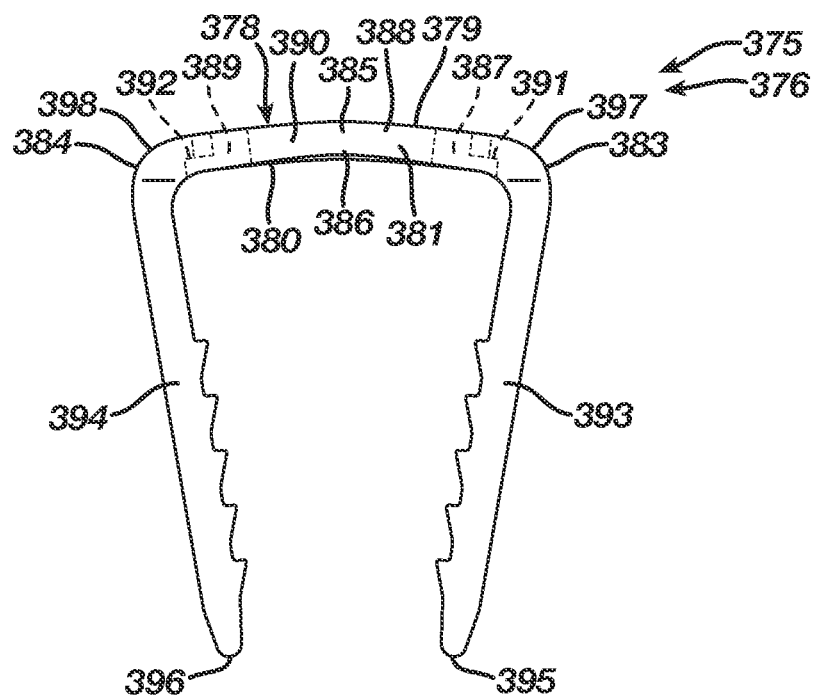
FIG. 16C is a side view thereof.
Figure 16D:
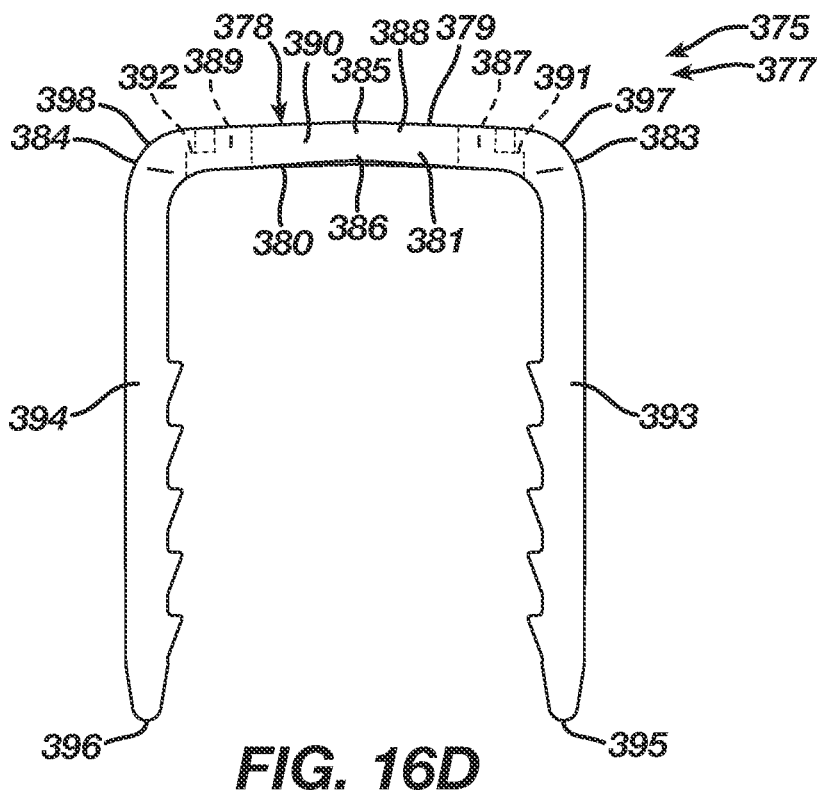
FIG. 16D is a side view illustrating the shape memory implant according to the fourth embodiment in an insertion shape.

FIGS. 16A-16C illustrate an orthopedic implant 375 according to a fourth embodiment in a natural shape 376, whereas FIG. 16D illustrates the orthopedic implant 375 in an insertion shape 377. The implant 375 in the fourth embodiment may be manufactured from a shape memory material with superelastic or temperature dependent properties (e.g., Nitinol) such that the implant 375 transitions between its natural shape 376 and its insertion shape 377. The implant 375 when deformed from its natural shape 376 to its insertion shape 377 stores energy deliverable to bone, bones, or bone pieces. In accordance with its manufacture from shape memory material, the implant 375 begins in its natural shape 376, is transitionable to its insertion shape 377, and, once implanted in bone, bones, or bone pieces, attempts to transition from its insertion shape 377 to its natural shape 376 whereby the implant 375 delivers the energy stored therein to the bone, bones, or bone pieces in order to affix the bone, bones, or bone pieces and promote a healing thereof. In the fourth embodiment, attempted transition of the implant 375 from its insertion shape 377 to its natural shape 376 continuously compresses the bone, bones, or bone pieces to promote fusion thereof.

The implant 375 includes a bridge 378 with upper and lower surfaces 379 and 380, first and second sides 381 and 382, and first and second ends 383 and 384. The implant 375 includes a transition section 385 located at a center section 386 of the implant 375 and thus the bridge 378. The implant 375 in the fourth embodiment includes an anchoring member in the form of a leg 393 extending from the first end 383 of the implant 375 and thus the bridge 378 in order to provide the implant 375 and thus the bridge 378 with an anchoring segment 397. Likewise, the implant 375 includes an anchoring member in the form of a leg 394 extending from the second end 384 of the implant 375 and thus the bridge 378 in order to provide the implant 375 and thus the bridge 378 with an anchoring segment 398. In the fourth embodiment, the legs 393 and 394 are formed integrally with the implant 375 and thus the bridge 378 at respective first and second ends 383 and 384. Each leg 393 and 394, which has a respective tip 395 and 396, may include barbs thereon that improve the pull-out resistance of the implant 375. The implant 375 includes anchoring members in the form of the legs 393 and 394 in order to facilitate a securing of the implant 375 with bone, bones, or bone pieces whereby the bridge 378 between the legs 393 and 394 traverses a fixation zone of the bone, bones, or bone pieces such that the implant 375, after its insertion and attempted transition from the insertion shape 377 to the natural shape 376, delivers energy to the bone, bones, or bone pieces at the fixation zone.

The implant 375, and thus the bridge 378, includes a first aperture 387 extending therethrough from the upper surface 379 to the lower surface 380 whereby the first aperture 387 is located adjacent the transition section 385 at a first side 388 thereof. The implant 375, and thus the bridge 378, includes a catch 391 protruding into the first aperture 387. Similarly, the implant 375, and thus the bridge 378, includes a second aperture 389 extending therethrough from the upper surface 379 to the lower surface 380 whereby the second aperture 389 is located adjacent the transition section 385 at a second side 390 thereof. The implant 375, and thus the bridge 378, includes a catch 392 protruding into the second aperture 389. The first aperture 387 and its catch 391 and the second aperture 389 and its catch 392 provide engagement points for the implant retainer 5 with the implant 375. As such, the first and second apertures 387 and 389 are spaced apart across the transition section 385 a distance that allows receipt therein, respectively, of the fasteners 29 and 45 when the fasteners 29 and 45 reside at their first distance. When the fasteners 29 and 45 reside at their second distance, the fasteners 29 and 45, respectively, engage the catches 391 and 392 thereby securing the implant retainer 5 with the implant 375. The implant retainer 5 and its fasteners 29 and 45 and the first and second apertures 387 and 389 are correspondingly designed with respect to their size, location, and distances to interact and engage such that the implant retainer 5 optimally constrains the implant 375 in its insertion shape 377.

The regular inherent shape of the implant 375, as illustrated in FIGS. 16A-16C, is its natural shape 376 where the transition section 385 locates the bridge 378 in a natural form consisting of a closed or angular profile whereby the first and second ends 383 and 384 reside at a first distance and places the legs 393 and 394 in a natural position whereby the legs 393 and 394 are convergent and spaced apart at a first distance. Nevertheless, as illustrated in FIG. 16D, the implant 375 is deformable under the action of superelasticity or temperature dependent shape memory to its insertion shape 377 where the transition section 385 deforms to store energy while also moving the bridge 378 from its natural form to an insertion form which is an open or substantially linear profile whereby the first and second ends 383 and 384 reside at a second distance that is greater than the first distance and placing the legs 393 and 394 in an insertion position whereby the legs 393 and 394 are substantially parallel and spaced apart at a second distance that is greater than the first distance. Since the insertion shape 377 is not the regular inherent shape of the implant 375, the bridge 378 typically is mechanically constrained using the implant retainer 5 whereby the implant retainer 5 maintains the bridge 378 in its insertion form. In particular, the implant retainer 5 inserts into the first and second apertures 387 and 389 and engages the catches 391 and 392 such that the implant retainer 5 holds the bridge 378, resulting in the implant retainer 5 constraining the deformed transition section 385 in order to maintain the implant 375 in its insertion shape 377. After implantation into bone, bones, or bone pieces and a release of the implant retainer 5, including if necessary a heating of the implant 375, the implant 375 delivers the energy stored in the transition section 385 whereby the bridge 378 attempts to transition from its insertion form to its natural form such that the implant 375 affixes the bone, bones, or bone pieces through an application of a compressive force thereto. While the implant 375 includes the first and second apertures 387 and 389 and the catches 391 and 392, the implant 375 may include four apertures and respective catches that provide additional engagement points for a more secure engagement of the implant 375 with an implant retainer including four fasteners.

Figure 17C:
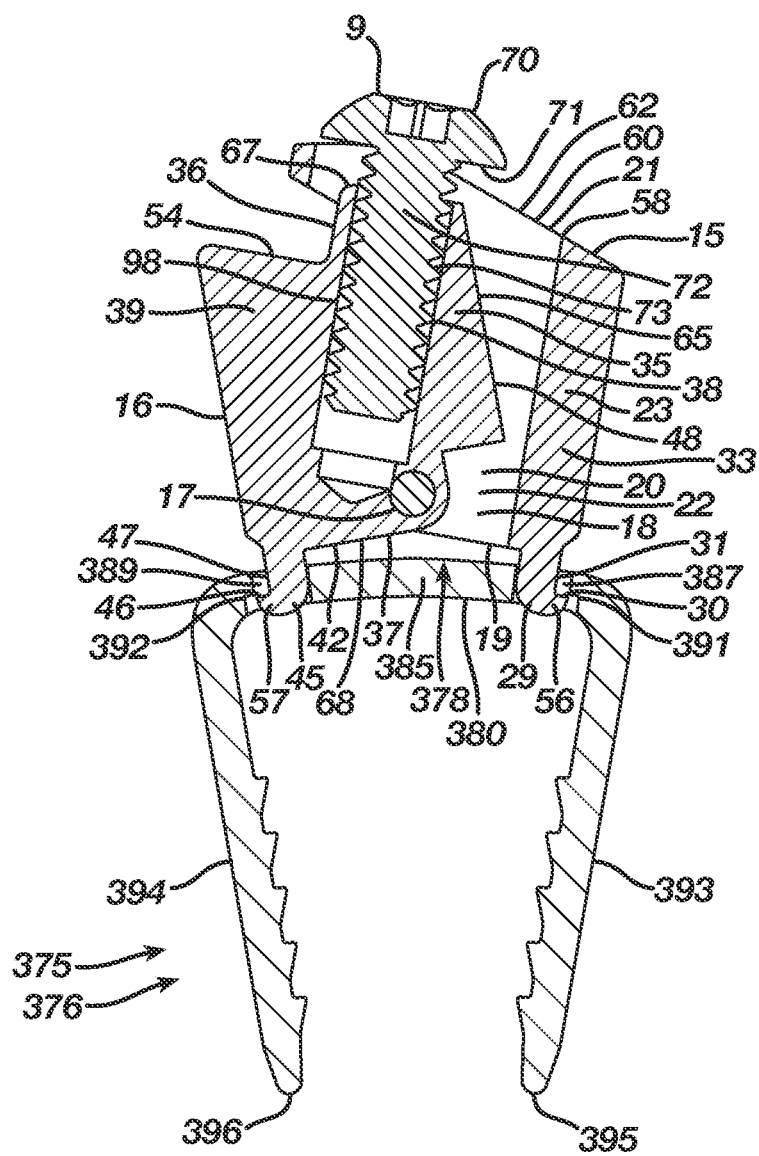
FIG. 17C is a side view in cross-section thereof.

When receiving the implant 375 in an orthopedic fixation system, the implant retainer 5 as illustrated in FIGS. 17A-17C begins in its unloaded position 6 wherein the implant grip 8 resides in its disengaged position 10 such that the fasteners 29 and 45 are in their unclasped position spaced apart at the first distance. In particular, after the implant retainer 5 is positioned adjacent the implant 375 at the upper surface 379 thereof, the fastener 29 of the frame 15 and the fastener 45 of the body 16, due to their unclasped position residing at the first distance, insert respectively into the first and second apertures 387 and 389 of the implant 375, whereby the cutouts 31 and 47 respectively are adjacent the first and second catches 391 and 392 while the detents 30 and 46 are positioned underneath the first and second catches 391 and 392 but separated therefrom. The fasteners 29 and 45 respectively extend below the end wall 23 of the wall 18 for the frame 15 and the wall 39 for the body 16 a length that permits their respective insertions into the first and second apertures 387 and 389 such that their detents 30 and 46 are located respectively below the first and second catches 391 and 392. Nevertheless, the lengths of the fasteners 29 and 45 are equal to or less than the thickness of the implant 375 between its upper and lower surfaces 379 and 380 whereby the fasteners 29 and 45 do not extend respectively from the first and second apertures 387 and 389 below the lower surface 380 of the implant 375 in order to ensure the implant 375 sits flush atop bone, bones, or bone pieces. Rotation of the head 70 for the actuator 9 in the first direction and the subsequent traversing of the head 70 along the bearing surface 60 from its unlocking position to its locking position progresses the fasteners 29 and 45 to their clasped position at the second distance such that the fasteners 29 and 45 respectively abut the first and second catches 391 and 392 at undersides thereof. As a result, the implant retainer 5, now in its loaded position 7 with the actuator 9 in its locking position holding the implant grip 8 in its engaged position 11 as illustrated in FIG. 18A-18C, has moved the implant 375, if necessary, to its insertion shape 377 and constrains the implant 375 in its insertion shape 377 via engagement of the implant retainer 5 with the implant 375 at the fasteners 29 and 45 and the bottoms 59 and 68 of the frame 15 and body 16 at the upper surface 379 of the implant 375.

Figure 18A:
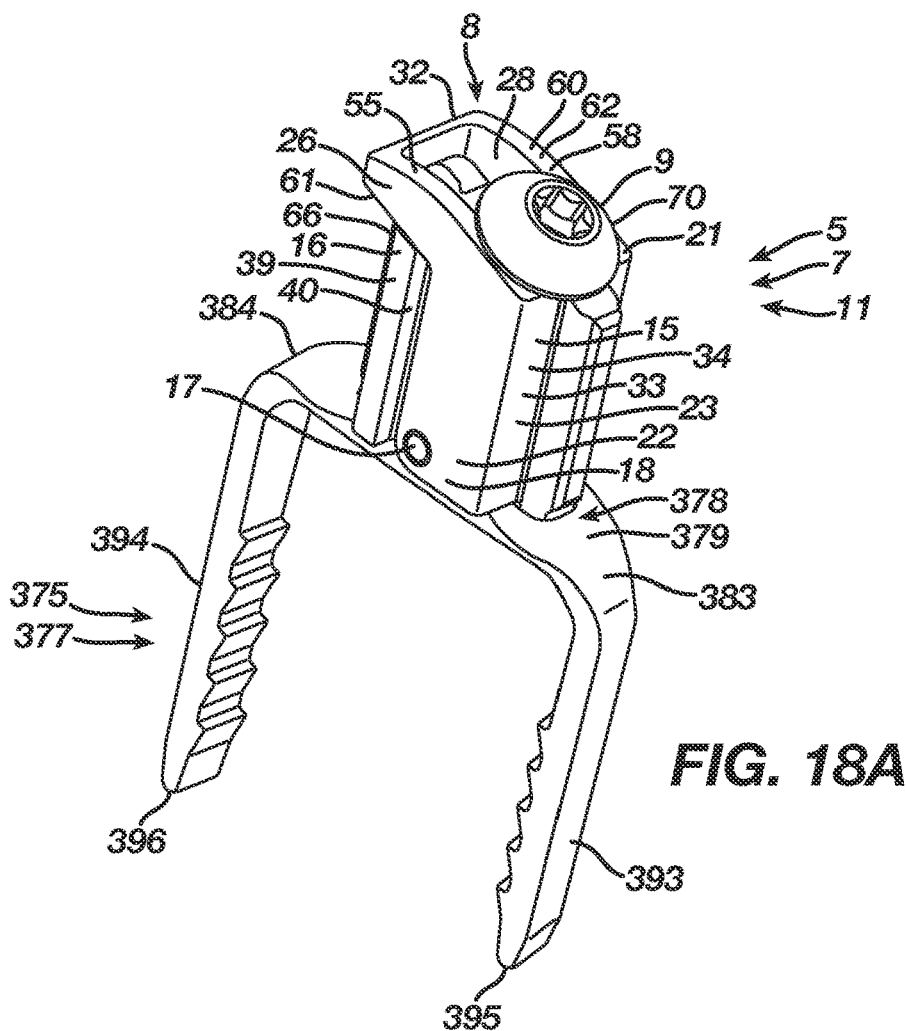
FIG. 18A is a top isometric view illustrating the implant retainer according to the first embodiment in a loaded position constraining the shape memory implant according to the fourth embodiment in its insertion shape.
Figure 18B:
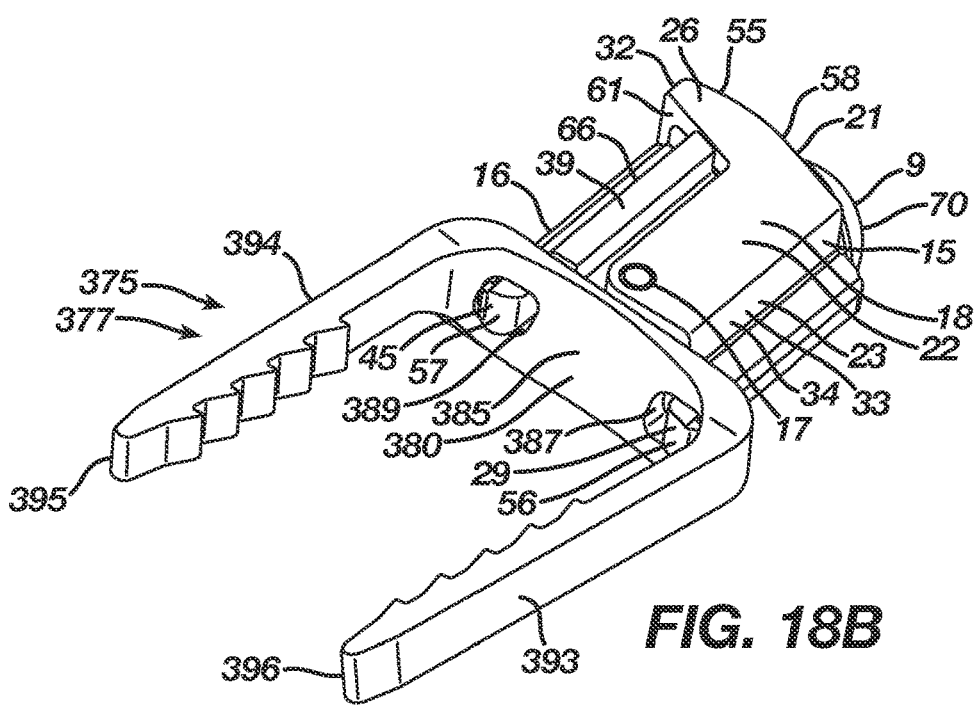
FIG. 18B is a bottom isometric view thereof.
Figure 18C:
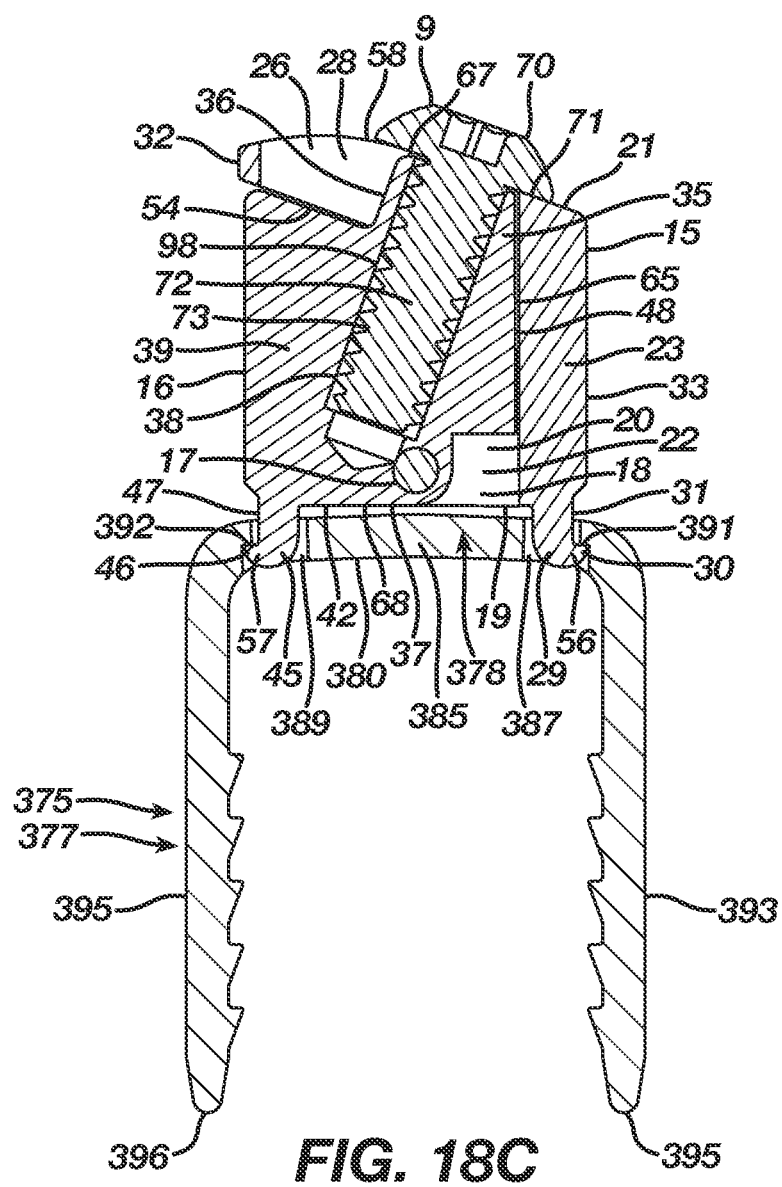
FIG. 18C is a side view in cross-section thereof.

When delivering the implant 375 to bone, bones, or bone pieces, the implant retainer 5 as illustrated in FIGS. 18A-18C begins in its loaded position 7 wherein the implant grip 8 in its engaged position 11 constrains the implant 375 in its insertion shape 377. Rotation of the head 70 for the actuator 9 in the second direction and the subsequent traversing of the head 70 along the bearing surface 60 from its locking position to its unlocking position progresses the fasteners 29 and 45 to their unclasped position at the first distance such that the fasteners 29 and 45 and thus the detents 30 and 46 respectively move away from and thus release the first and second catches 391 and 392 at undersides thereof. As a result, the implant retainer 5, now in its unloaded position 6 with the actuator 9 in its unlocking position holding the implant grip 8 in its disengaged position 10 as illustrated in FIGS. 17A-17C, removes from atop the upper surface 379 of the implant 375 while the fasteners 29 and 45 respectively discharge from the first and second apertures 387 and 389 such that the released implant 375 attempts transition from its insertion shape 377 to its natural shape 376 whereby the implant 375 delivers the energy stored therein to the bone, bones, or bone pieces.

Figure 19A:
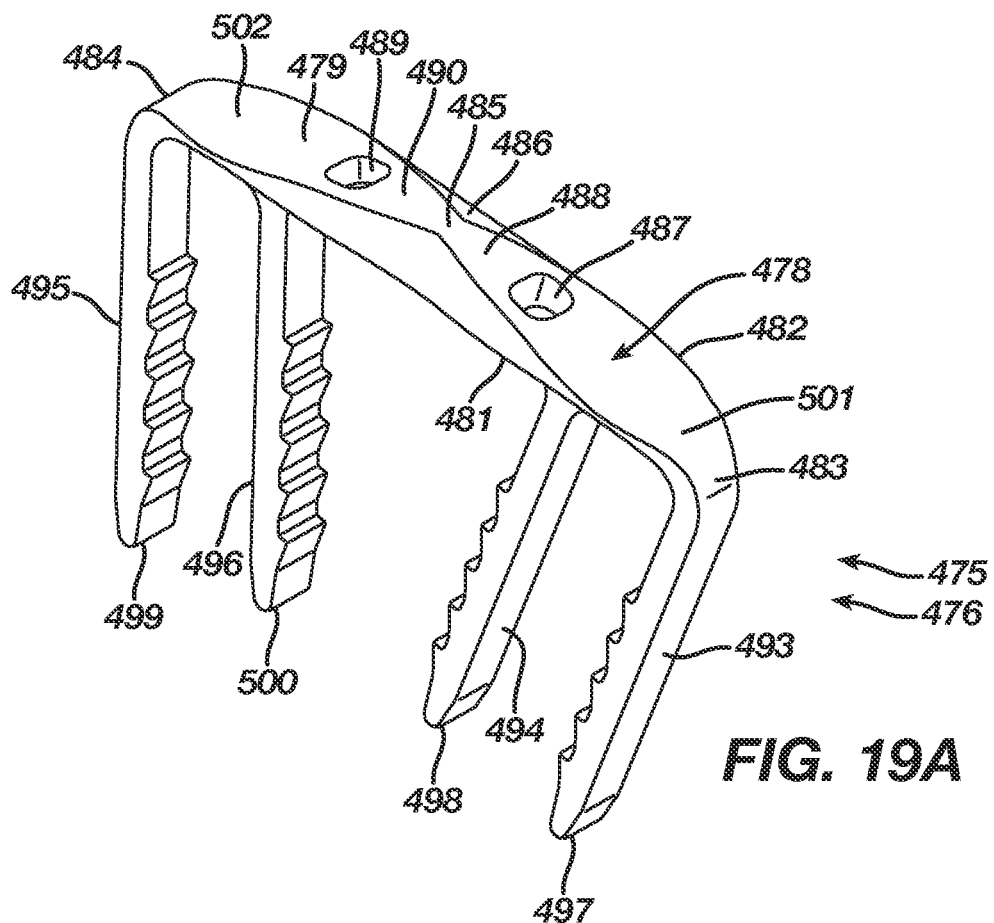
FIG. 19A is a top isometric view illustrating a shape memory implant according to a fifth embodiment in a natural shape.
Figure 19B:
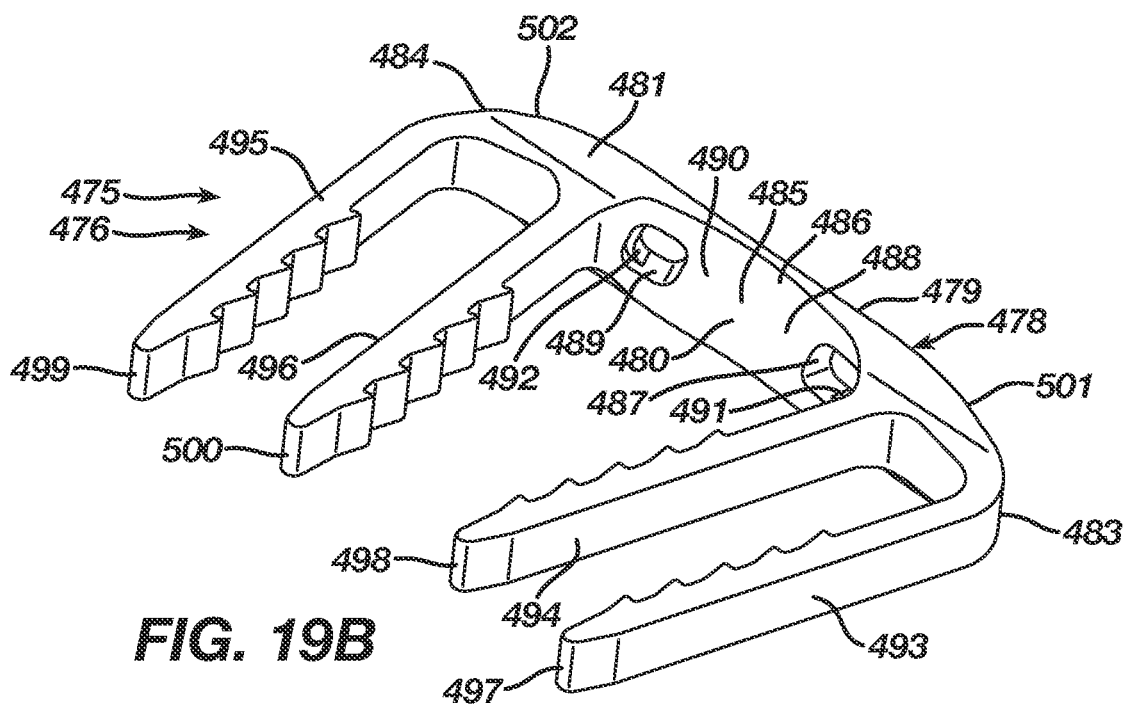
FIG. 19B is a bottom isometric view thereof.
Figure 19C:
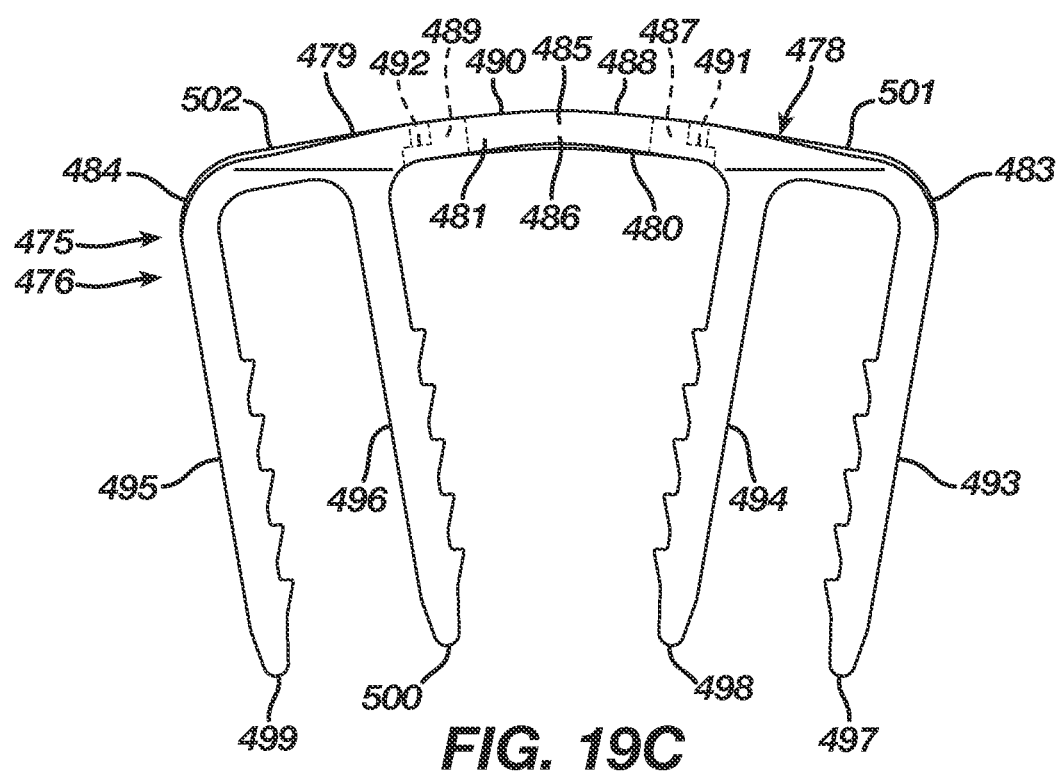
FIG. 19C is a side view thereof.
Figure 19D:
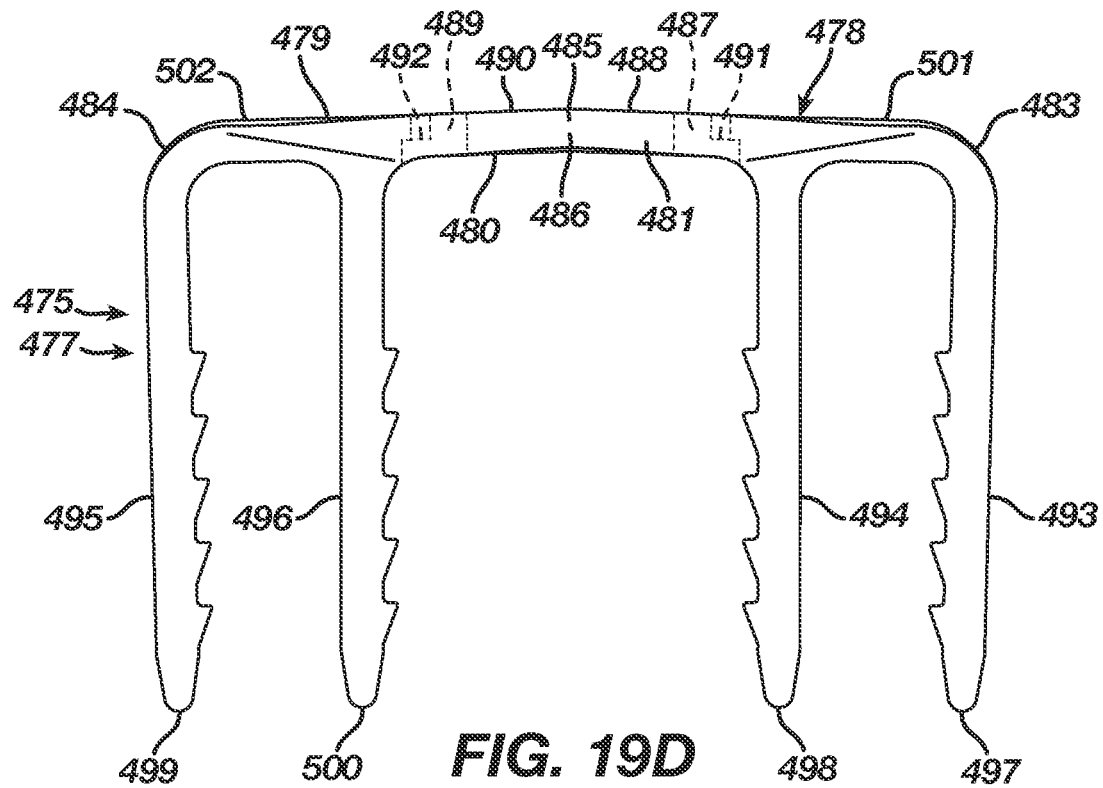
FIG. 19D is a side view illustrating the shape memory implant according to the fifth embodiment in an insertion shape.

FIGS. 19A-19C illustrate an orthopedic implant 475 according to a fifth embodiment in a natural shape 476, whereas FIG. 19D illustrates the orthopedic implant 475 in an insertion shape 477. The implant 475 in the fifth embodiment may be manufactured from a shape memory material with superelastic or temperature dependent properties (e.g., Nitinol) such that the implant 475 transitions between its natural shape 476 and its insertion shape 477. The implant 475 when deformed from its natural shape 476 to its insertion shape 477 stores energy deliverable to bone, bones, or bone pieces. In accordance with its manufacture from shape memory material, the implant 475 begins in its natural shape 476, is transitionable to its insertion shape 477, and, once implanted in bone, bones, or bone pieces, attempts to transition from its insertion shape 477 to its natural shape 476 whereby the implant 475 delivers the energy stored therein to the bone, bones, or bone pieces in order to affix the bone, bones, or bone pieces and promote a healing thereof. In the fifth embodiment, attempted transition of the implant 475 from its insertion shape 477 to its natural shape 476 continuously compresses the bone, bones, or bone pieces to promote fusion thereof.

The implant 475 includes a bridge 478 with upper and lower surfaces 479 and 480, first and second sides 481 and 482, and first and second ends 483 and 484. The implant 475 includes a transition section 485 located at a center section 486 of the implant 475 and thus the bridge 478. The implant 475 in the fifth embodiment includes anchoring members in the form of a leg 493 extending from the first end 483 of the implant 475 and thus the bridge 478 and a leg 494 extending from the implant 475 and thus the bridge 478 between the center section 486 and the first end 483 in order to provide the implant 475 and thus the bridge 478 with an anchoring segment 501. Likewise, the implant 475 includes an anchoring member in the form of a leg 495 extending from the second end 484 of the implant 475 and thus the bridge 478 and a leg 496 extending from the implant 475 and thus the bridge 478 between the center section 486 and the second end 484 in order to provide the implant 475 and thus the bridge 478 with an anchoring segment 502. In the fifth embodiment, the legs 493 and 495 are formed integrally with the implant 475 and thus the bridge 478 at respective first and second ends 483 and 484, while the legs 494 and 496 are formed integrally with the implant 475 and thus the bridge 478 between respective first and second ends 483 and 484 and the center section 486. Each leg 493-496, which has a respective tip 497-500, may include barbs thereon that improve the pull-out resistance of the implant 475. The implant 475 includes anchoring members in the form of the legs 493-496 in order to facilitate a securing of the implant 475 with bone, bones, or bone pieces whereby the bridge 478 between the legs 498 and 500 traverses a fixation zone of the bone, bones, or bone pieces such that the implant 475, after its insertion and attempted transition from the insertion shape 477 to the natural shape 476, delivers energy to the bone, bones, or bone pieces at the fixation zone.

The implant 475, and thus the bridge 478, includes a first aperture 487 extending therethrough from the upper surface 479 to the lower surface 480 whereby the first aperture 487 is located adjacent the transition section 485 at a first side 488 thereof. The implant 475, and thus the bridge 478, includes a catch 491 protruding into the first aperture 487. Similarly, the implant 475, and thus the bridge 478, includes a second aperture 489 extending therethrough from the upper surface 479 to the lower surface 480 whereby the second aperture 489 is located adjacent the transition section 485 at a second side 490 thereof. The implant 475, and thus the bridge 378, includes a catch 492 protruding into the second aperture 489. The first aperture 487 and its catch 491 and the second aperture 489 and its catch 492 provide engagement points for the implant retainer 5 with the implant 475. As such, the first and second apertures 487 and 489 are spaced apart across the transition section 485 a distance that allows receipt therein, respectively, of the fasteners 29 and 45 when the fasteners 29 and 45 reside at their first distance. When the fasteners 29 and 45 reside at their second distance, the fasteners 29 and 45, respectively, engage the catches 491 and 492 thereby securing the implant retainer 5 with the implant 475. The implant retainer 5 and its fasteners 29 and 45 and the first and second apertures 487 and 489 are correspondingly designed with respect to their size, location, and distances to interact and engage such that the implant retainer 5 optimally constrains the implant 475 in its insertion shape 477.

The regular inherent shape of the implant 475, as illustrated in FIGS. 19A-19C, is its natural shape 476 where the transition section 485 locates the bridge 478 in a natural form consisting of a closed or angular profile whereby the first and second ends 483 and 484 reside at a first distance and places the legs 493-494 and the legs 495-496 in a natural position whereby the legs 493-494 are convergent with the legs 495-496 and spaced apart therefrom at a first distance. Nevertheless, as illustrated in FIG. 19D, the implant 475 is deformable under the action of superelasticity or temperature dependent shape memory to its insertion shape 477 where the transition section 485 deforms to store energy while also moving the bridge 478 from its natural form to an insertion form which is an open or substantially linear profile whereby the first and second ends 483 and 484 reside at a second distance that is greater than the first distance and placing the legs 493-494 and the legs 495-496 in an insertion position whereby legs 493-494 are substantially parallel with the legs 495-496 and spaced apart therefrom at a second distance that is greater than the first distance. Since the insertion shape 477 is not the regular inherent shape of the implant 475, the bridge 478 typically is mechanically constrained using the implant retainer 5 whereby the implant retainer 5 maintains the bridge 478 in its insertion form. In particular, the implant retainer 5 inserts into the first and second apertures 487 and 489 and engages the catches 491 and 492 such that the implant retainer 5 holds the bridge 478, resulting in the implant retainer 5 constraining the deformed transition section 485 in order to maintain the implant 475 in its insertion shape 477. After implantation into bone, bones, or bone pieces and a release of the implant retainer 5, including if necessary a heating of the implant 475, the implant 475 delivers the energy stored in the transition section 485 whereby the bridge 478 attempts to transition from its insertion form to its natural form such that the implant 475 affixes the bone, bones, or bone pieces through an application of a compressive force thereto. While the implant 475 includes the first and second apertures 487 and 489 and the catches 491 and 492, the implant 475 may include four apertures and respective catches that provide additional engagement points for a more secure engagement of the implant 475 with an implant retainer including four fasteners.

Figure 20A:
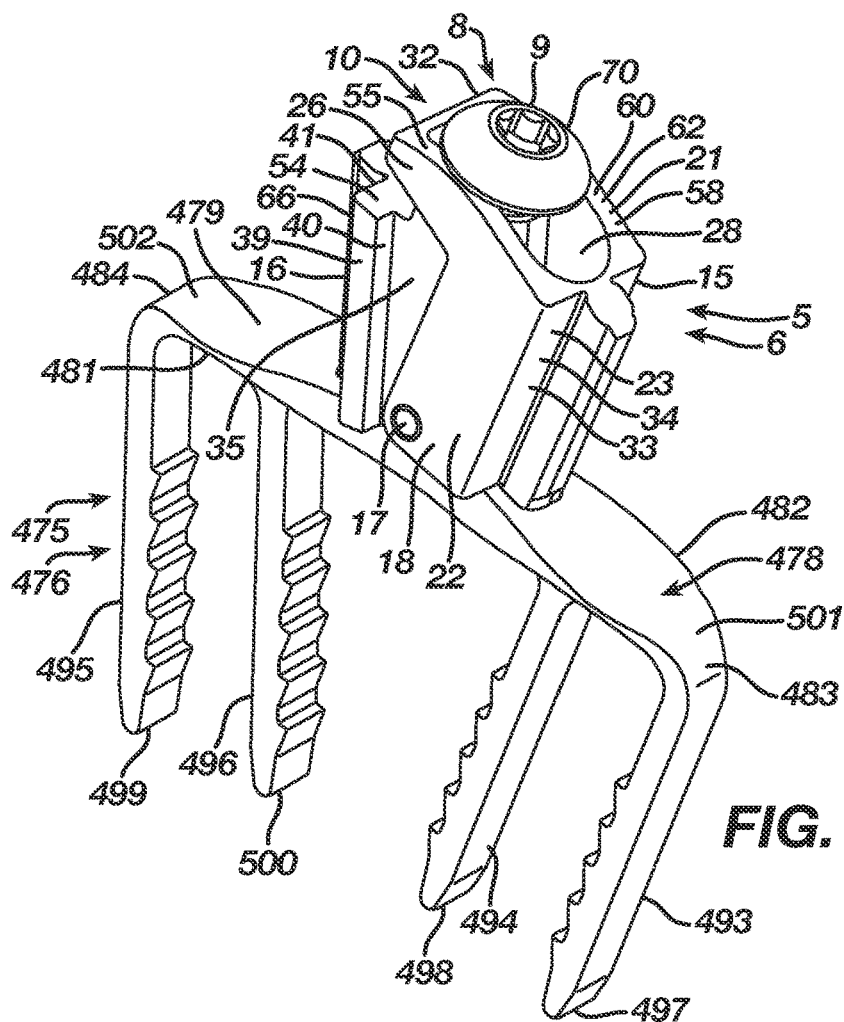
FIG. 20A is a top isometric view illustrating the implant retainer according to the first embodiment in an unloaded position relative to the shape memory implant according to the fifth embodiment in its natural shape.
Figure 20B:
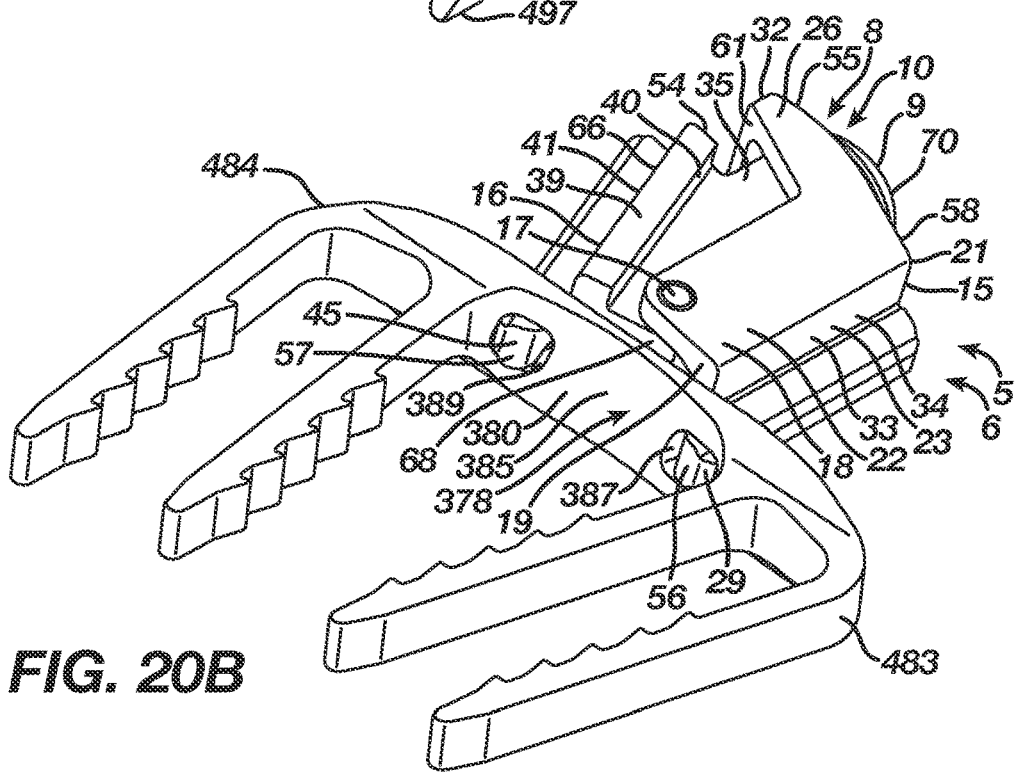
FIG. 20B is a bottom isometric view thereof.
Figure 20C:
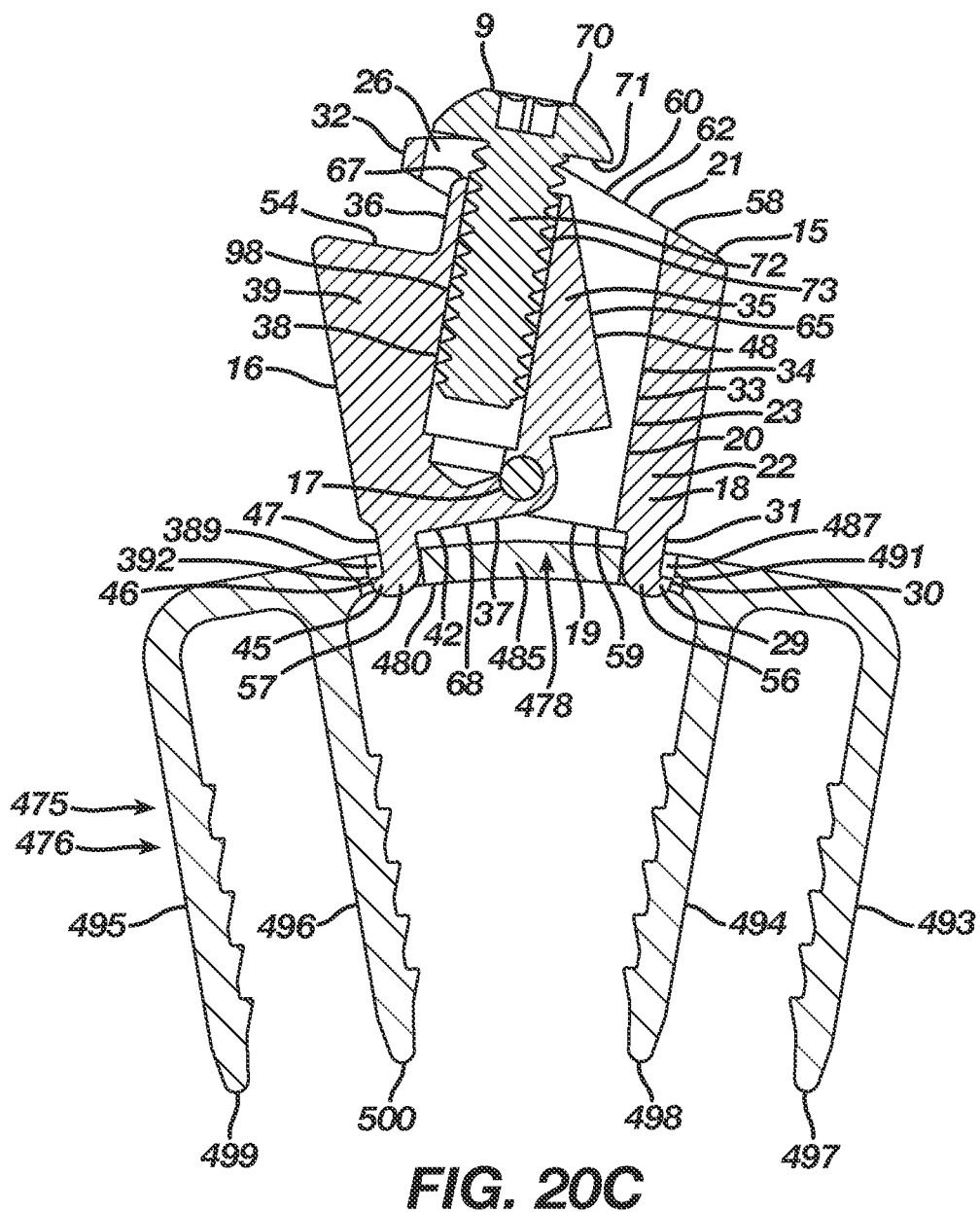
FIG. 20C is a side view in cross-section thereof.

When receiving the implant 475 in an orthopedic fixation system, the implant retainer 5 as illustrated in FIGS. 20A-20C begins in its unloaded position 6 wherein the implant grip 8 resides in its disengaged position 10 such that the fasteners 29 and 45 are in their unclasped position spaced apart at the first distance. In particular, after the implant retainer 5 is positioned adjacent the implant 475 at the upper surface 479 thereof, the fastener 29 of the frame 15 and the fastener 45 of the body 16, due to their unclasped position residing at the first distance, insert respectively into the first and second apertures 487 and 489 of the implant 475, whereby the cutouts 31 and 47 respectively are adjacent the first and second catches 491 and 492 while the detents 30 and 46 are positioned underneath the first and second catches 491 and 492 but separated therefrom. The fasteners 29 and 45 respectively extend below the end wall 23 of the wall 18 for the frame 15 and the wall 39 for the body 16 a length that permits their respective insertions into the first and second apertures 487 and 489 such that their detents 30 and 46 are located respectively below the first and second catches 491 and 492. Nevertheless, the lengths of the fasteners 29 and 45 are equal to or less than the thickness of the implant 475 between its upper and lower surfaces 479 and 480 whereby the fasteners 29 and 45 do not extend respectively from the first and second apertures 487 and 489 below the lower surface 480 of the implant 475 in order to ensure the implant 475 sits flush atop bone, bones, or bone pieces. Rotation of the head 70 for the actuator 9 in the first direction and the subsequent traversing of the head 70 along the bearing surface 60 from its unlocking position to its locking position progresses the fasteners 29 and 45 to their clasped position at the second distance such that the fasteners 29 and 45 respectively via the detents 30 and 46 abut the first and second catches 491 and 492 at undersides thereof. As a result, the implant retainer 5, now in its loaded position 7 with the actuator 9 in its locking position holding the implant grip 8 in its engaged position 11 as illustrated in FIG. 21A-21C, has moved the implant 475, if necessary, to its insertion shape 477 and constrains the implant 475 in its insertion shape 477 via engagement of the implant retainer 5 with the implant 475 at the fasteners 29 and 45 and the bottoms 59 and 68 of the frame 15 and body 16 at the upper surface 479 of the implant 475.

Figure 21A:
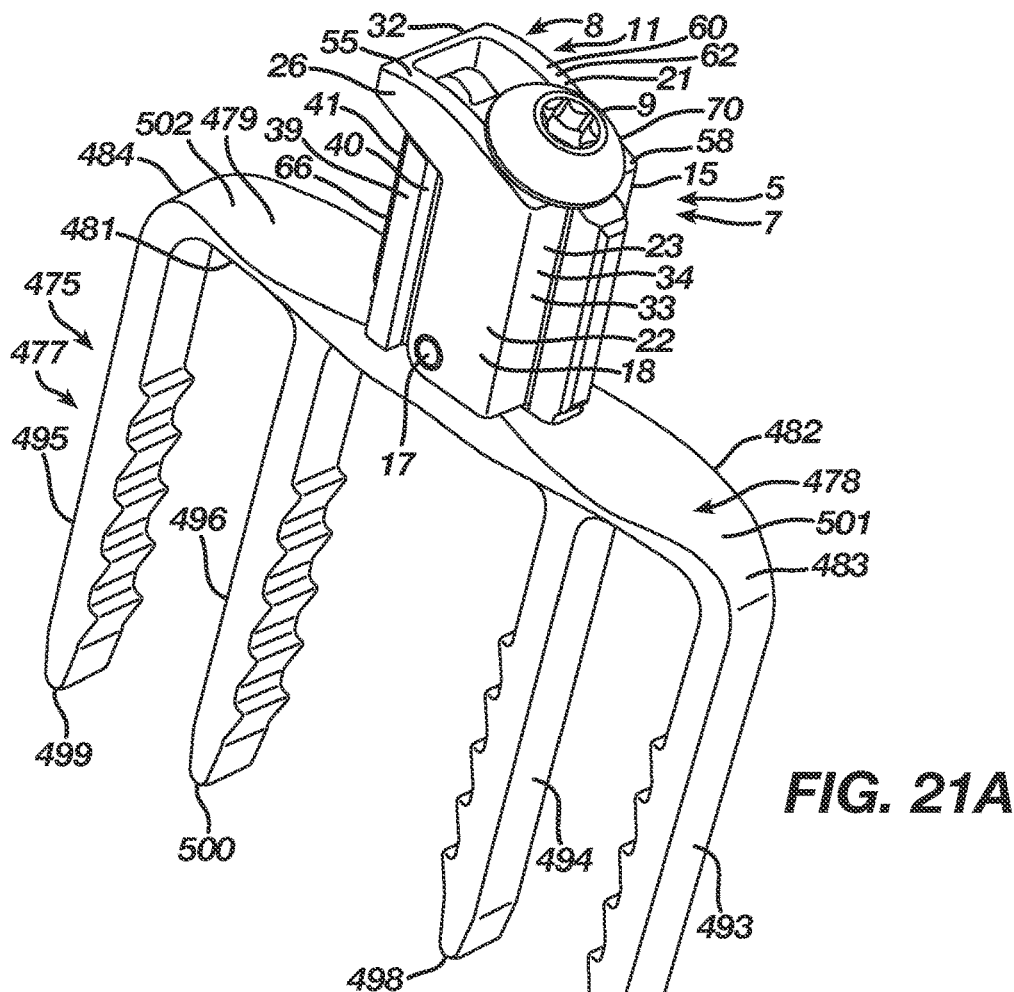
FIG. 21A is a top isometric view illustrating the implant retainer according to the first embodiment in a loaded position constraining the shape memory implant according to the fifth embodiment in its insertion shape.
Figure 21B:
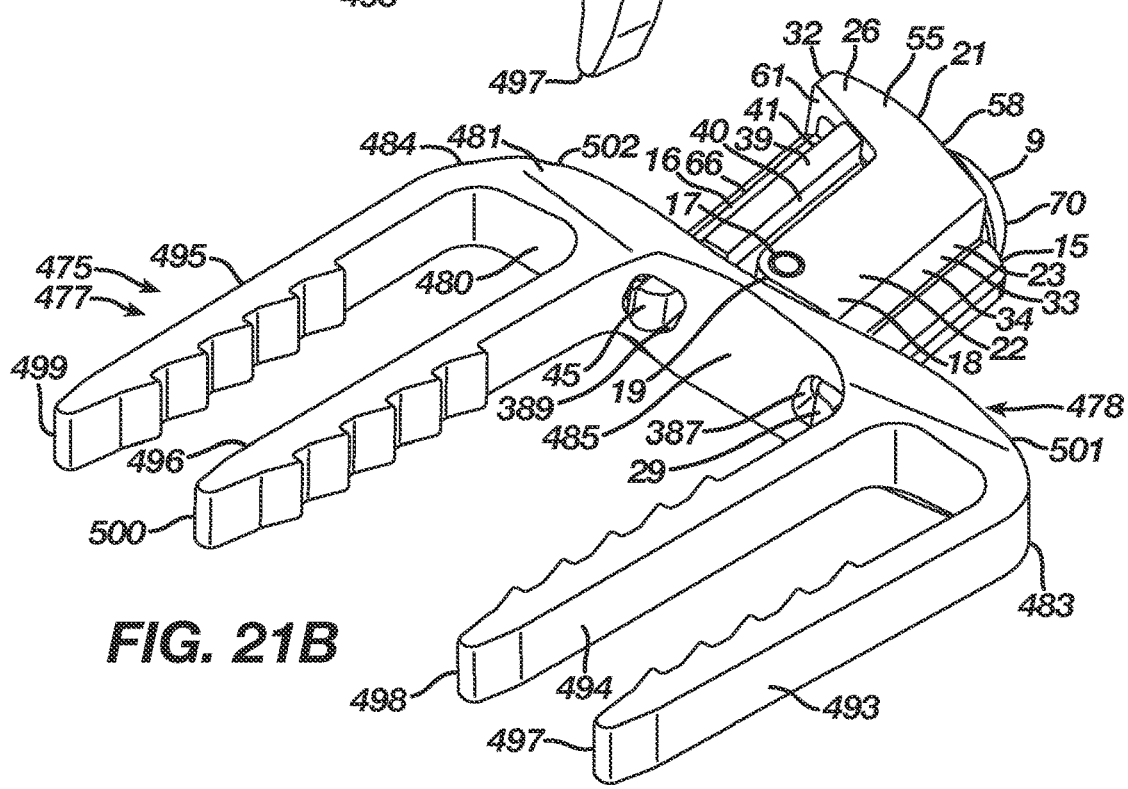
FIG. 21B is a bottom isometric view thereof.
Figure 21C:
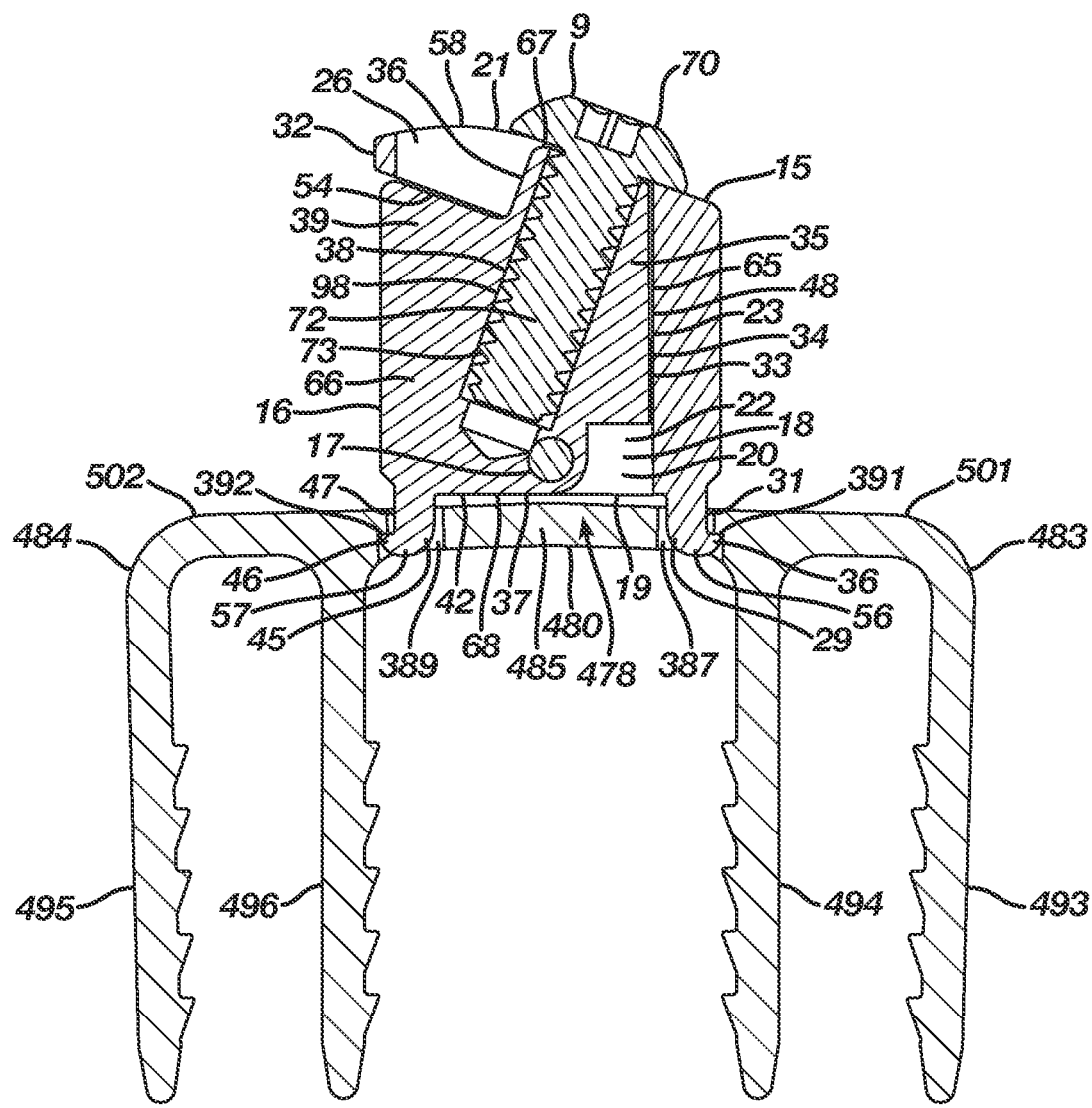
FIG. 21C is a side view in cross-section thereof.

When delivering the implant 475 to bone, bones, or bone pieces, the implant retainer 5 as illustrated in FIGS. 21A-21C begins in its loaded position 7 wherein the implant grip 8 in its engaged position 11 constrains the implant 475 in its insertion shape 477. Rotation of the head 70 for the actuator 9 in the second direction and the subsequent traversing of the head 70 along the bearing surface 60 from its locking position to its unlocking position progresses the fasteners 29 and 45 to their unclasped position at the first distance such that the fasteners 29 and 45 and thus the detents 30 and 46 respectively move away from and thus release the first and second catches 491 and 492 at undersides thereof. As a result, the implant retainer 5, now in its unloaded position 6 with the actuator 9 in its unlocking position holding the implant grip 8 in its disengaged position 10 as illustrated in FIGS. 20A-20C, removes from atop the upper surface 479 of the implant 475 while the fasteners 29 and 45 respectively discharge from the first and second apertures 487 and 489 such that the released implant 475 attempts transition from its insertion shape 477 to its natural shape 476 whereby the implant 475 delivers the energy stored therein to the bone, bones, or bone pieces.

Figure 22A:
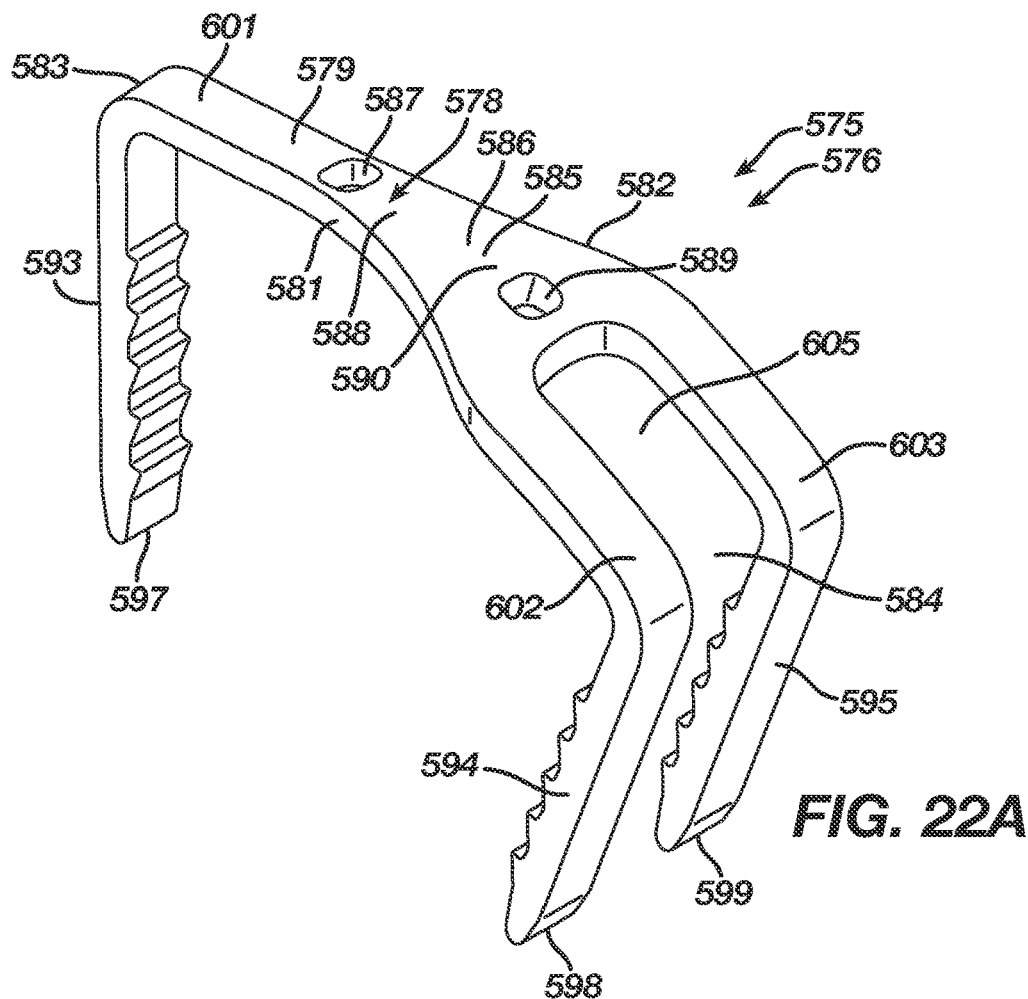
FIG. 22A is a top isometric view illustrating a shape memory implant according to a sixth embodiment in a natural shape.
Figure 22B:
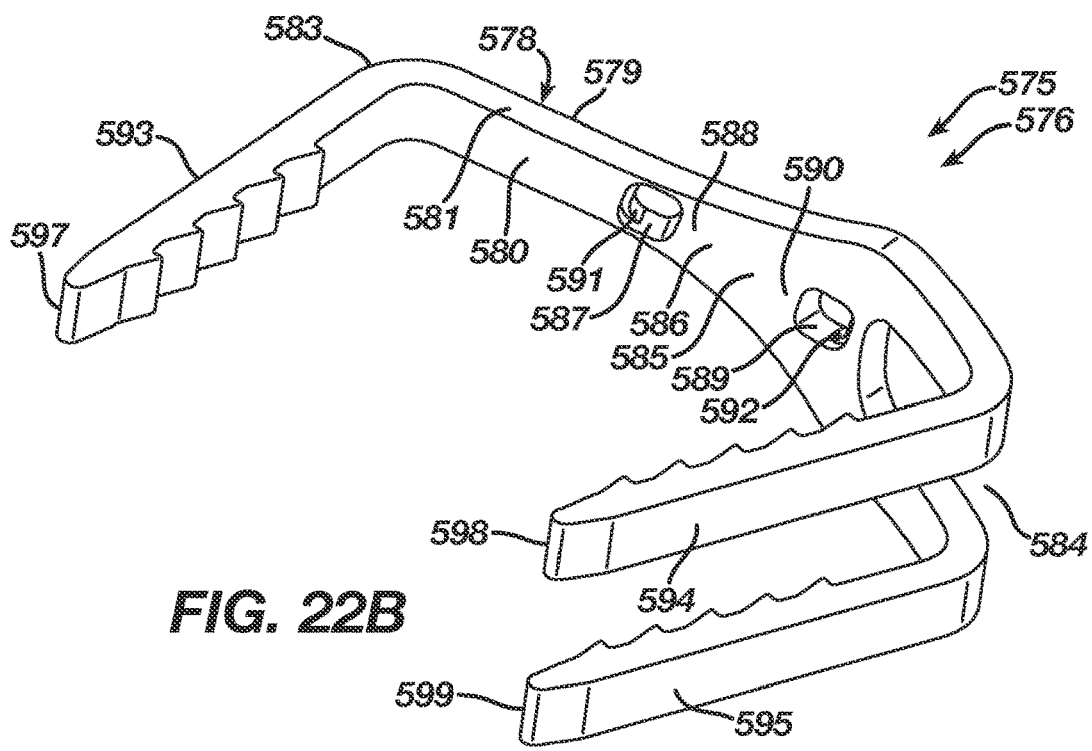
FIG. 22B is a bottom isometric view thereof.
Figure 22C:
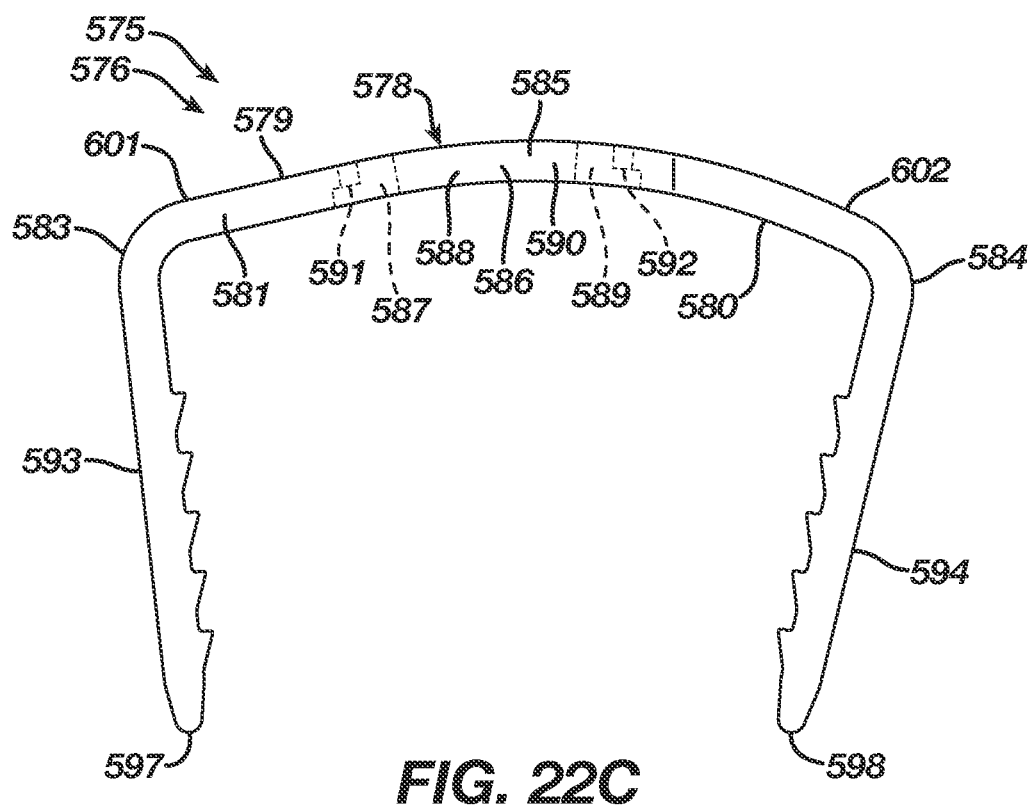
FIG. 22C is a side view thereof.
Figure 22D:
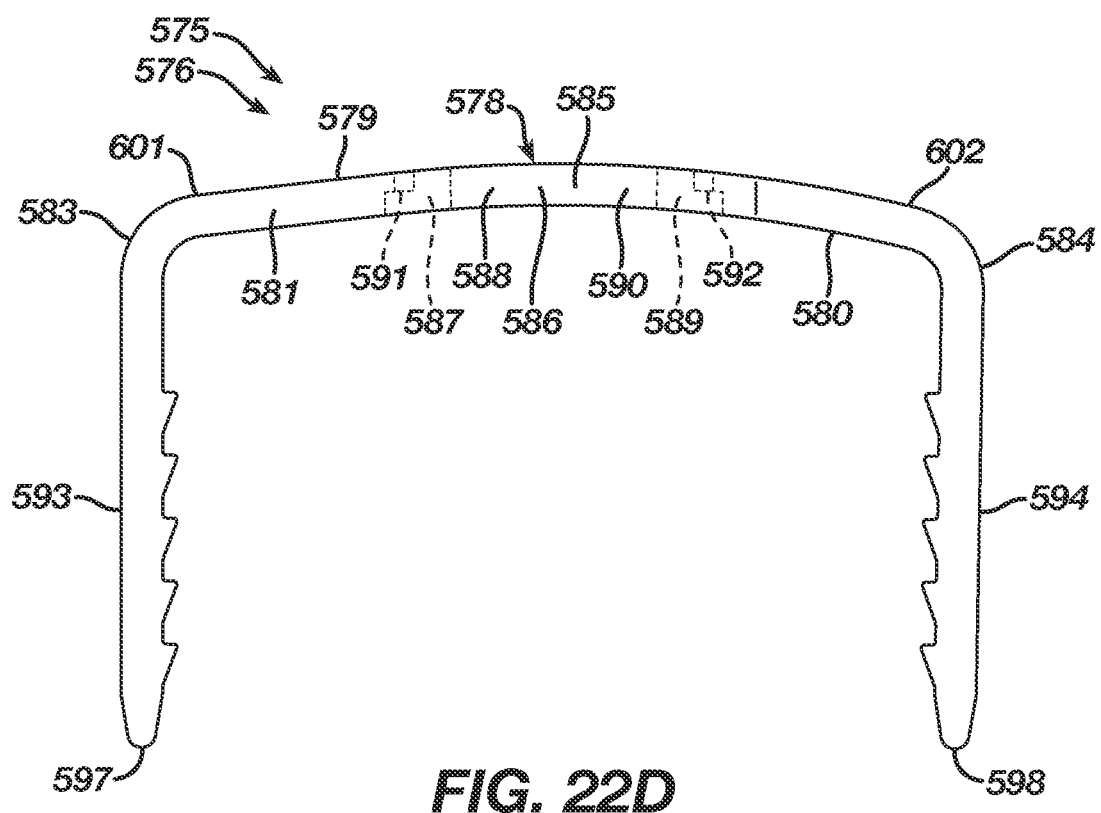
FIG. 22D is a side view illustrating the shape memory implant according to the sixth embodiment in an insertion shape.

FIGS. 22A-22C illustrate an orthopedic implant 575 according to a sixth embodiment in a natural shape 576, whereas FIG. 22D illustrates the orthopedic implant 575 in an insertion shape 577. The implant 575 in the sixth embodiment may be manufactured from a shape memory material with superelastic or temperature dependent properties (e.g., Nitinol) such that the implant 575 transitions between its natural shape 576 and its insertion shape 577. The implant 575 when deformed from its natural shape 576 to its insertion shape 577 stores energy deliverable to bone, bones, or bone pieces. In accordance with its manufacture from shape memory material, the implant 575 begins in its natural shape 576, is transitionable to its insertion shape 577, and, once implanted in bone, bones, or bone pieces, attempts to transition from its insertion shape 577 to its natural shape 576 whereby the implant 575 delivers the energy stored therein to the bone, bones, or bone pieces in order to affix the bone, bones, or bone pieces and promote a healing thereof. In the sixth embodiment, attempted transition of the implant 575 from its insertion shape 577 to its natural shape 576 continuously compresses the bone, bones, or bone pieces to promote fusion thereof.

The implant 575 includes a bridge 578 with upper and lower surfaces 579 and 580, first and second sides 581 and 582, and first and second ends 583 and 584. The implant 575 includes a transition section 585 located adjacent a center section 586 of the implant 575 and thus the bridge 578 between the center section 586 and the second end 584. The implant 575 in the sixth embodiment includes an anchoring member in the form of a first leg 593 extending from the first end 583 of the implant 575 and thus the bridge 578 in order to provide the implant 575 and thus the bridge 578 with a first anchoring segment 601 incorporating the first leg 593. The implant 575 includes anchoring members in the form of second and third legs 594 and 595 extending from the second end 584 of the implant 575 and thus the bridge 578 whereby the second and third legs 594 and 595 are aligned and located adjacent the second end 584 of the bridge 578. In the sixth embodiment, the implant 575, and thus the bridge 578, at the second end 584 divides via a cut-out 605 into a second anchoring segment 602 incorporating the second leg 594 and a third anchoring segment 603 incorporating the third leg 595, thereby producing a Y-shaped configuration for the implant 575. The first, second, and third legs 593-595 in the sixth embodiment are formed integrally with the implant 575 and thus the bridge 578 at respective first and second ends 583 and 584. Each of the first, second, and third legs 593-595, which has a respective tip 597-599, may include barbs thereon that improve the pull-out resistance of the implant 575. The implant 575 includes anchoring members in the form of the first, second, and third legs 593-595 in order to facilitate a securing of the implant 575 with bone, bones, or bone pieces whereby the bridge 578 between the first, second, and third legs 593-595 traverses a fixation zone of the bone, bones, or bone pieces such that the implant 575, after its insertion and attempted transition from the insertion shape 577 to the natural shape 576, delivers energy to the bone, bones, or bone pieces at the fixation zone.

The implant 575, and thus the bridge 578, includes a first aperture 587 extending therethrough from the upper surface 579 to the lower surface 580 whereby the first aperture 587 is located adjacent the transition section 585 at a first side 588 thereof. The implant 575, and thus the bridge 578, includes a catch 591 protruding into the first aperture 587. Similarly, the implant 575, and thus the bridge 578, includes a second aperture 589 extending therethrough from the upper surface 579 to the lower surface 580 whereby the second aperture 589 is located adjacent the transition section 585 at a second side 590 thereof. The implant 575, and thus the bridge 578, includes a catch 592 protruding into the second aperture 589. The first aperture 587 and its catch 591 and the second aperture 589 and its catch 592 provide engagement points for the implant retainer 5 with the implant 575. As such, the first and second apertures 587 and 589 are spaced apart across the transition section 585 a distance that allows receipt therein, respectively, of the fasteners 29 and 45 when the fasteners 29 and 45 reside at their first distance. When the fasteners 29 and 45 reside at their second distance, the fasteners 29 and 45, respectively, engage the catches 591 and 592 thereby securing the implant retainer 5 with the implant 575. The implant retainer 5 and its fasteners 29 and 45 and the first and second apertures 587 and 589 are correspondingly designed with respect to their size, location, and distances to interact and engage such that the implant retainer 5 optimally constrains the implant 575 in its insertion shape 577.

The regular inherent shape of the implant 575, as illustrated in FIGS. 22A-22C, is its natural shape 576 where the transition section 585 locates the bridge 578 in a natural form consisting of a closed or angular profile whereby the first and second ends 583 and 584 reside at a first distance and places the first leg 593 and the second and third legs 594-595 in a natural position whereby the first leg 593 is convergent with the second and third legs 594-595 and spaced apart therefrom at a first distance. Nevertheless, as illustrated in FIG. 22D, the implant 575 is deformable under the action of superelasticity or temperature dependent shape memory to its insertion shape 577 where the transition section 585 deforms to store energy while also moving the bridge 578 from its natural form to an insertion form which is an open or substantially linear profile whereby the first and second ends 583 and 584 reside at a second distance that is greater than the first distance and placing the first leg 593 and the second and third legs 595-595 in an insertion position whereby the first leg 593 is substantially parallel with the second and third legs 594-595 and spaced apart therefrom at a second distance that is greater than the first distance. Since the insertion shape 577 is not the regular inherent shape of the implant 575, the bridge 578 typically is mechanically constrained using the implant retainer 5 whereby the implant retainer 5 maintains the bridge 578 in its insertion form. In particular, the implant retainer 5 inserts into the first and second apertures 587 and 589 and engages the catches 591 and 592 such that the implant retainer 5 holds the bridge 578, resulting in the implant retainer 5 constraining the deformed transition section 585 in order to maintain the implant 575 in its insertion shape 577. After implantation into bone, bones, or bone pieces and a release of the implant retainer 5, including if necessary a heating of the implant 575, the implant 575 delivers the energy stored in the transition section 585 whereby the bridge 578 attempts to transition from its insertion form to its natural form such that the implant 575 affixes the bone, bones, or bone pieces through an application of a compressive force thereto. While the implant 575 includes the first and second apertures 587 and 589 and the catches 591 and 592, the implant 575 may include four apertures and respective catches that provide additional engagement points for a more secure engagement of the implant 575 with an implant retainer including four fasteners.

Figure 23A:
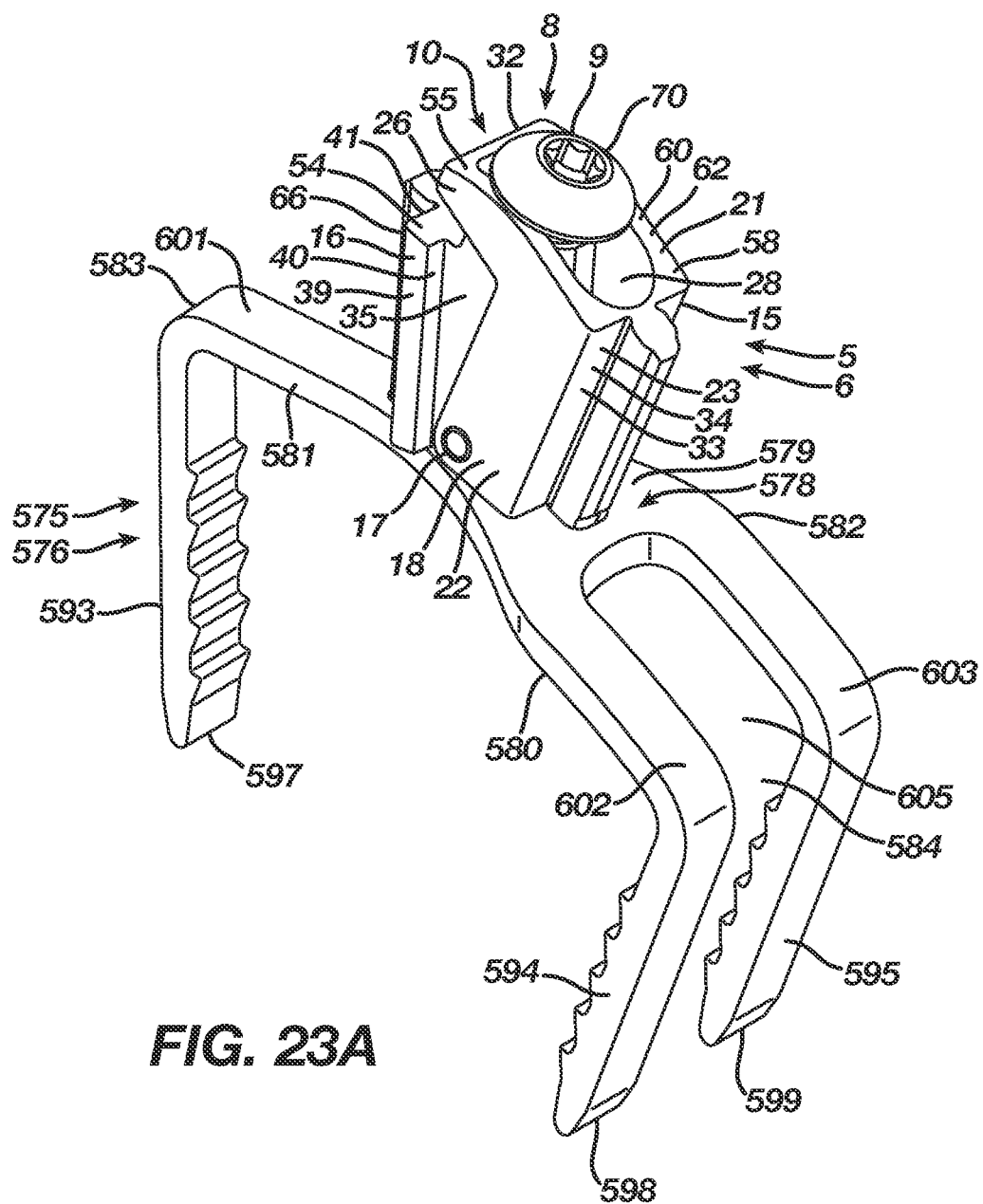
FIG. 23A is a top isometric view illustrating the implant retainer according to the first embodiment in an unloaded position relative to the shape memory implant according to the sixth embodiment in its natural shape.
Figure 23B:
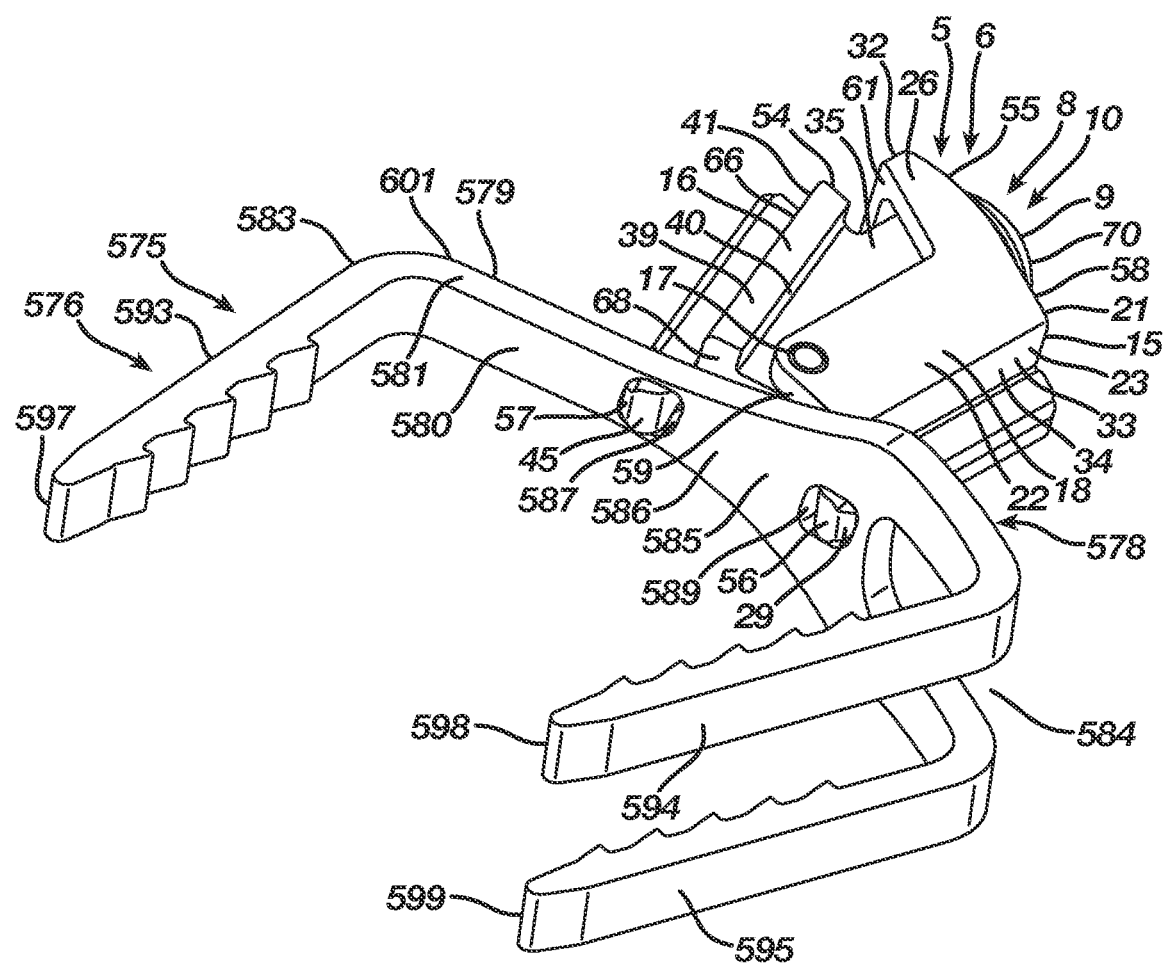
FIG. 23B is a bottom isometric view thereof.
Figure 23C:
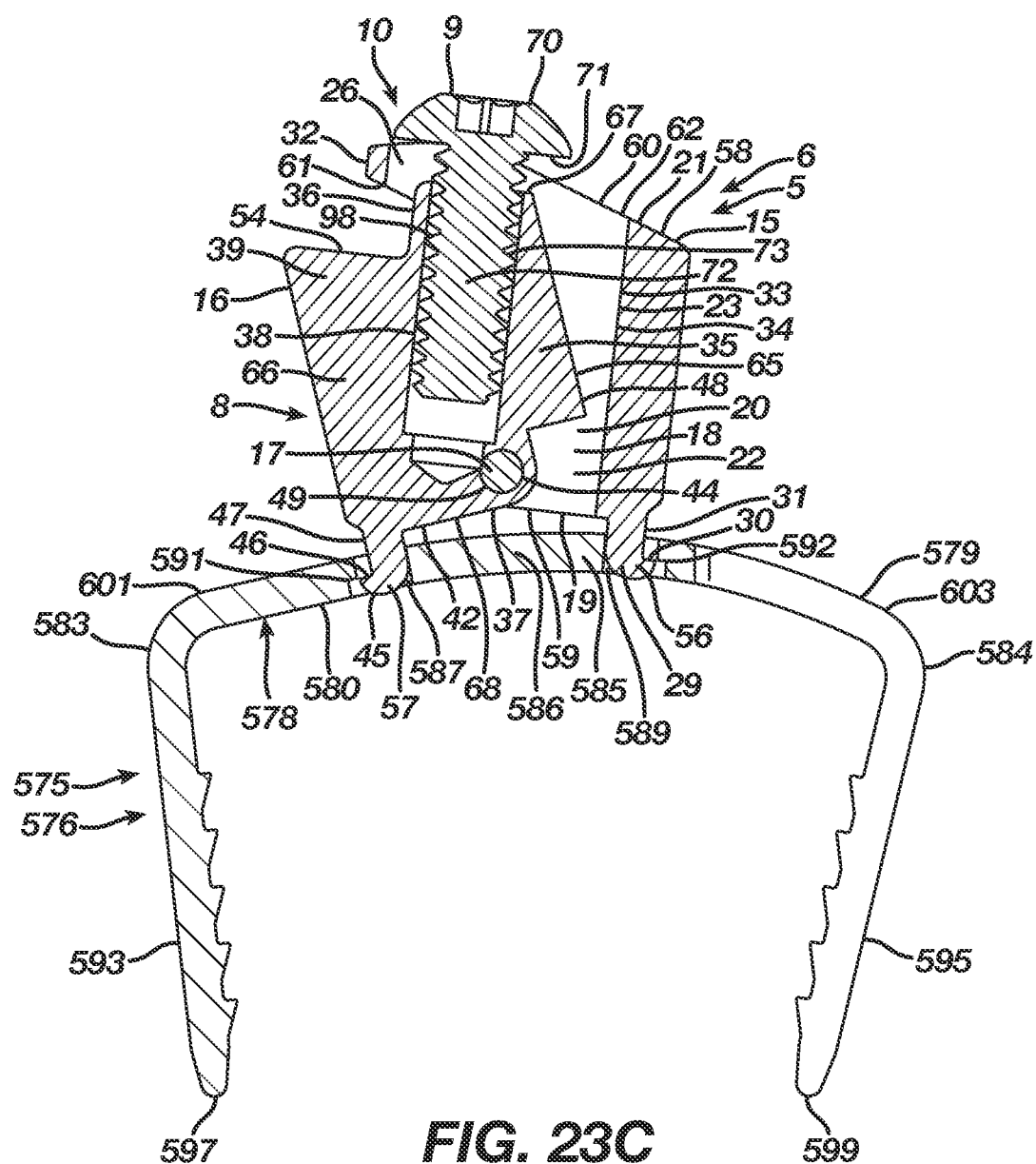
FIG. 23C is a side view in cross-section thereof.

When receiving the implant 575 in an orthopedic fixation system, the implant retainer 5 as illustrated in FIGS. 23A-23C begins in its unloaded position 6 wherein the implant grip 8 resides in its disengaged position 10 such that the fasteners 29 and 45 are in their unclasped position spaced apart at the first distance. In particular, after the implant retainer 5 is positioned adjacent the implant 575 at the upper surface 579 thereof, the fastener 29 of the frame 15 and the fastener 45 of the body 16, due to their unclasped position residing at the first distance, insert respectively into the first and second apertures 587 and 589 of the implant 575, whereby the cutouts 31 and 47 respectively are adjacent the first and second catches 591 and 592 while the detents 30 and 46 are positioned underneath the first and second catches 591 and 592 but separated therefrom. The fasteners 29 and 45 respectively extend below the end wall 23 of the wall 18 for the frame 15 and the wall 39 for the body 16 a length that permits their respective insertions into the first and second apertures 587 and 589 such that their detents 30 and 46 are located respectively below the first and second catches 591 and 592. Nevertheless, the lengths of the fasteners 29 and 45 are equal to or less than the thickness of the implant 575 between its upper and lower surfaces 579 and 580 whereby the fasteners 29 and 45 do not extend respectively from the first and second apertures 587 and 589 below the lower surface 580 of the implant 575 in order to ensure the implant 575 sits flush atop bone, bones, or bone pieces. Rotation of the head 70 for the actuator 9 in the first direction and the subsequent traversing of the head 70 along the bearing surface 60 from its unlocking position to its locking position progresses the fasteners 29 and 45 to their clasped position at the second distance such that the fasteners 29 and 45 respectively via the detents 30 and 46 abut the first and second catches 591 and 592 at undersides thereof. As a result, the implant retainer 5, now in its loaded position 7 with the actuator 9 in its locking position holding the implant grip 8 in its engaged position 11 as illustrated in FIG. 24A-24C, has moved the implant 575, if necessary, to its insertion shape 577 and constrains the implant 575 in its insertion shape 577 via engagement of the implant retainer 5 with the implant 575 at the fasteners 29 and 45 and the bottoms 59 and 68 of the frame 15 and body 16 at the upper surface 579 of the implant 575.

Figure 24A:
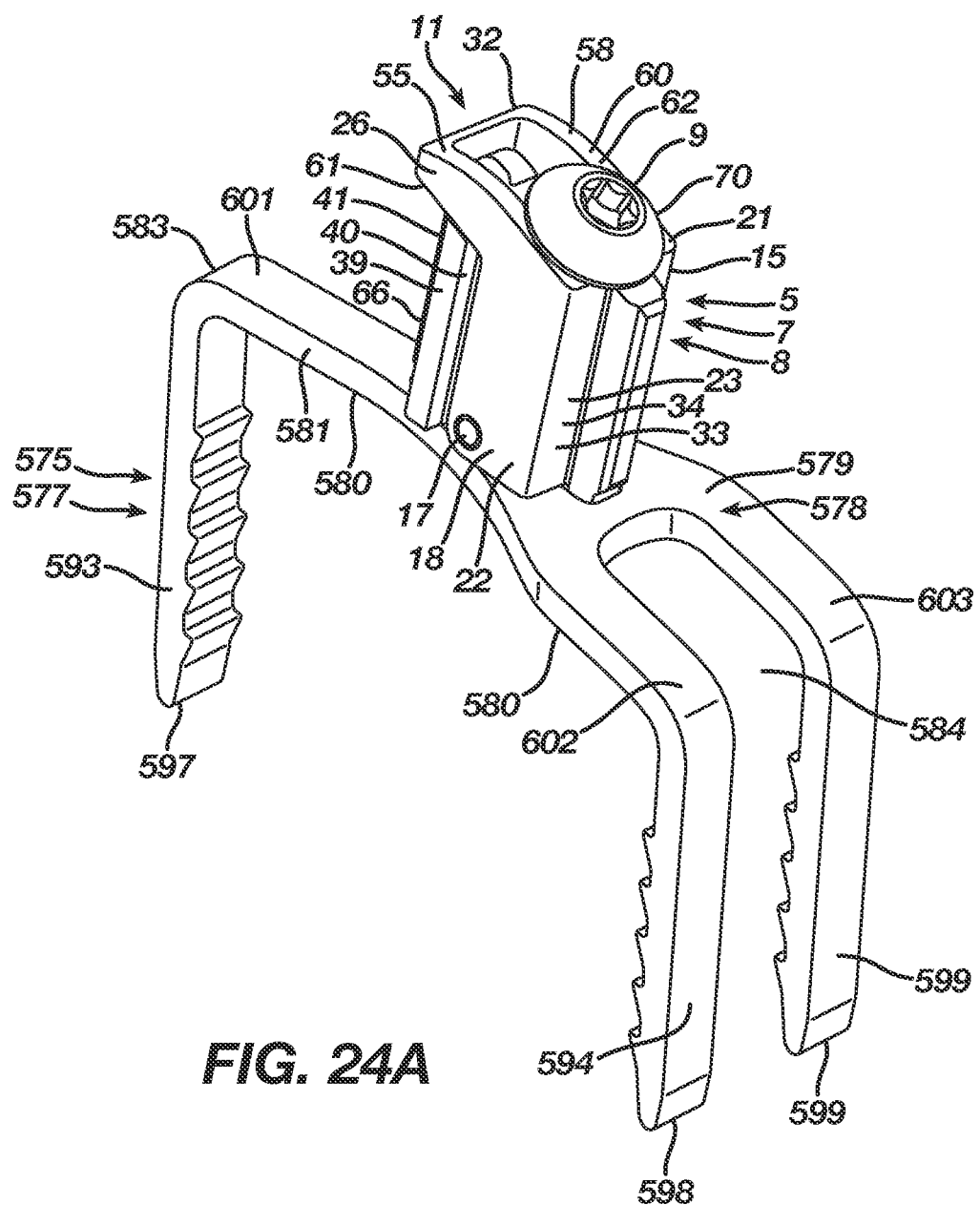
FIG. 24A is a top isometric view illustrating the implant retainer according to the first embodiment in a loaded position constraining the shape memory implant according to the sixth embodiment in its insertion shape.
Figure 24B:
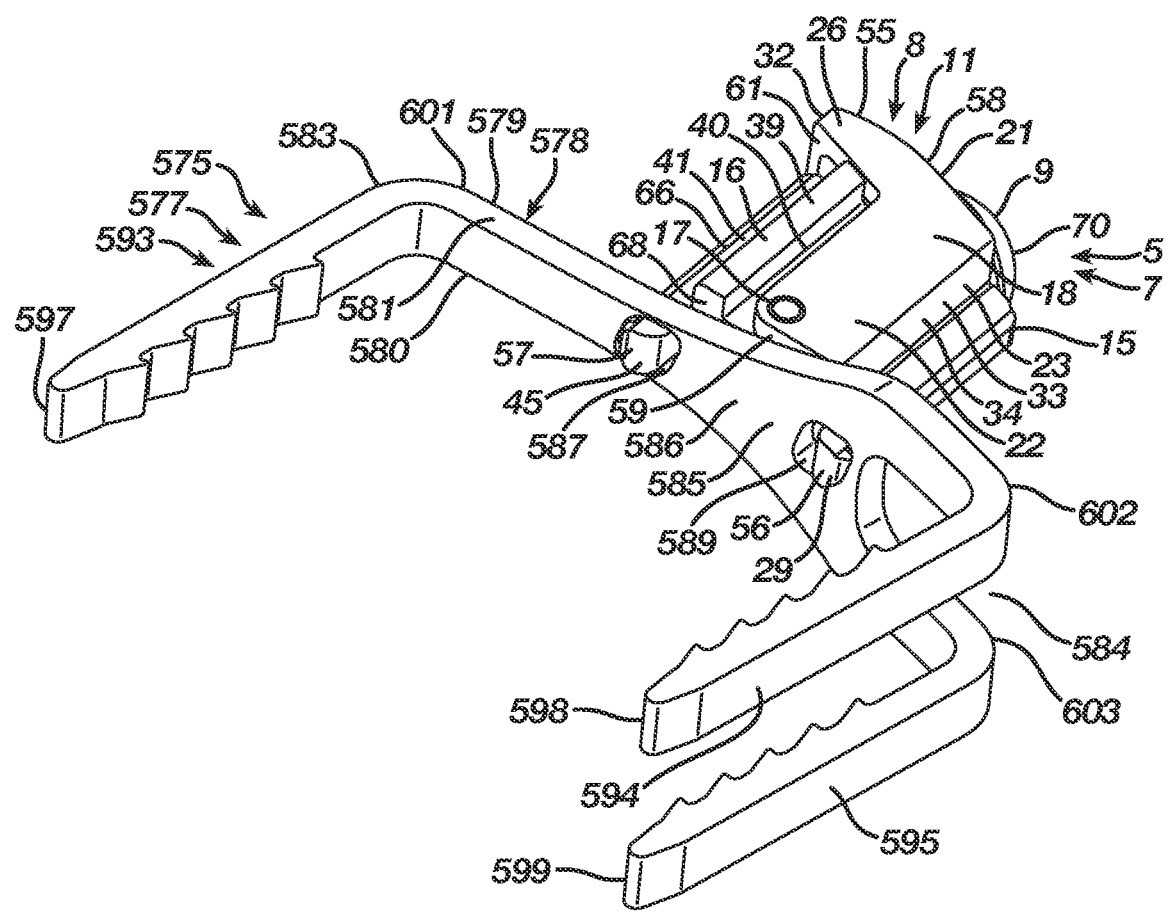
FIG. 24B is a bottom isometric view thereof.
Figure 24C:
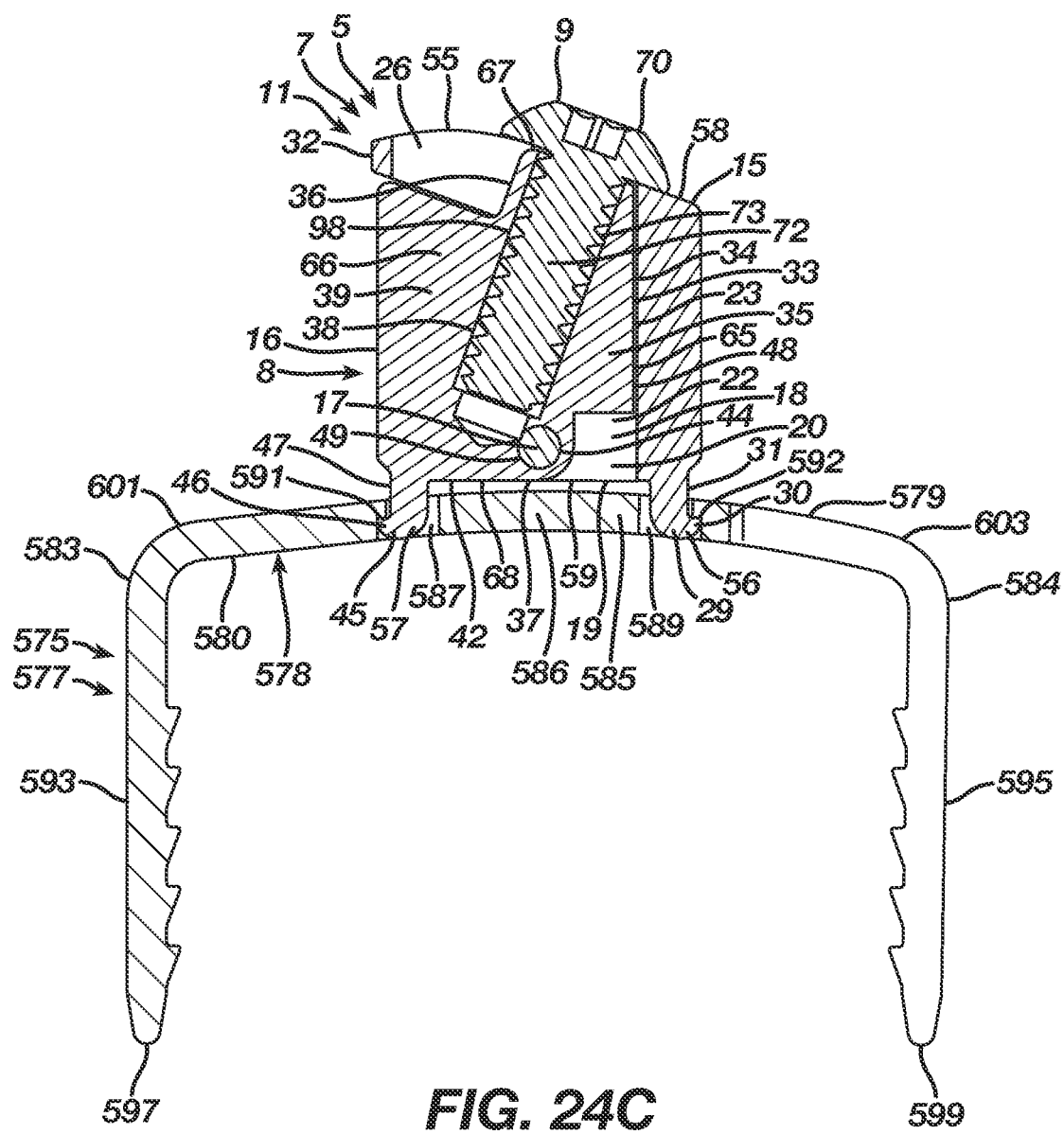
FIG. 24C is a side view in cross-section thereof.

When delivering the implant 575 to bone, bones, or bone pieces, the implant retainer 5 as illustrated in FIGS. 24A-24C begins in its loaded position 7 wherein the implant grip 8 in its engaged position 11 constrains the implant 575 in its insertion shape 577. Rotation of the head 70 for the actuator 9 in the second direction and the subsequent traversing of the head 70 along the bearing surface 60 from its locking position to its unlocking position progresses the fasteners 29 and 45 to their unclasped position at the first distance such that the fasteners 29 and 45 and thus the detents 30 and 46 respectively move away from and thus release the first and second catches 591 and 592 at undersides thereof. As a result, the implant retainer 5, now in its unloaded position 6 with the actuator 9 in its unlocking position holding the implant grip 8 in its disengaged position 10 as illustrated in FIGS. 23A-23C, removes from atop the upper surface 579 of the implant 575 while the fasteners 29 and 45 respectively discharge from the first and second apertures 587 and 589 such that the released implant 575 attempts transition from its insertion shape 577 to its natural shape 576 whereby the implant 575 delivers the energy stored therein to the bone, bones, or bone pieces.

Figure 25A:
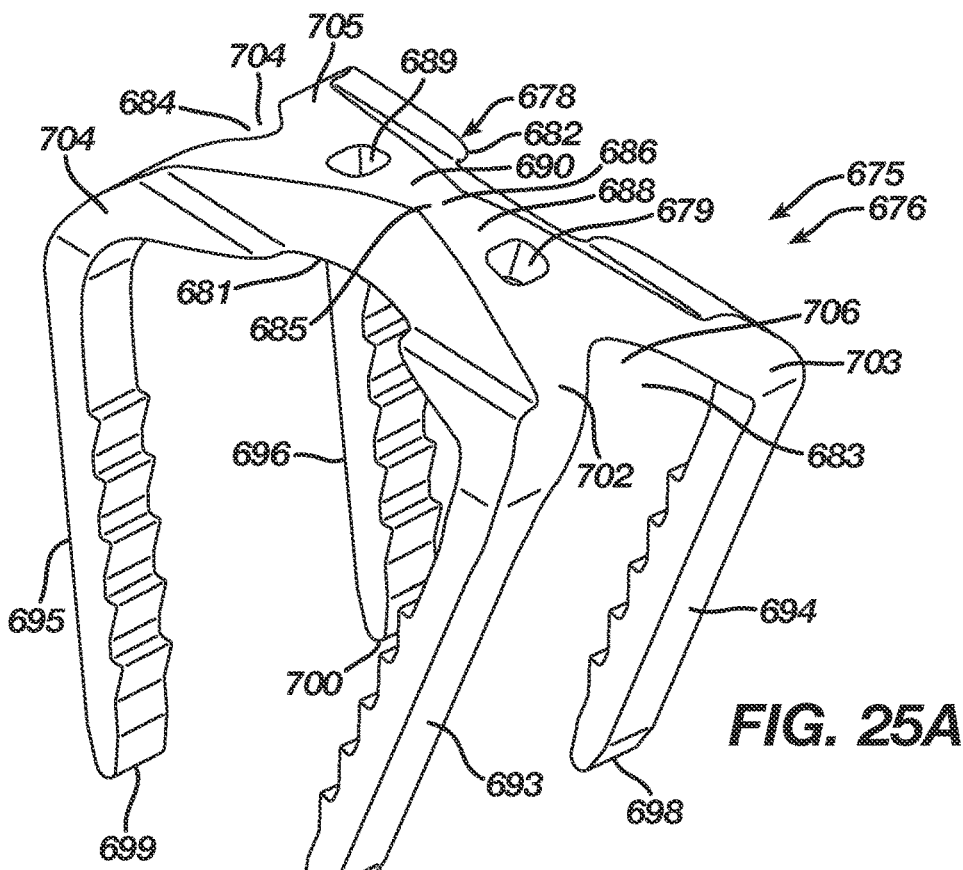
FIG. 25A is a top isometric view illustrating a shape memory implant according to a seventh embodiment in a natural shape.
Figure 25B:
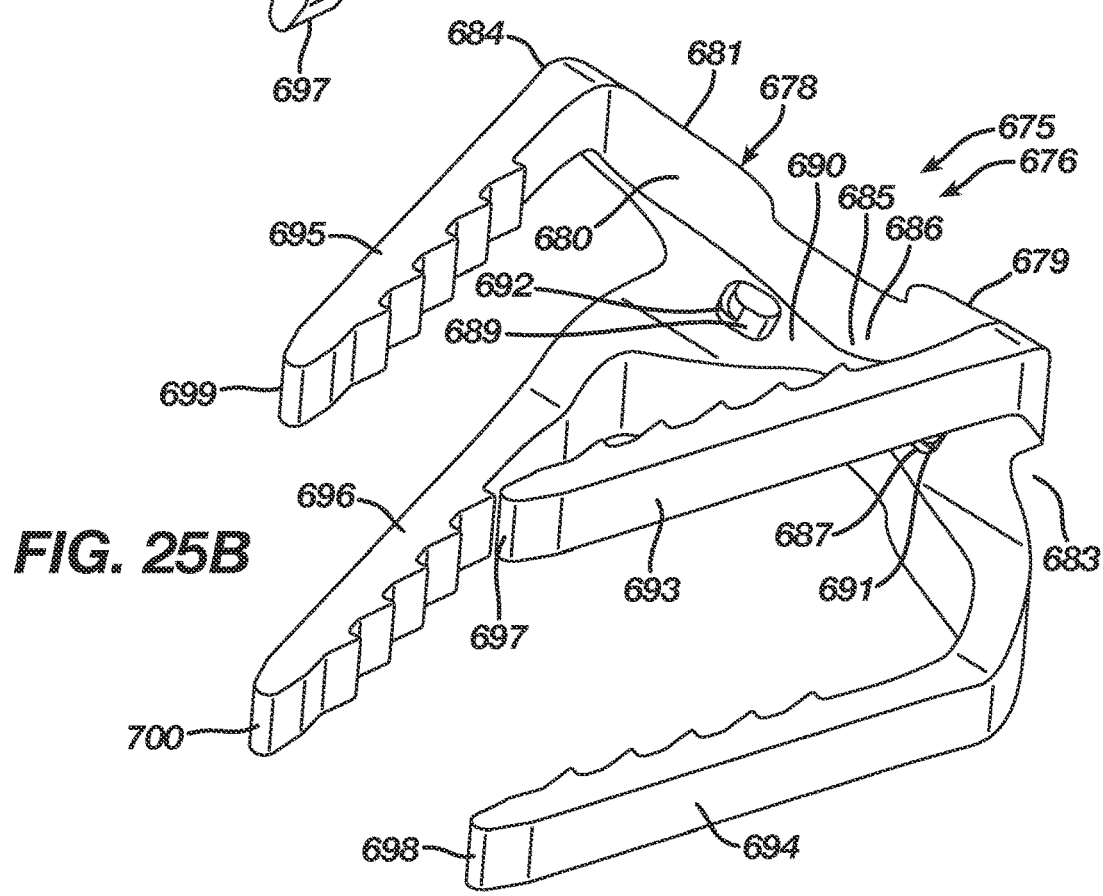
FIG. 25B is a bottom isometric view thereof.
Figure 25C:
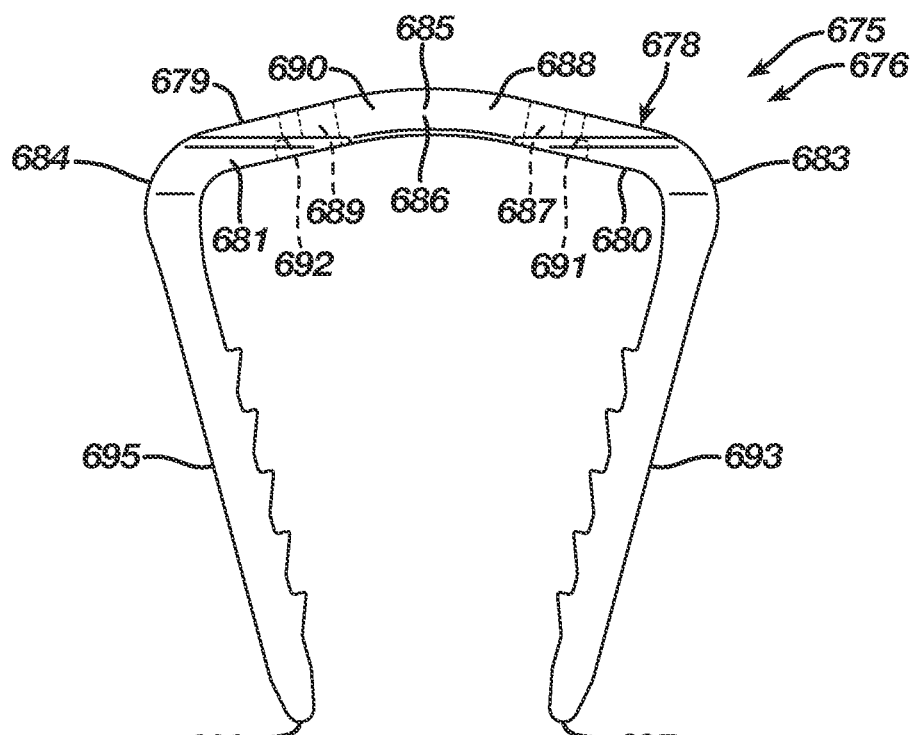
FIG. 25C is a side view thereof.
Figure 25D:
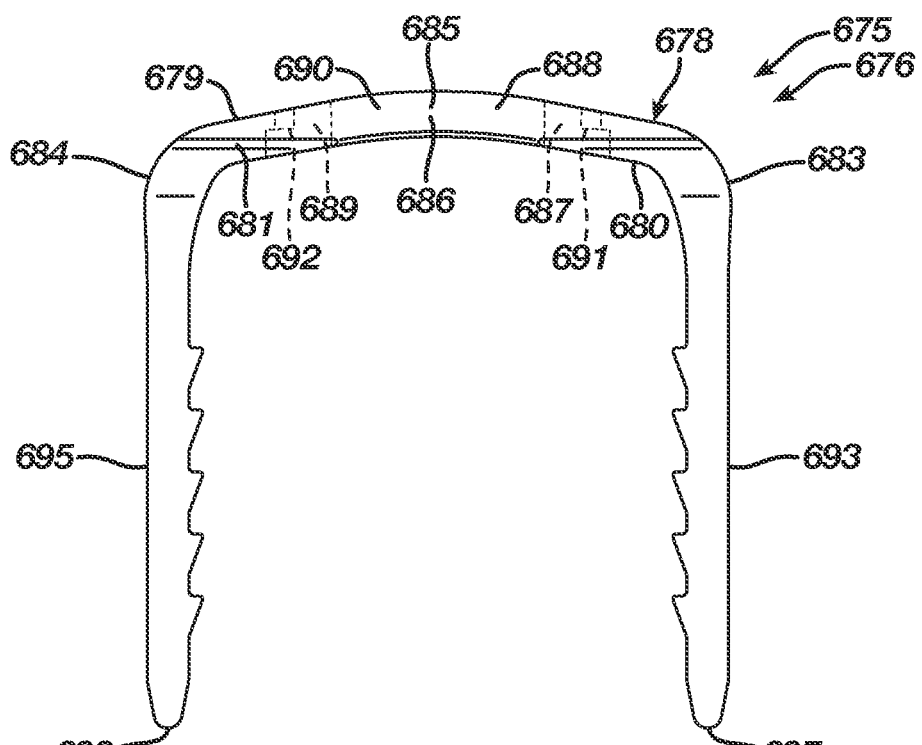
FIG. 25D is a side view illustrating the shape memory implant according to the seventh embodiment in an insertion shape.

FIGS. 25A-25C illustrate an orthopedic implant 675 according to a seventh embodiment in a natural shape 676, whereas FIG. 25D illustrates the orthopedic implant 675 in an insertion shape 677. The implant 675 in the seventh embodiment may be manufactured from a shape memory material with superelastic or temperature dependent properties (e.g., Nitinol) such that the implant 675 transitions between its natural shape 676 and its insertion shape 677. The implant 675 when deformed from its natural shape 676 to its insertion shape 677 stores energy deliverable to bone, bones, or bone pieces. In accordance with its manufacture from shape memory material, the implant 675 begins in its natural shape 676, is transitionable to its insertion shape 677, and, once implanted in bone, bones, or bone pieces, attempts to transition from its insertion shape 677 to its natural shape 676 whereby the implant 675 delivers the energy stored therein to the bone, bones, or bone pieces in order to affix the bone, bones, or bone pieces and promote a healing thereof. In the seventh embodiment, attempted transition of the implant 675 from its insertion shape 677 to its natural shape 676 continuously compresses the bone, bones, or bone pieces to promote fusion thereof.

The implant 675 includes a bridge 678 with upper and lower surfaces 679 and 680, first and second sides 681 and 682, and first and second ends 683 and 684. The implant 675 includes a transition section 685 located at a center section 686 of the implant 675 and thus the bridge 678. The implant 675 in the sixth embodiment includes anchoring members in the form of first and second legs 693 and 694 extending from the first end 683 of the implant 675 and thus the bridge 678 whereby the first and second legs 693 and 694 are aligned and located adjacent the first end 683 of the bridge 678. In the sixth embodiment, the implant 675, and thus the bridge 678, at the first end 683 divides via a cut-out 706 into a first anchoring segment 702 incorporating the first leg 693 and a second anchoring segment 703 incorporating the second leg 694, thereby producing an H-shaped configuration for the implant 675. The implant 675 includes anchoring members in the form of third and fourth legs 695 and 696 extending from the second end 684 of the implant 675 and thus the bridge 678 whereby the third and fourth legs 695 and 696 are aligned and located adjacent the second end 684 of the bridge 678. In the sixth embodiment, the implant 675, and thus the bridge 678, at the second end 684 divides via a cut-out 707 into a third anchoring segment 704 incorporating the third leg 695 and a fourth anchoring segment 705 incorporating the fourth leg 696, thereby producing an H-shaped configuration for the implant 675. The first, second, third, and fourth legs 693-696 are formed integrally with the implant 675 and thus the bridge 678 at respective first and second ends 683 and 684. Each of the first, second, third, and fourth legs 693-696, which has a respective tip 697-700, may include barbs thereon that improve the pull-out resistance of the implant 675. The implant 675 includes anchoring members in the form of the first, second, third, and fourth legs 693-696 in order to facilitate a securing of the implant 675 with bone, bones, or bone pieces whereby the bridge 678 between the first and second legs 693 and 694 and the third, and fourth legs 695 and 696 traverses a fixation zone of the bone, bones, or bone pieces such that the implant 675, after its insertion and attempted transition from the insertion shape 677 to the natural shape 676, delivers energy to the bone, bones, or bone pieces at the fixation zone.

The implant 675, and thus the bridge 678, includes a first aperture 687 extending therethrough from the upper surface 679 to the lower surface 680 whereby the first aperture 687 is located adjacent the transition section 685 at a first side 688 thereof. The implant 675, and thus the bridge 678, includes a catch 691 protruding into the first aperture 687. Similarly, the implant 675, and thus the bridge 678, includes a second aperture 689 extending therethrough from the upper surface 679 to the lower surface 680 whereby the second aperture 689 is located adjacent the transition section 685 at a second side 690 thereof. The implant 675, and thus the bridge 678, includes a catch 692 protruding into the second aperture 689. The first aperture 687 and its catch 691 and the second aperture 689 and its catch 692 provide engagement points for the implant retainer 5 with the implant 675. As such, the first and second apertures 687 and 689 are spaced apart across the transition section 685 a distance that allows receipt therein, respectively, of the fasteners 29 and 45 when the fasteners 29 and 45 reside at their first distance. When the fasteners 29 and 45 reside at their second distance, the fasteners 29 and 45, respectively, engage the catches 691 and 692 thereby securing the implant retainer 5 with the implant 675. The implant retainer 5 and its fasteners 29 and 45 and the first and second apertures 687 and 689 are correspondingly designed with respect to their size, location, and distances to interact and engage such that the implant retainer 5 optimally constrains the implant 675 in its insertion shape 677.

The regular inherent shape of the implant 675, as illustrated in FIGS. 25A-25C, is its natural shape 676 where the transition section 685 locates the bridge 678 in a natural form consisting of a closed or angular profile whereby the first and second ends 683 and 684 reside at a first distance and places the first and second legs 693 and 694 and the third and fourth legs 695 and 696 in a natural position whereby the first and second legs 693 and 694 are convergent with the third and fourth legs 695 and 696 and spaced apart therefrom at a first distance. Nevertheless, as illustrated in FIG. 25D, the implant 675 is deformable under the action of superelasticity or temperature dependent shape memory to its insertion shape 677 where the transition section 685 deforms to store energy while also moving the bridge 678 from its natural form to an insertion form which is an open or substantially linear profile whereby the first and second ends 683 and 684 reside at a second distance that is greater than the first distance and placing the first and second legs 693 and 694 and the third and fourth legs 695 and 696 in an insertion position whereby the first and second legs 693 and 694 is substantially parallel with the third and fourth legs 695 and 696 and spaced apart therefrom at a second distance that is greater than the first distance. Since the insertion shape 677 is not the regular inherent shape of the implant 675, the bridge 678 typically is mechanically constrained using the implant retainer 5 whereby the implant retainer 5 maintains the bridge 678 in its insertion form. In particular, the implant retainer 5 inserts into the first and second apertures 687 and 689 and engages the catches 691 and 692 such that the implant retainer 5 holds the bridge 678, resulting in the implant retainer 5 constraining the deformed transition section 685 in order to maintain the implant 675 in its insertion shape 677. After implantation into bone, bones, or bone pieces and a release of the implant retainer 5, including if necessary a heating of the implant 675, the implant 675 delivers the energy stored in the transition section 685 whereby the bridge 678 attempts to transition from its insertion form to its natural form such that the implant 675 affixes the bone, bones, or bone pieces through an application of a compressive force thereto. While the implant 675 includes the first and second apertures 687 and 689 and the catches 691 and 692, the implant 675 may include four apertures and respective catches that provide additional engagement points for a more secure engagement of the implant 675 with an implant retainer including four fasteners.

Figure 26A:
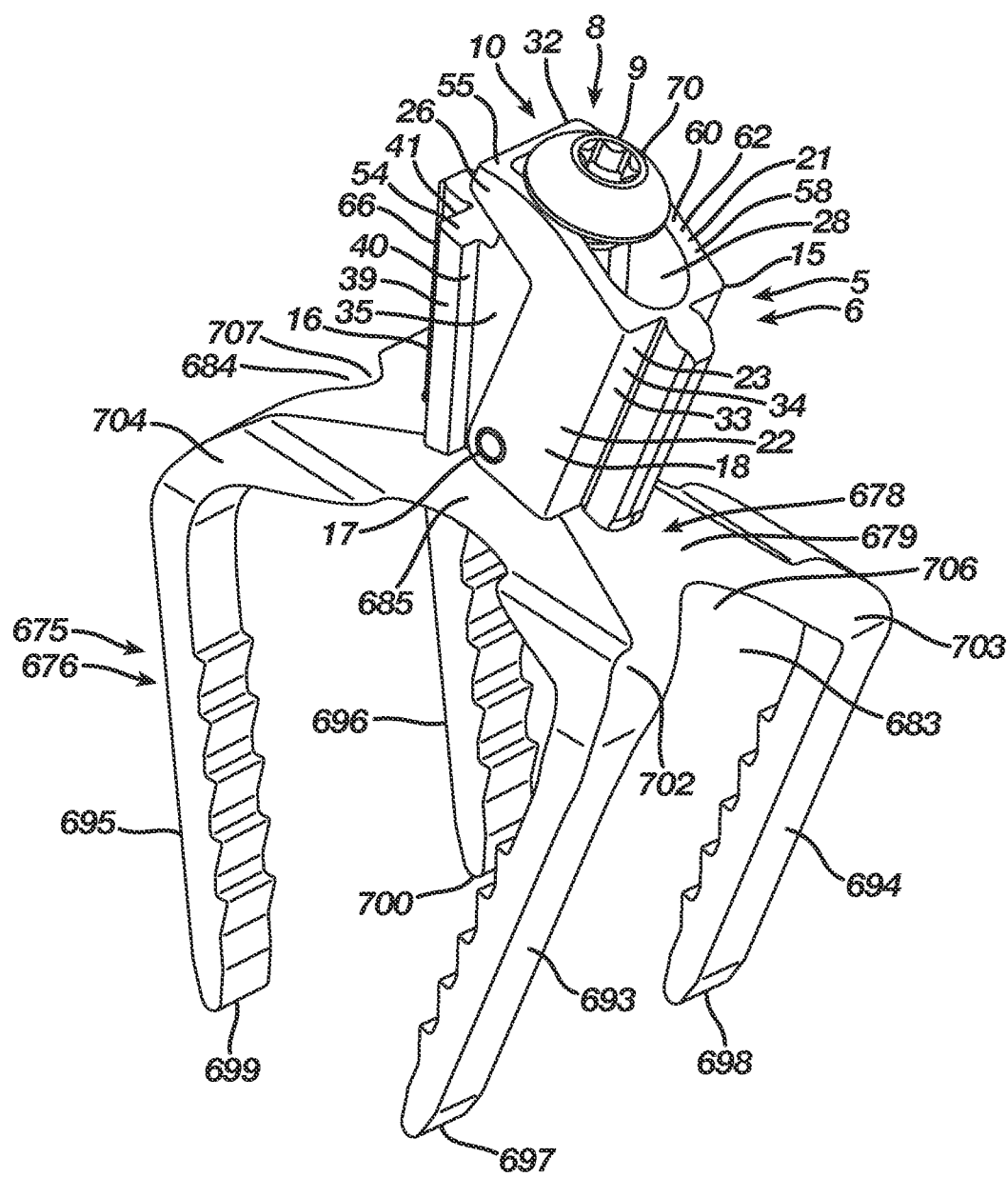
FIG. 26A is a top isometric view illustrating the implant retainer according to the first embodiment in an unloaded position relative to the shape memory implant according to the seventh embodiment in its natural shape.
Figure 26B:
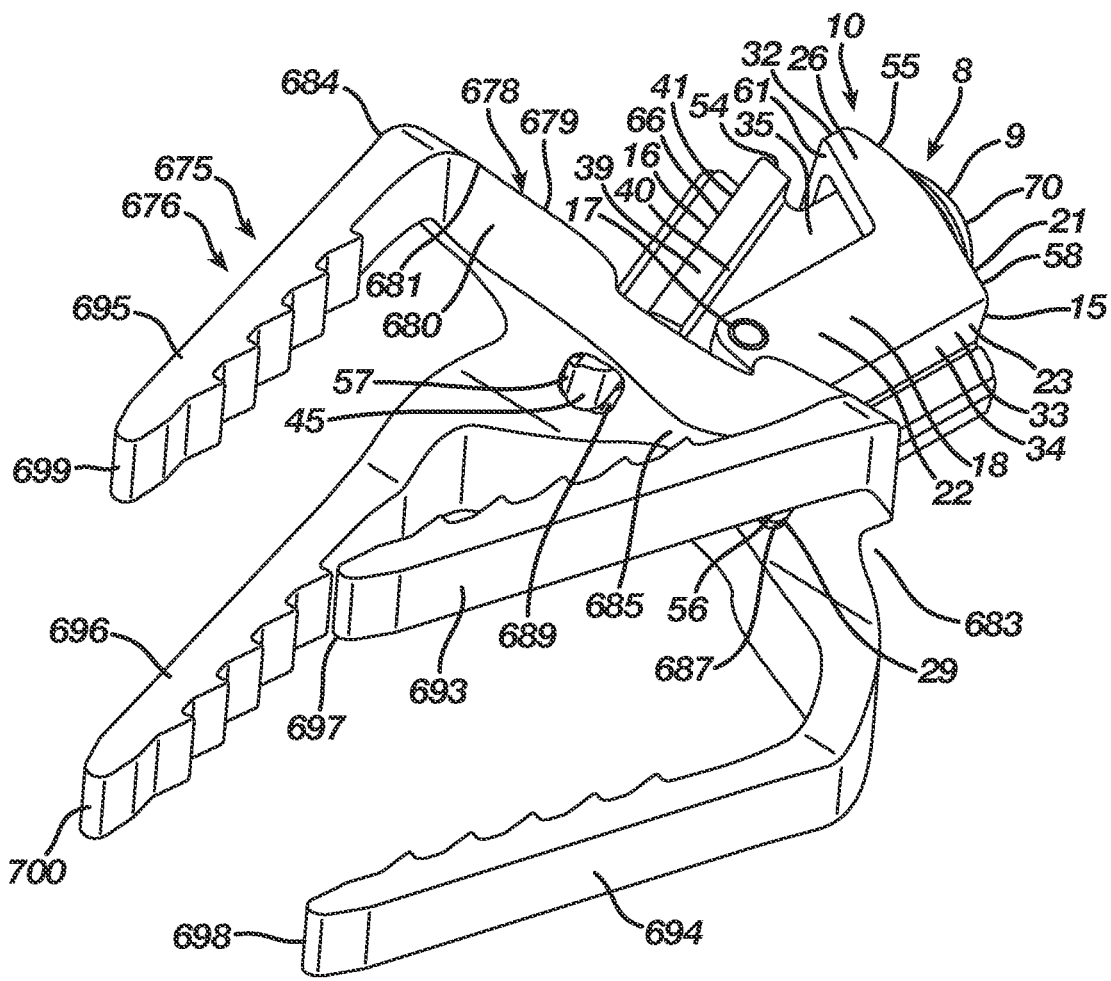
FIG. 26B is a bottom isometric view thereof.
Figure 26C:
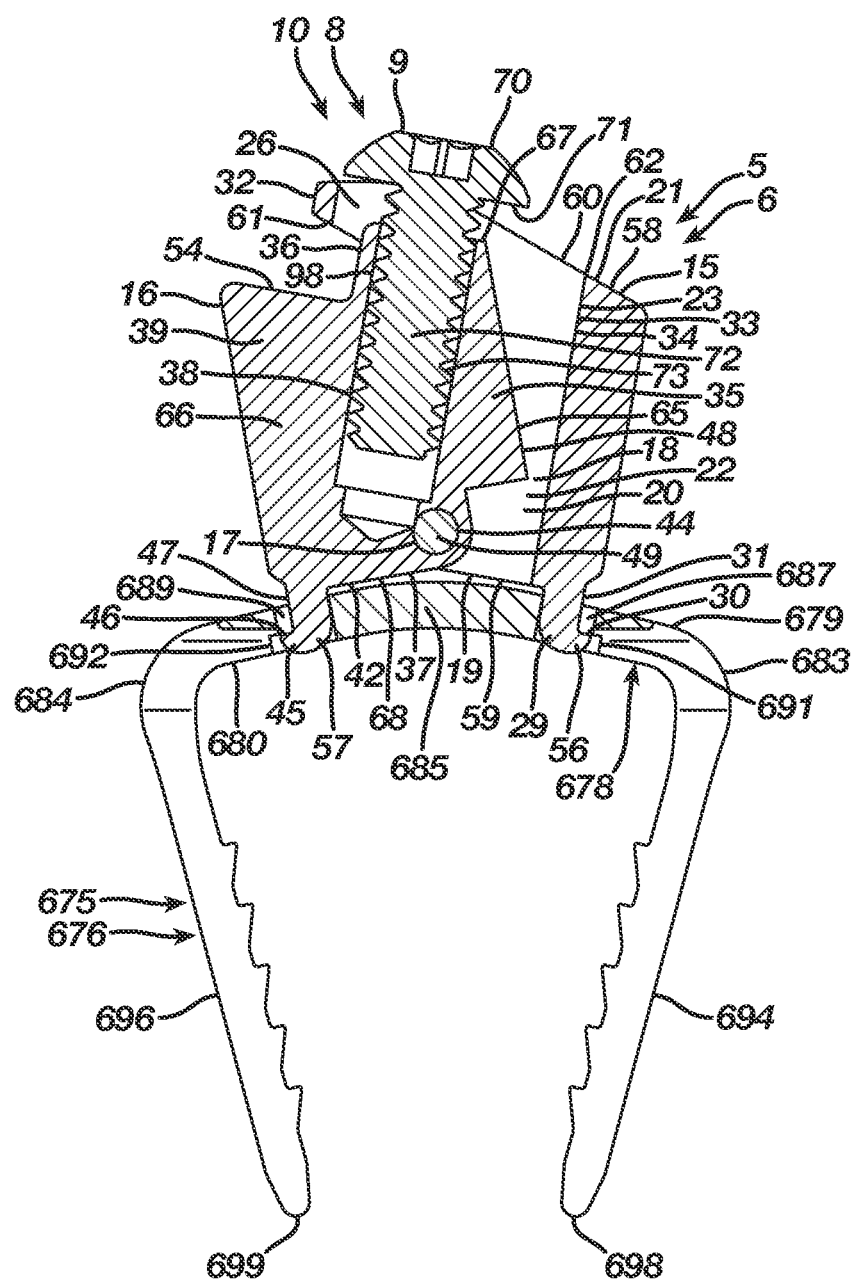
FIG. 26C is a side view in cross-section thereof.

When receiving the implant 675 in an orthopedic fixation system, the implant retainer 5 as illustrated in FIGS. 26A-26C begins in its unloaded position 6 wherein the implant grip 8 resides in its disengaged position 10 such that the fasteners 29 and 45 are in their unclasped position spaced apart at the first distance. In particular, after the implant retainer 5 is positioned adjacent the implant 675 at the upper surface 679 thereof, the fastener 29 of the frame 15 and the fastener 45 of the body 16, due to their unclasped position residing at the first distance, insert respectively into the first and second apertures 687 and 689 of the implant 675, whereby the cutouts 31 and 47 respectively are adjacent the first and second catches 691 and 692 while the detents 30 and 46 are positioned underneath the first and second catches 691 and 692 but separated therefrom. The fasteners 29 and 45 respectively extend below the end wall 23 of the wall 18 for the frame 15 and the wall 39 for the body 16 a length that permits their respective insertions into the first and second apertures 687 and 689 such that their detents 30 and 46 are located respectively below the first and second catches 691 and 692. Nevertheless, the lengths of the fasteners 29 and 45 are equal to or less than the thickness of the implant 675 between its upper and lower surfaces 679 and 680 whereby the fasteners 29 and 45 do not extend respectively from the first and second apertures 687 and 689 below the lower surface 680 of the implant 675 in order to ensure the implant 675 sits flush atop bone, bones, or bone pieces. Rotation of the head 70 for the actuator 9 in the first direction and the subsequent traversing of the head 70 along the bearing surface 60 from its unlocking position to its locking position progresses the fasteners 29 and 45 to their clasped position at the second distance such that the fasteners 29 and 45 respectively via the detents 30 and 46 abut the first and second catches 691 and 692 at undersides thereof. As a result, the implant retainer 5, now in its loaded position 7 with the actuator 9 in its locking position holding the implant grip 8 in its engaged position 11 as illustrated in FIG. 27A-27C, has moved the implant 675, if necessary, to its insertion shape 677 and constrains the implant 675 in its insertion shape 677 via engagement of the implant retainer 5 with the implant 675 at the fasteners 29 and 45 and the bottoms 59 and 68 of the frame 15 and body 16 at the upper surface 679 of the implant 675.

Figure 27A:
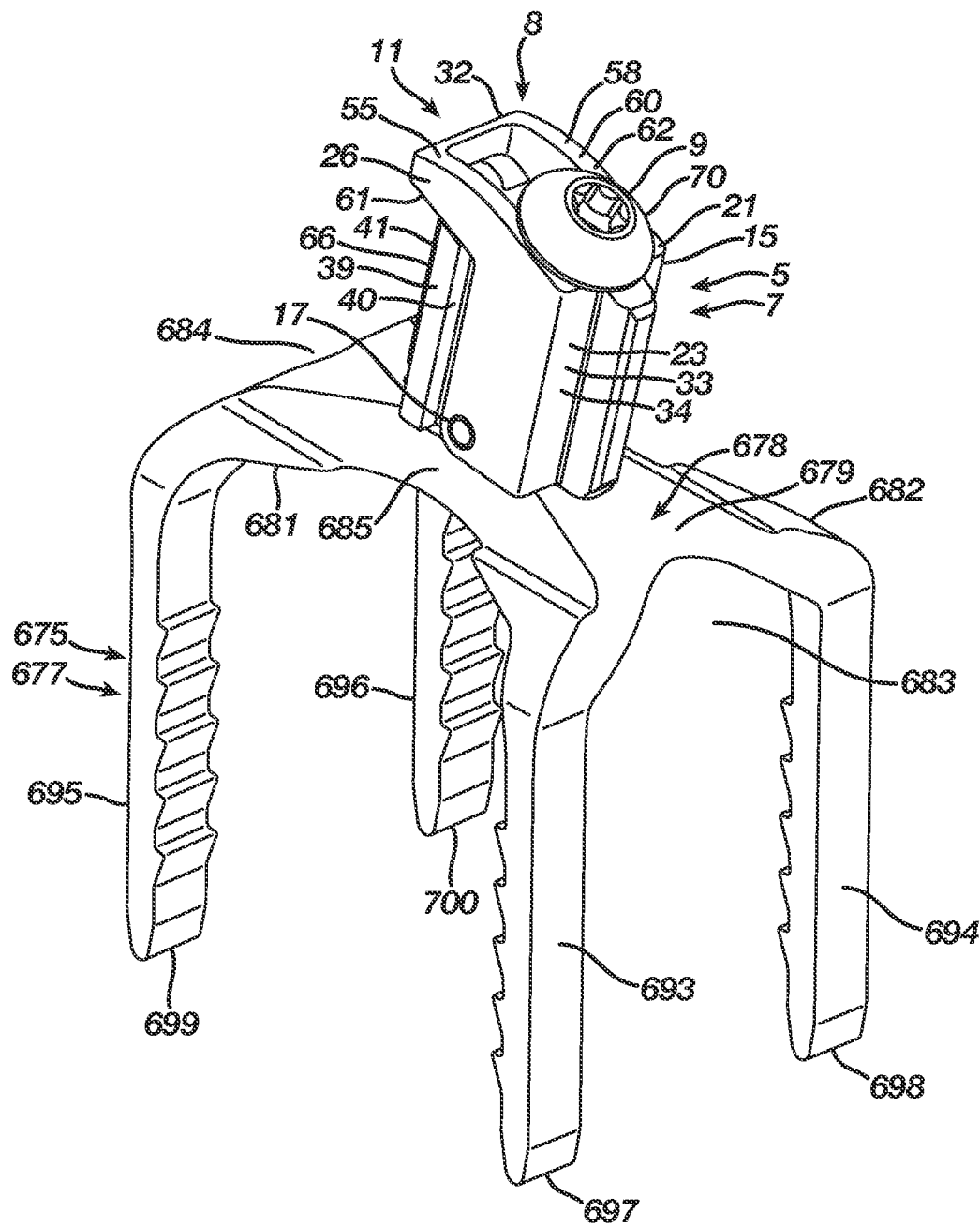
FIG. 27A is a top isometric view illustrating the implant retainer according to the first embodiment in a loaded position constraining the shape memory implant according to the seventh embodiment in its insertion shape.
Figure 27B:
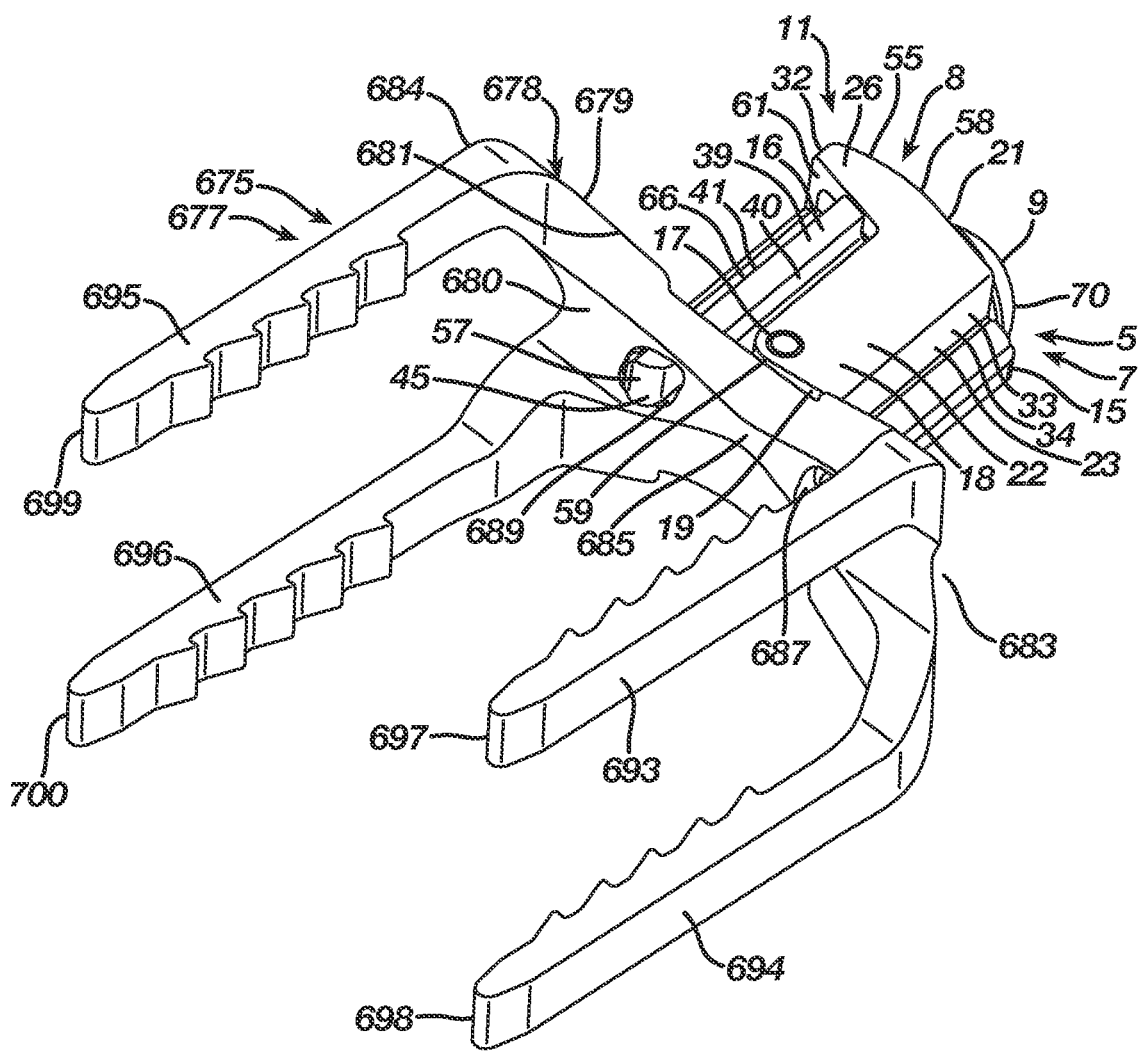
FIG. 27B is a bottom isometric view thereof.
Figure 27C:
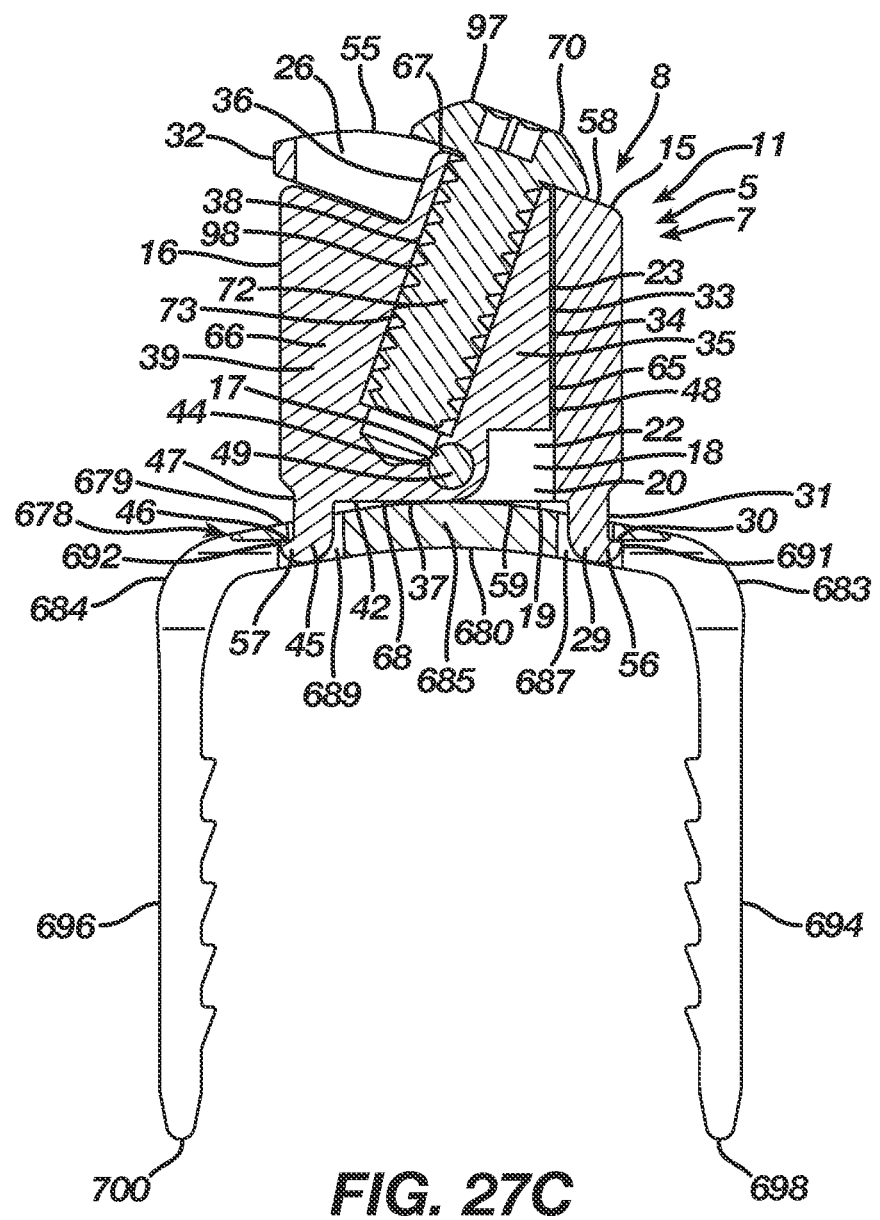
FIG. 27C is a side view in cross-section thereof.

When delivering the implant 675 to bone, bones, or bone pieces, the implant retainer 5 as illustrated in FIGS. 27A-27C begins in its loaded position 7 wherein the implant grip 8 in its engaged position 11 constrains the implant 675 in its insertion shape 677. Rotation of the head 70 for the actuator 9 in the second direction and the subsequent traversing of the head 70 along the bearing surface 60 from its locking position to its unlocking position progresses the fasteners 29 and 45 to their unclasped position at the first distance such that the fasteners 29 and 45 and thus the detents 30 and 46 respectively move away from and thus release the first and second catches 691 and 692 at undersides thereof. As a result, the implant retainer 5, now in its unloaded position 6 with the actuator 9 in its unlocking position holding the implant grip 8 in its disengaged position 10 as illustrated in FIGS. 26A-26C, removes from atop the upper surface 679 of the implant 675 while the fasteners 29 and 45 respectively discharge from the first and second apertures 687 and 689 such that the released implant 675 attempts transition from its insertion shape 677 to its natural shape 676 whereby the implant 675 delivers the energy stored therein to the bone, bones, or bone pieces.

Figure 28:
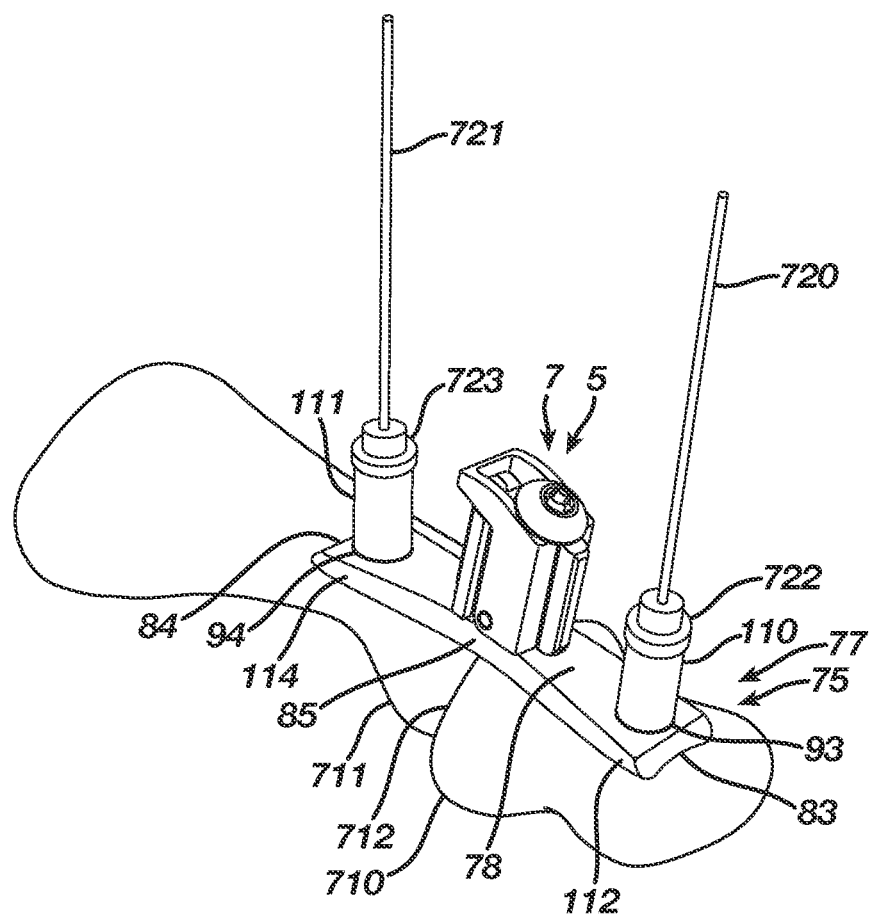
FIGS. 28-35 are isometric views illustrating implanting of the shape memory implant according to the first embodiment into bone, bones, or bone pieces using an implant retainer according to the first embodiment.

FIG. 28 illustrates the implant retainer 5 according to the first embodiment with the implant 75 of the first embodiment loaded thereon in an orthopedic fixation system whereby the implant retainer 5 in its loaded position 7 retains the implant 75 in its insertion shape 77 such that the implant 75 is ready for securing with bone, bones, or bone pieces, and, in particular, with a first bone 710 and a second bone 711, which are presented herein as an example. The implant 75 in addition to its loading on the implant retainer 5 includes the drill guides 110 and 111 respectively secured with the first and second openings 93 and 94 in order to facilitate a drilling of holes in the first and second bones 710 and 711.

A surgeon as illustrated in FIG. 28 aligns the first bone 710 with the second bone 711 at a fusion zone 712 in an orientation that promotes fixation of the first bone 710 with the second bone 711 and a proper healing thereof. The surgeon then places the implant 75 held in its insertion shape 77 by the implant retainer 5 across the first bone 710 and the second bone 711 with the transition section 85 of the bridge 78 located at the fusion zone 712. Upon placement of the implant 75, the surgeon secures the implant 75 with the first and second bone 710 and 711. In particular, a locating pin 720 inserts through the drill guide 110 and into the first bone 710 thereby securing the implant 75 at its anchoring segment 112 with the first bone 710. Likewise, a locating pin 721 inserts through the drill guide 111 and into the second bone 711 thereby securing the implant 75 at its anchoring segment 114 with the second bone 711. The locating pins 720 and 721 hold the implant 75 on the first and second bones 710 and 711 with the first and second bones 710 and 711 aligned in the orientation that promotes fixation. If desired, the surgeon may secure the locating pin 720 with the drill guide 110 via a collar 722 coupled with the drill guide 110 and the locating pin 721 with the drill guide 111 via a collar 723 coupled with the drill guide 111.

Figure 29:
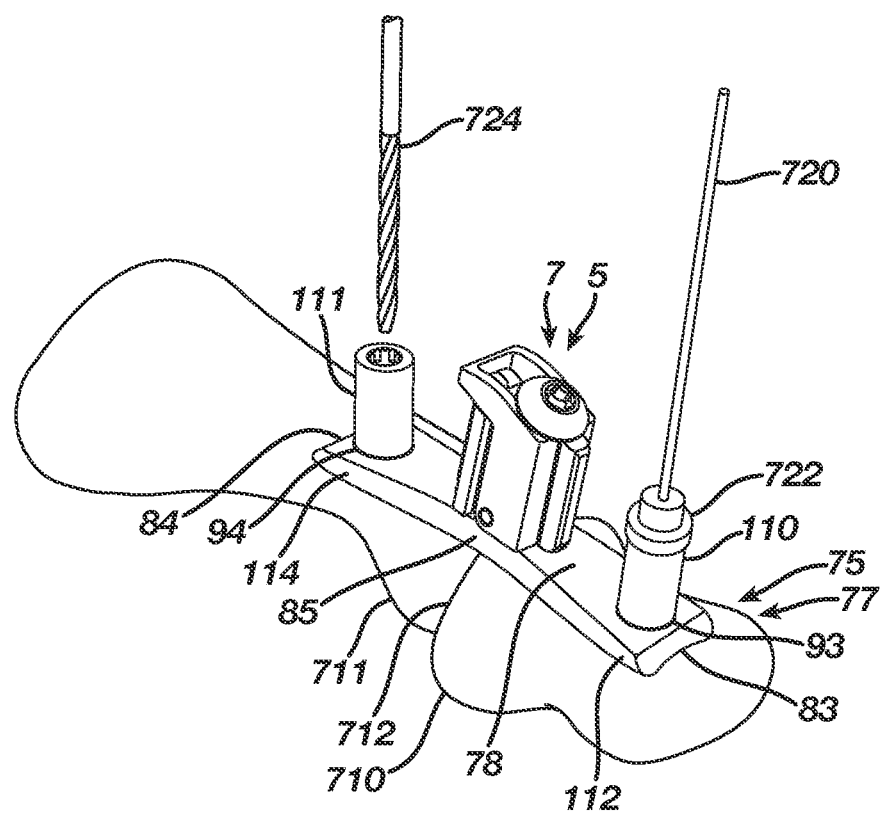
Figure 30:
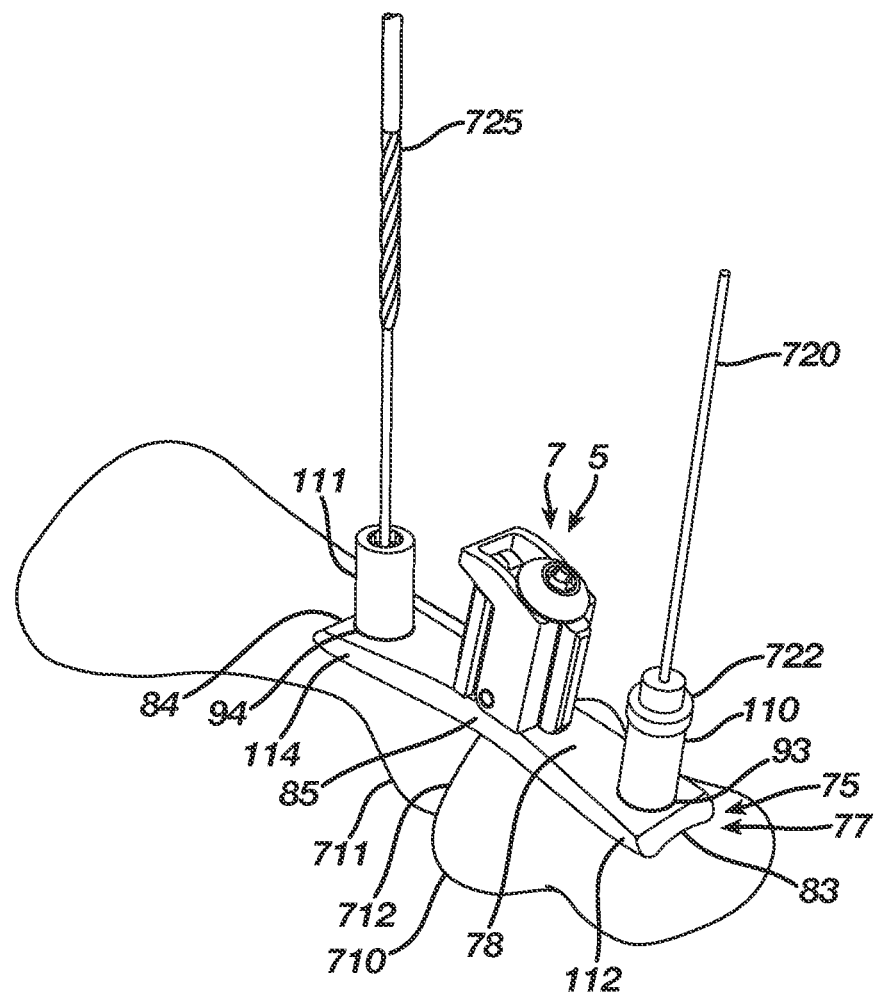

After securing the implant 75 with the first and second bones 710 and 711, the surgeon creates drill holes in the first and second bones 710 and 711. The surgeon in a first procedure as illustrated in FIG. 29 removes the locating pin 721 and the collar 723 if used, inserts a drill bit 724 through the drill guide 111 and second opening 94, and utilizes the drill bit 724 to form a drill hole in the second bone 711 at the second opening 94. Alternatively, the surgeon in a second procedure as illustrated in FIG. 30 removes the collar 723 if used, inserts a cannulated drill bit 725 over the locating pin 721 and through the drill guide 111 and second opening 94, and utilizes the drill bit 725 to form a drill hole in the second bone 711 at the second opening 94.

Figure 31:
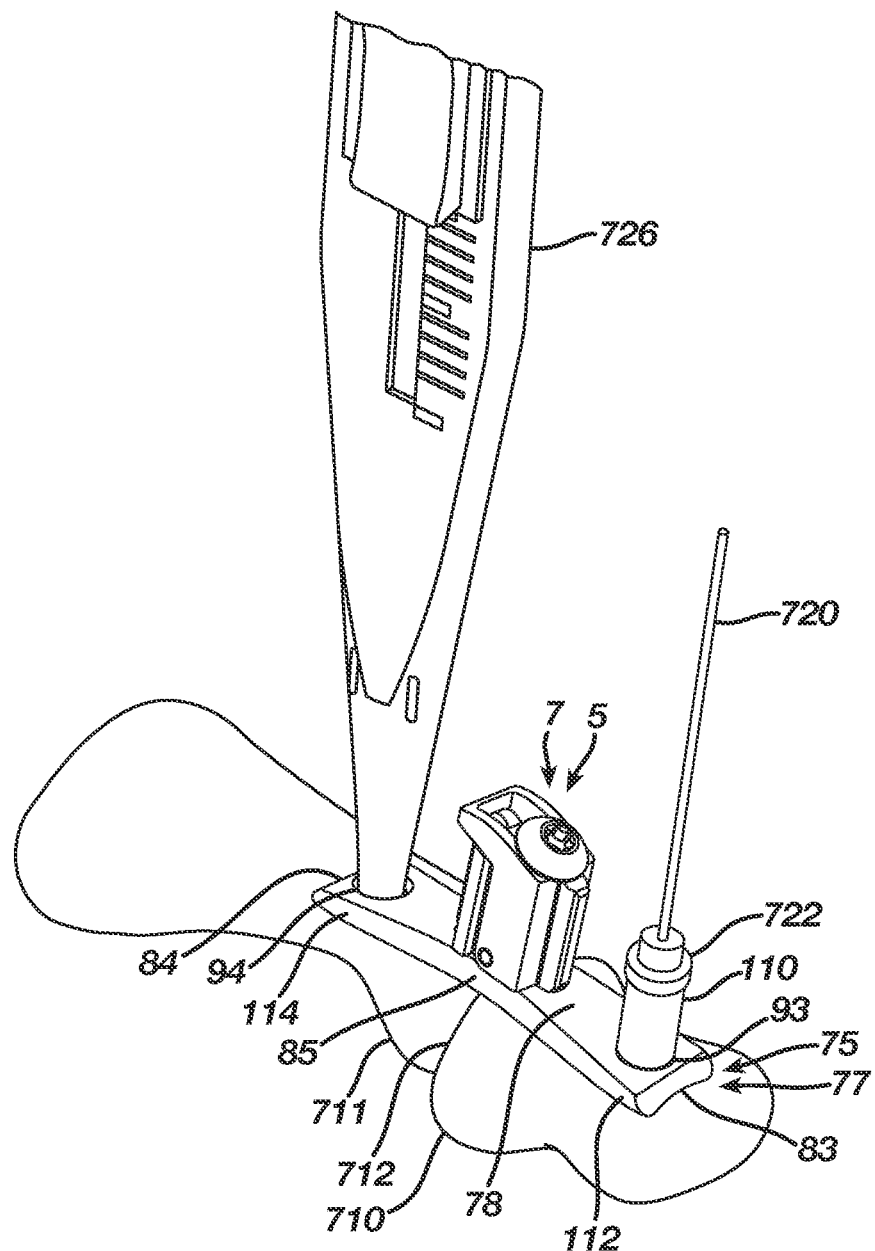
Figure 32:
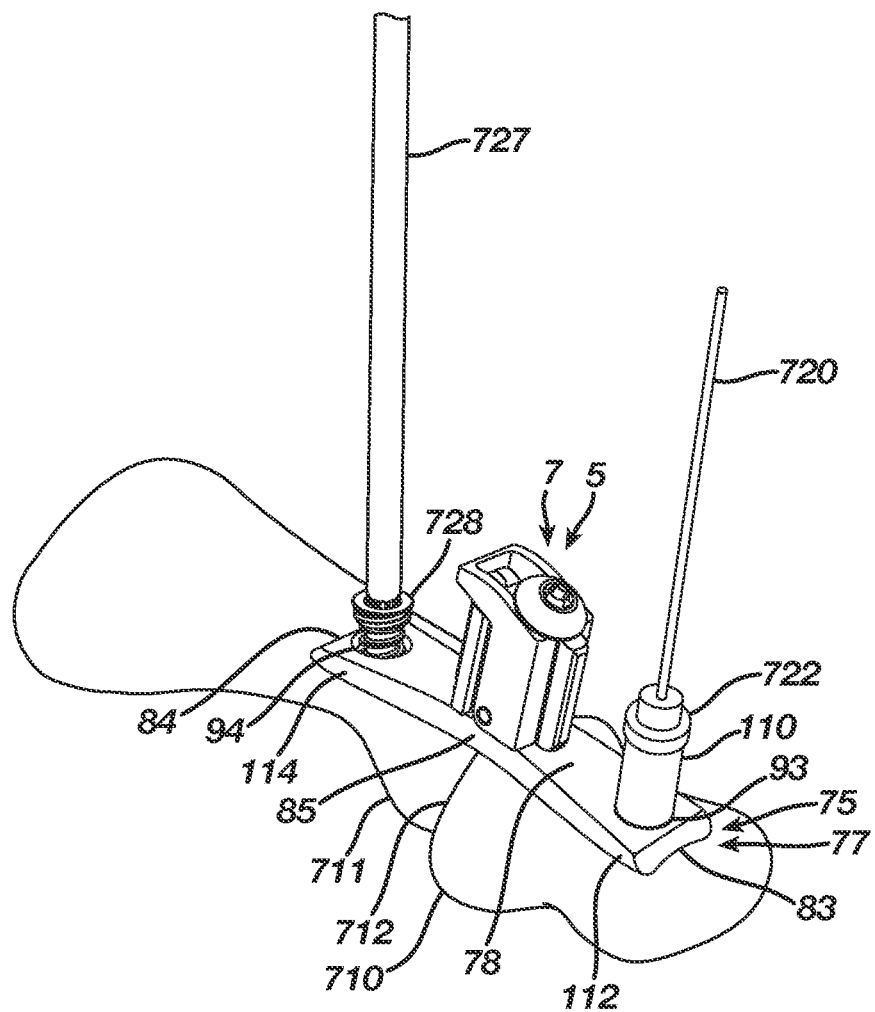

With a drill hole formed in the second bone 711 at the second opening 94, the surgeon as illustrated in FIG. 31 removes the drill guide 111 from the second opening 94 and utilizes a depth gauge 726 to determine the depth of the drill hole in the second bone 711. If the depth of the drill hole in the second bone 711 is incorrect, the surgeon re-forms the drill hole in the second bone 711. When the depth of the drill hole in the second bone 711 is correct, the surgeon confirms the alignment of the first and second bones 710 and 711 remains in the orientation that promotes fixation, and then, as illustrated in FIG. 32, the surgeon inserts, via an insertion tool 727 such as a screwdriver, an anchoring member in the form of a screw 728 through the second opening 94 and into the second bone 711 until the screw 728 at a head thereof resides substantially, completely within the second opening 94, whereby the screw 728 affixes the implant 75 at its anchoring segment 114 with the second bone 711.

Figure 33:
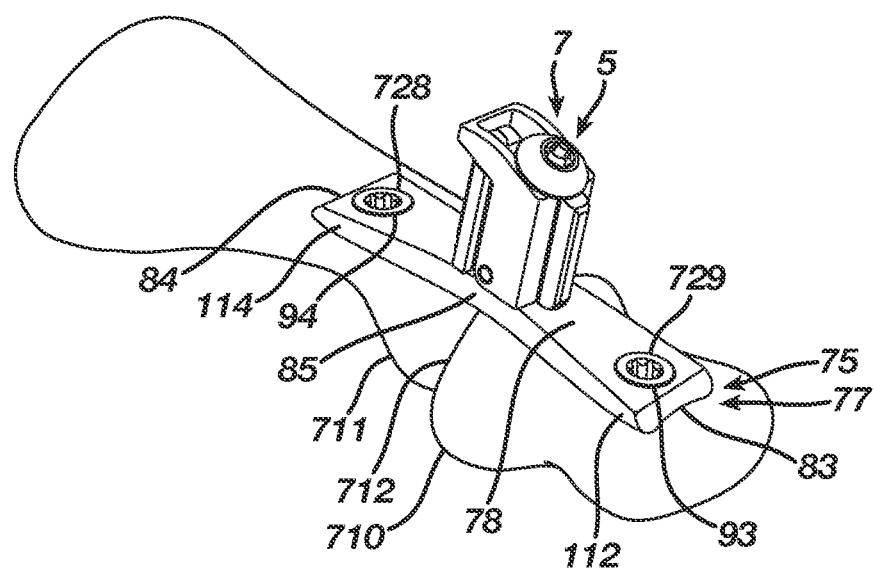

Once the surgeon affixes the implant 75 at its anchoring segment 114 with the second bone 711, the surgeon affixes the implant 75 at its anchoring segment 112 with the first bone 710. In particular, the surgeon forms a drill hole in the first bone 710 at the first opening 93 of the implant 75 employing either the first procedure illustrated in FIG. 29 or the second procedure illustrated in FIG. 30, except the first or second procedure involves the first bone 710, the implant 75 at its first opening 93, the drill guide 110, the locating pin 720, and the collar 722 if used. The surgeon then measures the correctness of the drill hole in the first bone 710 employing the procedure illustrated in FIG. 31, except the measurement involves the first bone 710. Once the depth of the drill hole in the first bone 710 is correct, the surgeon confirms the alignment of the first and second bones 710 and 711 remains in the orientation that promotes fixation, and then, employing the procedure illustrated in FIG. 32, except the procedure involves the first bone 710, the surgeon inserts, via the insertion tool 727, an anchoring member in the form of a screw 729 through the first opening 93 and into the first bone 710 until the screw 729 at a head thereof resides substantially, completely within the first opening 93, whereby, as illustrated in FIG. 33, the screw 729 affixes the implant 75 at its anchoring segment 112 with the first bone 710. While the foregoing shows forming a drill hole in the second bone 711 and inserting an anchoring member therein followed by forming a drill hole in the first bone 710 and inserting an anchoring member therein, one of ordinary skill in the art will recognize that the order of drill hole formation and anchoring member insertion may be reversed.

Figure 34:
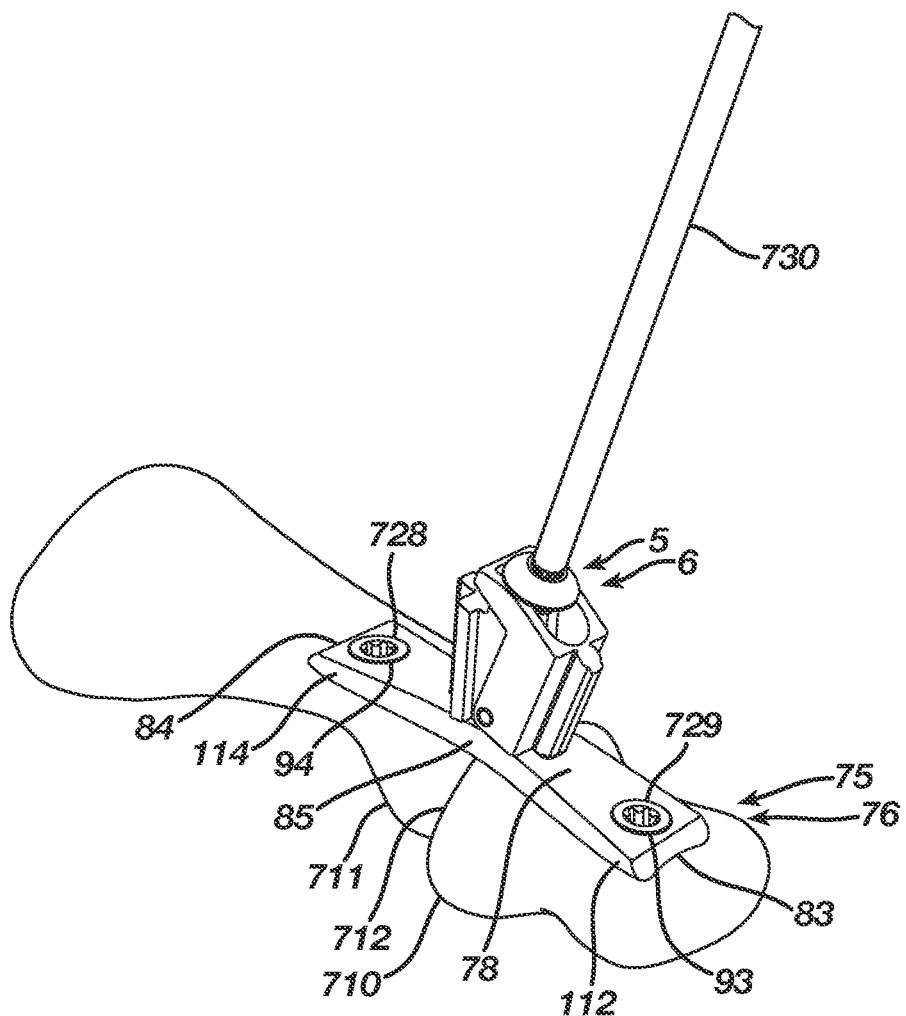
Figure 35:
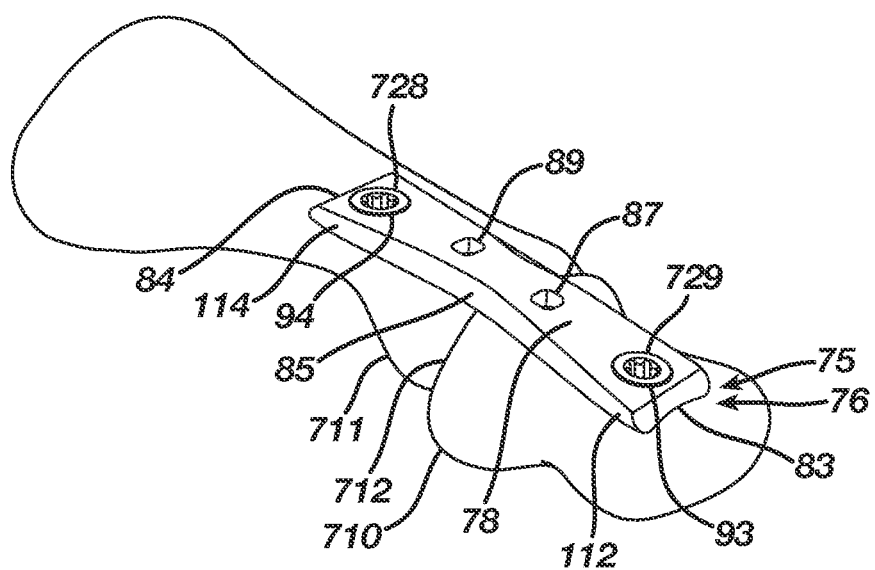

As illustrated in FIG. 33, the screw 729 secures the anchoring segment 112 at the first end 83 of the implant 75 with the first bone 710, whereas the screw 728 secures the anchoring segment 114 at the second end 84 of the implant 75 with the second bone 711, whereby the implant 75 resides on the first bone 710 and the second bone 711 with its transition section 85 located at the fusion zone 712, further whereby the implant retainer 5 in its loaded position 7 constrains the implant 75 in its insertion shape 77. The surgeon, as illustrated in FIG. 34, utilizes a rotation tool 730, such as a screwdriver, engageable with the head 70 of the actuator 9 to rotate the head 70 in the second direction as described previously, whereby the traversing of the head 70 along the bearing surface 60 from its locking position to its unlocking position progresses the fasteners 29 and 45 from their clasped position at the second distance to their unclasped position at the first distance such that the fasteners 29 and 45 and thus the detents 30 and 46 respectively move away from and thus release the first and second catches 91 and 92 at undersides thereof. The surgeon, now that the implant retainer 5 resides its unloaded position 6 whereby the actuator 9 in its unlocking position holds the implant grip 8 in its disengaged position 10, removes the implant retainer 5 from atop the implant 75 and the fasteners 29 and 45 from the first and second apertures 87 and 89. The implant 75, which is completely released from the implant retainer 5 as illustrated in FIG. 35, attempts transition from its insertion shape 77 to its natural shape 76 whereby the implant 75 delivers the energy stored in its transition section 85 to the first bone 710 and the second bone 711 such that the implant 75 affixes the first bone 710 and the second bone 711 through an application of a compressive force to the fixation zone 712. The implant retainer 5 accordingly improves insertion of the implant 75 because the implant retainer 5 does not release its constraint of the implant 75 until the implant 75 is completely affixed to the first and second bones 710 and 711 with its transition section 85 located across the fusion zone 712 thereof such that the implant retainer 5 prevents the implant 75 from prematurely delivering the energy stored therein to the first and second bones 710 and 711 at the fixation zone 712 thereof.

Figure 36:
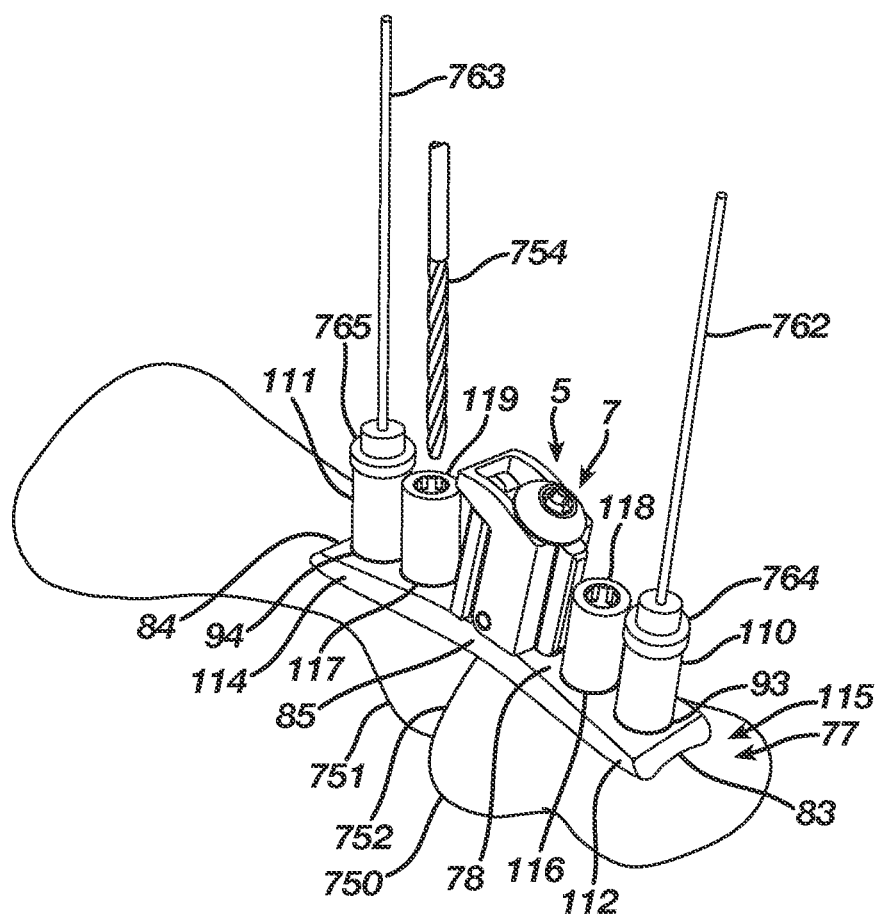
FIGS. 36-42 are isometric views illustrating implanting of a shape memory implant alternative to the first embodiment into bone, bones, or bone pieces using an implant retainer according to the first embodiment.

FIG. 36 illustrates the implant retainer 5 according to the first embodiment with an implant 115 alternative to the orthopedic implant 75 according to the first embodiment loaded thereon in an orthopedic fixation system. The implant 115 is substantially similar in design and operation relative to the implant 75 according to the first embodiment such that, for the sake of brevity, only differences therebetween will be described herein. Moreover, one of ordinary skill in the art will recognize that like parts of the implant 115 labeled with like numerals of the implant 75 incorporate a design and function as previously set forth in the detailed description of the implant 75 according to the first embodiment. The implant 115 includes the first and second openings 93 and 94 identical to the implant 75, however, in the alternative embodiment, the implant 115 further includes a third opening 116 at the anchoring segment 112 interior of the first opening 93 and a fourth opening 117 at the anchoring segment 114 that receive respectively additional drill guides 118 and 119 or anchoring members in the form of screws therethrough in order to more securely affix the implant 115 to bone, bones, or bone pieces. The implant retainer 5 in its loaded position 7 retains the implant 115 in its insertion shape 77 such that the implant 115 is ready for securing with bone, bones, or bone pieces, and, in particular, with a first bone 750 and a second bone 751, which are presented herein as an example. The implant 115 in addition to its loading on the implant retainer 5 includes the drill guides 110, 111, 118, and 119 respectively secured with the first, second, third, and fourth openings 93, 94, 116, and 117 in order to facilitate a drilling of holes in the first and second bones 750 and 751.

A surgeon as illustrated in FIG. 36 aligns the first bone 750 with the second bone 751 at a fusion zone 752 in an orientation that promotes fixation of the first bone 750 with the second bone 751 and a proper healing thereof. The surgeon then places the implant 115 held in its insertion shape 77 by the implant retainer 5 across the first bone 750 and the second bone 751 with the transition section 85 of the bridge 78 located at the fusion zone 752. Upon placement of the implant 115, the surgeon secures the implant 115 with the first and second bone 750 and 751. In particular, a locating pin 762 inserts through the drill guide 110 and into the first bone 750 thereby securing the implant 115 at its anchoring segment 112 with the first bone 750. Likewise, a locating pin 763 inserts through the drill guide 111 and into the second bone 751 thereby securing the implant 115 at its anchoring segment 114 with the second bone 751. The locating pins 762 and 763 hold the implant 115 on the first and second bones 750 and 751 with the first and second bones 750 and 751 aligned in the orientation that promotes fixation. If desired, the surgeon may secure the locating pin 762 with the drill guide 110 via a collar 764 coupled with the drill guide 110 and the locating pin 763 with the drill guide 111 via a collar 765 coupled with the drill guide 111.

Figure 37:
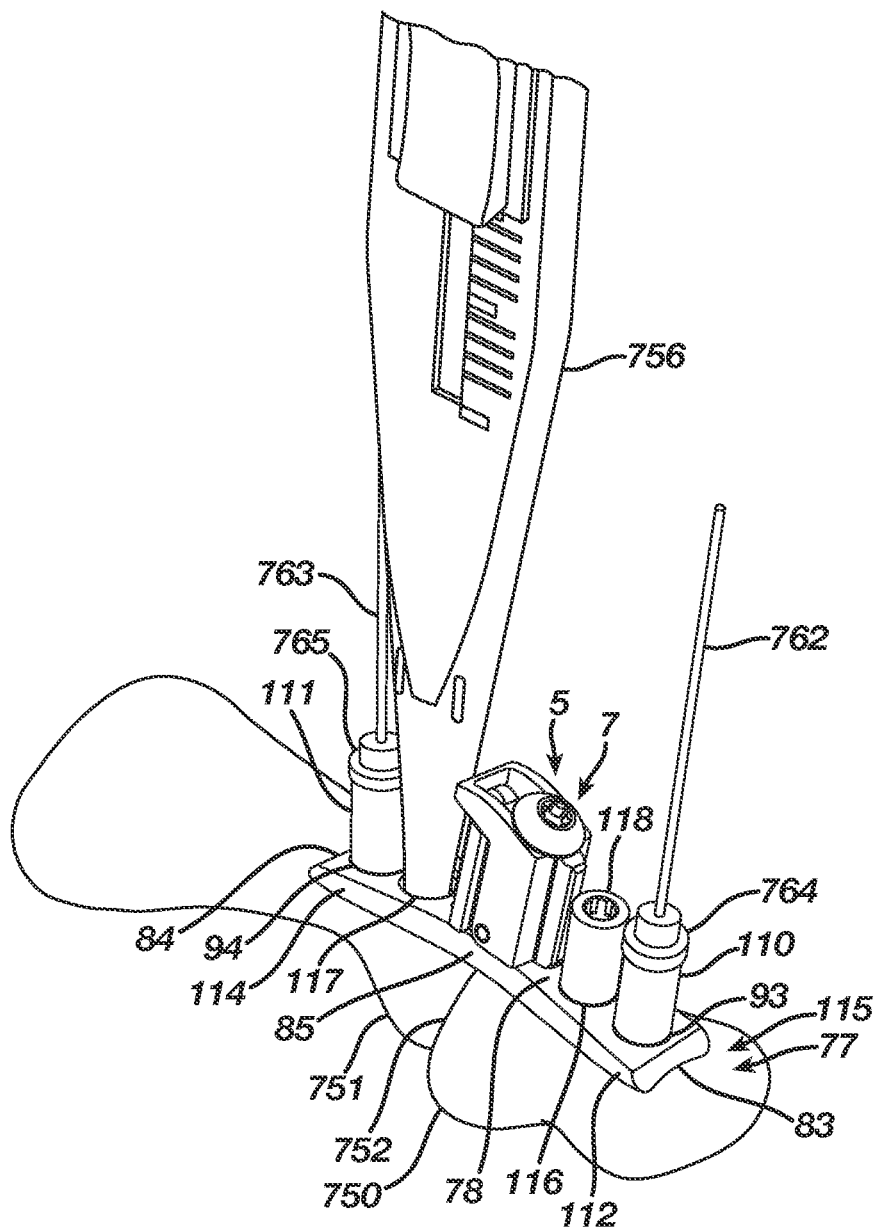
Figure 38:
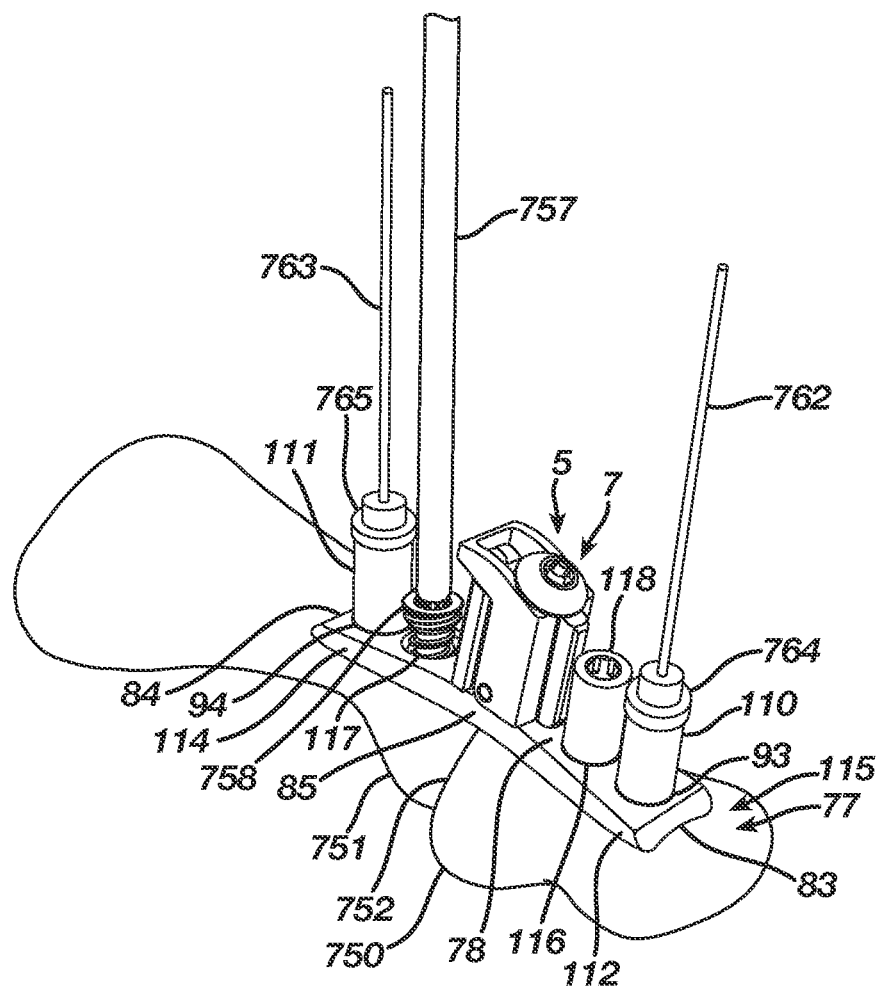

After securing the implant 115 with the first and second bones 750 and 751, the surgeon creates drill holes in the first and second bones 750 and 751. The surgeon as illustrated in FIG. 36 inserts a drill bit 754 through the drill guide 119 and the fourth opening 117 and then utilizes the drill bit 754 to form a drill hole in the second bone 751 at the fourth opening 117. With a drill hole formed in the second bone 751 at the fourth opening 117, the surgeon as illustrated in FIG. 37 removes the drill guide 119 from the fourth opening 117 and utilizes a depth gauge 756 to determine the depth of the drill hole in the second bone 751. If the depth of the drill hole in the second bone 751 is incorrect, the surgeon re-forms the drill hole in the second bone 751. When the depth of the drill hole in the second bone 751 is correct, the surgeon as illustrated in FIG. 38 inserts, via an insertion tool 757 such as a screwdriver, an anchoring member in the form of a screw 758 through the fourth opening 117 and into the second bone 751 until the screw 758 at a head thereof resides substantially, completely within the fourth opening 117, whereby the screw 758 affixes the implant 115 at its anchoring segment 114 with the second bone 751.

Once the surgeon affixes the implant 115 at its anchoring segment 114 with the second bone 751, the surgeon affixes the implant 115 at its anchoring segment 112 with the first bone 750. The surgeon inserts a drill bit 754 through the drill guide 118 and the third opening 116 and then utilizes the drill bit 754 to form a drill hole in the first bone 750 at the fourth opening 116. With a drill hole formed in the first bone 750 at the third opening 116, the surgeon removes the drill guide 118 from the fourth opening 117 and utilizes the depth gauge 756 to determine the depth of the drill hole in the first bone 750. If the depth of the drill hole in the first bone 751 is incorrect, the surgeon re-forms the drill hole in the first bone 750. When the depth of the drill hole in the first bone 750 is correct, the surgeon inserts, via the insertion tool 757, an anchoring member in the form of a screw 759 through the third opening 116 and into the first bone 750 until the screw 759 at a head thereof resides substantially, completely within the third opening 116, whereby the screw 759 affixes the implant 115 at its anchoring segment 112 with the first bone 750. While the foregoing shows forming a drill hole in the second bone 751 and inserting an anchoring member therein followed by forming a drill hole in the first bone 750 and inserting an anchoring member therein, one of ordinary skill in the art will recognize that the order of drill hole formation and anchoring member insertion may be reversed.

Figure 39:
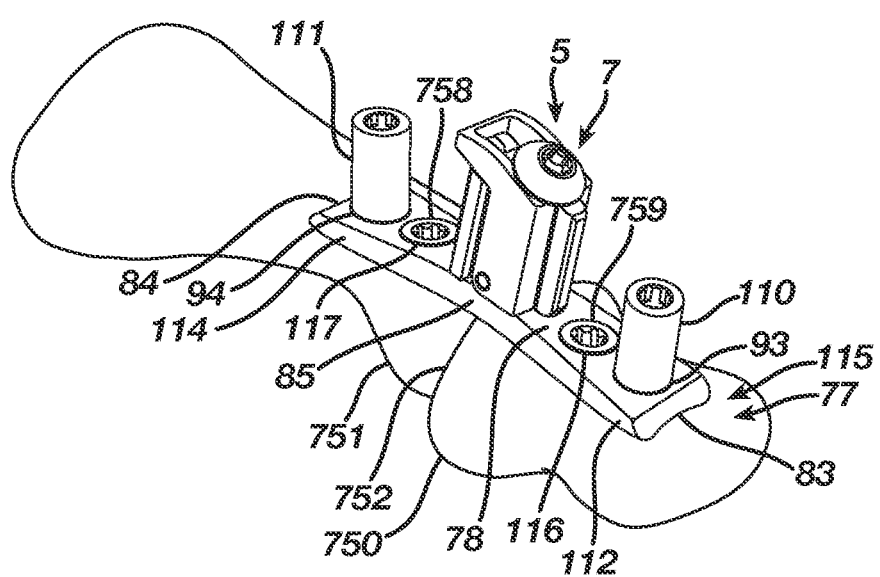

As illustrated in FIG. 39, the screw 759 secures the anchoring segment 112 at the first end 83 of the implant 115 with the first bone 750, whereas the screw 758 secures the anchoring segment 114 at the second end 84 of the implant 115 with the second bone 751, whereby the implant 115 resides on the first bone 750 and the second bone 751 with its transition section 85 located at the fusion zone 752 such that the first and second bones 710 and 711 remain aligned in the orientation that promotes their fixation. With the implant 115 affixed to the first and second bones 750, the surgeon removes the locating pin 763 and the collar 765 if used and then forms a drill hole in the second bone 751 at the second opening 94 of the implant 115 as previously described. After forming a drill hole in the second bone 751 with a correct depth, the surgeon inserts, via the insertion tool 757, an anchoring member in the form of a screw 760 through the second opening 94 and into the second bone 751 until the screw 760 at a head thereof resides substantially, completely within the second opening 94, whereby the screw 760 further affixes the implant 115 at its anchoring segment 114 with the second bone 751. Likewise, the surgeon removes the locating pin 762 and the collar 764 if used and then forms a drill hole in the first bone 750 at the first opening 93 of the implant 115 as previously described. After forming a drill hole in the first bone 750 with a correct depth, the surgeon inserts, via the insertion tool 757, an anchoring member in the form of a screw 761 through the first opening 93 and into the first bone 750 until the screw 761 at a head thereof resides substantially, completely within the first opening 93, whereby the screw 761 further affixes the implant 115 at its anchoring segment 112 with the first bone 751. While the foregoing shows forming a drill hole in the second bone 751 and inserting an anchoring member therein followed by forming a drill hole in the first bone 750 and inserting an anchoring member therein, one of ordinary skill in the art will recognize that the order of drill hole formation and anchoring member insertion may be reversed.

Figure 40:
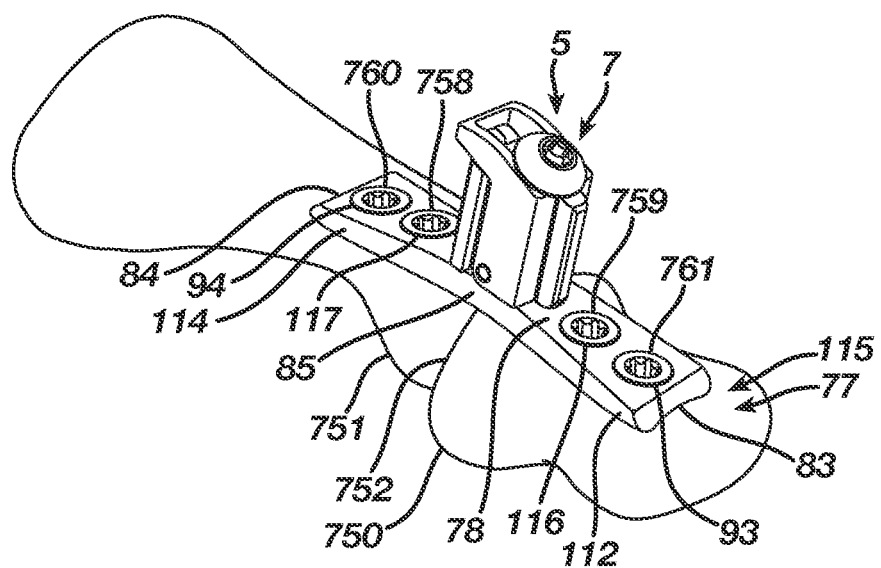
Figure 41:
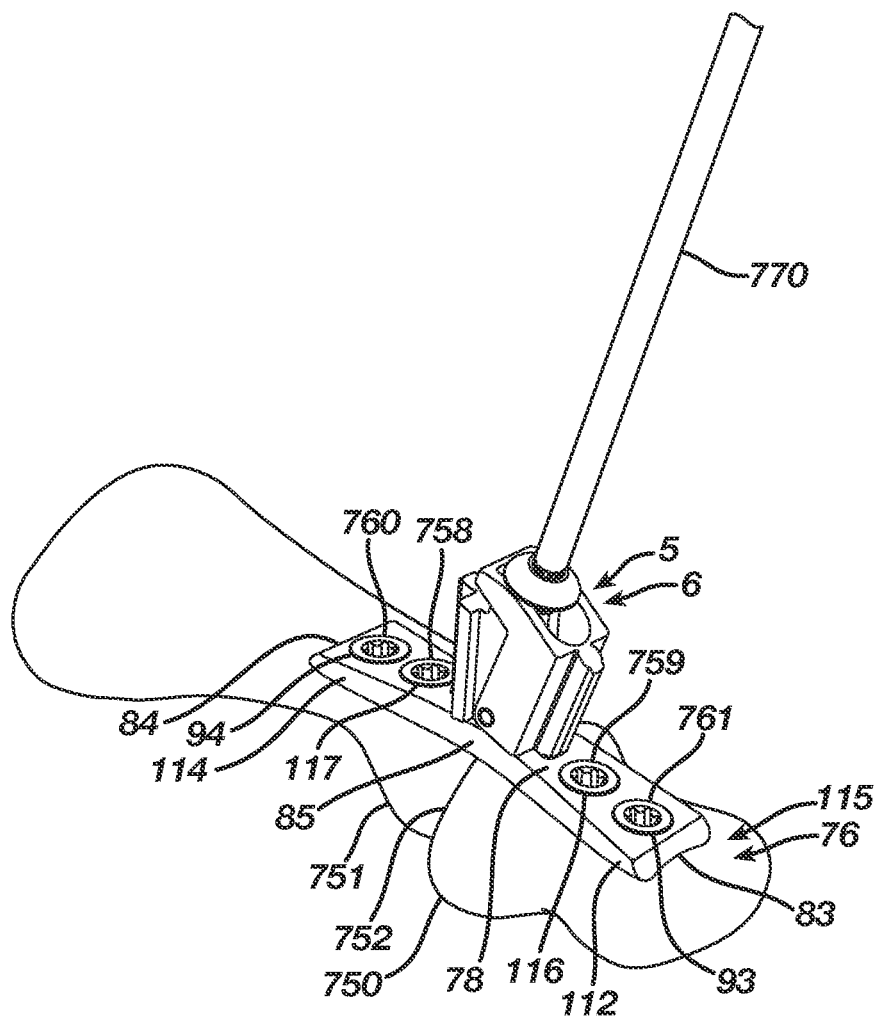
Figure 42:
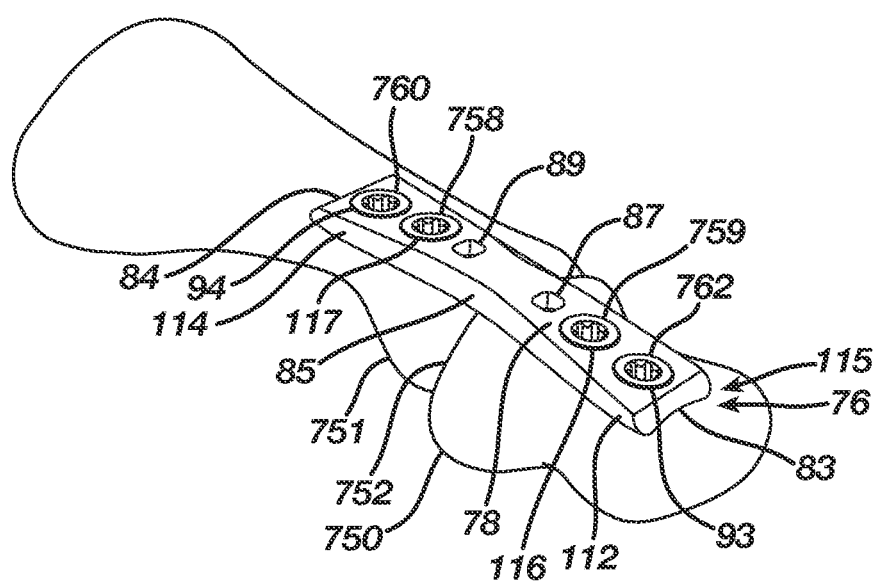

As illustrated in FIG. 40, the screws 759 and 761 secure the anchoring segment 112 at the first end 83 of the implant 115 with the first bone 750, whereas the screws 758 and 760 secure the anchoring segment 114 at the second end 84 of the implant 115 with the second bone 751, whereby the implant 115 resides on the first bone 750 and the second bone 751 with its transition section 85 located at the fusion zone 752, further whereby the implant retainer 5 in its loaded position 7 constrains the implant 115 in its insertion shape 77. The surgeon, as illustrated in FIG. 41, utilizes a rotation tool 770, such as a screwdriver, engageable with the head 70 of the actuator 9 to rotate the head 70 in the second direction as described previously, whereby the traversing of the head 70 along the bearing surface 60 from its locking position to its unlocking position progresses the fasteners 29 and 45 from their clasped position at the second distance to their unclasped position at the first distance such that the fasteners 29 and 45 respectively and thus the detents 30 and 46 move away from and thus release the first and second catches 91 and 92 at undersides thereof. The surgeon, now that the implant retainer 5 resides its unloaded position 6 whereby the actuator 9 in its unlocking position holds the implant grip 8 in its disengaged position 10, removes the implant retainer 5 from atop the implant 115 and the fasteners 29 and 45 from the first and second apertures 87 and 89. The implant 115, which is completely released from the implant retainer 5 as illustrated in FIG. 42, attempts transition from its insertion shape 77 to its natural shape 76 whereby the implant 115 delivers the energy stored in its transition section 85 to the first bone 750 and the second bone 751 such that the implant 115 affixes the first bone 750 and the second bone 751 through an application of a compressive force to the fixation zone 752. The implant retainer 5 accordingly improves insertion of the implant 115 because the implant retainer 5 does not release its constraint of the implant 115 until the implant 115 is completely affixed to the first and second bones 750 and 751 with its transition section 85 located across the fusion zone 752 thereof such that the implant retainer 5 prevents the implant 115 from prematurely delivering the energy stored therein to the first and second bones 750 and 751 at the fixation zone 752 thereof.

When implanting the implant 175 according to the second embodiment into a first bone and a second bone utilizing the implant retainer 150 according to the second embodiment, one of ordinary skill in the art will recognize that the implant retainer 150 operates substantially similar to the implant retainer 5 as previously described with respect to the implantation of the implant 75 except that the number of pre-drilled holes will correspond in location, spacing, and number based upon the configuration of the implant 175. Likewise, when implanting the implant 275 according to the third embodiment into a first bone and a second bone utilizing the implant retainer 250 according to the third embodiment, one of ordinary skill in the art will recognize that the implant retainer 250 operates substantially similar to the implant retainer 5 as previously described with respect to the implantation of the implant 75 except that the number of pre-drilled holes will correspond in location, spacing, and number based upon the configuration of the implant 275.

Figure 43:
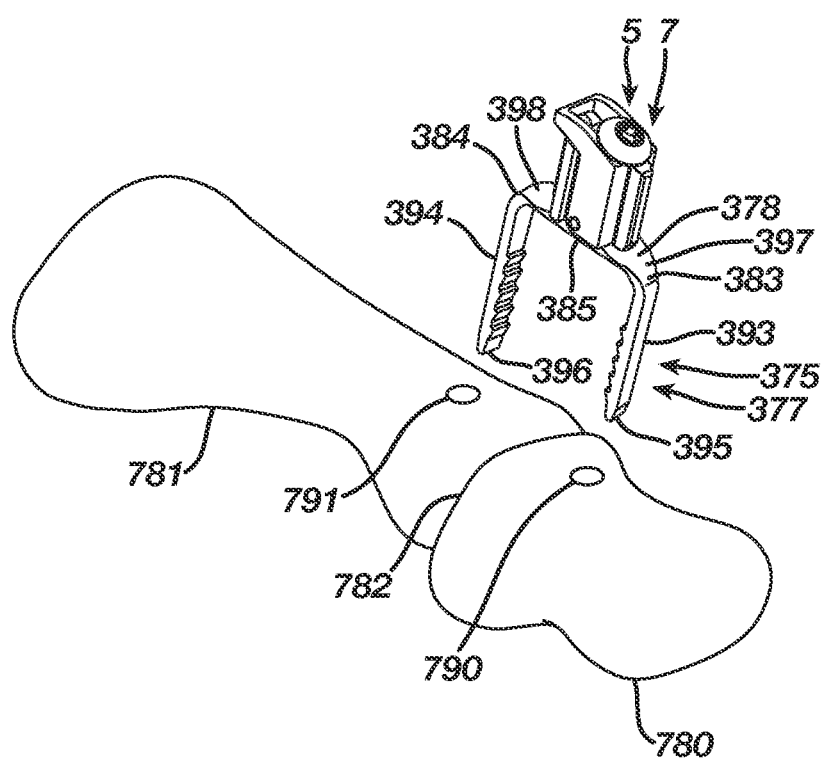
FIGS. 43-46 are isometric views illustrating implanting of the shape memory implant according to the fourth embodiment into bone, bones, or bone pieces using an implant retainer according to the first embodiment.
Figure 44:
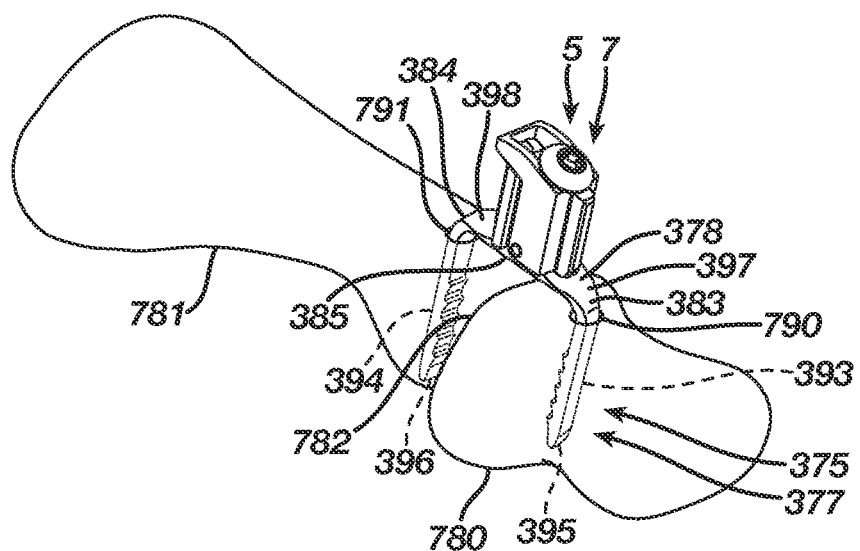

FIG. 43 illustrates the implant retainer 5 with the implant 375 of the fourth embodiment loaded thereon in an orthopedic fixation system whereby the implant retainer 5 constrains the implant 375 in its insertion shape 377 such that the implant 375 is ready for implantation into bone, bones, or bone pieces, and, in particular, into a first bone 780 and a second bone 781, which are presented herein as an example. A surgeon as illustrated in FIG. 43 aligns the first bone 780 with the second bone 781 at a fusion zone 782 in an orientation that promotes fixation of the first bone 701 with the second bone 702 and a proper healing thereof. The surgeon then drills a drill hole 790 in the first bone 780 and a drill hole 791 in the second bone 781. The drill holes 790 and 791 are drilled at spacings and locations desired for insertion of the leg 393 into the first bone 780 and the leg 394 into the second bone 781 whereby the bridge 378 of the implant 375 when the implant 375 resides in its insertion shape 377 spans the fusion zone 782 with the transition section 385 located at the fusion zone 782. While not required, the surgeon may create grooves in the first and second bones 780 and 781 that facilitate a more flush seating of the bridge 378 for the implant 375 relative to the first and second bones 780 and 781. The surgeon next utilizes the implant retainer 5 to position the tip 395 of the leg 394 for the implant 375 adjacent the pre-drilled hole 790 and the tip 396 of the leg 395 for the implant 375 adjacent the pre-drilled hole 791. After the tips 395 and 396 reside respectively at the pre-drilled hole 790 and 791, the surgeon as illustrated in FIG. 44 inserts the legs 393 and 394 respectively into the pre-drilled holes 790 and 791 using the implant retainer 5 until the bridge 378 abuts the first bone 780 and the second bone 781 with the transition section 385 located at the fusion zone 782. While an insertion of the implant 375 typically includes pre-drilling of the holes 790 and 791, the surgeon may use the implant retainer 5 to impact the legs 393 and 394 respectively into the first and second bones 780 and 781 at a desired location.

Figure 45:
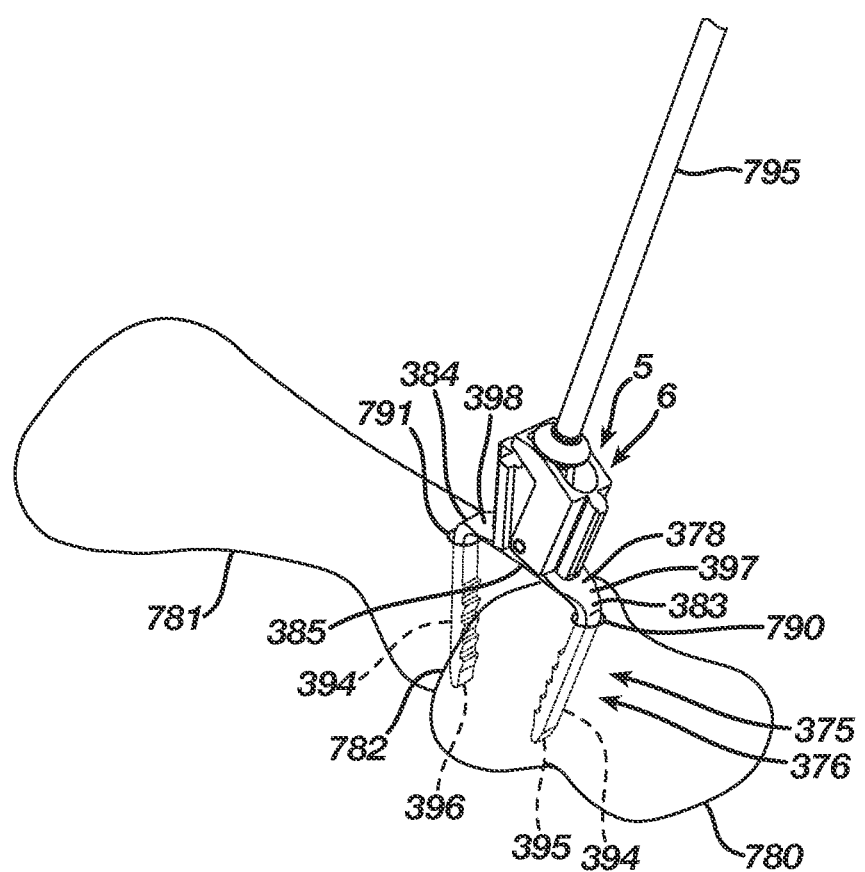
Figure 46:
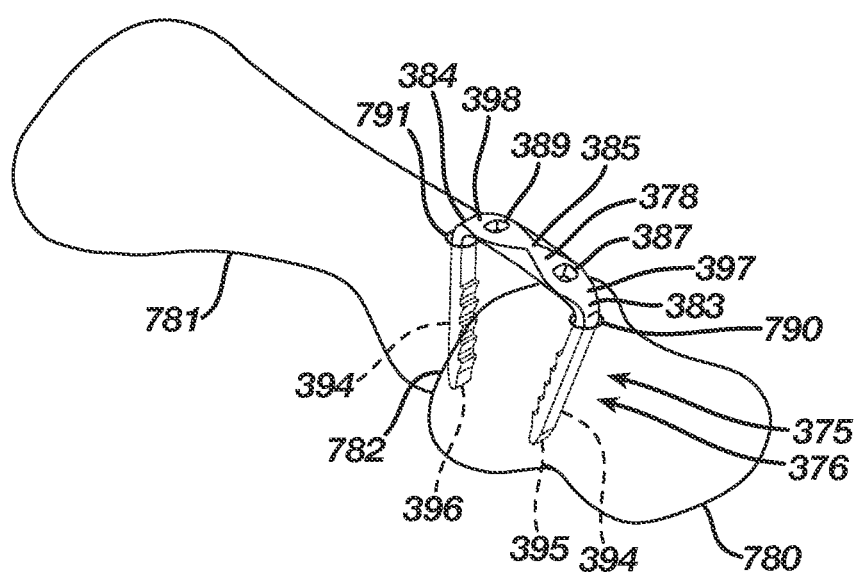

With the legs 393 and 394 inserted respectively into the pre-drilled holes 790 and 791, the leg 393 secures the anchoring segment 397 at the first end 383 of the implant 375 with the first bone 780, whereas the leg 394 secures the anchoring segment 398 at the second end 384 of the implant 375 with the second bone 781, whereby the implant 375 resides on the first bone 780 and the second bone 781 with its transition section 385 located at the fusion zone 782, further whereby the implant retainer 5 in its loaded position 7 constrains the implant 375 in its insertion shape 377. The surgeon, as illustrated in FIG. 45, utilizes a rotation tool 795, such as a screwdriver, engageable with the head 70 of the actuator 9 to rotate the head 70 in the second direction as described previously, whereby the traversing of the head 70 along the bearing surface 60 from its locking position to its unlocking position progresses the fasteners 29 and 45 from their clasped position at the second distance to their unclasped position at the first distance such that the fasteners 29 and 45 and thus the detents 30 and 46 respectively move away from and thus release the first and second catches 391 and 392 at undersides thereof. The surgeon, now that the implant retainer 5 resides its unloaded position 6 whereby the actuator 9 in its unlocking position holds the implant grip 8 in its disengaged position 10, removes the implant retainer 5 from atop the implant 375 and the fasteners 29 and 45 from the first and second apertures 387 and 389. The implant 375, which is completely released from the implant retainer 5 as illustrated in FIG. 46, attempts transition from its insertion shape 377 to its natural shape 376 whereby the implant 375 delivers the energy stored in its transition section 385 to the first bone 780 and the second bone 781 such that the implant 375 affixes the first bone 780 and the second bone 781 through an application of a compressive force to the fixation zone 782. The implant retainer 5 accordingly improves insertion of the implant 375 because the implant retainer 5 does not release its constraint of the implant 375 until the implant 375 is completely affixed to the first and second bones 780 and 781 with its transition section 385 located across the fusion zone 782 thereof such that the implant retainer 5 prevents the implant 375 from prematurely delivering the energy stored therein to the first and second bones 780 and 781 at the fixation zone 782 thereof.

When implanting the implant 475 according to the fifth embodiment into a first bone and a second bone utilizing the implant retainer 5 according to the first embodiment, one of ordinary skill in the art will recognize that the implantation of the implant 475 is substantially similar as previously described with respect to the implantation of the implant 375 except that the number of pre-drilled holes will correspond in location, spacing, and number based upon the configuration of the implant 475. Similarly, when implanting the implant 575 according to the sixth embodiment into a first bone and a second bone utilizing the implant retainer 5 according to the first embodiment, one of ordinary skill in the art will recognize that the implantation of the implant 575 is substantially similar as previously described with respect to the implantation of the implant 375 except that the number of pre-drilled holes will correspond in location, spacing, and number based upon the configuration of the implant 575. Likewise, when implanting the implant 675 according to the seventh embodiment into a first bone and a second bone utilizing the implant retainer 5 according to the first embodiment, one of ordinary skill in the art will recognize that the implantation of the implant 675 is substantially similar as previously described with respect to the implantation of the implant 375 except that the number of pre-drilled holes will correspond in location, spacing, and number based upon the configuration of the implant 675.

Although the present invention has been described in terms of the foregoing preferred embodiments, such description has been for exemplary purposes only and, as will be apparent to those of ordinary skill in the art, many alternatives, equivalents, and variations of varying degrees will fall within the scope of the present invention. That scope, accordingly, is not to be limited in any respect by the foregoing detailed description; rather, it is defined only by the claims that follow.

The invention claimed is:

1. An orthopedic fixation system, comprising:
   an orthopedic implant transitionable between a natural shape and an insertion shape whereby a transition of the orthopedic implant from the natural shape to the insertion shape stores deliverable energy and a transition of the orthopedic implant from the insertion shape to the natural shape delivers stored energy, the orthopedic implant, comprising:
      a bridge with a first end and a second end,
      a transition section disposed in the bridge, whereby the transition section deforms to move the orthopedic implant between the natural shape and the insertion shape,
      a first anchoring segment disposed at the first end of the bridge,
      a second anchoring segment disposed at the second end of the bridge,
      a first aperture extending through the bridge adjacent the transition section at a first side thereof, and
      a second aperture extending through the bridge adjacent the transition section at a second side thereof, the first aperture and the second aperture being spaced apart across the transition section;
   an implant retainer configured to engage the orthopedic implant at the first aperture and the second aperture and constrain the orthopedic implant in the insertion shape thereby preventing a transition of the orthopedic implant from the insertion shape to the natural shape;
   the implant retainer, comprising an implant grip and an actuator coupled with the implant grip, the actuator being operable to move the implant grip between a disengaged position whereby the implant grip releases the orthopedic implant and an engaged position whereby the implant grip constrains the orthopedic implant in the insertion shape;
   the implant grip, comprising a frame and a body pivotally secured at a pivot point, whereby the actuator is engageable with the frame and the body and operable to impart angular motion to the frame and the body about the pivot point such that the implant grip moves between the disengaged position and the engaged position; and
   the implant grip, further comprising a first fastener extending from the frame and adapted to engage the orthopedic implant at the first aperture and a second fastener extending from the body and adapted to engage the orthopedic implant at the second aperture, the first fastener and the second fastener being spaced apart at a first distance when the implant grip resides in the disengaged position and at a second distance greater than the first distance when the implant grip resides in the engaged position, wherein:
      upon operation of the actuator to move the implant grip to the disengaged position with the first fastener and the second fastener residing at the first distance, the first fastener inserts into and removes from the first aperture of the orthopedic implant and the second fastener inserts into and removes from the second aperture of the orthopedic implant, and
      upon operation of the actuator to move the implant grip to the engaged position with the first fastener and the second fastener residing at the second distance, the first fastener engages with the bridge of the orthopedic implant at the first aperture and the second fastener engages with the bridge of the orthopedic implant at the second aperture, whereby the implant grip secures with the orthopedic implant across the transition section of the bridge, further whereby the implant grip constrains the bridge and holds the orthopedic implant in the insertion shape to prevent a transition of the orthopedic implant from the insertion shape to the natural shape.

2. The orthopedic fixation system of claim 1, the orthopedic implant comprising a first catch protruding into the first aperture and a second catch protruding into the second aperture.

3. The orthopedic fixation system of claim 2, the first fastener comprising a first detent and the second fastener comprising a second detent whereby, upon operation of the actuator to move the implant grip to the disengaged position with the first fastener and the second fastener residing at the first distance, the first fastener inserts into and removes from the first aperture of the orthopedic implant such that the first detent bypasses the first catch and the second fastener inserts into and removes from the second aperture of the orthopedic implant such that the second detent bypasses the second catch, further whereby, upon operation of the actuator to move the implant grip to the engaged position with the first fastener and the second fastener residing at the second distance, the first detent interlocks with the first catch such that the first fastener engages with the bridge of the orthopedic implant at the first aperture and the second detent interlocks with the second catch such that the second fastener engages with the bridge of the orthopedic implant at the second aperture, whereby the implant grip secures with the orthopedic implant across the transition section of the bridge, further whereby the implant grip constrains the bridge and holds the orthopedic implant in the insertion shape to prevent a transition of the orthopedic implant from the insertion shape to the natural shape.

4. The orthopedic fixation system of claim 1, wherein:
the frame includes a front, a rear, a top, and a bottom, the front being elevated relative to the rear whereby the top angles downward between the front and the rear;
the frame defines a chamber;
the frame at the top thereof includes a slot communicating with the chamber;
the frame at the top thereof about the slot includes a bearing surface with a slope due to the front being elevated relative to the rear; and
the frame at the rear thereof includes the first fastener extending below the bottom of the frame.

5. The orthopedic fixation system of claim 4, wherein:
the body includes a front, a rear, a top, and a bottom;
the body defines an actuator aperture beginning at the top thereof and extending into the body, the actuator aperture being adapted to receive therein at least a portion of the actuator, whereby the actuator aperture facilitates linear travel of the actuator relative thereto;
the body is configured to insert into the chamber of the frame such that the actuator aperture of the body is accessible through the slot of the frame; and
the body at the rear thereof includes the second fastener extending below the bottom of the body.

6. The orthopedic fixation system of claim 5, the actuator, comprising a head coupled with a shaft, whereby the shaft inserts through the slot of the frame and into the actuator aperture of the body, further whereby the head resides atop the bearing surface at the top of the frame in abutting relationship therewith.

7. The orthopedic fixation system of claim 6, wherein:
the frame and the body, when the implant grip resides in the disengaged position, pivot relative thereto about the pivot point whereby the top of the body defining the actuator aperture is positioned in the slot adjacent the front of the frame and the front of the body is spaced apart from the rear of the frame;
the actuator, when the implant grip resides in the disengaged position, including the head thereof being located atop the bearing surface adjacent the front of the frame and the shaft thereof being inserted in the actuator aperture a first distance;
the frame and the body, when the implant grip resides in the engaged position, pivot relative thereto about the pivot point whereby the top of the body defining the actuator aperture is positioned in the slot adjacent the rear of the frame and the front of the body is positioned adjacent the rear of the frame; and
the actuator, when the implant grip resides in the engaged position, including the head thereof being located atop the bearing surface adjacent the rear of the frame and the shaft thereof being inserted in the actuator aperture a second distance greater than the first distance based upon the front of the frame being elevated relative to the rear of the frame.

8. The orthopedic fixation system of claim 7, wherein the actuator, in moving the implant grip from the disengaged position to the engaged position, being rotationally operable to facilitate a rotational motion of the head and a linear progression of the shaft, whereby:
the head traverses the bearing surface of the frame from adjacent the front of the frame to adjacent the rear of the frame and the shaft progresses within the actuator aperture from the first distance to the second distance based upon the abutting relationship of the head with the bearing surface of the frame and the slope of the bearing surface being negative relative to the head,
the pivot point of the frame and the body translates the rotational motion of the head and the linear progression of the shaft into a linear motion imparted to the frame and the body that pivots the frame and the body about the pivot point along a decreasing arc until the top of the body defining the actuator aperture traverses the slot from adjacent the front of the frame to adjacent the rear of the frame and the front of the body inserts into the chamber of the frame adjacent the rear of the frame, and
the first fastener and the second fastener progress from the first distance to the second distance such that the first fastener engages with the bridge of the orthopedic implant at the first aperture and the second fastener engages with the bridge of the orthopedic implant at the second aperture.

9. The orthopedic fixation system of claim 7, wherein the actuator, in moving the implant grip from the engaged position to the disengaged position, being rotationally operable to facilitate a rotational motion of the head and a linear retraction of the shaft, whereby:
the head traverses the bearing surface of the frame from adjacent the rear of the frame to adjacent the front of the frame and the shaft retracts within the actuator aperture from the second distance to the first distance based upon the abutting relationship of the head with the bearing surface of the frame and the slope of the bearing surface being positive relative to the head,
the pivot point of the frame and the body translates the rotational motion of the head and the linear retraction of the shaft into a linear motion imparted to the frame and the body that pivots the frame and the body about the pivot point along an increasing arc until the top of the body defining the actuator aperture traverses the slot from adjacent the rear of the frame to adjacent the front of the frame and the front of the body is spaced apart from the rear of the frame, and
the first fastener and the second fastener progress from the second distance to the first distance such that the first fastener disengages from the bridge of the orthopedic implant at the first aperture and the second fastener disengages from the bridge of the orthopedic implant at the second aperture.

10. The orthopedic fixation system of claim 7, the orthopedic implant comprising a first catch protruding into the first aperture and a second catch protruding into the second aperture.

11. The orthopedic fixation system of claim 10, the first fastener comprising a first detent and the second fastener comprising a second detent.

12. The orthopedic fixation system of claim 11, wherein the actuator, in moving the implant grip from the disengaged position to the engaged position, being rotationally operable to facilitate a rotational motion of the head and a linear progression of the shaft, whereby:
the head traverses the bearing surface of the frame from adjacent the front of the frame to adjacent the rear of the frame and the shaft progresses within the actuator aperture from the first distance to the second distance based upon the abutting relationship of the head with the bearing surface of the frame and the slope of the bearing surface being negative relative to the head,
the pivot point of the frame and the body translates the rotational motion of the head and the linear progression of the shaft into a linear motion imparted to the frame and the body that pivots the frame and the body about the pivot point along a decreasing arc until the top of the body defining the actuator aperture traverses the slot from adjacent the front of the frame to adjacent the rear of the frame and the front of the body inserts into the chamber of the frame adjacent the rear of the frame, and
the first fastener and the second fastener progress from the first distance to the second distance such that the first detent interlocks with the first catch thereby engaging with the bridge of the orthopedic implant at the first aperture and the second detent interlocks with the second catch thereby engaging with the bridge of the orthopedic implant at the second aperture.

13. The orthopedic fixation system of claim 11, wherein the actuator, in moving the implant grip from the engaged position to the disengaged position, being rotationally operable to facilitate a rotational motion of the head and a linear retraction of the shaft, whereby:
the head traverses the bearing surface of the frame from adjacent the rear of the frame to adjacent the front of the frame and the shaft retracts within the actuator aperture from the second distance to the first distance based upon the abutting relationship of the head with the bearing surface of the frame and the slope of the bearing surface being positive relative to the head,
the pivot point of the frame and the body translates the rotational motion of the head and the linear retraction of the shaft into a linear motion imparted to the frame and the body that pivots the frame and the body about the pivot point along an increasing arc until the top of the body defining the actuator aperture traverses the slot from adjacent the rear of the frame to adjacent the front of the frame and the front of the body is spaced apart from the rear of the frame, and
the first fastener and the second fastener progress from the second distance to the first distance such that the first detent releases the first catch thereby disengaging with the bridge of the orthopedic implant at the first aperture and the second detent releases the second catch thereby disengaging with the bridge of the orthopedic implant at the second aperture.

14. The orthopedic fixation system of claim 1, the orthopedic implant, comprising:
the first anchoring segment comprising a first opening extending through the bridge at the first end thereof, the first opening adapted to receive a screw therethrough; and
the second anchoring segment comprising a second opening extending through the bridge at the second end thereof, the second opening adapted to receive a screw therethrough.

15. The orthopedic fixation system of claim 14, the orthopedic implant, comprising:
the first anchoring segment comprising a third opening extending through the bridge at the first end thereof exterior of the first opening, the third opening adapted to receive a screw therethrough; and
the second anchoring segment comprising a fourth opening extending through the bridge at the second end thereof exterior of the second opening, the fourth opening adapted to receive a screw therethrough.

16. The orthopedic fixation system of claim 14, the orthopedic implant, comprising a third anchoring segment disposed at the first end of the bridge adjacent the first anchoring segment, the third anchoring segment comprising a third opening extending through the bridge at the first end thereof adjacent the first opening, the third opening adapted to receive a screw therethrough.

17. The orthopedic fixation system of claim 16, the orthopedic implant, comprising a fourth anchoring segment disposed at the second end of the bridge adjacent the second anchoring segment, the fourth anchoring segment comprising a fourth opening extending through the bridge at the second end thereof adjacent the second opening, the fourth opening adapted to receive a screw therethrough.

18. The orthopedic fixation system of claim 1, the orthopedic implant, comprising:
the first anchoring segment comprising a first leg extending from the bridge at the first end thereof; and
the second anchoring segment comprising a second leg extending from the bridge at the second end thereof.

19. The orthopedic fixation system of claim 18, the orthopedic implant, comprising:
the first anchoring segment comprising a third leg extending from the bridge interior of the first leg; and
the second anchoring segment comprising a fourth leg extending from the bridge interior of the second leg.

20. The orthopedic fixation system of claim 18, the orthopedic implant, comprising a third anchoring segment disposed at the first end of the bridge adjacent the first anchoring segment, the third anchoring segment comprising a third leg extending from the bridge at the first end thereof adjacent the first leg.

21. The orthopedic fixation system of claim 20, the orthopedic implant, comprising a fourth anchoring segment disposed at the second end of the bridge adjacent the second anchoring segment, the fourth anchoring segment comprising a fourth leg extending from the bridge at the second end thereof adjacent the second leg.

* * * * *